United States Patent
Kwiatkowski et al.

(10) Patent No.: US 11,957,735 B2
(45) Date of Patent: *Apr. 16, 2024

(54) RELEASABLE GLP-1 CONJUGATES

(71) Applicant: QuiaPEG Pharmaceuticals AB, Uppsala (SE)

(72) Inventors: Marek Kwiatkowski, Uppsala (SE); Christian Sund, Varby (SE)

(73) Assignee: QuiaPEG Pharmaceuticals AB, Uppsala (SE)

(*) Notice: Subject to any disclaimer, the term of this patent is extended or adjusted under 35 U.S.C. 154(b) by 142 days.

This patent is subject to a terminal disclaimer.

(21) Appl. No.: 17/559,692

(22) Filed: Dec. 22, 2021

(65) Prior Publication Data

US 2022/0118055 A1  Apr. 21, 2022

Related U.S. Application Data

(63) Continuation of application No. 16/568,935, filed on Sep. 12, 2019, now Pat. No. 11,357,828.

(60) Provisional application No. 62/771,972, filed on Nov. 27, 2018, provisional application No. 62/730,935, filed on Sep. 13, 2018, provisional application No. 62/730,341, filed on Sep. 12, 2018.

(51) Int. Cl.
*A61K 38/00* (2006.01)
*A61K 38/26* (2006.01)
*A61K 47/60* (2017.01)

(52) U.S. Cl.
CPC .............. *A61K 38/26* (2013.01); *A61K 47/60* (2017.08)

(58) Field of Classification Search
CPC .................. A61K 38/26; A61K 47/60
See application file for complete search history.

(56) References Cited

U.S. PATENT DOCUMENTS

| | | |
|---|---|---|
| 4,647,447 A | 3/1987 | Gries et al. |
| 4,946,778 A | 8/1990 | Ladner et al. |
| 5,208,020 A | 5/1993 | Chari et al. |
| 5,304,121 A | 4/1994 | Sahatjian |
| 5,395,619 A | 3/1995 | Zalipsky et al. |
| 5,475,092 A | 12/1995 | Chari et al. |
| 5,585,499 A | 12/1996 | Chari et al. |
| 5,846,545 A | 12/1998 | Chari et al. |
| 5,886,026 A | 3/1999 | Hunter et al. |
| 5,922,897 A | 7/1999 | Hu et al. |
| 6,099,562 A | 8/2000 | Ding et al. |
| 6,165,501 A | 12/2000 | Tirosh et al. |
| 6,180,095 B1 | 1/2001 | Greenwald et al. |
| 6,211,244 B1 | 4/2001 | Van Wagenen et al. |
| 6,267,958 B1 | 7/2001 | Andya et al. |
| 6,320,041 B1 | 11/2001 | Hogrefe et al. |
| 6,803,031 B2 | 10/2004 | Rabinowitz et al. |
| 7,745,394 B2 | 6/2010 | Doronina et al. |
| 8,043,833 B2 | 10/2011 | Schwartz et al. |
| 8,198,242 B2 | 6/2012 | Wendt et al. |
| 8,349,910 B2 | 1/2013 | Carrico et al. |
| 8,377,917 B2 | 2/2013 | Hersel et al. |
| 8,410,047 B2 | 4/2013 | Bock et al. |
| 8,754,190 B2 | 6/2014 | Ashley et al. |
| 8,846,941 B2 | 9/2014 | Kwiatkowski |
| 8,906,847 B2 | 12/2014 | Cleemann et al. |
| 9,062,094 B2 | 6/2015 | Rau et al. |
| 9,173,953 B2 | 11/2015 | Rau et al. |
| 9,220,789 B2 | 12/2015 | Kwiatkowski |
| 9,387,245 B2 | 7/2016 | Johnson et al. |
| 9,790,324 B2 | 10/2017 | Kwiatkowski |
| 9,849,187 B2 | 12/2017 | Kwiatkowski |
| 9,872,924 B2 | 1/2018 | Naito et al. |
| 10,010,621 B2 | 7/2018 | Kwiatkowski |
| 10,835,578 B2 | 11/2020 | Rau et al. |
| 2003/0165849 A1 | 9/2003 | Zhang et al. |
| 2006/0063147 A1 | 3/2006 | Chernov et al. |

(Continued)

FOREIGN PATENT DOCUMENTS

| | | |
|---|---|---|
| CN | 104725628 | 6/2015 |
| CN | 106559984 | 4/2017 |

(Continued)

OTHER PUBLICATIONS

Alouane and Jullien, "Self-immolative spacers: kinetic aspects, structure-property relationships, and applications," Angewandte Chemie International Edition, Jun. 2015, 54(26):7492-509.

(Continued)

*Primary Examiner* — Jeanette M Lieb
(74) *Attorney, Agent, or Firm* — Fish & Richardson P.C.

(57) ABSTRACT

The present application provides compounds of Formula (I):

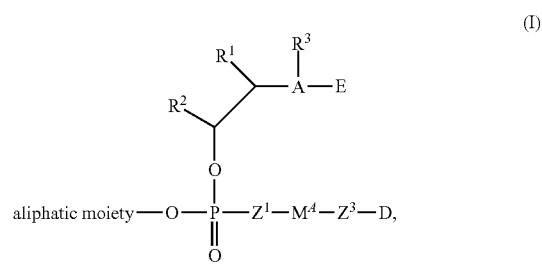

or pharmaceutically acceptable salts thereof, wherein D is a residue of a GLP-polypeptide or an analog thereof, which underdo hydrolysis under physiological conditions to release the GLP-polypeptide or analog thereof and which are useful in the treatment of disorders that could be beneficially treated with the GLP-polypeptide or analog thereof.

20 Claims, 12 Drawing Sheets

Specification includes a Sequence Listing.

(56) References Cited

U.S. PATENT DOCUMENTS

| | | |
|---|---|---|
| 2006/0079486 A1 | 4/2006 | Zalipsky |
| 2007/0092486 A1 | 4/2007 | Yesland |
| 2007/0276139 A1 | 11/2007 | Song et al. |
| 2008/0113027 A1 | 5/2008 | Asharian et al. |
| 2009/0312236 A1 | 12/2009 | Beals et al. |
| 2010/0240730 A1 | 9/2010 | Beigelman et al. |
| 2012/0178940 A1 | 7/2012 | Kwiatkowski |
| 2013/0195888 A1 | 8/2013 | Wang et al. |
| 2014/0030278 A1 | 1/2014 | Kwiatkowski |
| 2014/0194610 A1 | 7/2014 | Verdine et al. |
| 2014/0249093 A1 | 9/2014 | Vetter et al. |
| 2015/0057221 A1 | 2/2015 | Cleemann et al. |
| 2015/0232615 A1 | 8/2015 | Kwiatkowski |
| 2016/0354477 A1 | 12/2016 | Kwiatkowski |
| 2018/0200378 A1 | 7/2018 | Bennett et al. |
| 2018/0251598 A1 | 9/2018 | Kwiatkowski |
| 2018/0360974 A1 | 12/2018 | Kwiatkowski et al. |
| 2018/0369402 A1 | 12/2018 | Kwiatkowski |
| 2019/0125887 A1 | 5/2019 | Kwiatkowski |
| 2020/0108124 A1 | 4/2020 | Kwiatkowski et al. |
| 2021/0170045 A1 | 6/2021 | Kwiatkowski et al. |

FOREIGN PATENT DOCUMENTS

| | | |
|---|---|---|
| CN | 107129538 | 9/2017 |
| CN | 107614020 | 1/2018 |
| CN | 110545850 | 12/2019 |
| JP | 10175987 | 6/1998 |
| JP | 2001-516492 | 9/2001 |
| JP | 2007-284402 | 11/2007 |
| JP | 2007-530485 | 11/2007 |
| JP | 2016-01 7036 | 2/2016 |
| TW | 201625315 | 7/2016 |
| WO | WO 1995/023160 | 8/1995 |
| WO | WO 2002/083954 | 10/2002 |
| WO | WO 2004/030617 | 4/2004 |
| WO | WO 2004/073620 | 9/2004 |
| WO | WO 2007/059912 | 5/2007 |
| WO | WO 2007/075534 | 7/2007 |
| WO | WO 2009/095479 | 8/2009 |
| WO | WO 2010/006282 | 1/2010 |
| WO | WO 2010/033217 | 3/2010 |
| WO | WO 2010/135541 | 11/2010 |
| WO | WO 2012/080836 | 6/2012 |
| WO | WO 2013/037267 | 3/2013 |
| WO | WO 2013/186632 | 12/2013 |
| WO | WO 2014/130064 | 8/2014 |
| WO | WO 2015/095755 | 6/2015 |
| WO | WO 2015/195904 | 12/2015 |
| WO | WO 2016/110577 | 7/2016 |
| WO | WO 2017/031034 | 2/2017 |
| WO | WO 2017/118693 | 7/2017 |
| WO | WO 2017/118698 | 7/2017 |
| WO | WO 2017/191460 | 11/2017 |
| WO | WO 2018/163131 | 9/2018 |
| WO | WO 2019/171358 | 9/2019 |

OTHER PUBLICATIONS

American Chemical Society. Chemical Abstract Service. RN 200130-23-0. Entered into STN/first available to public on Jan. 22, 1998. (Year: 1998).
Ananda et al., "Analysis of functionalization of methoxy-PEG as maleimide-PEG," Anal. Biochem., 2008, 374:231-242.
Ansel Introduction to Pharmaceutical Dosage Forms, Fourth Edition 1985, 126.
Atherton et al., "The Fluorenylmethoxycarbonyl Amino Protecting Group," in The Peptides, S. Udenfriend and J. Meienhofer, Academic Press, New York, 1987, 40 pages.
Authorized Officer A. Van Der Heijden. International Search Report and Written Opinion in International Application No. PCT/IB2011/003206, dated Jun. 19, 2012, 18 pages.
Axup et al., "Synthesis of site-specific antibody-drug conjugates using unnatural amino acids," Proc. Nat. Acad. Sci. USA, Oct. 2, 2012, 109(40):16101-16106.
Beck et al., "Strategies and challenges for the next generation of antibody-drug conjugates," Nat. Rev. Drug Discovery, May 2017, 16(5):315-337.
Blom et al., "Preparative LC-MS Purification: Improved Compound Specific Method Optimization," J. Combi. Chem., 2004, 6:874-883.
Chen et al., "Surface hydration: Principles and applications toward low-fouling/nonfouling biomaterials," Polymer, Oct. 2010, 51(23):5283-93.
Choi et al., "PEGylation of G-CSF using cleavable olgi-lactic acid linkage," Journal of Controlled Release, 2003, 271-284.
Cole et al., "The EBV-Hybridoma Technique and its Application to Human Lung Cancer," in Monoclonal Antibodies and Cancer Therapy, Proceedings of the Roche-UCLA Symposium, Park City, UT, Jan. 26-Feb. 2, 1985, 77-96.
Conolly et al., "Chemical synthesis of oligonucleotides containing a free sulphydryl group and subsequent attachment of thiol specific probes," Nucleic Acids Res., 1985, 13(12):4485-4502.
Conrad et al., "Studies on the stability of trialkyl phosphates and di-(2'deoxythymidine) phosphotriesters in alkaline and neutral solution. A model study for hydrolysis of phosphotriesters in DNA and on the influence of a β hydroxyethyl ester group," Chem. Bio. Interactions, 1986, 60:57-65.
Corso et al., "Protease-Cleavable Linkers Modulate the Anticancer Activity of Non-Internalizing Antibody-Drug Conjugates," Bioconjug. Chemistry, Jul. 2017, 28(7):1826-1833.
Dahlback, "Inherited thrombophilia: resistance to activated protein C as a pathogenic factor of venous thromboembolism," Blood, 1995, 85:607-614.
De Graaf et al. Pharmacol. Rev. Oct. 2016; 68(4): 954-1013.
Dods and Donnelly, "The peptide agonist-binding site of the glucagon-like peptide-1 (GLP-1) receptor based on site-directed mutagenesis and knowledge-based modelling," Bioscience reports, Feb. 2016, 36(1):e00285.
Dong et al., "Sequence-defined multifunctional polyethers via liquid-phase synthesis with molecular sieving," Nat. Chemistry, Dec. 3, 2018, 11:136-145.
Drioli et al., "Pure, homo-bifunctional poly(ethylene glycol) orthogonally protected: synthesis and characterisation," Reactive & Functional Polymers, 2001, 48:119-128.
Ducreux et al., "The Inhibitory Potencies of Monoclonal Antibodies to the Macrophage Adhesion Molecule Sialoadhesin Are Greatly Increased Following PEGylation," Bioconjugate Chem., 2008, 19:2088-2094.
Ducry et al., "Antibody-Drug Conjugates: Linking Cytotoxic Payloads to Monoclonal Antibodies," Bioconjug. Chemistry, Jan. 2010, 21(1):5-13.
Esmon et al., "Isolation of a membrane-bound cofactor for thrombin-catalyzed activation of protein C," J Biol Chem., 1982, 257:859-864.
Fan et al., "Anticancer drug delivery systems based on inorganic nanocarriers with fluorescent tracers," AIChE Journal, Mar. 2018, 64(3):835-859.
Fee and Van Alstine, "Prediction of the viscosity radius and the size exclusion chromatography behavior of PEGylated proteins," Bioconjugate chemistry, Nov. 2004, 15(6):1304-13.
Fee and Van Alstine, "PEG-proteins: Reaction engineering and separation issues," Chemical Engineering Science, 2006, 61:924-934.
Fidanza et al., "Functionalization of Oligonucleotides by the Incorporation of Thio-Specific Report Groups," Methods in Molecular Biology, 1994, 26, 121-143.
Finn, "Human Tumor Antigens Yesterday, Today, and Tomorrow," Cancer Immunol. Research, May 2017, 5(5):347-354.
Fiore et al., "The biochemical basis for the apparent defect of soluble mutant tissue factor in enhancing the proteolytic activities of factor VIIa," J Biol Chem., 1994, 269:143-149.
Garegg et al., "Nucleoside hydrogenphosphonates in Oligonucleotide Synthesis," Chem. Scr., 1986, 26:59-62.

(56) References Cited

OTHER PUBLICATIONS

Gaur, "Introduction of 5'-Terminal Amino and Thiol Groups into Synthetic Oligonucleotides," Nucleosides, Nucleotides & Nucleic Acids, 1991, 10(4):895-909.
GenBank Accession No. FE203799.1, "B393E12 Antarctic fish *Dissostichus mawsoni* adult brain library Dissostichus mawsoni cDNA, mRNA sequence," dated Mar. 10, 2011, 2 pages.
Gold, "SELEX: How It Happened and Where It will Go," J. Mol. Evolution, Oct. 2015, 81(5-6):140-143.
Gouy et al., "Special feature of mixed phosphotriester derivatives of cytarabine," Bioorganic & Medicinal Chemistry, 2009, 6340-6347.
Greenwald et al., "A New Aliphatic Amino Prodrug System for the Delivery of Small Molecules and Proteins Utilizing Novel PEG Derivatives," J. Med. Chem., 2004, 47:726-734.
Gupta et al., "Chemically Modified DNA Aptamers Bind Interleukin-6 with High Affinity and Inhibit Signaling by Blocking Its Interaction with Interleukin-6 Receptor," J. Biol. Chemistry, Mar. 2014, 289(12):8706-8719.
Hann et al., "1,3-Anhydro-2,4-methylene-D,L-xylitol and Related Compounds," J. Am. Chem. Soc., 1950, 72:561-566.
Hatakeyama et al., "Development of a novel systemic gene delivery system for cancer therapy with a tumor-specific cleavable PEG-lipid," Gene Therapy, 2007, 14:68-77.
Hayashi et al., "Syntheses of prodrug-type phosphotriester oligonucleotides responsive to intracellular reducing environment for improvement of cell membrane permeability and nuclease resistance," Bioorganic Med. Chem. Letters, Jul. 15, 2017, 27(14):3135-3138.
Hecker et al., "Prodrugs of Phosphates and Phosphonates," J. Med. Chem., 2008, 51:2328-2345.
Hoey et al., "Chemistry of X-Ray Contrast Media," Handbook of Experimental Pharmacology, 1984, 73:23-125.
Hovinen et al., "Versatile Strategy for Oligonucleotide Derivatization. Introduction of Lanthanide(III) Chelates to Oligonucleotides," Organic Lett., 2001, 3(16):2473-2476.
Hurwitz et al., "The effect in vivo of chemotherapeutic drug-antibody conjugates in two murine experimental tumor systems," Int. J. Cancer, Jun. 1978, 21(6):747-755.
Huse et al., "Generation of a Large Combinatorial Library of the Immunoglobulin Repertoire in Phage Lambda," Science, Dec. 8, 1989, 246(4935):1275-1281.
Illum, "Is nose-to-brain transport of drugs in man a reality?," J. Pharm. Pharmacol., Jan. 2004, 56(1):3-17.
Illum, "Transport of drugs from the nasal cavity to the central nervous system," Eur. J. Pharm. Sci., Jul. 2000, 11(1):1-18.
International Search Report & Written Opinion in International Application No. PCT/IB2019/057715 dated Feb. 28, 2020, 16 pages.
Jagur-Grudzinski, "Biomedical application of functional polymers," Reactive & Functional Polymers, 1999, 39:99-138.
Jain et al., "Current ADC Linker Chemistry," Pharm. Research, Mar. 11, 2015, 32(11):3526-3540.
Kachalova et al., "A New and Efficient Method for Synthesis of 5'Conjugates of Oligonucleotides through Amide-Bond Formation on Solid Phase," Helv. Chim. Acta, 2002, 85:2409-2416.
Kadajji et al., "Water Soluble Polymers for Pharmaceutical Applications," Polymers, Nov. 11, 2011, 3(4):1972-2009.
Khomutov, "Derivatives of Hydroxylamine, Synthesis of o-substituted hydroxylamines," Journal of General Chemistry 1961, 31:1992-1995.
Kohler et al., "Continuous cultures of fused cells secreting antibody of predefined specificity," Nature, Aug. 7, 1975, 256(5517):495-497.
Kolakowski et al., "The methylene alkoxy carbamate self-immolative unit: utilization for the targeted delivery of alcohol-containing payloads with antibody-drug conjugates," Angewandte Chemie International Edition, Jul. 2016, 55(28):7948-51.
Kolodych et al., "CBTF: new amine-to-thiol coupling reagent for preparation of antibody conjugates with increased plasma stability," Bioconjug. Chemistry, Feb. 2015, 26(2):197-200.
Koo et al., "Disulfide-cross-linked PEG-poly(amino acid)s copolymer micelles for glutathione-mediated intracellular drug delivery," Chem. Commun., 2008, 6570-6572.
Kozbor et al., "The production of monoclonal antibodies from human lymphocytes," Immunol. Today, Mar. 1983, 4(3):72-79.
Kraszewski et al., "Phosphoryl tris-triazole—a new phosphorylating reagent," Tet. Lett., Jan. 1980, 21(30):2935-2936.
Krempsky et al., "Biotin and fluorescein labeling of biomolecules by active esters of 1-phenypyrazolin-5-ones," Tet. Lett., 1996, 37(12):4313-4316.
Kumari et al., "Biodegradable polymeric nanoparticles based drug delivery systems," Colloids Surf. B Biointerfaces, Jan. 2010, 75(1):1-18.
Kwant et al., "Controlled levels of protein modification through a chromatography mediated bioconjugation," Royal Society of Chemistry, Chem. Sci., Apr. 2015, 6:2596-2601.
Leader et al., "Protein therapeutics: a summary and pharmacological classification," Nature Reviews, Jan. 2008, 7(1):21-39.
Lee et al., "Synthesis, characterization, and pharmacokinetic studies of PEGylated glucagon-like peptide-1," Bioconjugate chemistry, Mar. 2005, 16(2):377-82.
Leisvuori et al., "Chemical and enzymatic stability of amino acid derived phosphoramidates of antiviral nucleoside 5'-monophosphates bearing a biodegradable protecting group," Organic & Biomolecular Chemistry, 2010, 8:2131-2141.
Levy et al., "The Specific Cytotoxic Effects of Daunomycin Conjugated to Antitumor Antibodies," Cancer Research, May 1975, 35(5):1182-1186.
Li et al., "Incretin-based therapy for type 2 diabetes mellitus is promising for treating neurodegenerative diseases," Reviews in the Neurosciences, Oct. 2016, 27(7):689-711.
Li et al., "PEG Linker Improves Antitumor Efficacy and Safety of Affibody-Based Drug Conjugates," Int. J. Mol. Sciences, Feb. 3, 2021, 22(4):1540, 18 pages.
Liang et al. "PAMAM Dendrimers and Branched Polyethyleneglycol (Nanoparticles) Prodrugs of (+13-D-(2R, 4R)-dioxolanethymine (DOT) and Their Anti-HIV Activity", Antiviral Chemistry and Chemotherapy., 17:321-329, 2006.
Lunardi et al., "PLGA nano/microparticles loaded with cresyl violet as a tracer for drug delivery: Characterization and in-situ hyperspectral fluorescence and 2-photon localization," Mater. Sci. Eng. C Mater. Biol. Applications, Jan. 1, 2017, 70(Pt 1):505-511.
Lyon et al., "Reducing hydrophobicity of homogeneous antibody-drug conjugates improves pharmacokinetics and therapeutic index," Nat. Biotechnology, Jul. 2015, 33(7):733-735.
Lyon et al., "Self-hydrolyzing maleimides improve the stability and pharmacological properties of antibody-drug conjugates," Nat. Biotechnology, Sep. 6, 2014, 32(10):1059-1062.
Mackman and Cihlar, "Prodrug Strategies in the Design of Nucleoside and Nucleotide Antiviral Therapeutics," Annual Reports in Medicinal Chemistry, 2004, 39:306-321.
Manning et al.., "Stability of Protein Pharmaceuticals: An Update," Pharm. Research, Apr. 2010, 27(4):544-575.
Marcus et al., "Turning Low-Molecular-Weight Drugs into Prolonged Acting Prodrugs by Reversible Pegylation: A Study with Gentamicin," J. Med. Chem, 2008, 51:4300-4305.
Mathe et al., "Effect on mouse leukemia 1210 of a combination by diazo-reaction of amethopterin and gamma-globulins from hamsters inoculated with such leukemia by heterografts," C. R. Hebd. Seances Acad. Sciences, Mar. 1958, 246(10):1626-1628 (with English translation of Abstract).
McCombs et al., "Antibody Drug Conjugates: Design and Selection of Linker, Payload and Conjugation Chemistry," AAPS Journal, Mar. 2015, 17(2):339-351.
McGuigan et al., "Synthesis and biological evaluation of some phosphate triester derivatives of the anti-viral drug AraA," Nucl. Acids Res., 1989, 17(15):6065-6075.
McMillen et al., "Identifying regions of membrane proteins in contact with phospholipid head groups: covalent attachment of a new class of aldehyde lipid labels to cytochrome c oxidase," Biochemistry, Jan. 14, 1986, 25(1):182-193.

(56) References Cited

OTHER PUBLICATIONS

Mendelsohn et al., "Investigation of Hydrophilic Auristatin Derivatives for Use in Antibody Drug Conjugates," Bioconjug. Chemistry, Jan. 6, 2017, 28(2):371-381.
Nakai, S., et al. "Synthesis and Polymerization of 2-Aminoethyl 2-(p-Methacryloyloxybenzoyloxy)ethyl Hydrogen Phosphate." Makromol. Chem. (1978), vol. 179, pp. 2349-2353. (Year: 1978).
Nesher et al., "Reversible Pegylation Prolongs the Hypotensive Effect of Atrial Natriuretic Peptide," Bioconjugate Chem, 2008, 19:342-348.
Oumzil et al., "Reduction-triggered delivery using nucleoside-lipid based carriers possessing a cleavable PEG coating," Journal of Controlled Release, 2011, 123-130.
PCT International Preliminary Report on Patentability in International Appln. No. PCT/IB2019/057715, dated Mar. 9, 2021, 7 pages.
Peng "Vaccines targeting IgE in the treatment of asthma and allergy" Human Vaccines, 2009, vol. 5, pp. 302-309.
Peptide Institute, Inc. "List of Enzyme Inhibitors and Substrates," Aug. 2013, 22 pages.
Petursson et al., "Protecting Groups in Carbohydrate Chemistry," J. Chem. Educ., 1997, 74(11):1297.
Podyminogin et al., "Attachment of benzaldehyde-modified oligodeoxynucleotide probes to semicarbazide-coated glass,"Nucl. Acids Res., 2001, 29(24):5090-5098.
Pusuluri et al., "Treating Tumors at Low Drug Doses Using an Aptamer-Peptide Synergistic Drug Conjugate," Angew. Chem. Int. Edition, Jan. 28, 2019, 58(5):1437-1441.
Raddetz et al., "Hydrazide oligonucleotides: new chemical modification for chip array attachment and conjugation," Nucleic Acids Res., 2002, 30(21):4793-4802.
Rayudu, Radiotracers for Medical Applications, vol. I, pp. 201.
Remington's Pharmaceutical Sciences, 19th Edition (Mack Publishing Company, 1995 (Table of Contents only).
Roberts et al., "Chemistry for peptide and protein PEGylation," Advanced Drug Delivery Reviews, 2002, 54:459-476.
Roland et al., "A novel linker for the solid-phase synthesis of a library of 3'-thiophosphorylated dinucleotides," Tet. Lett., May 2001, 42(22):3669-3672.
Rudmann et al., "High Molecular Weight Polyethylene Glycol Cellular Distribution and PEG-associated Cytoplasmic Vacuolation Is Molecular Weight Dependent and Does Not Require Conjugation to Proteins," Toxicol. Pathology, Jun. 2013, 41(7):970-983.
Sakaitani et al., "One-pot Conversion of N-Benzyloxycarbonyl Group into N-Tert-Butoxycarbonyl Group," Tetrahedron Lett., 1988, 29:2983.
Sandstrom, "Omalizumab in the management of patients with allergic (IgE-mediated) asthma," J Asthma Allergy, 2009, 2:49-62.
Sanofi, "Sanofi-aventis Acquires from Ascendis Pharma Worldwide Rights on Drug-Delivery Technology in Diabetes and Related Disorders," broutcher dated Dec. 2010, 4 pages.
Santos, "Protein PEGylation for the design of biobetters: from reaction to purification processes," Braz. J. Pharm. Sciences, Nov. 2018, 54(Special):e01009, 17 pages.
Sebastian et al., "Catumaxomab: a bispecific trifunctional antibody," Drugs Today (Barc), 2009, 45(8):589-97 (Abstract Only).
Shechter et al., "Reversible pegylation of insulin facilitates its prolonged action in vivo," European Journal of Pharmaceutics and Biopharmaceutics, 2008, 70:19-28.
Singh et al. "New Method to Prepare Peptide-Oligonucleotide Conjugates through Glyoxylic Oxime Formation," J. Org. Chem., 2004, 69:8544-8546.
Sow et al., "Synthesis of RGD amphiphilic cyclic peptide as fibrinogen or fibronectin antagonist," Lett. Pept. Science, Dec. 1997, 4:455-461.
Spinelli et al. "Aldehydic Oligonucleotide: A Key Intermediate for the Preparation of Oligonucleotide Conjugates Through Oxime Bond Formation," Nucleosides, Nucleotides and Nucleic Acids, 2007, 26:883-887.
Srinivasarao et al., "Ligand-Targeted Drug Delivery," Chem. Reviews, Oct. 11, 2017, 117(19):12133-12164.
Stahl et al., "General Procedure for the Synthesis of Mono-N-acylated 1,6-Diaminohexanes," J. Org. Chem., 1978, 43:2285.
Storring et al., "Epoetin alfa and beta differ in their erythropoietin isoform compositions and biological properties," Br J Haematol., 1998, 100(1):79-89.
Strohl, "Current progress in innovative engineered antibodies," Protein Cell, Jan. 2018, 9(1):86-120.
Substantive correspondence to and from the USPTO in U.S. Appl. No. 15/918,944, from Feb. 15, 2019 to Nov. 9, 2021, 121 pages.
Suzawa et al., "Enhanced tumor cell selectivity of Adriamycin-monoclonal antibody conjugate via a poly(ethylene glycol)-based cleavable linker," Journal of Controlled Release, 2002, 229-242.
Suzawa et al., "Synthesis and HPLC analysis of enzymatically cleavable linker consisting of poly(ethylene glycol) and dipeptide for the development of immunoconjugate," Journal of Controlled Release, 2000, 27-41.
Swanson, "Enhancement Agents for Ultrasound: Fundamentals," Pharmaceuticals in Medical Imaging, 1990, pp. 682-687.
Taira et al., "Electrode modification by long-chain, dialkyl disulfide reagent having terminal dinitrophenyl group and its application to impedimetric immunosensors," Analytical Sciences, Apr. 1993, 9(2):199-206.
Tao et al., "α-Aldehyde Terminally Functional Methacrylic Polymers from Living Radical Polymerization: Application in Protein Conjugation 'Pegylation'," J. Am. Chem. Soc., 2004, 126:13220-13221.
Tjulandin et al., "Epoetin Theta with a New Dosing Schedule in Anaemic Cancer Patients Receiving Nonplatinum-Based Chemotherapy: A Randomised Controlled Trial," Arch Drug Inf., 2011, 4(3):33-41.
Tsuchikama et al., "Antibody-drug conjugates: recent advances in conjugation and linker chemistries," Protein Cell, Jan. 2018, 9(1):33-46.
Tyler et al., "In Vivo Enhancement of Ultrasonic Image Luminance by Aqueous Solutions with High Speed of Sound," Ultrasonic Imaging, 1981, 3:323-29.
Van Witteloostuijn et al., "Half-life extension of biopharmaceuticals using chemical methods: Alternatives to PEGylation," ChemMedChem, Nov. 2016, 11(22):2474-2495.
Vernet et al., "Large-Scale Biophysical Evaluation of Protein PEGylation Effects: In Vitro Properties of 61 Protein Entities," Mol. Pharmaceutics, Apr. 4, 2016, 13(5):1587-1598.
Wagner et al., "Pronucleotides: Toward the In Vivo Delivery of Antiviral and Anticancer Nucleotides," Med Res Rev, 2000, 6:417-451.
Werner and Chantelau, "Differences in bioactivity between human insulin and insulin analogues approved for therapeutic use—compilation of reports from the past 20 years," Diabetol Metab Syndr, 2011, 3:13, 10 pages.
Wong et al., "Acid cleavable PEG-lipids for applications in a ternary gene delivery vector," Mol. BioSyst., 2008, 532-541.
Xu et al., "Esterase-catalyzed dePEGylation of pH-sensitive vesicles modified with cleavable PEG-lipid derivatives," Journal of Controlled Release, 2008, 238-245.
Yamamoto et al., "One-step Synthesis of 5'-Azido-nucleosides," J. Chem. Soc. Perkin Trans. 1, 1980, 306-310.
Zalipsky et al., "Thiolytically Cleavable Dithiobenzyl Urethane-Linked Polymer-Protein Conjugates as Macromolecular Prodrugs: Reversible PEGylation of Proteins," Bioconjugate Chem, 2007, 18:1869-1878.
Zhu et al., "PEGylated versus non-PEGylated drugs: A cross-sectional analysis of adverse events in the FDA Adverse Event Reporting System (FAERS) Database," Int. J. Clin. Pharmacol. Therapeutics, Apr. 23, 2020, 58(6):332-342.
Zwierzak et al., "Phosphorous acid amides—II: Synthesis of momoalkyl phosphoroamidites (RO)(R2'N)P(O)H," Tetrahedron, 1967, 23:2243-2252.
U.S. Appl. No. 15/918,944, filed Mar. 12, 2018, Marek Kwiatkowski, Published as U.S. Patent Application Publication No. 2018/0360974.
U.S. Appl. No. 16/978,991, filed Sep. 8, 2020, Marek Kwiatkowski, Published as U.S. Patent Application Publication No. 2021/0170045.

(56) References Cited

OTHER PUBLICATIONS

American Chemical Society. Chemical Abstract Service. RN 15458-75-0. First entered into STN/first availability to the public: Nov. 16, 1984. (Year: 1984).

Jing et al., "[Advances in reaserch of GLP-1 receptor agonists]," Central South Pharmacy, May 2017, 15(5):553-560 (with English Abstract).

| Compound | Theoretical monoisotopic mass [Da] | Structure |
|---|---|---|
| full size liraglutide, AA7-37 | 3748.946 | 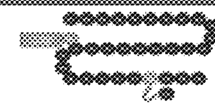 |
| liraglutide fragment, AA9-37 (truncation of AA7-8) | 3540.850 | 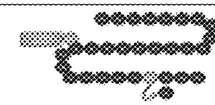 |
| liraglutide fragment, AA13-37 (truncation of AA7-12) | 3106.670 | 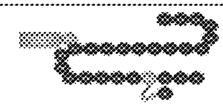 |
| liraglutide fragment, AA25-37 (truncation of AA7-24) | 1869.124 | 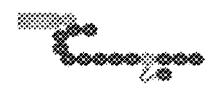 |

FIG. 1

Circles = liraglutide (SEQ ID NO:3)
Squares = Compound 7

FIG. 12
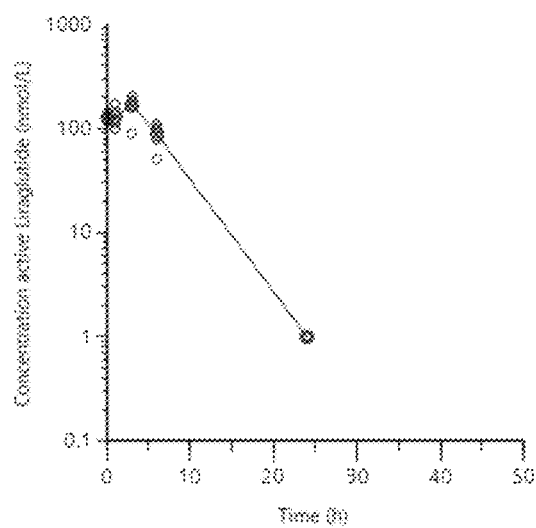
$t_{1/2} = 2.9$
Group 1
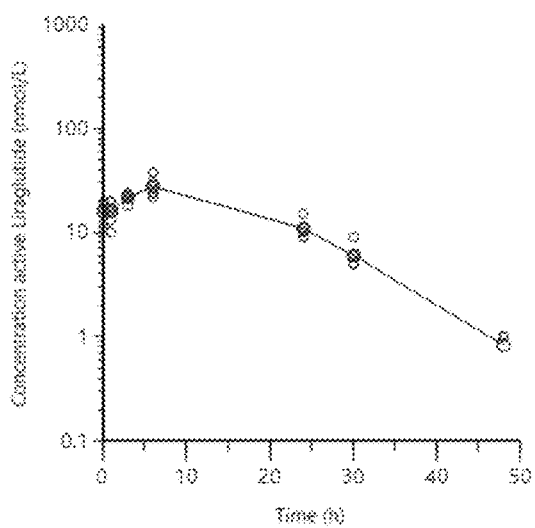
$t_{1/2} = 7.3$
Group 2

RELEASABLE GLP-1 CONJUGATES

CLAIM OF PRIORITY

This application is a continuation of U.S. patent application Ser. No. 16/568,935, filed on Sep. 12, 2019, which claims priority to U.S. Provisional Patent Application Ser. No. 62/730,341, filed on Sep. 12, 2018, U.S. Provisional Patent Application Ser. No. 62/730,935, filed on Sep. 13, 2018, and U.S. Provisional Patent Application Ser. No. 62/771,972, filed on Nov. 27, 2018, the entire contents of which are hereby incorporated by reference.

SEQUENCE LISTING

The instant application contains a Sequence Listing which has been submitted electronically in ASCII format and is hereby incorporated by reference in its entirety. Said ASCII copy, created on Oct. 22, 2019, is named 31152-0034WO1_SL.txt and is 21,377 bytes in size.

TECHNICAL FIELD

This document relates to conjugates of a glucagon-like-peptide (GLP), for example, a glucagon-like-peptide 1 (GLP-1) polypeptide or analogs thereof (e.g., GLP-1 analogs) bound directly or indirectly to an aliphatic polymer (e.g., polyethylene glycol), wherein the GLP-1 polypeptide or analogs thereof can be released from the conjugate in vivo. Such conjugates are referred to herein as "releasable GLP-1 conjugates". This document further includes methods and materials for making and using such releasable GLP-1 conjugates.

BACKGROUND

The World Health Organization has estimated that in 2014 over 400 million adults were living with diabetes, compared to 108 million in 1980 (1). Ninety percent of these persons have type 2 diabetes. This is not only related to population growth as age standardized diabetes grew from 4.7% to 8.5% of the adult population. Much of this is related to wealth gains in developing countries, including China and India, being spent on diabetes-causing diets (e.g. sugar-rich drink consumption) which also lead to increased weight and other medical problems such as cardio-vascular disease. Cardiovascular complications are a leading cause of morbidity and mortality in these people (2). New treatments for diabetes are needed to combat this disease and its complications.

In general, diabetes and insulin treatment can be associated with weight gain whereas glucagon-like-peptide 1 receptor (GLP-1R) agonists are often associated with weight loss. This has triggered enhanced interest in using GLP-1R agonists for treatment of weight gain, as well as for diabetes. At least one GLP-1R agonist (Liraglutide) has been approved for treatment of both type 2 diabetes as well as obesity. Nearly one third of the World's population (over 2 billion people) can be considered as obese or significantly overweight (7). Over 340 million children and adolescents (5-19 years old) were overweight or obese in 2016 (7). Although obesity can often be treated with diet modification some acute conditions, in danger of rapidly leading to diabetes and serious diseases, may benefit from pharmaceutical support treatment.

Pharmacokinetic properties of proteins may be controlled by their conjugation to certain polymers, for example, polyethylene glycol (PEG) (Fee and Van Alstine, *Chemical Engineering Science*, 61:924-934 (2006)). Several approaches to PEGylation of biologically active molecules have been described. However, in some cases the presence of the PEG (hydrophilic polymer) "blocks" significant conjugate "surface area" and significantly hinders the conjugate properties such as solubility (Fee and Van Alstine, Bioconjugate Chemistry, 2004 (15), 1304-1313. This may negatively affect and offset any increase in circulation life-time, decrease in nonspecific proteolysis, or other enhanced properties resulting from the PEGylation. One example in regard to glucagon-like-peptide-1 (GLP-1) is described in Lee et al., Bioconjugate Chem., 2006 (16), 377-382. In this example, the authors were able to covalently link PEG 2000 to GLP-1 via reactive amino groups at the amino terminal of the polypeptide, where natural proteolysis occurs and PEG inhibition of such proteolysis would be beneficial, and at various lysine residues. The PEG-lys modified-GLP-1 conjugates had insulinotropic activity similar to native GLP-1, whereas the PEG-aminoterminal modified-GLP-1 conjugates exhibited reduced potency. Methods for designing, preparing, and using the releasable conjugates are provided herein.

SUMMARY

Provided herein are conjugates of a glucagon-like-peptide (GLP), for example, glucagon-like-peptide 1 (GLP-1) polypeptide or analogs thereof (e.g., GLP-1 analogs) bound indirectly (e.g., though a linking moiety) to an aliphatic polymer (e.g., polyethylene glycol, PEG), wherein the GLP polypeptide or analogs thereof can be released from the conjugate in vivo. In some embodiments, the GLP polypeptide or analog thereof is a GLP-1 polypeptide or analog thereof. Such conjugates are referred to herein as "releasable GLP-1 conjugates". This document further includes methods and materials for making and using such releasable GLP conjugates.

The releasable conjugates provided herein are based on the discovery that 3' phosphotriester groups of a ribonucleoside are unstable in the presence of free vicinal 2' hydroxyl moieties and can decompose following intramolecular nucleophilic attack of a 2' hydroxyl moiety at the 3' phosphotriester group. The subsequent decomposition reaction is thought to be controlled by the geometry of the attacking nucleophile and the phosphorus atom, with the vicinal configuration being the most reactive species and analog arabino-geometries being practically unreactive. The conjugates provided herein advantageously provide release of a GLP-1 polypeptide or analogs thereof from a PEG or similar hydrophilic polymer-containing conjugate with little to no trace of the previously existing linker and polymer system on the GLP-1 polypeptide or analogs thereof. One such example is shown in Scheme 1 as follows:

Scheme 1

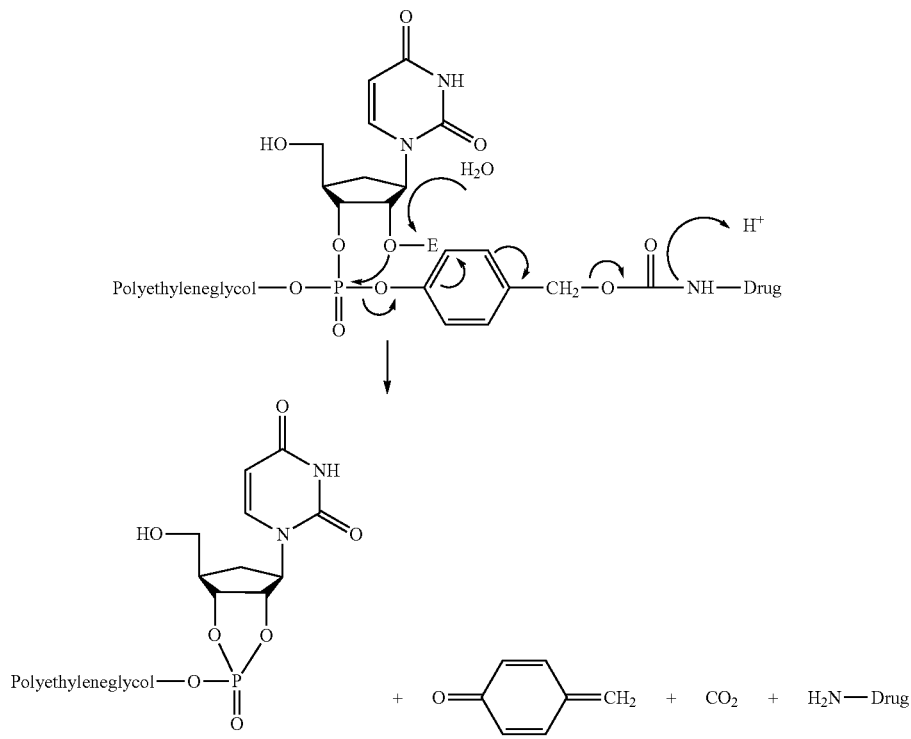

In this example, cleavage of group E, the trigger moiety, results in a nucleophilic attack of the liberated hydroxyl on the phosphorus atom leading to the formation of a cyclic phosphotriester, quinone methide, carbon dioxide ($CO_2$), and the GLP-1 polypeptide or analog thereof. The cyclic phosphotriester may be further hydrolyzed at physiological pH resulting in the opening of the 5-membered ring and formation of both isomeric phosphodiesters. Quinone methide may also be further hydrolyzed (e.g., reacting with water) at physiological pH to form 4-(hydroxymethyl)phenol.

Such a system provides several advantages over alternative conjugates for drug release. For example, the system is modifiable and cleavage can be altered based upon the identity of the trigger moiety, "E", as exemplified above. For example, E can contain an enzyme-labile group, an acid labile functionality, or a pH-labile (e.g., base-labile) functional group. Moreover, as group E is not bound directly to the polymer (e.g., polyethylene glycol), the need to extensively modify each E for every conjugate is avoided as the basic (non-derivatized) form of any E moiety can be appended to the conjugates as described herein. In addition, the use of non-substituted trigger groups offers the potential for better control over the kinetics of prodrug disintegration and liberation of the free biologically active molecule in vivo. Finally, the releasable conjugates provided herein exhibit substantial synthetic freedom. For example, looking at Scheme 1 above, it is not required to have the E moiety introduced selectively on the 2' hydroxyl along with introduction of the phosphotriester on the 3' hydroxyl of the linker moiety. In fact, the opposite placement behaves similarly, making both positional isomers, whether alone or in combination, suitable and useful as releasable conjugates.

Provided herein is a compound of Formula (I)

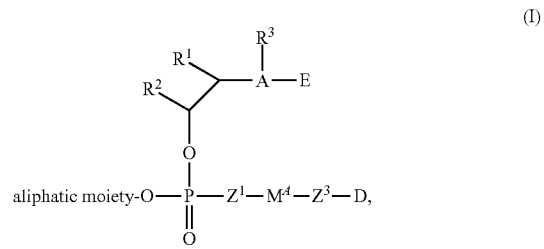

or a pharmaceutically acceptable salt thereof, wherein:
the aliphatic moiety is selected from a polymer, $R^P$, and a group selected from:
  polymer-L-$(CH_2)_m$— and polymer-L-$(CH_2-CH_2-O)_p-(CH_2)_m$—;
$R^P$ is selected from optionally substituted $C_{1-6}$ alkyl, optionally substituted $C_{1-3}$ alkyl-O—$(CH_2-CH_2-O)_p-(CH_2)_m$—, and optionally substituted $C_{3-7}$ cycloalkyl;
L is a linking group;
m and p are each independently an integer from 1 to 10;
D comprises a residue of a GLP-1 polypeptide or an analog thereof;
$Z^1$ is selected from O, S, and $N(R^N)$;
$Z^3$ is selected from O and $N(R^N)$, or $Z^3$ is absent;
A is O or N, wherein when A is O then $R^3$ is absent;
$R^N$ is selected from H and optionally substituted $C_{1-6}$ alkyl;
$R^3$ is selected from H and $C_{1-6}$ alkyl, or
$R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring;

$M^A$ is a self-immolative group having any one of formulae (a)-(i):

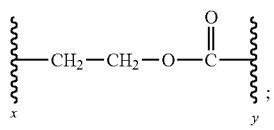
(a)

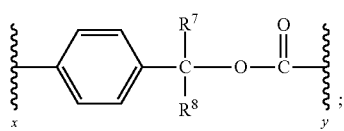
(b)

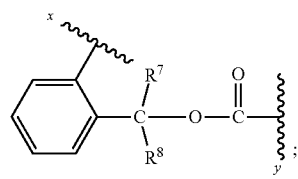
(c)

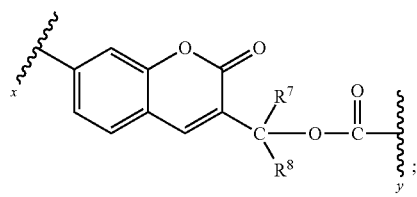
(d)

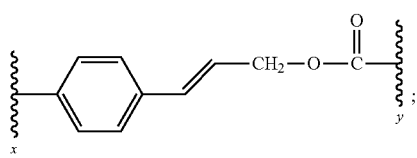
(e)

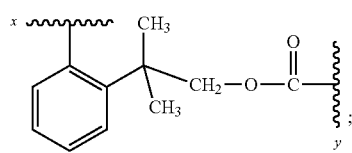
(f)

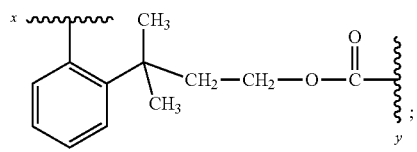
(g)

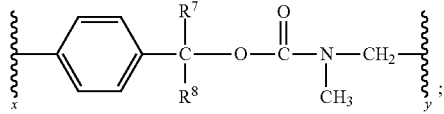
(h)

-continued

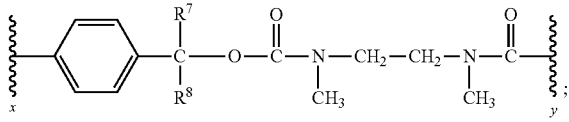
(i)

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

Also provided herein is a compound of Formula (II):

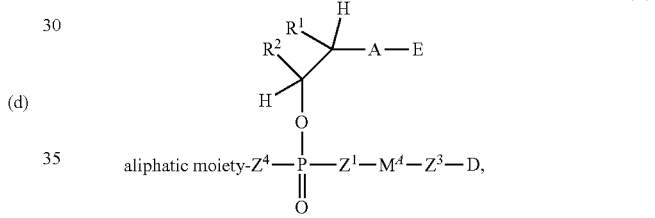
(II)

or a pharmaceutically acceptable salt thereof, wherein:

the aliphatic moiety is selected from a polymer, $R^P$, and a group selected from:
polymer-L-$(CH_2)_m$— and polymer-L-$(CH_2$—$CH_2$—$O)_p$—$(CH_2)_m$—;

$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;

L is a linking group;

m and p are each independently an integer from 1 to 10;

D comprises a residue of a biologically active drug;

$Z^1$ is selected from O, S, and $N(R^N)$;

$Z^3$ is selected from O and $N(R^N)$, or $Z^3$ is absent;

$Z^4$ is selected from O and S;

A is selected from O and $N(R^N)$;

$R^N$ is selected from H and optionally substituted $C_{1-4}$ alkyl;

$M^A$ is a diradical selected from:
  i. a self-immolative group having any one of formulae (a)-(i):

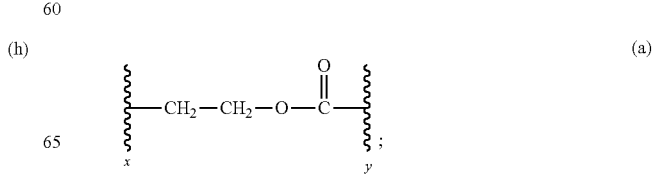
(a)

-continued

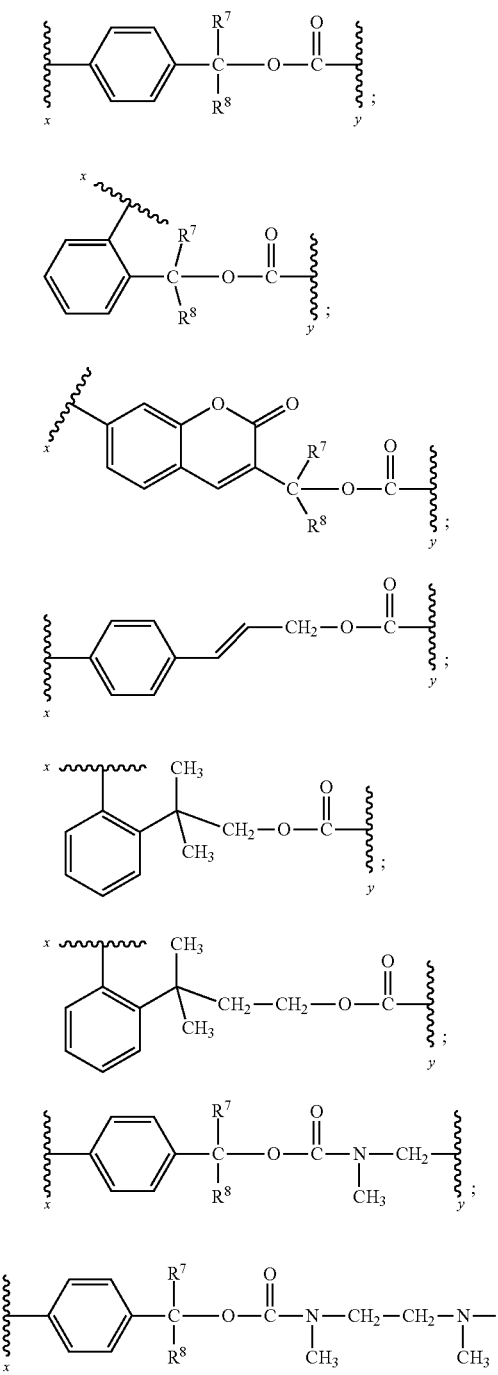

and
ii. a stable diradical selected from any one of formulae (j)-(l):

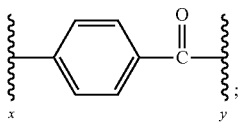

-continued

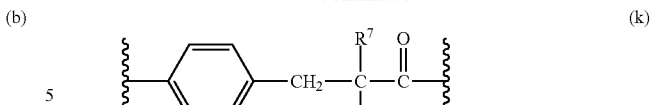
and

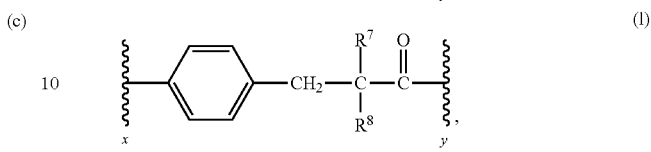

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H, $C_{1-6}$ alkyl, amino, ($C_{1-6}$ alkyl)amino, di-($C_{1-6}$ alkyl)amino, acylamino, and a protected amino group; and E is a cleavable moiety.

Further provided herein is a pharmaceutical composition comprising a compound of Formula (I) or Formula (II), or a pharmaceutically acceptable salt thereof, and a pharmaceutically acceptable carrier.

This disclosure also provides a method of treating a disease or condition in a subject in need thereof, the method comprising administering to the subject a therapeutically effective amount of a compound of Formula (I) or Formula (II), or a pharmaceutically acceptable salt thereof, or a pharmaceutical composition as described herein. In some embodiments, the disease or condition is selected from diabetes and obesity.

The disclosure also provides a method of making a compound of formula:

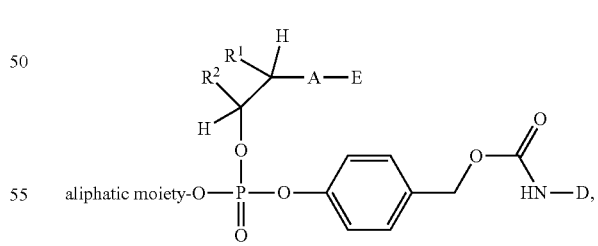

or a pharmaceutically acceptable salt thereof, wherein the aliphatic moiety, $R^1$, $R^2$, A, E, and D are described herein.

Unless otherwise defined, all technical and scientific terms used herein have the same meaning as commonly understood by one of ordinary skill in the art to which the present application pertains. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 1 is a table illustrating the observed isoforms of liraglutide after digestion with the proteolytic enzyme dipeptidyl peptidase IV DPP-IV.

FIG. 12 contains graphs plotting the amount (nmol/L) of active liraglutide detected in samples collected at the indicated times from rats administered liraglutide (SEQ ID NO:3; Group 1) or compound 7 (Group 2). The half-life for each is provided.

DETAILED DESCRIPTION

Definitions

Figure 2:
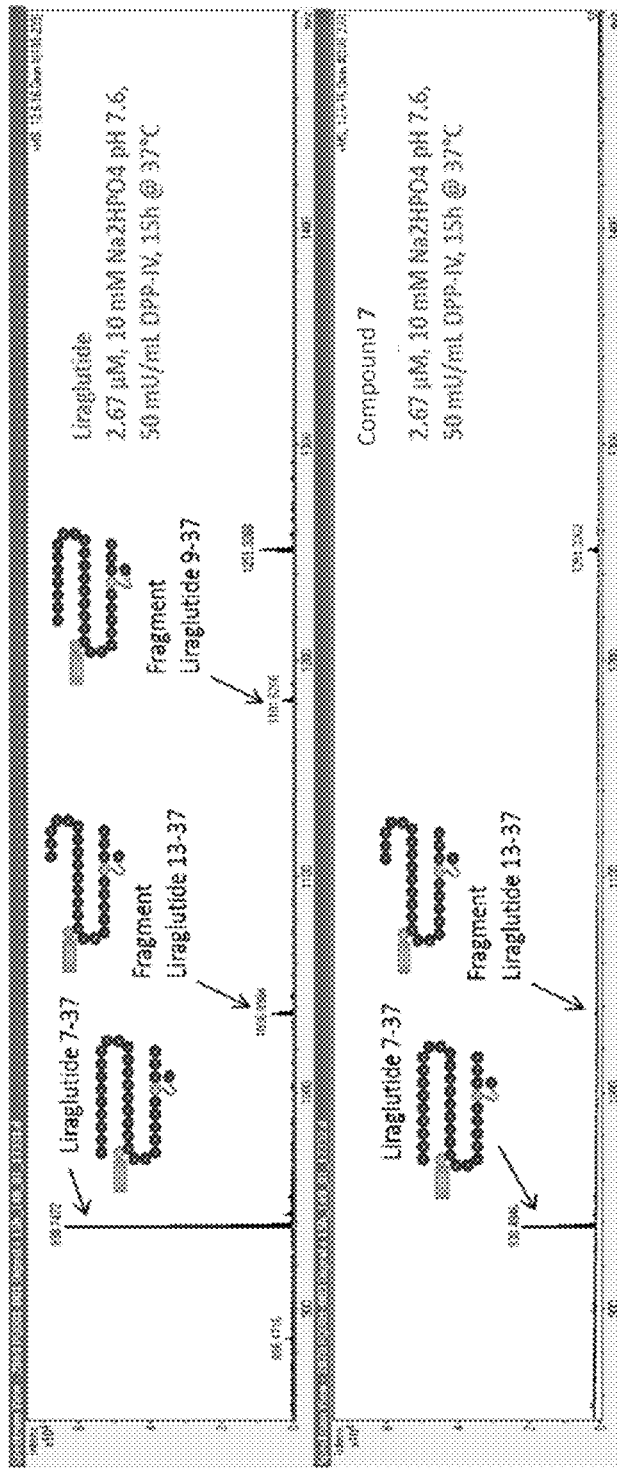
FIG. 2 shows the spectrum of 2.67 µM liraglutide and compound 7 after 15 h of digest with 50 mU/mL DPP-IV in 10 mM $Na_2HPO_4$ pH 7.6 at 37° C.

The term "$C_{n-m}$ alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_{1-12}$ for straight chain; $C_{3-12}$ for branched chain). For example, the term $C_{1-12}$ includes alkyl groups containing 1 to 12 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms. The term "$C_{n-m}$ alkenylene" refers to divalent alkenyl linking groups.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tent-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di($C_{n-m}$-alkyl)amino" refers to a group of formula —N(alkyl)$_2$, wherein the two alkyl groups each have, independently, n to m carbon atoms. In some embodiments, each alkyl group independently has 1 to 6, 1 to 4, or 1 to 3 carbon atoms.

As used herein, the term "thio" refers to a group of formula SH.

As used herein, the term "amino" refers to a group of formula —NH$_2$.

As used herein, the term "carboxy" or "carboxyl" refers to a —C(O)OH group.

As used herein, "halo" or "halogen" refers to F, Cl, Br, or I. In some embodiments, halo is F, Cl, or Br. In some embodiments, halo is F or Cl.

The term "n-membered" where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a 3-12 membered monocyclic or bicyclic cycloalkyl. In some embodiments, the cycloalkyl is a $C_{3-7}$ monocyclic cycloalkyl. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, cyclooctyl, cyclooctenyl, and the like. In some embodiments, cycloalkyl is cyclopropyl, cyclobutyl, cyclopentyl, cyclohexyl, cyclooctyl, or cyclooctenyl. In some embodiments, the cycloalkyl is a cyclooctenyl ring fused with 1 or 2 benzene rings. In some embodiments, the cycloalkyl is a 3-8 membered or 3-7 membered monocyclic cycloalkyl group (e.g., $C_{3-8}$ or $C_{3-7}$ cycloalkyl). In some embodiments, the cycloalkyl is a 8-12-membered bicyclic cycloalkyl. In some embodiments, the cycloalkyl is a 8-16-membered bicyclic or tricyclic cycloalkyl (e.g., $C_{8-16}$ cycloalkyl).

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 membered monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered heteroaryls are pyridyl, pyrazinyl, pyrimidinyl, triazinyl and pyridazinyl. The term "heteroarylene" refers to a divalent heteroaryl linking group.

The term "aromatic" refers to a carbocycle or heterocycle having one or more polyunsaturated rings having aromatic character (i.e., having (4n+2) delocalized π (pi) electrons where n is an integer).

The term "aliphatic" refers to organic compounds (including polymers) in which carbon atoms and heteroatoms form open chains and which do not contain polyunsaturated rings having aromatic character. Aliphatic compounds may be linear or cyclic, saturated or unsaturated, straight chain or branched.

As used herein, the term "polymer" refers to a macromolecule containing a plurality of repeating subunits.

The term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl and the like. In some embodiments, aryl groups have from 6 to about 20 carbon atoms, from 6 to about 15 carbon atoms, or from 6 to about 10 carbon atoms. In some embodiments, the aryl group is phenyl. The term "arylene" refers to a divalent aryl linking group.

As used herein, "heterocycloalkyl" or "aliphatic heterocycle" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido groups (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the non-aromatic heterocycle, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the heterocycloalkyl is a 8-12-membered heterocycloalkyl (e.g., bicyclic heterocycloalkyl). In some embodiments, the heterocycloalkyl is a 8-16-membered heterocycloalkyl (e.g., bicyclic or tricyclic heterocycloalkyl). In some embodiments, the 8-12 membered bicyclic heterocycloalkyl is a 8-12 membered fused heterocycloalkylaryl group or a 8-12 membered fused heterocycloalkylheteroaryl group. In some embodiments, the heterocycloalkyl is a 9-12 membered bicyclic heterocycloalkyl. In some embodiments, the 9-10 membered bicyclic heterocycloalkyl is a 9-10 membered fused heterocycloalkylaryl group or a 9-10 membered fused heterocycloalkylheteroaryl group. The term "heterocycloalkylene" refers to a divalent heterocycloalkyl linking group.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), and/or 2) ameliorating the disease; for example, ameliorating a disease, condition, disorder or symptom in an individual who is experiencing or displaying the pathology or symptomatology of the disease, condition or disorder (i.e., reversing the pathology and/or symptomatology).

The terms "protecting group" and "protective group" refer to a moiety that reversibly chemically modifies a functional group in order to obtain chemoselectivity or in order to reduce degradation in one or more subsequent chemical reactions. Suitable protecting groups are well known in the art (see, e.g., Greene and Wuts, *Protective Groups in Organic Synthesis,* 3rd Ed., John Wiley & Sons, New York, N.Y., 1999, which is incorporated herein by reference in its entirety).

The term "leaving group", as used herein, refers to a molecule or a molecular fragment (e.g., an anion) that is displaced in a chemical reaction as a stable species taking with it the bonding electrons. Examples of leaving groups include an arylsulfonyloxy group or an alkylsulfonyloxy group, such as a mesylate or a tosylate group. Common anionic leaving groups also include halides such as Cl—, Br—, and I—.

As used herein, the term "ribose ring system" refers to, e.g., an optionally substituted ribofuranose, arabinofuranose, xylofuranose or lyxofuranose ring system having the following general structure:

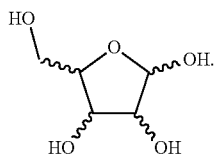

In some embodiments, the ribose ring system comprises a part of an optionally substituted ribonucleoside having the following structure:

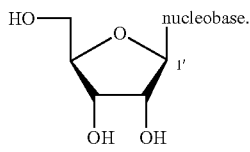

In other embodiments, the ribose ring system comprises a part of an optionally substituted lyxonucleoside having the following structure:

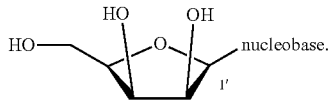

In some embodiments, the ribose ring system comprises a part of an optionally substituted arabinonucleoside having the following structure:

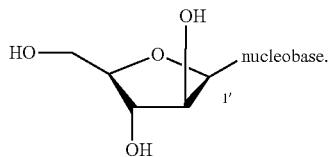

In some embodiments, the ribose ring system comprises a part of an optionally substituted xylonucleoside having the following structure:

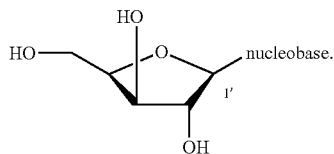

In some embodiments, the nucleobase in a ribonucleoside, arabinonucleoside, xylonucleoside or a lyxonucleoside is adenine, cytosine, guanine, thymine or uracil covalently attached to the ribose/lyxose ring at position 1'.

As used herein, the term "self-immolative" refers to a moiety or residue that provides stable bond formation between two groups of a compound or conjugate, but which becomes labile upon activation (e.g., nucleophilic attack) leading to rapid cleavage of the moiety or residue and separation of the two groups. The chemistry of self-immolative groups is described, for example, in Alouane, A. et al., "Self-immolative spacers: kinetic aspects, structure-property relationships, and applications", *Angew. Chem. Int. Ed.,* 2015, 54, 7492-7509 and Kolakowski, R. V. et al., "The methylene alkoxy carbamate self-immolative unit: Utilization of the targeted delivery of alcohol-containing payloads with antibody-drug conjugates", *Angew. Chem. Int. Ed.,* 2016, 55, 7948-7951.

As used herein, the term "optionally substituted" refers to a group (e.g., alkyl group, cycloalkyl group, alkylene group, aryl group, heteroaryl group, and the like), where one or more hydrogens on the designated atom, usually a carbon, oxygen, or nitrogen atom, may be replaced with a designated substituent, provided that the designated atom's normal valency is not exceeded, and that the substitution results in a stable compound. When a substituent is keto or oxo (i.e., =O), then 2 hydrogens on the atom are replaced. The one or more substituents can be independently selected from $C_{1-6}$ alkyl, $C_{1-4}$ haloalkyl, $C_{3-7}$ cycloalkyl, $C_{2-6}$ alkenyl, $C_{2-6}$ alkynyl, $C_{6-10}$ aryl, 4 to 7 membered heterocycloalkyl, substituted 5- to 14-membered heteroaryl, halo, CN, $NO_2$, $OR^a$, $SR^a$, $C(O)R^a$, $C(O)NR^aR^a$, $C(O)OR^a$, $OC(O)R^a$, $OC(O)NR^aR^a$, $N_3$, $NHR^a$, $NR^aR^a$, $NR^aC(O)R^a$, $NR^aC(O)OR^a$, $NR^aC(O)NR^aR^a$, $NR^aS(O)_2R^a$, $S(O)_2R^a$, and $S(O)_2NR^aR^a$, wherein each $R^a$ is independently selected from H, $C_{1-6}$ alkyl, $C_{3-7}$ cycloalkyl, $C_{6-10}$ aryl, 4 to 7 membered heterocycloalkyl, substituted 5- to 14-membered heteroaryl, $C_{1-4}$ haloalkyl, $C_{2-6}$ alkenyl and $C_{2-6}$ alkynyl.

In some embodiments, the one or more optional substituents are selected from $C_{1-6}$ alkyl, $C_{1-4}$ haloalkyl, OH, $NO_2$, CN. and acetyl.

In some embodiments, the optional substituent is SH.

In some embodiments, the optional substituent is an azide ($N_3$).

In some embodiments, the optional substituent is a group of formula:

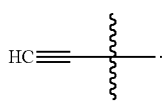 [SMILES: *C#C]

In some embodiments, the optional substituent is a maleimide of formula:

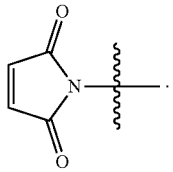 [SMILES: *N1C(=O)C=CC1=O]

In some embodiments, the optional substituent is a cyclooctyne, such as is dibenzocyclooctyne (DBCO), difluorobenzocyclooctyne (DIFBO), biarylazacyclooctynone (BARAC), dibenzocyclooctyne (DIBO), difluorinated cyclooctyne (DIFO), monofluorinated cyclooctyne (MOFO), dimethoxyazacyclooctyne (DIMAC) or aryl-less octyne (ALO), each of which is optionally substituted with 1, 2, 3, 4 or 5 optional substituents described herein.

In some embodiments, the optional substituent is a cyclooctyne selected from the group consisting of:

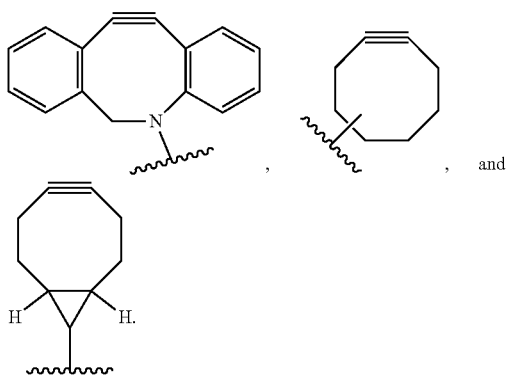

and

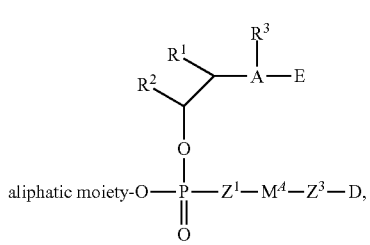

As used herein, the term "about" is meant to account for variations due to experimental error. As used herein, the singular forms "a," "an," and "the" include plural referents unless the context clearly dictates otherwise.

Compounds

Compounds of Formula (I)

In one general aspect, the present application provides a compound of Formula (I):

(I)

aliphatic moiety-O—P(=O)(O)—Z$^1$—M$^4$—Z$^3$—D, with substituents R$^1$, R$^2$, R$^3$, A—E as shown or a pharmaceutically acceptable salt thereof, wherein:

the aliphatic moiety is selected from a polymer, R$^P$, and a group selected from:

polymer-L-(CH$_2$)$_m$— and polymer-L-(CH$_2$—CH$_2$—O)$_p$—(CH$_2$)$_m$—;

R$^P$ is selected from optionally substituted C$_{1-6}$ alkyl, optionally substituted C$_{1-3}$ alkyl-O—(CH$_2$—CH$_2$—O)$_p$—(CH$_2$)$_m$—, and optionally substituted C$_{3-7}$ cycloalkyl;

L is a linking group;

m and p are each independently an integer from 1 to 10;

D comprises a residue of a GLP-1 polypeptide or an analog thereof;

Z$^1$ is selected from O, S, and N(R$^N$);

Z$^3$ is selected from O and N(R$^N$), or Z$^3$ is absent;

A is O or N, wherein when A is O then R$^3$ is absent;

R$^N$ is selected from H and optionally substituted C$_{1-6}$ alkyl;

R$^3$ is selected from H and C$_{1-6}$ alkyl, or

R$^3$ and R$^1$, together with A and the carbon atom to which R$^1$ is attached, form an optionally substituted 4 to 7 membered aliphatic heterocyclic ring; or R$^3$ and R$^2$, together with A, the carbon atom to which R$^1$ is attached, and the carbon atom to which R$^2$ is attached, form an optionally substituted 4 to 8 membered aliphatic heterocyclic ring;

M$^4$ is a self-immolative group having any one of formulae (a)-(i):

(a)

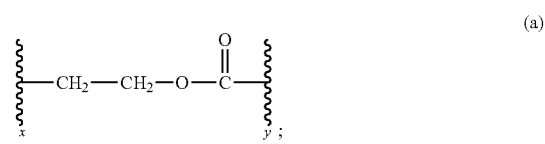

(b)

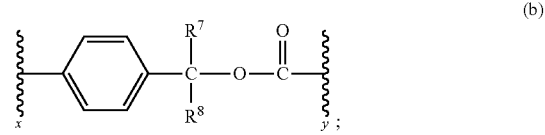

(c)

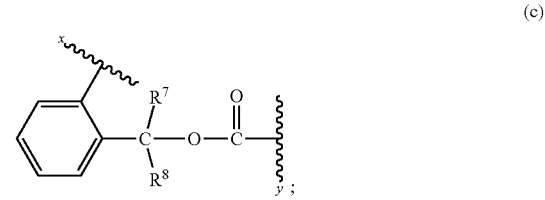

(d)

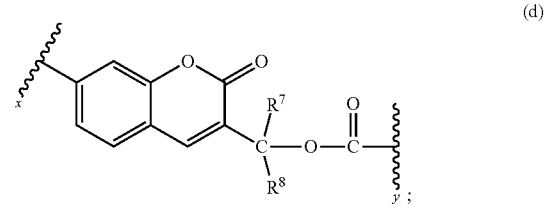

(e)

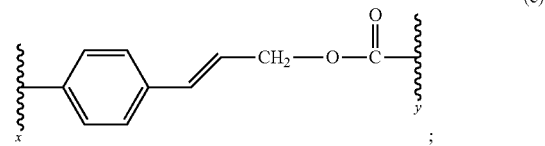

-continued

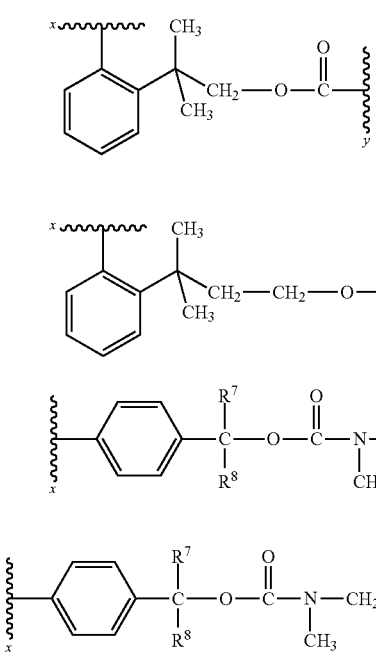

(f)

(g)

(h)

(i)

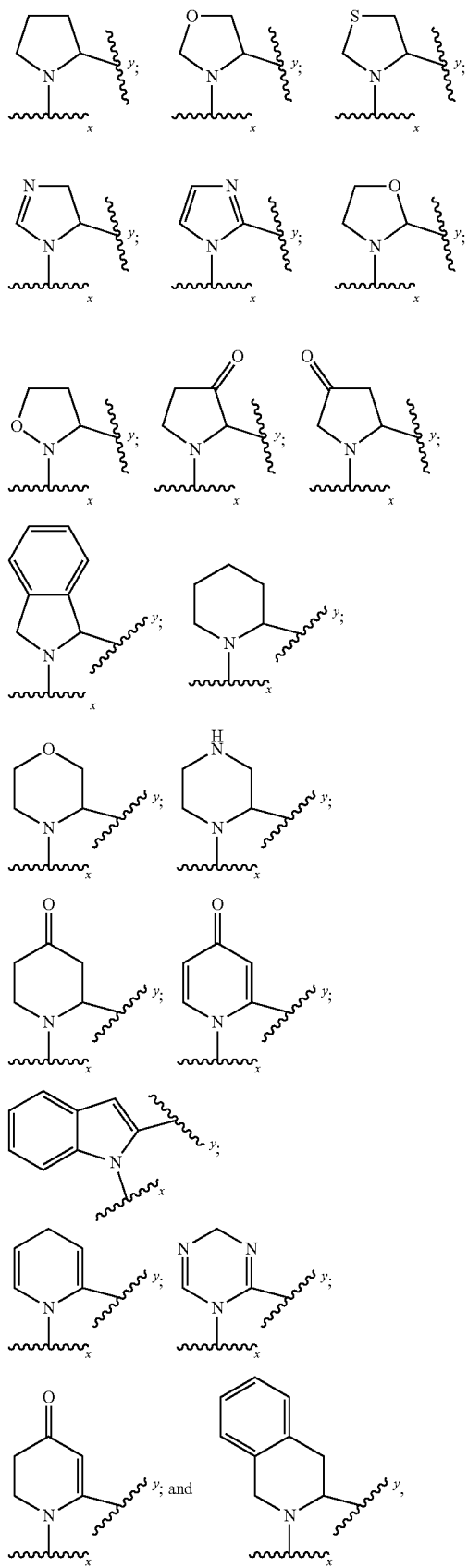

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

In some embodiments of Formula (I), $R^P$, L, m, p, D, $Z^1$, $Z^3$, A, $R^N$, $M^A$, $R^1$, $R^2$, $R^7$, $R^8$ and E are as described herein for a compound of Formula (I), and $R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring.

In some embodiments of Formula (I), A is N. In other embodiments, A is O.

In some embodiments of Formula (I), A is $NR^3$.

In some embodiments of Formula (I), when A is $NR^3$, $R^3$ and $R^1$, together with A and the carbon atom to which $R^1$ is attached, form an optionally substituted 4 to 7 membered aliphatic heterocyclic ring. In some aspects of these embodiments, the 4 to 7 membered aliphatic heterocyclic ring is selected from the group consisting of:

wherein x denotes a point of attachment to E, and y denotes a point of attachment to the carbon atom to which $R^1$ is attached.

In some embodiments of Formula (I), when A is $NR^3$, $R^3$ and $R^2$, together with A, the carbon atom to which $R^1$ is attached, and the carbon atom to which $R^2$ is attached, form an optionally substituted 4 to 8 membered aliphatic heterocyclic ring.

In some embodiments, the compound of Formula (I) has any one of the following formulae:

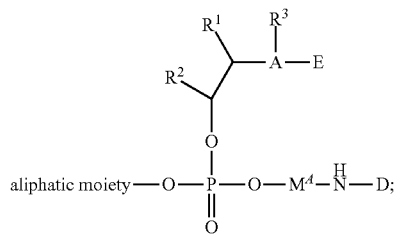

(I-1)

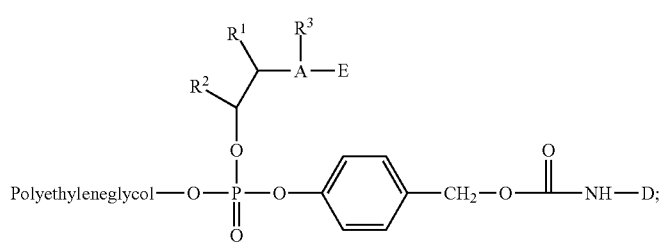

(I-2)

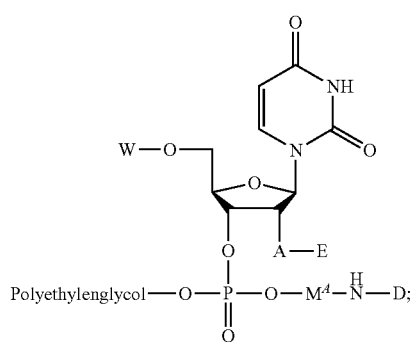

(I-3)

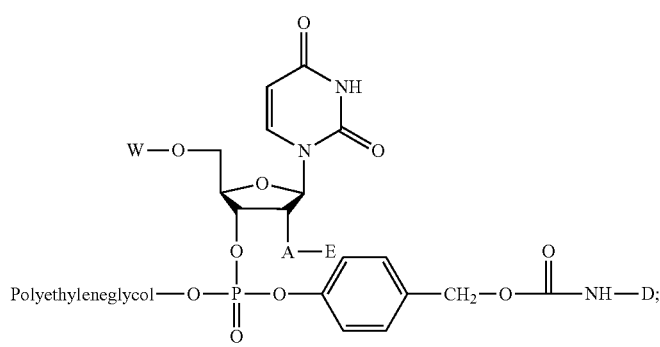

(I-4)

-continued
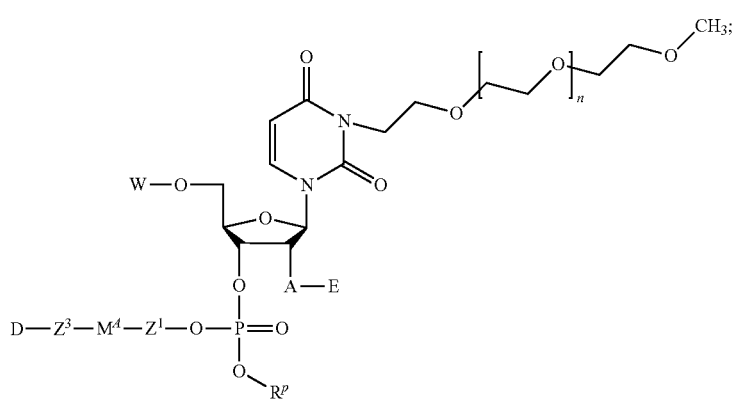
(I-5)
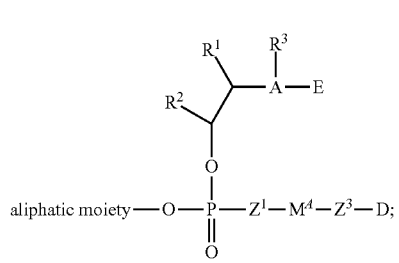
(I-6)
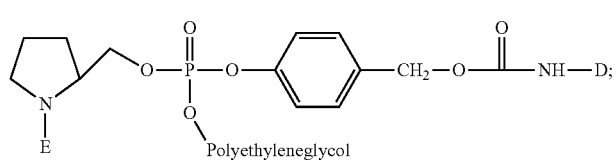
(I-7)
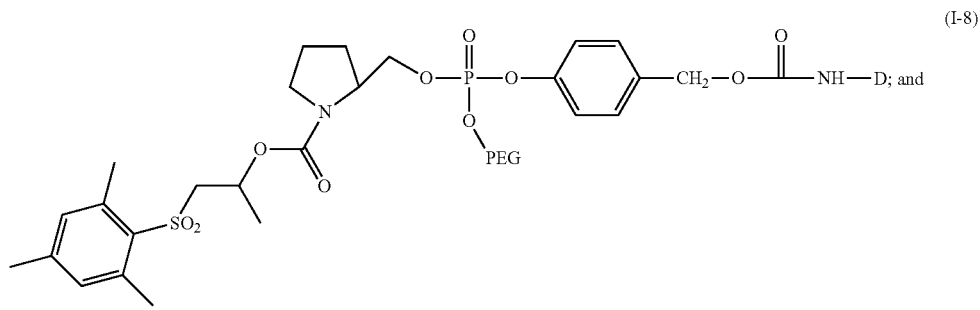
(I-8)
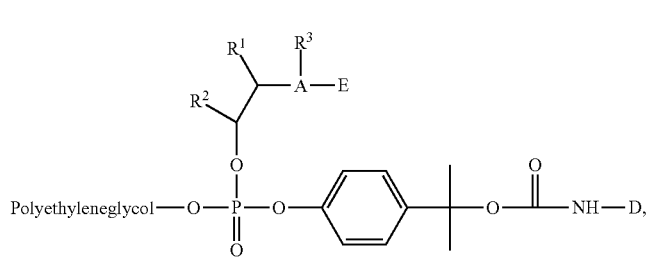
(I-9)
or a pharmaceutically acceptable salt thereof.

In some embodiments, the compound of Formula (I) is any one of the compounds of Formula (II) described herein.
Compounds of Formula (II)
In one general aspect, the present application provides a compound of Formula (II):

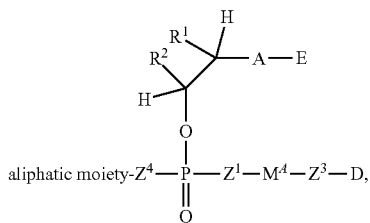

(II)

or a pharmaceutically acceptable salt thereof, wherein:
the aliphatic moiety is selected from a polymer, $R^P$, and a group selected from:
  polymer-L-$(CH_2)_m$— and polymer-L-$(CH_2$—$CH_2$—$O)_p$—$(CH_2)_m$—;
$R^P$ is selected from optionally substituted $C_{1-6}$ alkyl, optionally substituted $C_{1-3}$ alkyl-O—$(CH_2$—$CH_2$—$O)_p$—$(CH_2)_m$—, and optionally substituted $C_{3-7}$ cycloalkyl;
L is a linking group;
m and p are each independently an integer from 1 to 10;
D comprises a residue of a GLP-1 polypeptide or analog thereof;
$Z^1$ is selected from O, S, and $N(R^N)$;
$Z^3$ is selected from O and $N(R^N)$, or $Z^3$ is absent;
$Z^4$ is selected from O and S;
A is selected from O and $N(R^N)$;
$R^N$ is selected from H and optionally substituted $C_{1-4}$ alkyl;
$M^A$ is a diradical selected from:
  a) a self-immolative group having any one of formulae (a)-(i):

(a)

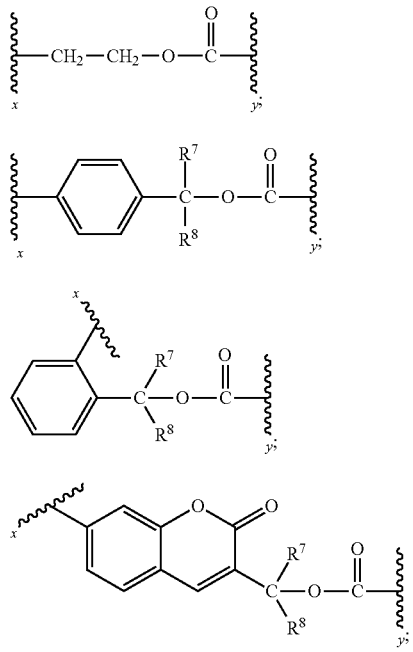

(b)

(c)

(d)

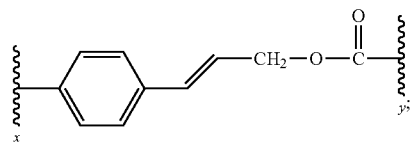

(e)

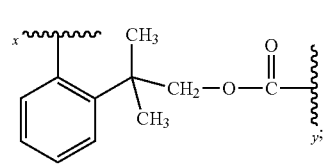

(f)

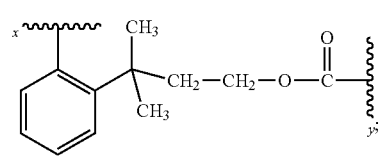

(g)

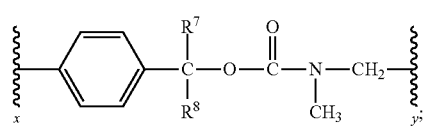

(h)

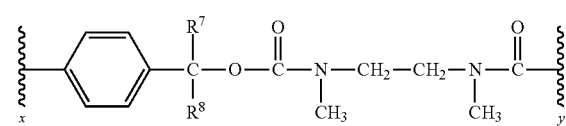

(i)

wherein x denotes a point of attachment to $Z^1$ and y denotes a point of attachment to $Z^3$; and
  b) a stable diradical selected from any one of formulae (j)-(l):

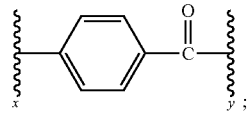

(j)

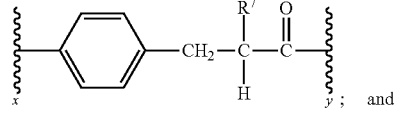

(k)

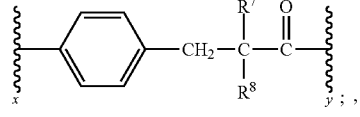

(l)

; and wherein x denotes a point of attachment to $Z^1$ and y denotes a point of attachment to $Z^3$;
$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;
or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or R$^1$ and R$^2$ are joined together to form a ribose ring system;

R$^7$ and R$^8$ are independently selected from H, C$_{1-6}$ alkyl, amino, (C$_{1-6}$ alkyl)amino, di-(C$_{1-6}$ alkyl)amino, acylamino, and a protected amino group; and E is a cleavable moiety.

In some embodiments of Formula (I) or Formula (II), wherein the aliphatic moiety is selected from a polymer, R$^P$, and a group of formula polymer-L-(CH$_2$)$_m$—; R$^P$ is selected from optionally substituted C$_{1-6}$ alkyl and optionally substituted C$_{3-7}$ cycloalkyl; and m is an integer from 1 to 10.

In some embodiments of Formula (I) or Formula (II), D comprises a residue of any one of the GLP-1 polypeptides or analogs thereof described herein (e.g., D comprises a residue of liraglutide). In some embodiments of Formula (I) or Formula (II), D is a residue of any one of the GLP-1 polypeptides or analogs thereof described herein (e.g., D is a residue of liraglutide).

In some embodiments of Formula (I) or Formula (II), the aliphatic moiety is a group of formula: polymer-L-(CH$_2$)$_m$—. In some aspects of these embodiments, L is a linking group comprising a heterocycloakylene or a heteroarylene. For example, L is a linking group comprising a succinimide or a triazole. In some embodiments, L is a linking group of any one of the following formulae:

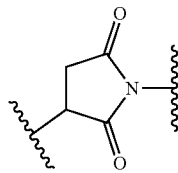 and 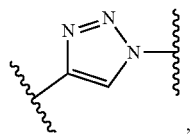, wherein ⸹ indicates a point of attachment of the linking group to the polymer or to the CH$_2$ group.

In some embodiments, the linking group L is a linking group of formulae:

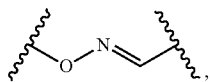 [SMILES: */C=N/O*], wherein ⸹ indicates a point of attachment of the linking group to the polymer or to the CH$_2$ group.

In some embodiments, L comprises a group of formula (L$^1$):

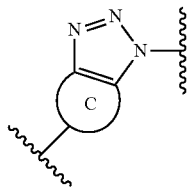

(L$^1$)

wherein ring C is selected from the group consisting of an optionally substituted C$_{8-16}$ cycloalkyl and an optionally substituted 8-16-membered heterocycloalkyl, and ⸹ indicates a point of attachment of the linking group to the polymer or to the CH$_2$ group. In some aspects of these embodiments, C$_{8-16}$ cycloalkyl is a cyclooctenyl which is optionally fused with 1 or 2 benzene rings. In other aspects of these embodiments, C$_{8-16}$ cycloalkyl is a cyclooctenyl which is optionally substituted with 1, 2 or 3 substituents selected from halogen, OH, C$_{1-3}$ alkyl and C$_{1-3}$ alkoxy. For example, cyclooctenyl may be substituted with 1 or 2 fluoro, or with 1 or 2 methoxy groups.

In some embodiments, the group of formula (L$^1$) is selected from any one of the following formulae:

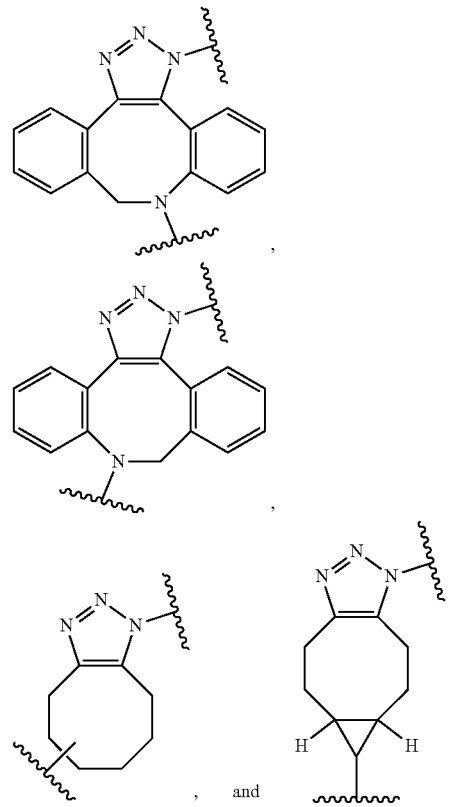

In some embodiments, the group of formula (L$^1$) is

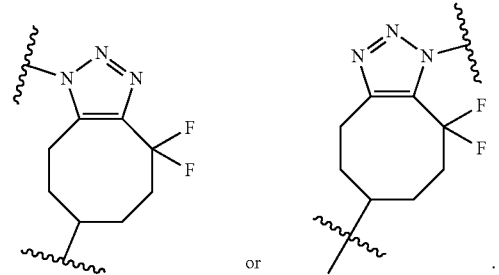 [SMILES: *C1CCc2c(nnn2*)C(F)(F)CC1 ; *C1CCc2nnn(*)c2C(F)(F)CC1]

In some embodiments, the group of formula (L$^1$) is

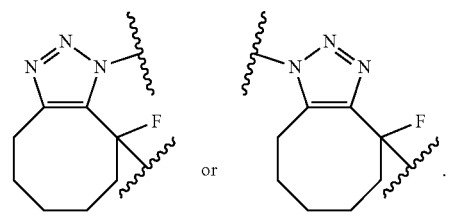 [SMILES: *n1nnc2c1C(*)(F)CCCCC2 ; *n1nnc2c1CCCCCC2(*)F]

In some embodiments, the group of formula (L¹) is

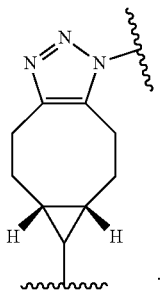

In some embodiments, the group of formula (L¹) is

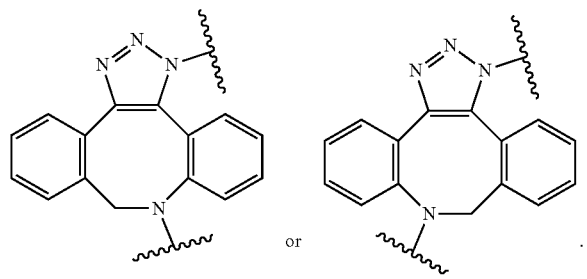 [SMILES: *N1Cc2ccccc2-c2nnn(*)c2-c2ccccc21 ; *N1Cc2ccccc2-c2c(nnn2*)-c2ccccc21]

In some embodiments, the group of formula (L¹) is

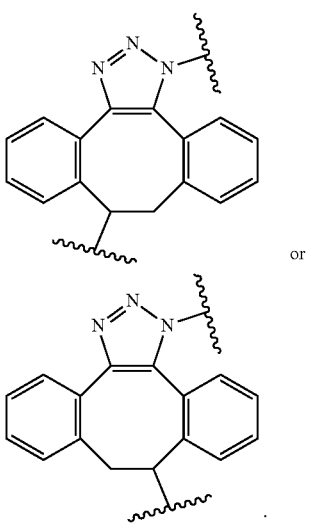

In some embodiments, the group of formula (L¹) is

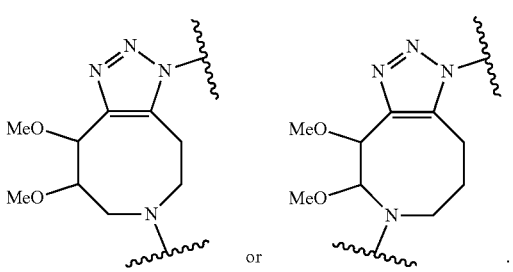 [SMILES: *N1CCc2c(nnn2*)C(OC)C(OC)C1 ; *N1CCCc2c(nnn2*)C(OC)C1OC]

In some embodiments, m is an integer from 1 to 6. For example, m is 1, 2, 3, 4, 5, or 6. In some embodiments, m is an integer from 1 to 4.

In some embodiments, the aliphatic moiety is any one of the following formulae:

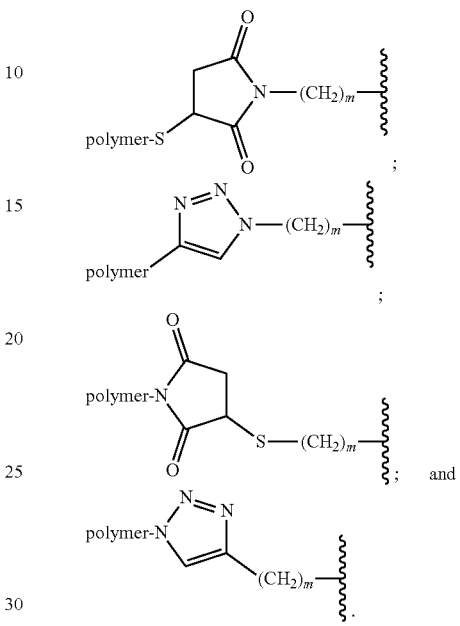

In some embodiments, the aliphatic moiety is any one of the following formulae:

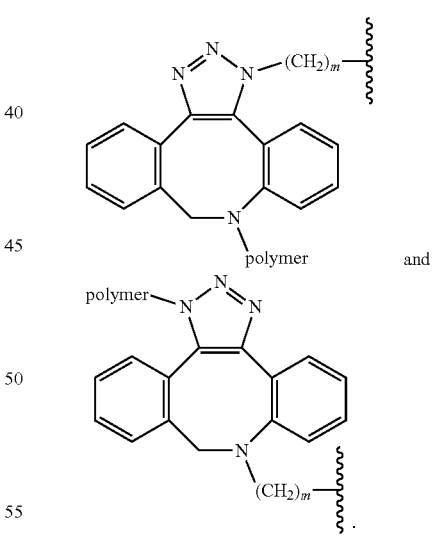

In some embodiments of Formula (I) or Formula (II), the aliphatic moiety is a polymer (e.g., any one of the polymers described herein). The polymer in the aliphatic moiety can be selected from poly(alkylene glycol), poly(oxyethylated polyol), poly(olefinic alcohol), poly(α-hydroxy acid), poly(vinyl alcohol), polyoxazoline, or copolymers thereof. In some embodiments, the polymer in the aliphatic moiety is polyethylene glycol. For example, the aliphatic moiety comprises a linear polyethylene glycol or a branched polyethylene glycol.

In some embodiments of Formula (I) or Formula (II), the aliphatic moiety is $R^P$. In some embodiments, $R^P$ is an optionally substituted $C_{1-6}$ alkyl or an optionally substituted $C_{3-7}$ cycloalkyl. For example, $R^P$ is selected from $C_{1-6}$ alkyl, $C_{1-6}$ cyanoalkyl and $C_{3-7}$ cycloalkyl. When the aliphatic moiety is $R^P$, the aliphatic moiety can be $C_{1-6}$ alkyl (e.g., methyl, ethyl, propyl, isopropyl, n-butyl, isobutyl, tert-butyl, amyl or hexyl). For example, the aliphatic moiety can be cyanoethyl. In some embodiments, the aliphatic moiety can be 2-cyanoethyl. In other embodiments, the aliphatic moiety is $C_{3-7}$ cycloalkyl (e.g., cyclopropyl, cyclobutyl, cyclopentyl or cyclohexyl). In some embodiments, $R^P$ is isopropyl. In some embodiments, $R^P$ is cyanoethyl.

In some embodiments, $R^P$ is selected from the group of any one of the following formulae:

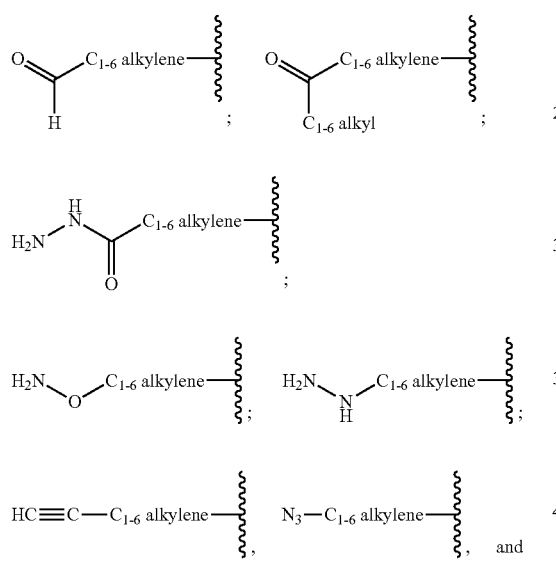

In some embodiments, $R^P$ is selected from the group of any one of the following formulae:

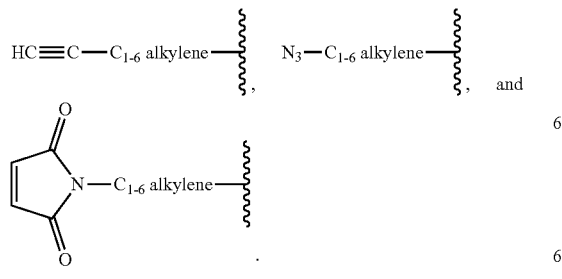

In some embodiments, $R^P$ is a substituted $C_{1-6}$ alkyl of formula:

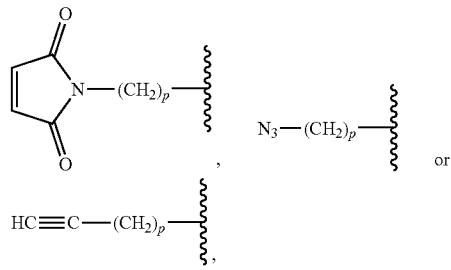

wherein p is an integer from 1 to 6. For example, p is 1, 2, 3, 4, 5 or 6. In some embodiments, p is an integer from 1 to 4.

In some embodiments, $R^P$ is selected from any one of the following formulae:

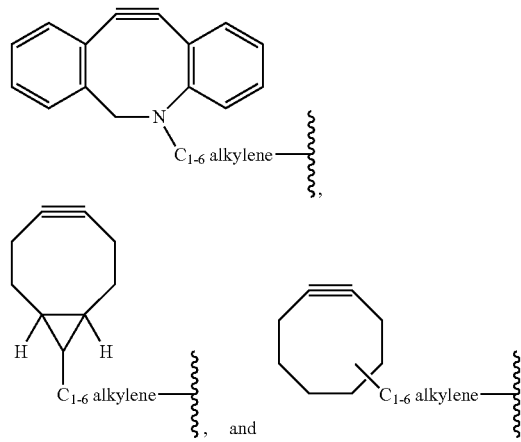

In some embodiments, $R^P$ is selected from any one of the following formulae:

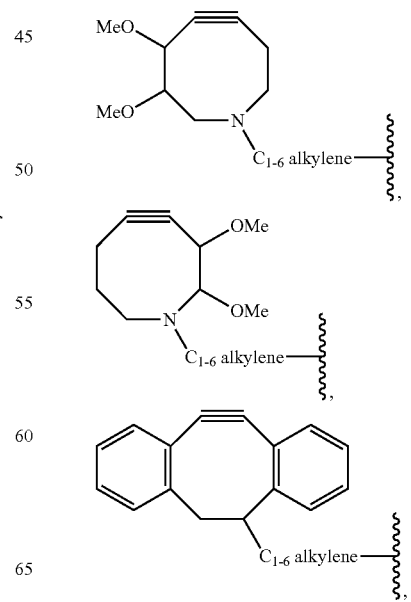

-continued

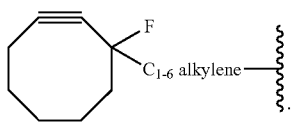

In some embodiments, $R^P$ is

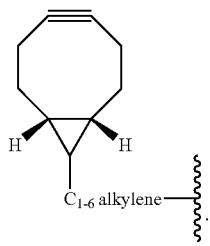

In some embodiments, $R^P$ is

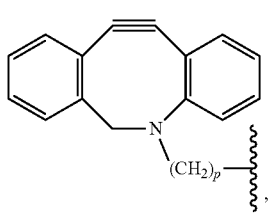

wherein p is an integer from 1 to 6.

In some embodiments of Formula (I) or Formula (II), $Z^1$ is selected from O, S, and $N(R^N)$. In some embodiments, $Z^1$ is O. In some embodiments, $Z^1$ is NH. In some embodiments, $Z^1$ is $N(C_{1-6}$ alkyl). In some embodiments, $Z^1$ is S.

In some embodiments of Formula (I) or Formula (II), $Z^3$ is selected from O and $N(R^N)$. In some embodiments, $Z^3$ is absent. In some embodiments, $Z^3$ is O. In some embodiments, $Z^3$ is NH. In some embodiments, $Z^3$ is $N(C_{1-6}$ alkyl).

In some embodiments of Formula (I) or Formula (II), $Z^1$ is O and $Z^3$ is NH. In some embodiments, $Z^1$ is NH and $Z^3$ is O. In some embodiments, $Z^1$ is O and $Z^3$ is absent. In some embodiments, $Z^1$ is O and $Z^3$ is O. In some embodiments, $Z^1$ is NH and $Z^3$ is NH. In some embodiments, $Z^1$ is NH and $Z^3$ is absent. In some embodiments, $Z^1$ is S and $Z^3$ is O. In some embodiments, $Z^1$ is S and $Z^3$ is NH. On some embodiments, $Z^1$ is S and $Z^3$ is ab sent.

In some embodiments of Formula (I), $Z^4$ is O. In other embodiments of Formula (I), $Z^4$ is S.

In some embodiments of Formula (I) or Formula (II), $M^4$ is a diradical characterized in that, alone or together with $Z^1$, upon nucleophilic attack on the phosphorus atom in Formula (I) or Formula (II), $M^4$ (along with $Z^3$-D) creates a better leaving group than any one of the aliphatic moieties described herein. For example, as shown in Scheme 2 below, upon nucleophilic attack on the phosphorus atom by the 2' hydroxyl group of the ribose unit, both 2-hydroxy propionate and the polyethylene glycol fragments create equally good leaving groups and the nucleophilic substitution reaction is non-selective.

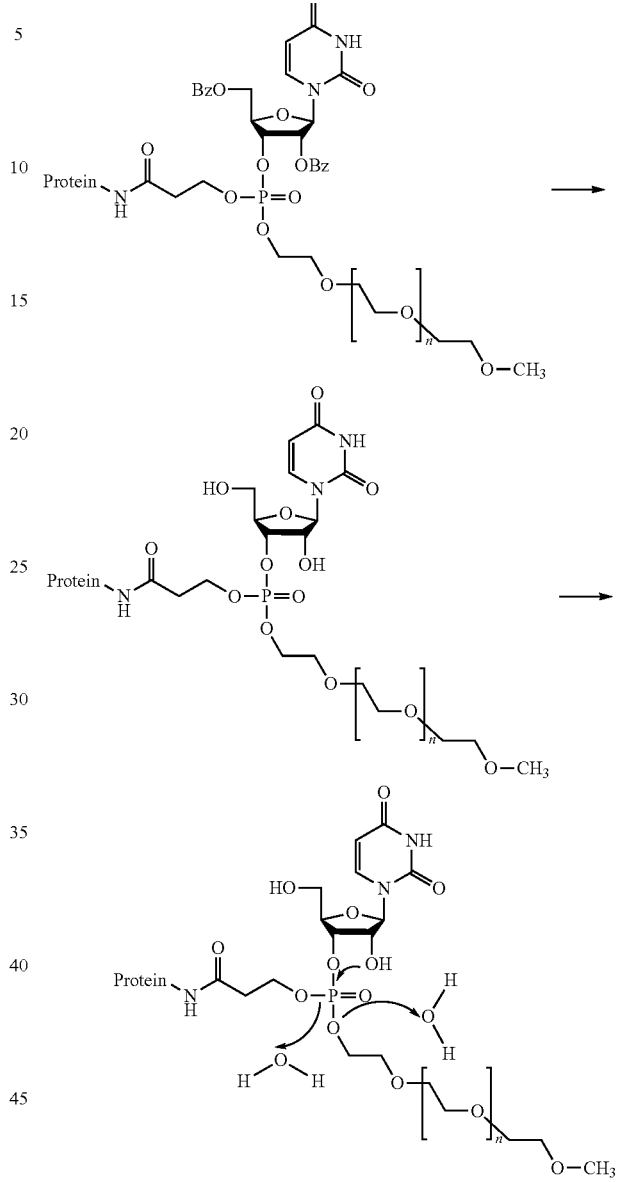

In contrast, in some embodiments of Formula (I) or Formula (II) as described herein, a group comprising the —$Z^1$-$M^4$- fragment is a better leaving group than the aliphatic moiety (e.g., a polyethylene glycol), such that under similar conditions as compared to Scheme 2, upon nucleophilic attack on the phosphorus atom by the 2' hydroxyl group of the ribose unit, the polyethylene glycol fragment remains covalently attached to the phosphorus atom, while the group comprising the —$Z^1$-$M^4$- fragment is selectively cleaved.

In some embodiments of Formula (I) or Formula (II), $M^4$ is a diradical, characterized in that, alone or together with $Z^1$, upon nucleophilic attack on the phosphorus atom in Formula (I) or Formula (II), $M^4$ (along with $Z^3$-D) creates a better leaving group than polyethylene glycol. In some embodiments, the conjugate acid of the $Z^1$-$M^4$-$Z^3$-D moiety, represented by the formula H$Z^1$-$M^4$-$Z^3$-D, has a lower pKa value than the conjugate acid of the aliphatic moiety that is conjugated to a compound of Formula (I) or Formula (II). In some embodiments, the group $HZ^1$-$M^4$-$Z^3D$ has a lower pKa value than a polyethylene glycol or an alcohol. In some aspects of these embodiments, $Z^1$ is oxygen and $M^4$ comprises an aromatic moiety (e.g., $M^4$ comprises a phenylene). In some embodiments, $Z^1$ is nitrogen and $M^4$ comprises an aromatic moiety (e.g., $M^4$ comprises a phenylene), and the conjugated base of the compound of formula $HZ^1$-$M^4$-$Z^3$-D is a better leaving group than any one of the aliphatic moieties described herein due to delocalization of the lone pair of electrons on the nitrogen atom of $Z^1$ into the aromatic ring of $M^4$.

In some embodiments, the compound of Formula (I) or Formula (II) comprises a single immolative functionality. In some embodiments of Formula (I) or Formula (II), $M^4$ is a self-immolative group. In some embodiments, $M^4$ is any one of the self-immolative groups described, for example, in Alouane, A. et al., "Self-immolative spacers: kinetic aspects, structure-property relationships, and applications", *Angew. Chem. Int. Ed.*, 2015, 54, 7492-7509. In other embodiments, $M^4$ is any one of the self-immolative groups described, for example, in Kolakowski, R. et al., "The Methylene Alkoxy Carbamate Self-Immolative Unit: Utilization for the Targeted Delivery of Alcohol-Containing Payloads with Antibody-Drug Conjugates", *Angew. Chem. Int. Ed.*, 2016, 55 (28), 7948-7951.

In some embodiments, $M^4$ is a self-immolative group having any one of formulae (a)-(i):

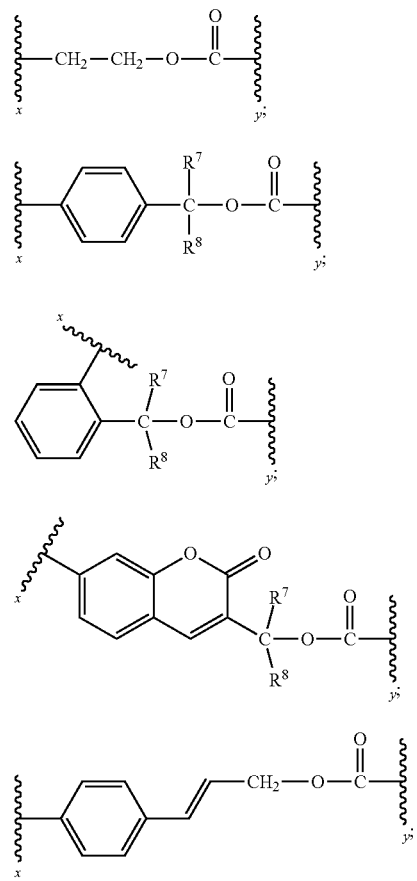

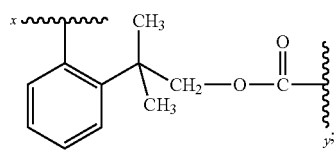

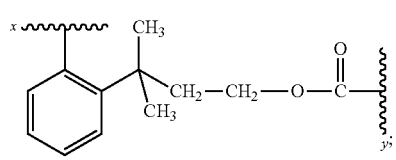

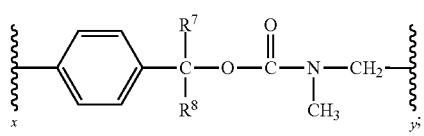

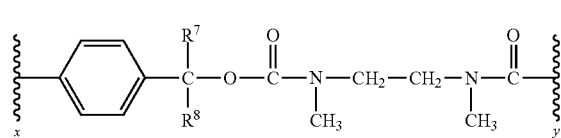

wherein x denotes a point of attachment to $Z^1$ and y denotes a point of attachment to $Z^3$.

In some embodiments of Formula (I) or Formula (II), the self-immolative group is characterized in that the cleavage of the P—$Z^1$ bond generates a cascade of decomposition reactions (e.g., a hydrolysis cascade as described herein) ultimately leading to:
i) release of the conjugate base of the compound $HZ^3$-D when $Z^3$ is present; or
ii) release of the conjugate base of the compound HO—(C=O)-D when $Z^3$ is absent.

In some embodiments, the conjugated base of the compound of formula $HZ^3$-D is a moiety of formula $^-Z^3$-D. In some embodiments, the conjugated base of the compound of formula HO—(C=O)-D is a moiety of formula $^-$O—(C=O)-D.

In some embodiments of Formula (I) or Formula (II), $Z^3$ is present (e.g., $Z^3$ is O or NH) and $M^4$ is a self-immolative group. In some embodiments, the self-immolative group is characterized in that the cleavage of the P—$Z^1$ bond generates a cascade of decomposition reactions ultimately leading to the release of the conjugate base of the compound $HZ^3$-D.

In some aspects of these embodiments, cleavage of the P—$Z^1$ bond results in the formation of $Z^1$=$M^{4'}$, $CO_2$ and the conjugate base of compound $HZ^3$-D, where $M^{4'}$ is a fragment of a self-immolative group (e.g. self-immolative group of any of formula (a)-(g)) which lacks a moiety of formula:

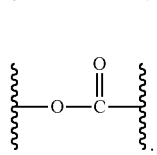

In one example, $M^A$ is a self-immolative group of formula (b), and $M^{A'}$ is a fragment of formula:

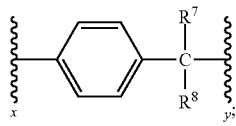

wherein x denotes a point of attachment to $Z^1$ and y denotes a point of attachment to $Z^3$.

In one example, $M^A$ is a self-immolative group of formula (b), and $M^{A'}$ is a fragment of formula:

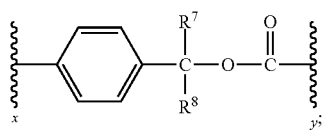

(b)

wherein x denotes a point of attachment to $Z^1$ and y denotes a point of attachment to $Z^3$.

In one example, $M^A$ is a self-immolative group of formula (d), and $M^{A'}$ is a fragment of formula:

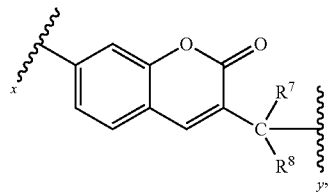

wherein x denotes a point of attachment to $Z^1$ and y denotes a point of attachment to $Z^3$.

In some embodiments, in the compound $Z^1=M^{A'}$, the second bond between $Z^1$ and $M^{A'}$ connects $Z^1$ and any one of atoms of the $M^{A'}$ group. For instance, when $M^A$ is a self-immolative group of formula (a), the second bond between $Z^1$ and $M^{A'}$ connects $Z^1$ and the carbon atom of formula (a) that was in position β to $Z^1$ prior to the decomposition reaction:

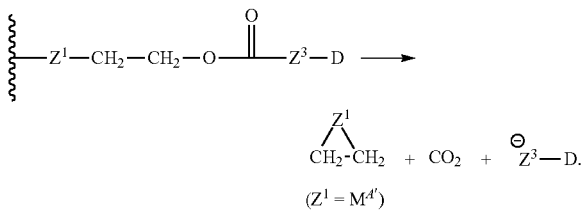

In another example of the compound $Z^1=M^{A'}$, when $M^A$ is a self-immolative group of formula (b-1), the second bond between $Z^1$ and $M^{A'}$ connects $Z^1$ and the carbon atom in $M^{A'}$ to which $Z^1$ is attached, and the remaining bonds in $M^{A'}$ are delocalized:

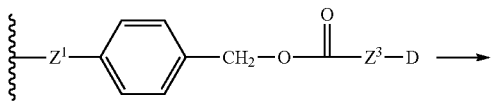

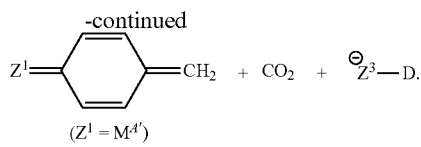

In other aspects of the above embodiments, cleavage of the P—$Z^1$ bond results in the formation of the conjugate base of the compound $HZ^3$-D and a compound of formula:

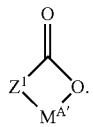

In some embodiments of Formula (I) or Formula (II), $Z^3$ is absent, and $M^A$ is a self-immolative group. In some embodiments, the self-immolative group is characterized in that the cleavage of the P—$Z^1$ bond generates a cascade of decomposition reactions ultimately leading to the release of the conjugare base of the compound HO—(C=O)-D. In some aspects of these embodiments, the cleavage of the P—$Z^1$ bond results in the formation of $Z^1=M^{A'}$ (as described herein) and the conjugate base of the compound HO—(O=C)-D.

In some embodiments of Formula (I) or Formula (II), $Z^1$ is S and $M^A$ is a self-immolative group of formula (a):

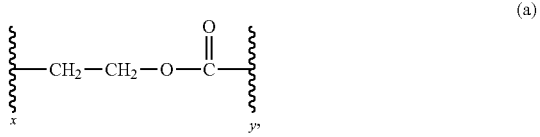

(a)

wherein x denotes a point of attachment to $Z^1$ and y denotes a point of attachment to $Z^3$.

In some embodiments of Formula (I) or Formula (II), the self-immolative group of formula (b) has the formula (b-1):

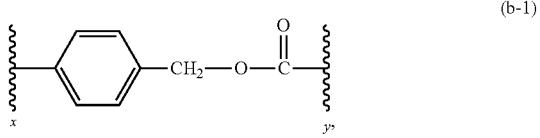 [SMILES: *C(=O)OCc1ccc(*)cc1]

(b-1)

wherein x denotes a point of attachment to $Z^1$ and y denotes a point of attachment to $Z^3$.

In some embodiments of Formula (I) or Formula (II), the self-immolative group of formula (b) has the formula (b-2):

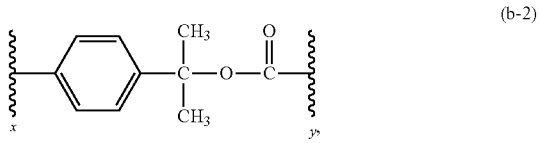 [SMILES: *C(=O)OC(C)(C)c1ccc(*)cc1]

(b-2)

wherein x denotes a point of attachment to $Z^1$ and y denotes a point of attachment to $Z^3$.

In some embodiments of Formula (I) or Formula (II), the self-immolative group of formula (c) has the formula (c-1):

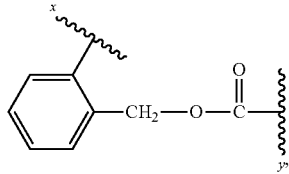
(c-1)

wherein x denotes a point of attachment to $Z^1$ and y denotes a point of attachment to $Z^3$.

In some embodiments of Formula (I) or Formula (II), the self-immolative group of formula (d) has the formula (d-1):

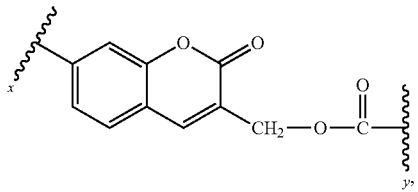
(d-1)

wherein x denotes a point of attachment to $Z^1$ and y denotes a point of attachment to $Z^3$.

In some embodiments of Formula (I) or Formula (II), $Z^1$ is O or NH and $M^A$ is a self-immolative group of any one of formula (b)-(i). In some embodiments, $Z^1$ is O or NH, $Z^3$ is absent, and $M^A$ is a self-immolative group of any one of formula (b)-(i).

In some embodiments of Formula (I) or Formula (II), $Z^1$ is O or NH, $Z^3$ is absent, and $M^A$ is a self-immolative group of formula (b), wherein $R^7$ and $R^8$ are each $C_{1-6}$ alkyl, or a formula (b-2).

In some embodiments of Formula (I) or Formula (II), $Z^1$ is O, $Z^3$ is NH or absent, and $M^A$ is a self-immolative group of formula (b), wherein $R^7$ and $R^8$ are each H, or a formula (b-1).

In some embodiments of Formula (I) or Formula (II), $Z^1$ is O, $Z^3$ is O, and $M^A$ is a self-immolative group of formula (h-1):

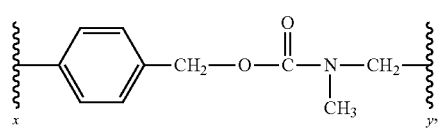
(h-1)

wherein x denotes a point of attachment to $Z^1$ and y denotes a point of attachment to $Z^3$.

In some embodiments of Formula (I) or Formula (II), $Z^1$ is O, $Z^3$ is O, and $M^A$ is a self-immolative group of formula (i-1):

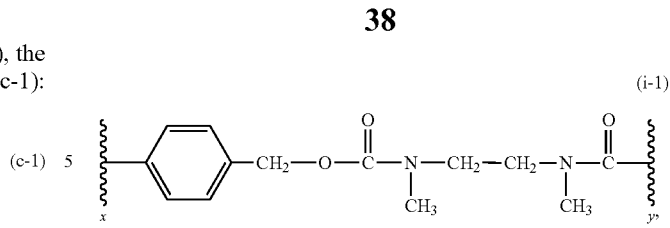
(i-1)

wherein x denotes a point of attachment to $Z^1$ and y denotes a point of attachment to $Z^3$.

In some embodiments of Formula (I) or Formula (II), $Z^1$ is NH, $Z^3$ is O, and $M^A$ is a self-immolative group of formula (h-1). In some embodiments, wherein $Z^1$ is NH, $Z^3$ is O, and $M^A$ is a self-immolative group of formula (i-1).

In some embodiments of Formula (I), $M^A$ is a stable diradical. For example, the stable diradical is not a self-immolative group (e.g. upon nucleophilic attack on the phosphorus atom in Formula (I), the stable diradical does not lead to the cleavage of the $Z^1$-$M^A$ bond, or the $M^A$-$Z^3$ bond). In some embodiments, the stable diradical is characterized in that the cleavage of the P—$Z^1$ bond generates a conjugate base of the compound of formula H$Z^1$-$M^A$-$Z^3$-D, which is stable and does not undergo the decomposition reaction.

In some embodiments, $M^A$ is a stable diradical having any one of formulae (j)-(l):

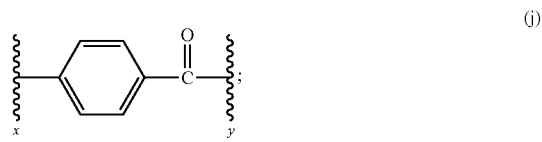
(j)

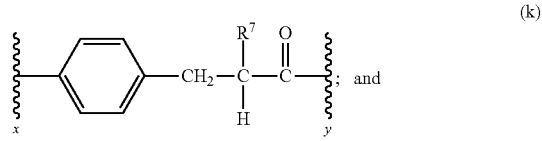
(k)

and

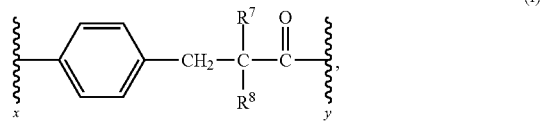
(l)

wherein x denotes a point of attachment to $Z^1$ and y denotes a point of attachment to $Z^3$. In some aspects of these embodiments, $Z^1$ and $Z^3$ are independently O or NH (e.g., $Z^1$ is O and $Z^3$ is NH). In some embodiments, when $M^A$ is a stable diradical of formula (j), $Z^1$ is O. In some embodiments, when $M^A$ is a stable diradical of formula (j), $Z^1$ is NH.

In some embodiments of Formula (I), $M^A$ is a stable diradical having the formula (m):

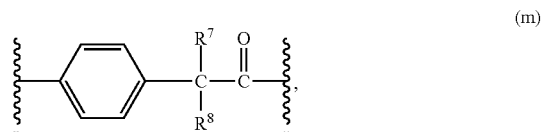
(m)

wherein x denotes a point of attachment to $Z^1$ and y denotes a point of attachment to $Z^3$. In some aspects of these embodiments, $Z^1$ and $Z^3$ are independently O or NH (e.g., $Z^1$ is O and $Z^3$ is NH). In some embodiments, when $M^A$ is a stable diradical of formula (m), $Z^1$ is O and $R^7$ and $R^8$ are each hydrogen.

In some embodiments of Formula (I) or Formula (II), $R^7$ and $R^8$ are independently selected from H, $C_{1-6}$ alkyl, amino, ($C_{1-6}$ alkyl)amino, di-($C_{1-6}$ alkyl)amino, acylamino, and a protected amino group (e.g., the protecting group for the amino group may be selected from any one of the amino-protecting groups described, for example, in Greene and Wuts, *Protective Groups in Organic Synthesis*, 3rd Ed., John Wiley & Sons, New York, N.Y., 1999). In some embodiments, $R^7$ and $R^8$ are independently selected from H, methyl, amino, and acylamino. In some embodiments of Formula (I) or Formula (II), $R^7$ and $R^8$ are independently selected from H and $C_{1-6}$ alkyl. In some embodiments, $R^7$ and $R^8$ are independently selected from H and methyl. In some embodiments, $R^7$ and $R^8$ are each H.

In some embodiments of Formula (I) or Formula (II), $R^7$ is selected from $C_{1-6}$ alkyl, $C_{3-7}$ cycloalkyl, amino, acylamino, and a protected amino group, and $R^8$ is H. In some embodiments, $R^8$ is selected from $C_{1-6}$ alkyl, $C_{3-7}$ cycloalkyl, amino, acylamino, and a protected amino group, and $R^7$ is H.

In some embodiments of Formula (I) or Formula (II), $R^8$ is H and $R^7$ is $C_{1-6}$ alkyl (e.g., methyl, ethyl, propyl, isopropyl or tert-butyl). In some embodiments, $R^7$ is H and $R^8$ is $C_{1-6}$ alkyl (e.g., methyl, ethyl, propyl, isopropyl or tut-butyl). In some embodiments, $R^7$ and $R^8$ are both H. In some embodiments, $R^7$ and $R^8$ are both $C_{1-6}$ alkyl. In another example, $R^7$ and $R^8$ are both methyl. In another example, $R^7$ is methyl, and $R^8$ is ethyl. In some embodiments, $R^7$ and $R^8$ are both $C_{3-7}$ cycloalkyl (e.g., cyclopropyl or cyclobutyl).

In some embodiments of Formula (I) or Formula (II), $R^7$ and $R^8$ are each independently H or acylamino (e.g., acetylamino, propionylamino, or butyramino). In some embodiments, $R^7$ is amino or acetylamino. In some embodiments, $R^8$ is amino or acetylamino. In some embodiments, $R^7$ is acetylamino and $R^8$ is H. In some embodiments, $R^7$ is H. In some embodiments, $R^8$ is H.

In some embodiments of Formula (I) or Formula (II), $M^A$ is a self-immolative group of any one of formulae (b), (c) or (d), and $R^7$ and $R^8$ are both $C_{1-6}$ alkyl (e.g., methyl, ethyl, propyl, isopropyl or tut-butyl). In some embodiments, $M^A$ is a stable diradical of formula (k) or formula (l), and $R^7$ and $R^8$ are independently selected from H or acylamino (e.g., acetylamino, propionylamino, or butyramino).

In some embodiments of Formula (I), the stable diradical of formula (k) has the formula (k-1):

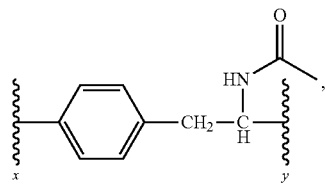

(k-1)

wherein x denotes a point of attachment to $Z^1$ and y denotes a point of attachment to $Z^3$.

In some embodiments of Formula (I) or Formula (II), $R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl. In some embodiments, $R^1$ and $R^2$ are each hydrogen. In some embodiments, $R^1$ and $R^2$ together form a chemical bond (i.e., a carbon-carbon double bond is formed between the carbon to which $R^1$ is attached and the carbon atom to which $R^2$ is attached).

In some embodiments of Formula (I) or Formula (II), $R^1$ and $R^2$ are joined together with the carbon atoms to which they are attached to form an optionally substituted $C_{3-7}$ cycloalkyl ring, an optionally substituted 4- to 7-membered aliphatic heterocyclic ring, an optionally substituted $C_{6-10}$ aryl or an optionally substituted 5- to 14-membered heteroaryl. In some embodiments, $R^1$ and $R^2$ together form a $C_{3-7}$ cycloalkyl ring (e.g., cyclopropyl, cyclobutyl, cyclopentyl and cyclohexyl). In some embodiments, $R^1$ and $R^2$ together form a 4- to 7-membered aliphatic heterocyclic ring (e.g., pyrrolidine, piperidine, tetrahydrofuran and tetrahydropyran).

In some embodiments of Formula (I) or Formula (II), $R^1$ and $R^2$ are joined together to form a ribose ring system (e.g., adenosine, guanosine, 5-methyluridine, uridine, 5-methylcytidine, cytidine, inosine, xanthosine, and wybutosine, each of which is substituted as described herein). In some embodiments, the ribonucleoside is uridine. In some embodiments, $R^1$ and $R^2$ together form a ribose ring system of formula:

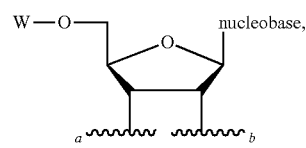

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl). Without being bound by any theory, it is believed that a lyxofuranose-based nucleotide has similar reactivity when compared to the ribofuranose analogues described herein.

Similarly, in one example, it is possible to assume that the 5'-OH can be involved in the intramolecular attack on a phosphotriester even if it is located 3 carbons away. This is more demanding that the typical 2-carbon distance interaction described herein, but this lyxo-isomer could facilitate the reaction by reversing the orientation of the 3' OH. Thus, 2'-deoxy,3'-xylo nucleosides are a suitable alternative to a ribonucleotide ribose scaffold described above for use in the cleavable unit.

In some embodiments of Formula (I) or Formula (II), the nucleobase is selected from the group consisting of adenine, cytosine, guanine, thymine, uracil, and other natural and non-natural nucleobases.

In some embodiments of Formula (I) or Formula (II), the nucleobase can be provided in its chemically protected form (e.g., benzoyl or fatty acyl).

In some embodiments of Formula (I) or Formula (II), the nucleobase is uracil. In some embodiments, the nucleobase is selected from the group consisting of adenine, cytosine, guanine, thymine and uracil. In some embodiments, the nucleobase is selected from the group consisting of 5-methylcytosine, pseudouridine, dihydrouridine, inosine, 7-methylguanosine, hypoxanthine and xanthine.

In some embodiments of Formula (I) or Formula (II), the nucleobase comprises a fluorescent group (e.g., a traditional fluorophore). In some embodiments, the nucleobase is a fluorescent analog of adenine, cytosine, guanine, thymine or uracil.

In some embodiments of Formula (I) or Formula (II), $R^1$ and $R^2$ together form a ribose ring system of any one of the following formulae:

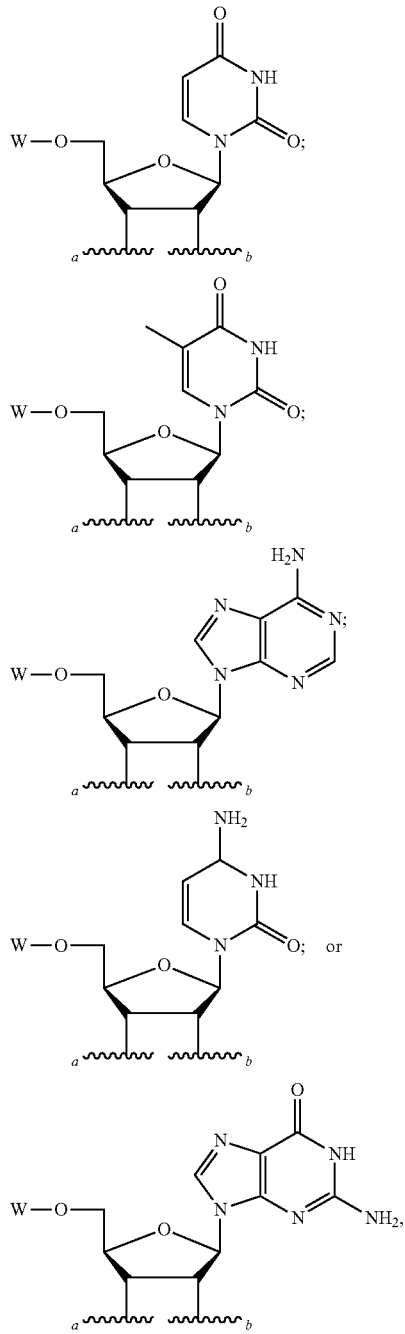

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl).

In some embodiments of Formula (I) or Formula (II), $R^1$ and $R^2$ together form a ribose ring system of any one of the following formulae:

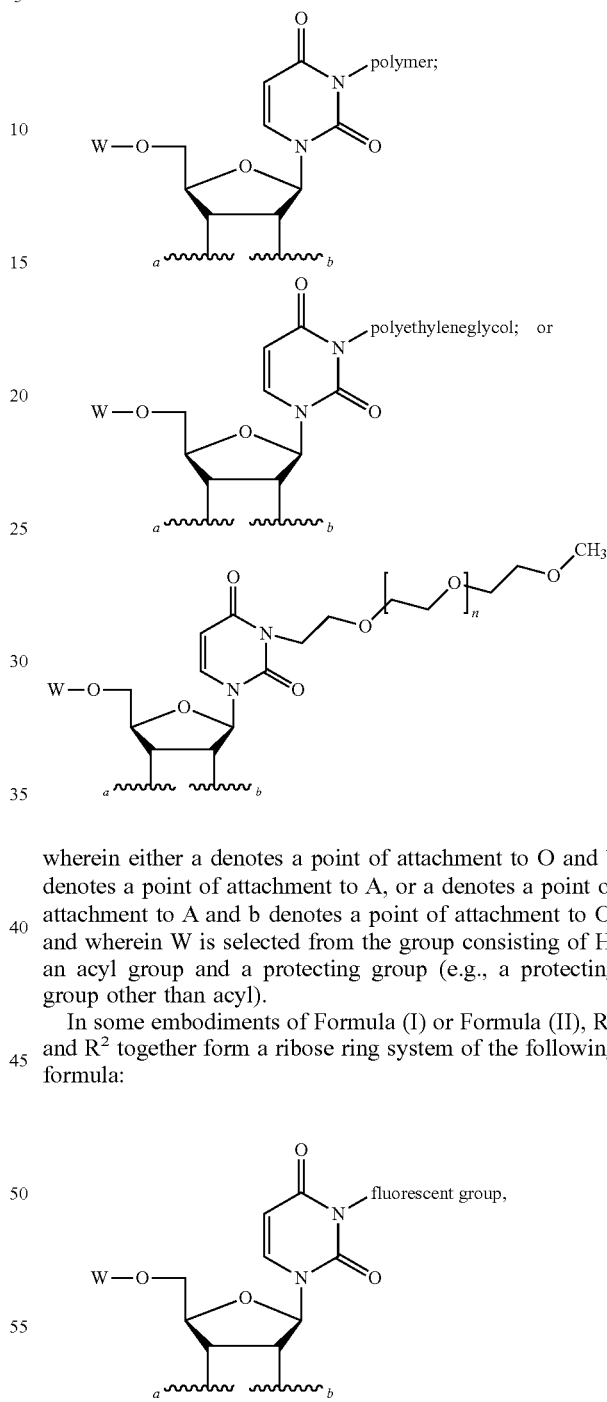

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl).

In some embodiments of Formula (I) or Formula (II), $R^1$ and $R^2$ together form a ribose ring system of the following formula:

wherein either a denotes a point of attachment to O and b denotes a point of attachment to A, or a denotes a point of attachment to A and b denotes a point of attachment to O, and wherein W is selected from the group consisting of H, an acyl group and a protecting group (e.g., a protecting group other than acyl). In some aspects of the above embodiments, the aliphatic moiety is $R^P$. For example, $R^P$ is $C_{1-6}$ alkyl (e.g., ethyl or isopropyl). In another example, $R^P$ is cyanoethyl. In other aspects of the above embodiments, the aliphatic moiety is a polymer (e.g., polyethylene glycol). In other aspects of the above embodiments, the aliphatic moiety is a group of formula: polymer-L-(CH$_2$)$_m$—.

In some embodiments of Formula (I) or Formula (II), W is a protecting group. For example, W may be a hydroxyl protecting group such as methoxymethyl ether (MOM), benzyloxymethyl ether (BOM), benzyl ether, p-methoxybenzyl ether (PMB), trityl ether, silyl ether (e.g., TMS, TIPS), or any of the hydroxyl protecting groups described, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. In some embodiments, W is an alcohol protecting group selected from the group consisting of t-butyldimethylsilyl, diethylisopropylsilyl, triphenylsilyl, formate, methoxymethylcarbonate, t-butylcarbonate, 9-fluorenylmethylcarbonate, N-phenylcarbamate, 4,4'-dimethoxytrityl, monomethoxytrityl, trityl, and pixyl.

In some embodiments, W is hydrogen.

In some embodiments, W is an acyl group.

In some embodiment of Formula (I) or Formula (II), W is any one of the acyl groups described herein (e.g., W is an acyl group selected from formyl, acetyl, propionyl, acrylyl, pivaloyl, and benzoyl). In some embodiments, W is pivaloyl or benzoyl. In some embodiments, W and E are the same (e.g., W and E are each an acyl group). In some embodiments, W is an acyl group and E is a cleavable group other than an acyl group. In some embodiments, an acyl group is hydrolyzable in the presence of any one of the numerous hydrolase enzymes existing in vivo.

In some embodiments of Formula (I) or Formula (II), A is selected from O and N(R$^N$). In some embodiments, A is O. In some embodiments, A is N(R$^N$). In some embodiments, A is NH. In some embodiments, A is N(C$_{1-6}$ alkyl). In some embodiments, A is N(CH$_3$). In some embodiments, A is N(CH$_2$CH$_3$).

In some embodiments, when A is N(R$^N$), R$^N$ and R$^1$, together with A and the carbon atom to which R$^1$ is attached, form an optionally substituted 4 to 7 membered aliphatic heterocyclic ring. In some aspects of these embodiments, the 4 to 7 membered aliphatic heterocyclic ring is selected from the group consisting of:

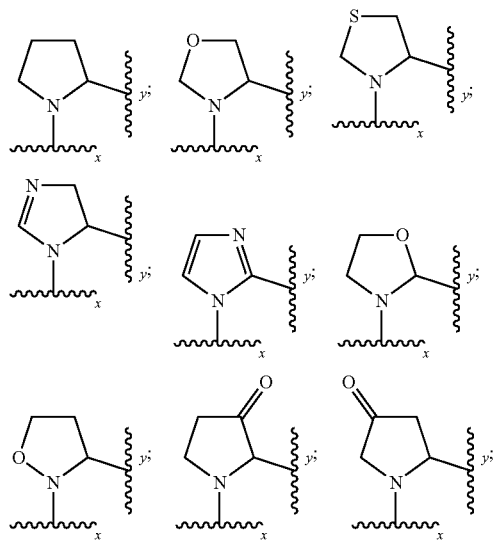

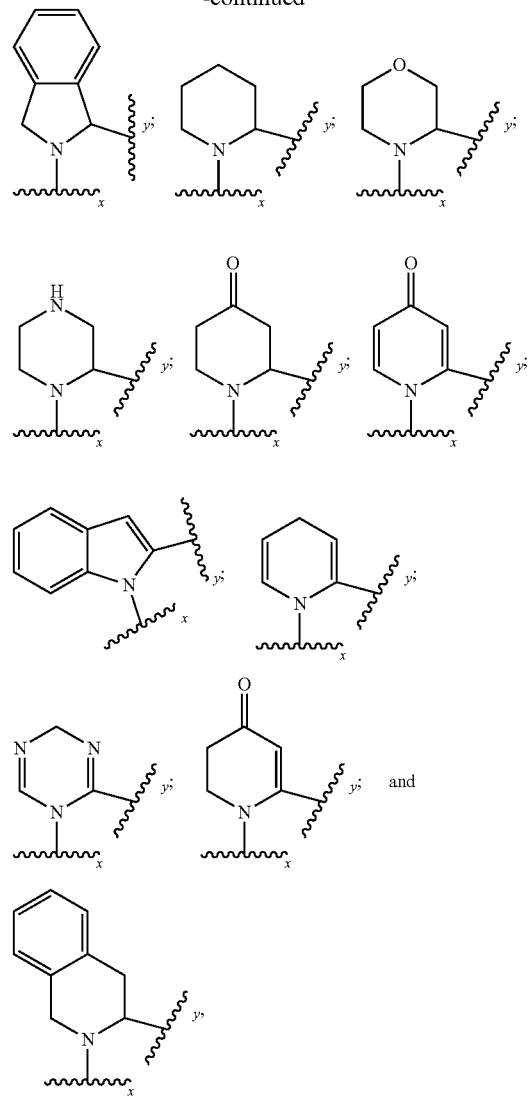

wherein x denotes a point of attachment to E, and y denotes a point of attachment to the carbon atom to which R$^1$ is attached.

In some embodiments, R$^N$ and R$^2$, together with A, the carbon atom to which R$^1$ is attached, and the carbon atom to which R$^2$ is attached, form an optionally substituted 4 to 8 membered aliphatic heterocyclic ring.

In some embodiments, when A comprises N, the moiety:

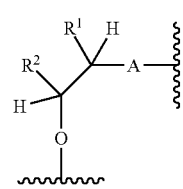

is an 2-amino alcohol which is not serine or a derivative thereof, threonine or a derivative thereof, or cis-amino indanol or a derivative thereof. In some embodiments, the 2-amino alcohol is not aminoethanol.

In some embodiments, the compound of Formula (II) has Formula (II-1a):

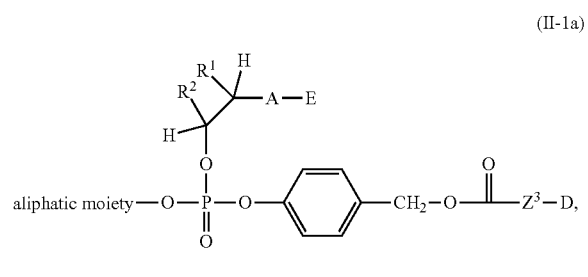

(II-1a)

or a pharmaceutically acceptable salt thereof.

In some embodiments, the compound of Formula (II) has Formula (II-1b):

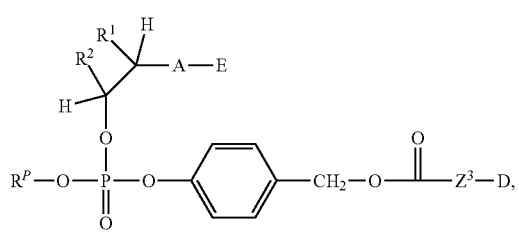

(II-1b)

or a pharmaceutically acceptable salt thereof.

In some embodiments, the compound of Formula (II) has Formula (II-1c):

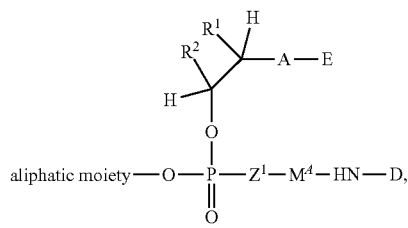

(II-1c)

or a pharmaceutically acceptable salt thereof.

In some embodiments, the compound of Formula (II) has Formula (II-2a):

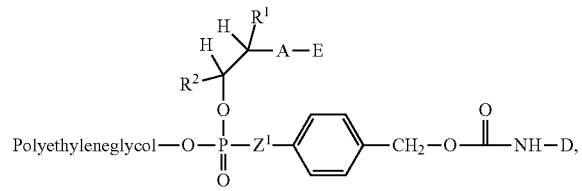

(II-2a)

or a pharmaceutically acceptable salt thereof.

In some embodiments, the compound of Formula (II) has Formula (II-2b):

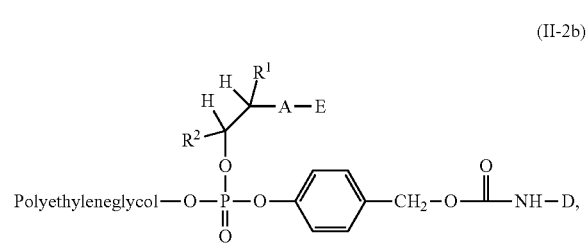

(II-2b)

or a pharmaceutically acceptable salt thereof.

In some embodiments, the compound of Formula (II) has Formula (II-3a):

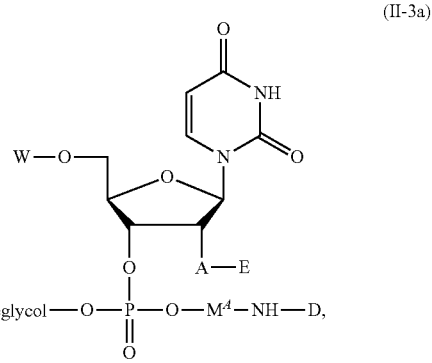

(II-3a)

or a pharmaceutically acceptable salt thereof.

In some embodiments, the compound of Formula (II) has Formula (II-3b):

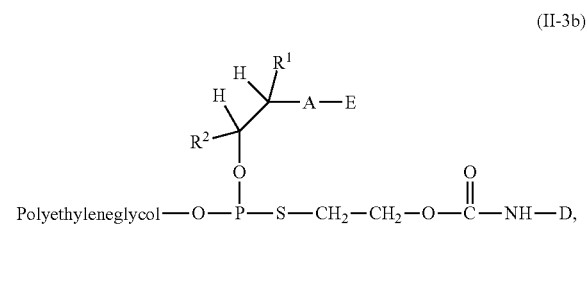

(II-3b)

or a pharmaceutically acceptable salt thereof.

In some embodiments, the compound of Formula (II) has Formula (II-4a):

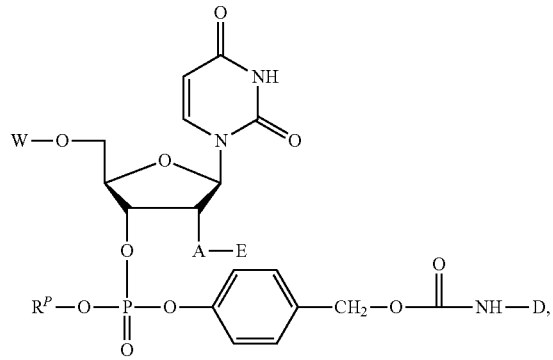

(II-4a)

or a pharmaceutically acceptable salt thereof.

In some embodiments, the compound of Formula (II) has Formula (II-4b):

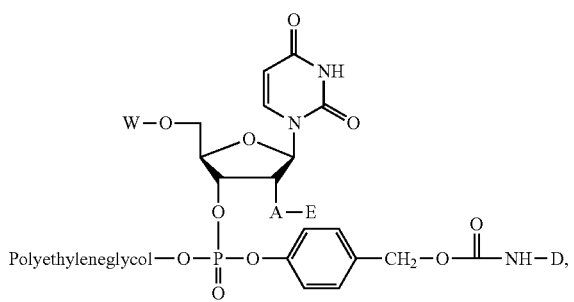

(II-4b)

or a pharmaceutically acceptable salt thereof.

In some embodiments, the compound of Formula (II) has any one of the following Formulae (II-5) to (II-7):

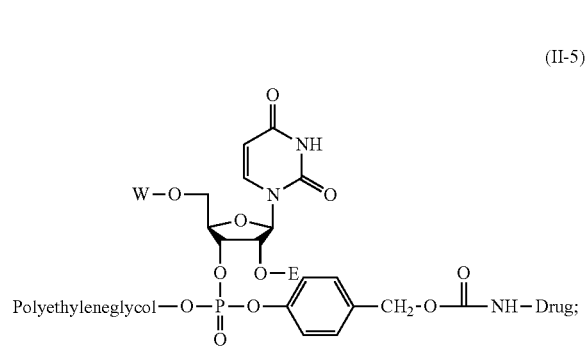

(II-5)

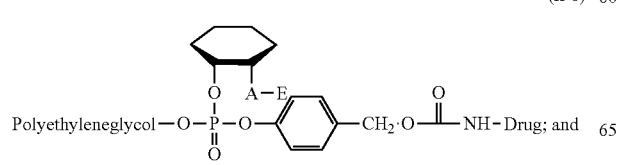

(II-6)

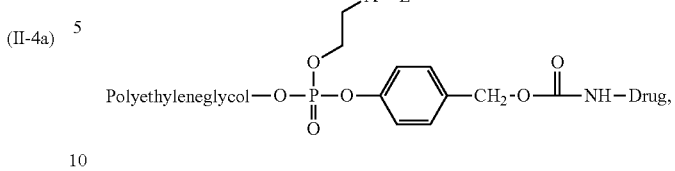

(II-7)

wherein for (II-7), A is O, or a pharmaceutically acceptable salt thereof.

In some embodiments, the compound of Formula (II) has Formula (II-8):

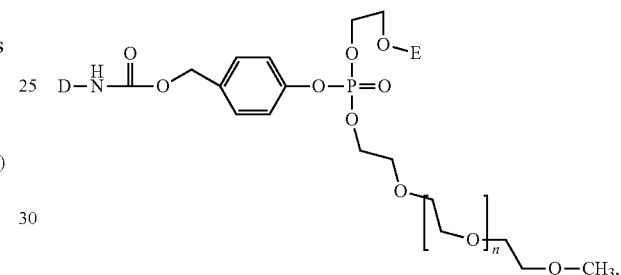

(II-8)

or a pharmaceutically acceptable salt thereof.

In some embodiments, the compound of Formula (II) has Formula (II-9):

(II-9)

or a pharmaceutically acceptable salt thereof.

In some embodiments, the compound of Formula (II) has Formula (II-10):

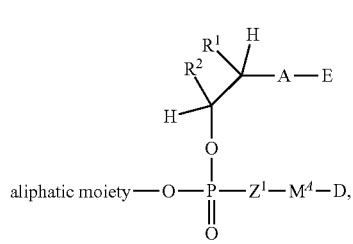

(II-10)

or a pharmaceutically acceptable salt thereof.

In some embodiments, the compound of Formula (II) has Formula (II-10a):

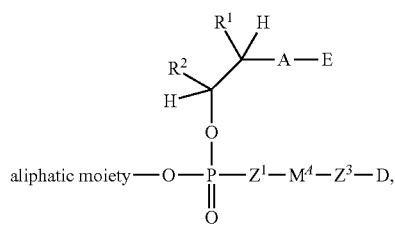

(II-10a)

or a pharmaceutically acceptable salt thereof.

In some embodiments, the compound of Formula (II) has Formula (II-11a):

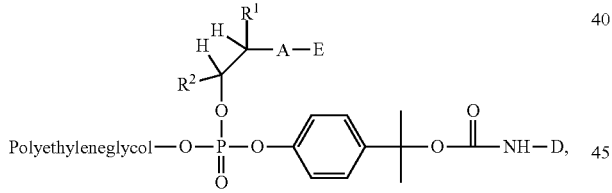

(II-11a)

or a pharmaceutically acceptable salt thereof.

In some embodiments, the compound of Formula (II) has Formula (II-11):

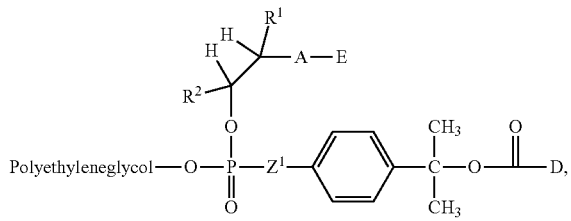

(II-11)

or a pharmaceutically acceptable salt thereof.

In some embodiments, the compound of Formula (II) has Formula (II-12a):

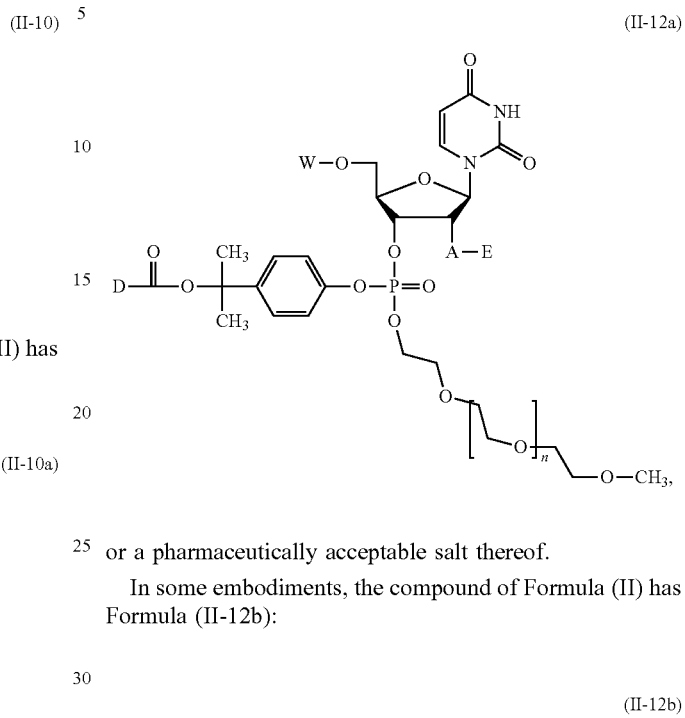

(II-12a)

or a pharmaceutically acceptable salt thereof.

In some embodiments, the compound of Formula (II) has Formula (II-12b):

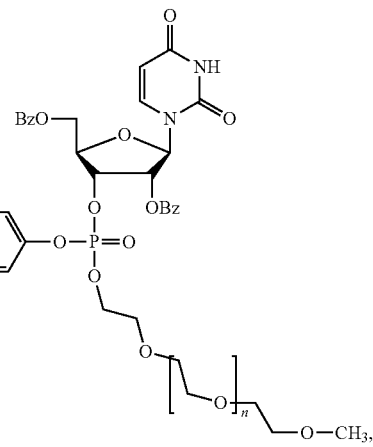

(II-12b)

or a pharmaceutically acceptable salt thereof.

In some embodiments, the compound of Formula (II) has Formula (II-13):

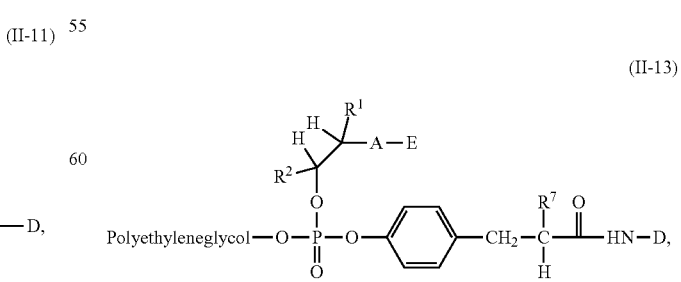

(II-13)

or a pharmaceutically acceptable salt thereof.

In some embodiments, wherein the compound of Formula (II) has Formula (II-14):

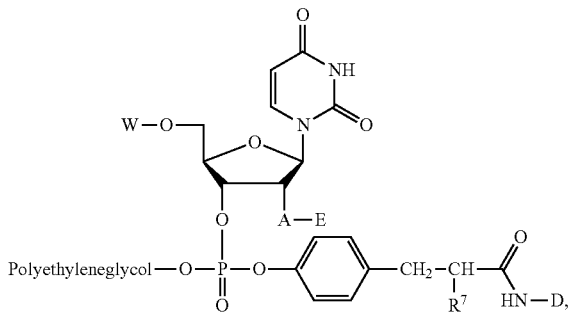

(II-14)

or a pharmaceutically acceptable salt thereof.

In some embodiments, the compound of Formula (II) has Formula (II-15):

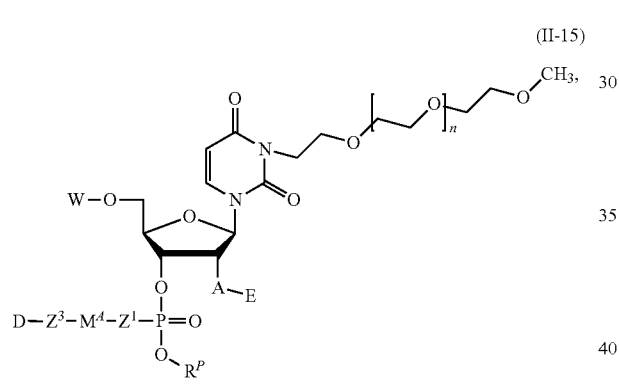

(II-15)

or a pharmaceutically acceptable salt thereof.

In some embodiments, the compound of Formula (II) has Formula (II-16):

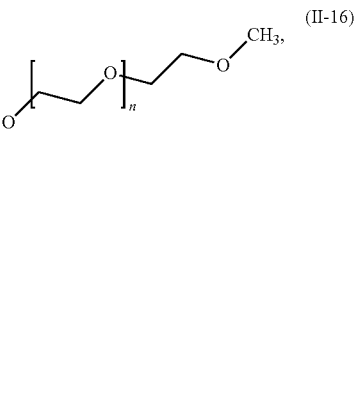

(II-16)

or a pharmaceutically acceptable salt thereof. In some aspects of these embodiments, $R^P$ is an optionally substituted $C_{1-6}$ alkyl (e.g., isopropyl or cyanoethyl).

In some embodiments, the compound of Formula (II) has Formula (II-17):

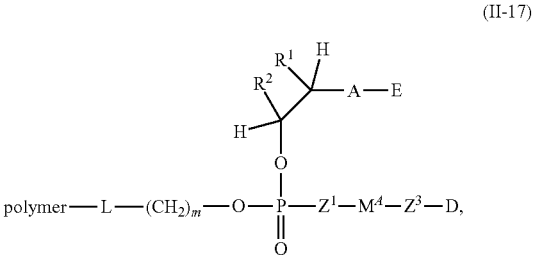

(II-17)

or a pharmaceutically acceptable salt thereof.

In some embodiments, the compound of Formula (II) has Formula (II-18):

(II-18)

or a pharmaceutically acceptable salt thereof.

In some embodiments, $R^N$ is H. In some embodiments, $R^N$ is $C_{1-6}$ alkyl (e.g., methyl, ethyl, propyl, isopropyl).

In some embodiments, the compound of Formula (II) has Formula (II-19a) is:

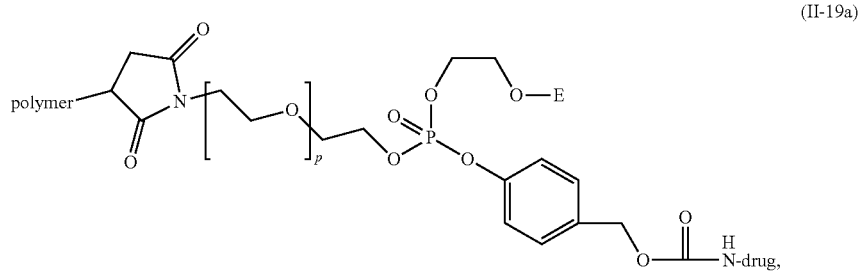

(II-19a)

or a pharmaceutically acceptable salt thereof.

In some embodiments, the compound of Formula (I) or Formula (II) is not:

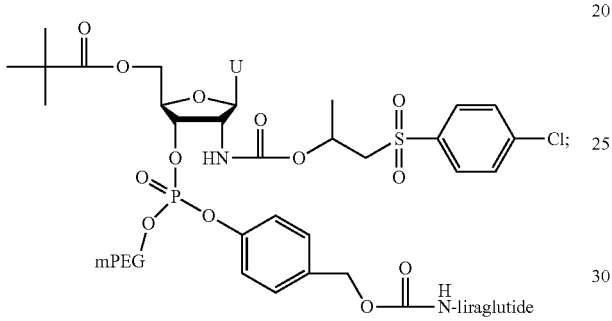

or a pharmaceutically acceptable salt thereof, wherein U is uracil.

Cleavable E-Groups

In some embodiments of Formula (I) or Formula (II), E is a cleavable moiety that upon cleavage liberates a free AH group, where H is hydrogen. The cleavable moiety E can include, for example:

1) An E moiety cleavable by any one of the following enzymes:

a) Esterases

All esters, carbonates and methyloxy esters can be hydrolyzed by an esterase enzyme. The reactivity of these functional groups in the enzymatic reaction can be modulated by selection of a carboxylic acid component of the ester functional group containing different electron donating groups or by making the ester sterically hindered. Both the acid component and the alcohol component of the ester may be sterically hindered.

b) Reductases

Methyl-dithioethers, methyl azido group and 2-oxymethyleneantraquinone carbonates (MAQC) are examples of cleavable moieties E, that both can be cleaved by a reductase enzyme. For example, a moiety E cleavable by a reductase is a methyl azido group, or the moiety E may be of the following formulae:

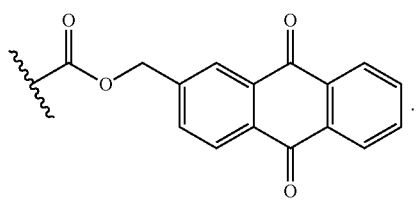 [SMILES: *C(=O)OCc1ccc2c(c1)C(=O)c1ccccc1C2=O]

c) Glycosidases

If A-E represents a heteroatom substituted by a sugar residue forming a glycosidic bond with the rest of the compound of Formula (I) or Formula (II), then an action of a glycosidase in vivo can cleave E and liberate the free A-H.

2) Moieties E cleavable by bases but at physiological pH, via the β-elimination mechanism (e.g., a β-eliminative trigger).

a) For example, moiety E may be a fluorenylmethyl carbamide-type trigger having the following formula:

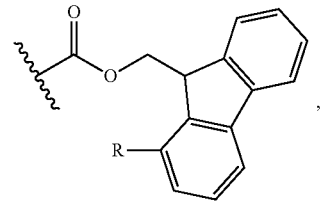

wherein R is selected from H, $C_{1-10}$ alkyl, OH, $NO_2$, CN, halogen and acetyl. Introduction of electron-withdrawing substituents R can increase the rate of β-elimination and liberation of free AH. In another example, the following moiety E possesses the electron withdrawing $—SO_2—$ group:

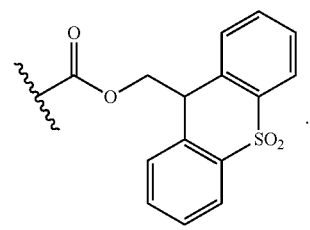 [SMILES: *C(=O)OCC1c2ccccc2S(=O)(=O)c2ccccc21]

b) Substituted β-phenylsulfonyl ethyl carbamates and carbonates:

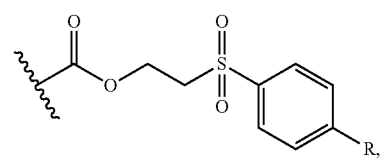

wherein R is selected from H, $C_{1-10}$ alkyl, OH, $NO_2$, CN, halogen and acetyl. These functional groups cleave via a β-elimination mechanism at about pH 7.4 and the rate of this process can be controlled by the substituent R on the phenyl ring.

In some embodiments, E is cleavable by an enzyme selected from the group consisting of an esterase, a specific or an unspecific peptidase, a reductase, an oxidase, a glycosidase, a hydrolase, a glycosyl transferase, and a transaminase. In some embodiments, E is cleavable by an enzyme selected from the group consisting of an esterase, a reductase, an oxidase, a glycoside, a hydrolase and glycosyl transferase.

3) Acid-Cleavable Moieties.

Any acid-cleavable alcohol protecting group can be used as cleavable moiety E. For example, acetals, orto-esters and phenyl substituted ethers can be used. Examples of such cleavable moieties include protecting groups such as THF, MTHP or MDMP, and also more labile acetals such as methoxy isopropyl acetal or methoxy cyclohexenyl acetal. Other examples of cleavable moieties E of this type that are cleaved in an acidic environment include dimethoxytrityl, trimethoxytrityl and pixyl groups.

In some embodiments, E contains a dithio group, cleavable by a biogenic thiol. In some embodiments of Formula (I) or Formula (II), moiety E is cleavable by a glutathione.

In some embodiments, E is a group of any one of the following formulae:

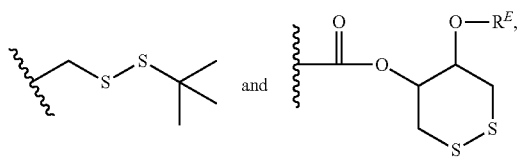

and wherein $R^E$ is selected from the group consisting of $C_{1-6}$ alkyl and benzyl. In some embodiments, $R^E$ is $C_{1-6}$ alkyl. In some embodiments, $R^E$ is benzyl.

In some embodiments, A is O, and E is a group of formula:

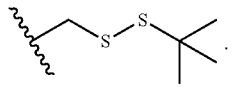 [SMILES: *CSSC(C)(C)C]

In some aspects of these embodiments, A is NH, and E is a group of formula:

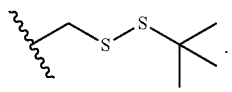 [SMILES: *CSSC(C)(C)C]

In some embodiments of Formula (I) or Formula (II), E is cleavable by an enzyme selected from the group consisting of an esterase, a reductase, an oxidase and a glycosidase or glycosyl transferase. In other embodiments, E is non-enzymatically cleavable at acidic or physiological pH. In some embodiments, E is an acyl group, an O-methyl-acyl group, a methyl azido group, a sugar residue, a protected acetal, or a carbonate ester. In some of these embodiments, A is O. In other embodiments, A is NH.

In some embodiments of Formula (I) or Formula (II), an acyl group is selected from the group consisting of formyl, acetyl, chloroacetyl, dichloroacetyl, trichloroacetyl, cyanoacetyl, mono-methyl malonate, mono-ethyl malonate, methoxyacetyl, ethoxyacetyl, t-butoxyacetyl, phenoxyacetyl, t-butylphenoxyacetyl, glycolate, acetylglycolate, propionate, 2-chloropropionate, 3-chloropropionate, 2-cyanopropionate, 3-cyanopropionate, N-acetyl-glycinate, N-trifluoroacetyl glycinate, N-acetyl alanylate, N-trifluoroacetyl alanylate, N-acetyl phenylalanylate, N-trifluoroacetyl phenylalanylate, N-acetyl valinylate, N-trifluoroacetyl valinylate, N-acetyl valinyl-citrunyllate, N-trifluoroacetyl valinyl-citrunyllate, butyrate, isobutyrate, pivaloate, levulinate, monomethyl oxalate, mono-ethyloxalate, mono-methyl succinate, mono-ethyl succinate, hydroxyl butyrate, acetoxybutyrate, acetylbutyrate, hexanoate, palmitate, stearate, benzoate, chloro-benzoate, dichloro-benzoate, pentachlorobenzoate, cyano-benzoate, aminobenzoate, acetamino-benzoate, mono-methyl-phthalate, mono-ethyl-phthalate, methoxy-benzoate, trimethoxybenzoate, trifluoromethylbenzoate, dimethylaminobenzoate, and methylsulfonylbenzoate. In some embodiments, E is an acyl group selected from formyl, acetyl, propionyl, acrylyl, pivaloyl, and benzoyl.

In some embodiments of Formula (I) or Formula (II), E is cleavable by an esterase enzyme. For example, E is an acyl group (e.g., any of the acyl groups described herein), a carbonate ester or an O-methyl-acyl ester.

In some embodiments of Formula (I) or Formula (II), E is cleavable by a reductase.

In some aspects of these embodiments, A is O and E is a group of formula:

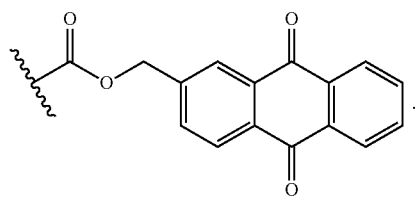 [SMILES: *C(=O)OCc1ccc2c(c1)C(=O)c1ccccc1C2=O]

In some aspects of these embodiments, A is NH and E is a group of formula:

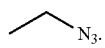

In some embodiments of Formula (I) or Formula (II), E is cleavable by a glutathione. In some aspects of these embodiments, A is NH. In other aspects of these embodiments, E is a moiety of formula:

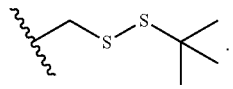 [SMILES: *CSSC(C)(C)C]

In some embodiments of Formula (I) or Formula (II), E is cleavable by a glycosidase. In some aspects of these embodiments, E is a residue of a sugar (e.g., glucose, galactose or mannose).

In some embodiments of Formula (I) or Formula (II), E is cleavable at physiological pH via the β-elimination mechanism. For example, E is selected from the group of any one of the following formulae:

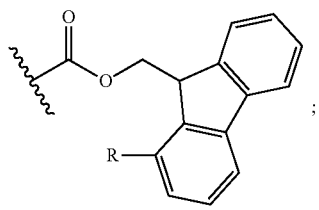

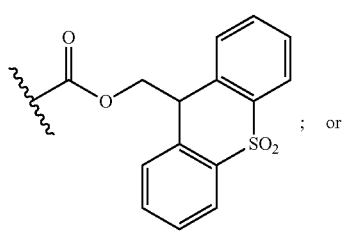
; or

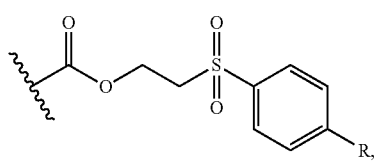

wherein R is selected from H, $C_{1-10}$ alkyl, OH, $NO_2$, CN, halogen and acetyl. In another example of moieties cleavable at physiological pH, E is an acyl group (e.g., any one of acyl groups described herein, such as pivaloyl or benzoyl).

In another example of moieties cleavable at physiological pH via the β-elimination mechanism, A is $NR^N$ or $NR^3$ and E is a cleavable moiety of formula:

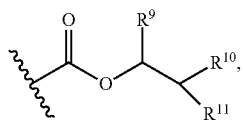

wherein:

$R^9$ is selected from H, an optionally substituted $C_{6-10}$ aryl, and an optionally substituted $C_{1-6}$ alkyl;

$R^{10}$ and $R^{11}$ are each independently selected from H, CN, $NO_2$, $COR^{12}$, $SOR^{12}$ or $SO_2R^{12}$, an optionally substituted $C_{1-6}$ alkyl, an optionally substituted $C_{6-10}$ aryl, and an optionally substituted 5- to 14-membered heteroaryl; or $R^{10}$ and $R^{11}$ together with the carbon atom to which they are attached form an optionally substituted $C_{3-7}$ cycloalkyl ring which is fused with one or more optionally substituted $C_{6-10}$ aryl rings;

$R^{12}$ is selected from an optionally substituted $C_{1-6}$ alkyl and an optionally substituted $C_{6-10}$ aryl. In some aspects of these embodiments, A is NH, and $R^9$ is selected from H and an optionally substituted $C_{6-10}$ aryl.

In some embodiments of Formula (I) or Formula (II), E is a cleavable moiety of any one of the following formulae (E-1) to (E-12), (E-37), and (E-39) to (E-41):

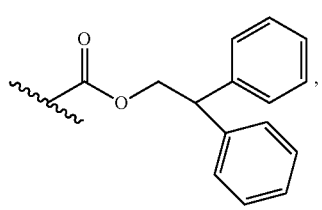 (E-1)

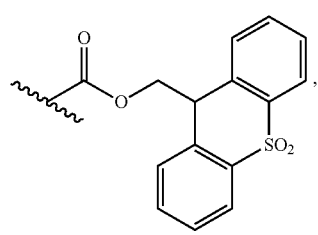 (E-2)

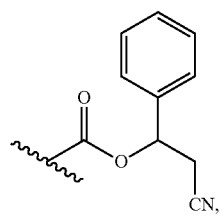 (E-3)

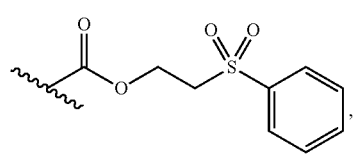 (E-4)

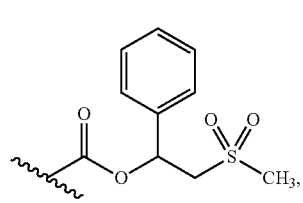 (E-5)

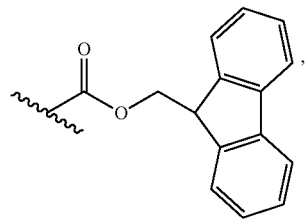 (E-6)

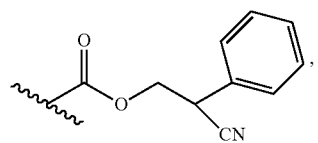 (E-7)

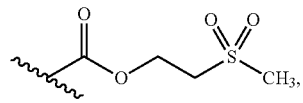 (E-8)

(E-9) 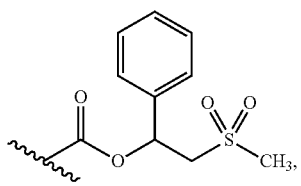

(E-10) 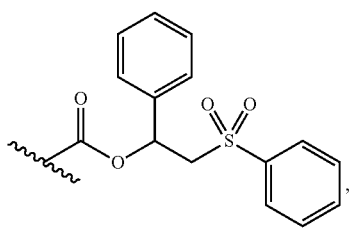

(E-11) 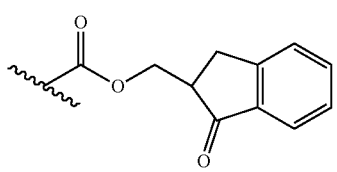

(E-12) 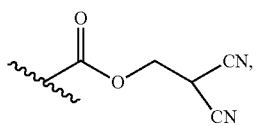

(E-37) 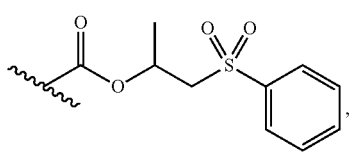

(E-39) 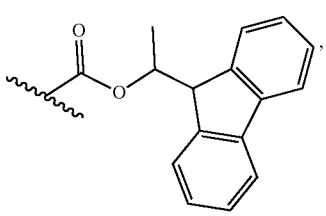

(E-40) 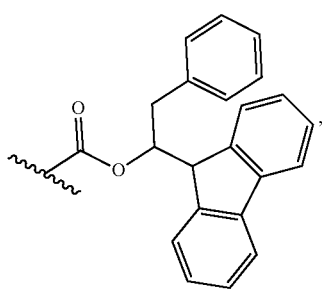

(E-41) 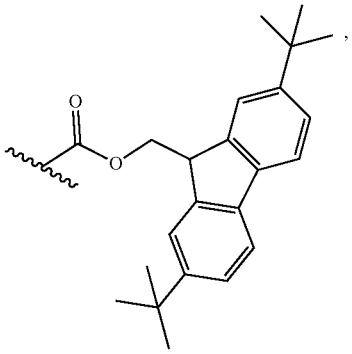

wherein any one of the phenyl rings in the formulae (E-1) to (E-12), (E-37) and (E-39) to (E-41) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl. In some aspects of these embodiments, E is a cleavable moiety of any one of formulae (E-1) to (E-12). In some embodiments, the substituents on the phenyl rings of the formulae (E-1) to (E-12), (E-37), and (E-39) to (E-41) modify stability and lability for the cleavable groups. In one example, cleavable moiety E may be a fluorenylmethyl carbamide-type having the following formula:

(E-6a) 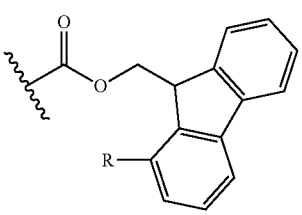

In one example, cleavable moiety E may be a fluorenylmethyl carbamide-type having the following formula:

(E-6b) 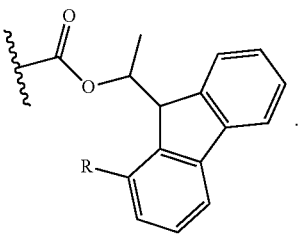

Introduction of electron-withdrawing substituents R such as, e.g., cyano, halogen, nitro, sulfonyl or acyl can increase the rate of β-elimination and liberation of free AH. In contrast, introduction of electron-donating substituents R such as, e.g., $C_{1-6}$ alkyl or silyl can stabilize the moiety E against β-elimination.

Substituted β-phenylsulfonyl ethyl carbamates and carbonates, such as such as (4-X-phenyl)sulfonylethoxycarbonyl (PSEC or XPSEC) groups, are examples of these useful moieties:

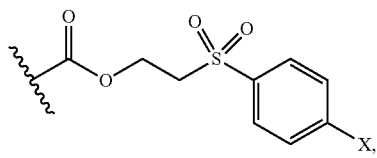

(E-4a)

wherein the substituent X is selected from the group consisting of H, $C_{1-10}$ alkyl, $C_{1-10}$ haloalkyl, $C_{1-10}$ alkoxy, OH, $NO_2$, CN, halogen and acyl. In some embodiments, X is selected from H, Cl and methoxy.

In some embodiments, the PSEC group is a group of formula:

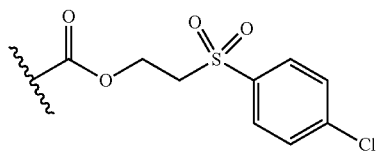

(chloro-PSEC)

or

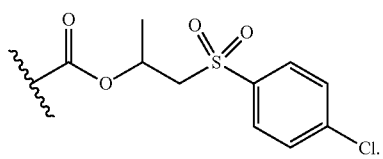

(E-38)

In some embodiments of Formula (I) or Formula (II), any one of the phenyl rings in the formulae (E-1) to (E-12), (E-37), or (E-39) to (E-41) is optionally substituted with 1, 2, 3, or substituents selected from F, Cl, CN, acetyl, $NO_2$ and $CF_3$. For example, (E-1) can be substituted with F to result in formula (E-42):

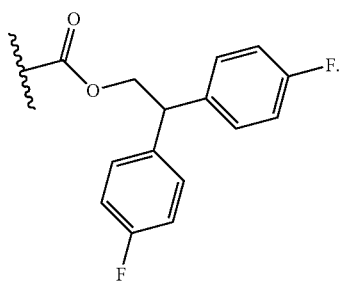 [SMILES: *C(=O)OCC(c1ccc(F)cc1)c1ccc(F)cc1]

In some embodiments of Formula (I) and Formula (II), E is not (E-38).

In some embodiments of Formula (I) or Formula (II), E is cleavable at acidic pH. For example, E is a moiety selected from an acetal, an ortho-ester, and a substituted triphenyl methylether. In a further example of moieties E cleavable at acidic pH, E may be selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, trimethoxytrityl and pixyl.

In some embodiments of Formula (I) or Formula (II), a moiety E that is cleavable by bases at physiological pH via the β-elimination mechanism, or is cleavable in an autocatalytic manner that starts with deprotonation of the most basic amino group in the E group. In one example, such an E moiety is an oligoamide (e.g., diamide or triamide). In some aspects of these embodiments, A is nitrogen (e.g., A is NH). For example, E is any one of the oligoamides described in US Publication No. US 2015/0057221, US Publication No. US 2014/0249093, U.S. Pat. Nos. 8,377,917, 8,906,847, 9,173,953, or 9,062,094, all of which are incorporated by reference herein. In one example, E is a cleavable moiety selected from any one of the following formulae (E-13) to (E-36):

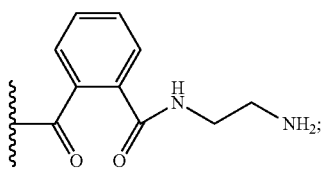

(E-13)

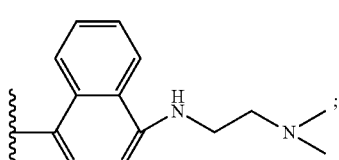

(E-14)

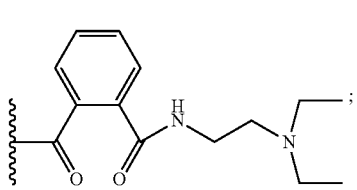

(E-15)

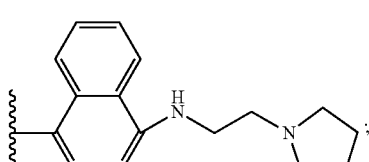

(E-16)

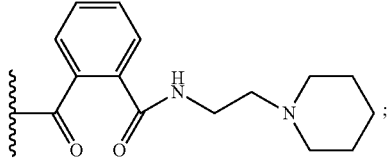

(E-17)

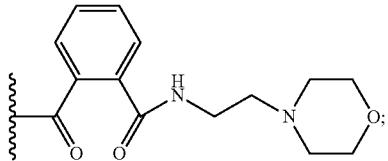

(E-18)

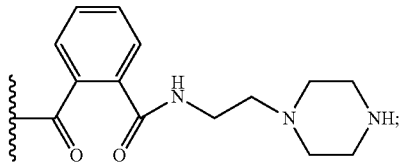

(E-19)

(E-20)
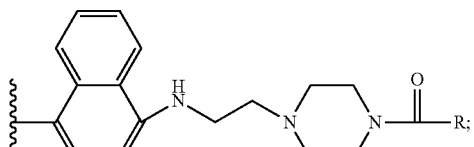
(E-21)
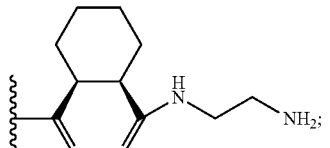
(E-22)
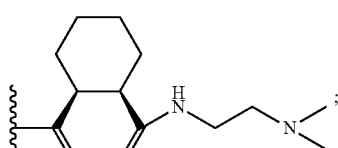
(E-23)
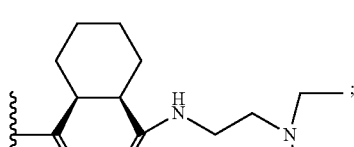
(E-24)
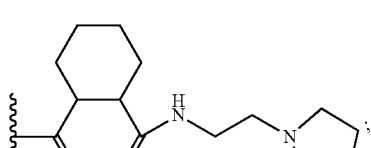
(E-25)
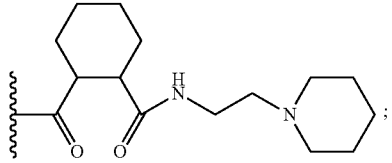
(E-26)
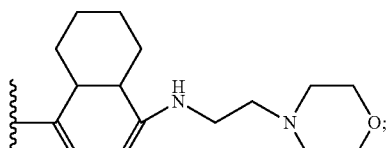
(E-27)
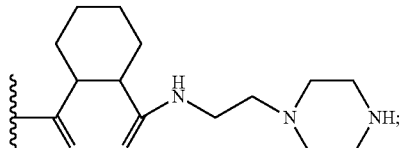
(E-28)
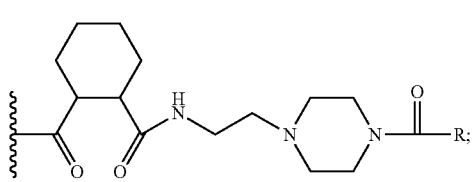
(E-29)
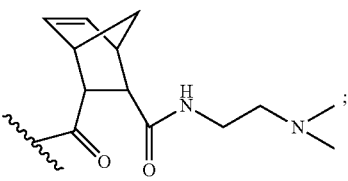
(E-30)
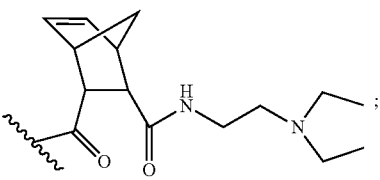
(E-31)
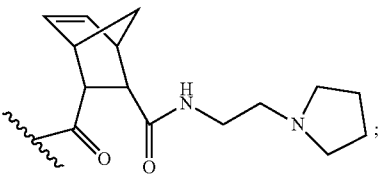
(E-32)
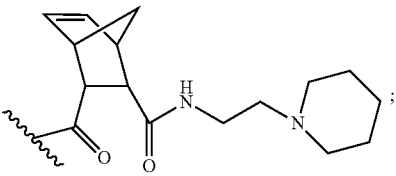
(E-33)
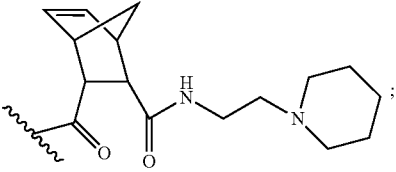
(E-34)
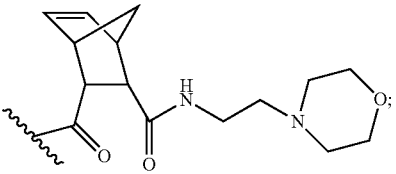
(E-35)
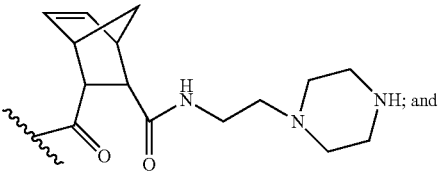
(E-36)
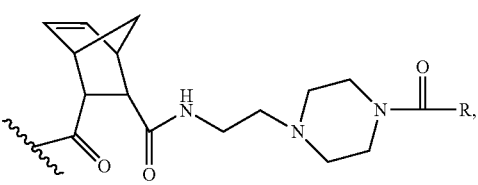
wherein R is as described herein.
In some embodiments of Formula (I) or Formula (II), a moiety E that is cleavable at physiological pH, e.g., via the β-elimination mechanism, is any one of the β-eliminative moiety described, for example, in U.S. Pat. Nos. 9,387,245 or 8,754,190, both of which are incorporated herein by reference.

In some embodiments of Formula (I) or Formula (II), a moiety E is attached to A using a group of formula ($L^E$):

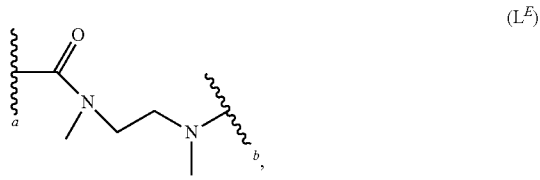

wherein a denotes a point of attachment to A, and b denotes a point of attachment to E. In some aspects of these embodiments, A is O. In other aspects of these embodiments, upon cleavage of the moiety E, the group of formula $L^E$ undergoes decomposition reaction to yield $CO_2$ and a compound of formula:

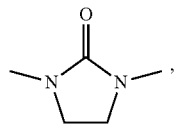

thus liberating a free $A^-$ group, which may then undergo a nucleophilic attack on the poshorus atom in the compound of Formula (I) or Formula (II). The $A^-$ group may also be protonated to yield the group AH prior to the nucleophilic attack.

In one example, in the compound of Formula (II-8a) the chloro-PSEC cleavable moiety E is attached to A using the group of formula $L^E$. When the chloro-PSEC moiety in the compound (II-8a) is cleaved non-enzymatically via the β-elimination mechanism, the resultant decomposition of the moiety $L^E$ may occur, for example, as shown in Scheme 3.

In some embodiments, any one of cleavable moieties (E-1) to (E-36) may be attached to A using a moiety of formula ($L^E$).

In some embodiments, an E moiety may be cleaved via enzymatic catalysis, through a β-elimination mechanism at physiological pH, or may be hydrolyzed at an acidic pH. For example, when a compound of Formula (I) or Formula (II) is subjected to enzymatic conditions at physiological pH, the E-group in the compound may be cleaved by the enzyme or cleaved by β-elimination, or both, depending on which reaction is kinetically favorable under the given conditions. In another example, when a compound of Formula (I) or Formula (II) is subjected to enzymatic conditions at acidic pH, the E-group in the compound may be cleaved by the enzyme or hydrolyzed, or both, depending on the difference in activation energy for the enzymatic hydrolysis reaction and the acidic hydrolysis reaction.

GLP-1 Polypeptide or Analogs thereof

In some embodiments of Formula (I) or Formula (II), D comprises a residue of any one of the glucagon-like-peptide 1 (GLP-1) polypeptide or analogs thereof described herein. The residue of a GLP-1 polypeptide or analogs thereof in Formula (I) or Formula (II) may be shown as "D" or "Drug", which symbols are used herein interchangeably.

In some embodiments of Formula (I) or Formula (II), $HZ^3$— may represent an amino group or a hydroxyl group of the side chain of an amino acid within the polypeptide backbone (e.g., lysine), and D represents the rest of the polypeptide backbone. For example, $HZ^3$— may be a ε-amino group of a lysine. In another example, $HZ^3$— may be an OH— group of a serine.

In some embodiments of Formula (I) or Formula (II), $HZ^3$— may represent an amino group or a hydroxyl group of the terminus of the polypeptide backbone (e.g., the terminal amine of histidine), and D represents the rest of the polypeptide backbone. For example, $HZ^3$— may be the N-terminal amine group of the N-terminal amino acid (e.g., histidine). In another example, $HZ^3$— may be an OH— group of the C-terminal carboxylic acid of the terminal amino acid of the polypeptide.

Scheme 3

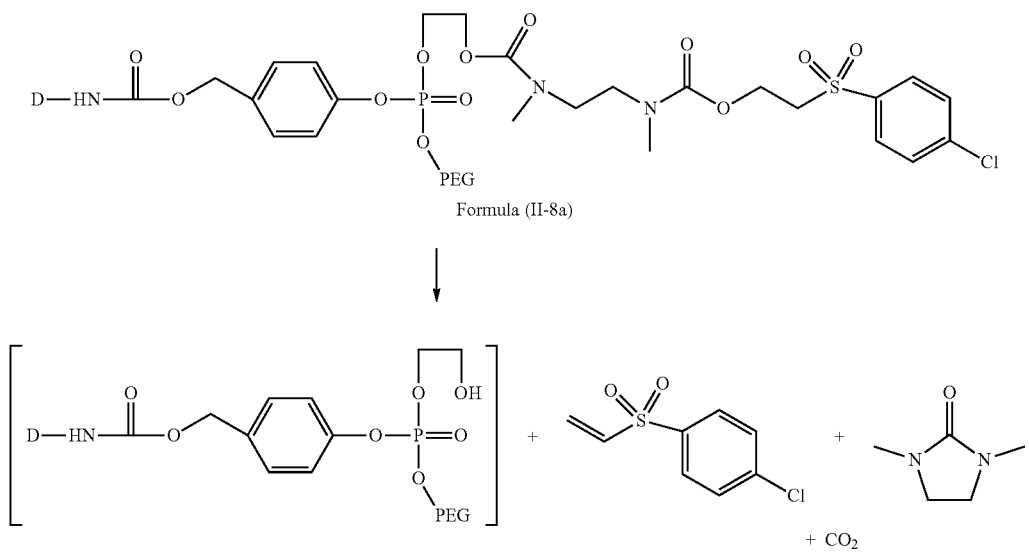

Formula (II-8a)

+ $CO_2$

In some embodiments of a compound of Formula (I) or Formula (II), when $Z^3$ is absent, prior to being conjugated to form the compound of Formula (I) or Formula (II), the GLP-1 polypeptide or analogs thereof may be described as a compound of formula $H_2N$-D. In this example, the moiety of formula:

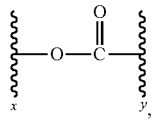 [SMILES: *OC(*)=O]

in the self-immolative group $M^4$ of any one of the formulae (a)-(g) represents the part of the drug, after the drug is being conjugated to form the compound of Formula (I) or Formula (II). In this moiety, x represents a point of attachment to $M^{4'}$ (as described herein) of the self-immolative group, or to the H— of the drug $H_2N$-D prior to conjugation, and y represents a point of attachment to D.

In some embodiments of a compound of Formula (I) or Formula (II), when $Z^3$ is absent, prior to being conjugated to form the compound of Formula (I) or Formula (II), the GLP-1 polypeptide or analogs thereof may be described as a compound of formula $H_2N$-D. In this case, when the GLP-1 polypeptide or analogs thereof has the formula $H_2N$-D, the moiety $H_2N$— represents a terminal amine group of the GLP-1 polypeptide or analog thereof, and D comprises a residue of the GLP-1 polypeptide or analogs thereof.

In one example, prior to being conjugated to form a compound of Formula (I) or Formula (II) as described herein, the GLP-1 polypeptide or analogs thereof may be described as a compound of formula $HZ^3$D, wherein $HZ^3$— represents a reactive amino- or hydroxyl-group of the GLP-1 polypeptide or analogs thereof (when $Z^3$ is nitrogen or oxygen, respectively), and D comprises a residue of the GLP-1 polypeptide or analogs thereof. In one example, prior to being conjugated to form a compound of Formula (I) or Formula (II) as described herein, the GLP-1 polypeptide or analogs thereof may be described as a compound of formula $HZ^3$D, wherein $HZ^3$— represents a reactive amino- or hydroxyl-group of the GLP-1 polypeptide or analogs thereof (when $Z^3$ is nitrogen or oxygen, respectively), and D is a residue of the GLP-1 polypeptide or analogs thereof.

Non-limiting examples of GLP-1 polypeptides or analogs thereof include:

```
GLP-1 (1-37):
                                      (SEQ ID NO: 1)
HDEFERHAEGTFTSDV SSYLEGQAAK EFIAWLVKGR G

GLP-1 (7-37):
                                      (SEQ ID NO: 2)
HAEGTFTSDV SSYLEGQAAK EFIAWLVKGR G
``` wherein this sequence corresponds to amino acids 7-37 of the GLP-1 (1-37) polypeptide sequence.

Liraglutide (VICTOZA®; K26 liraglutide) is a GLP-1 polypeptide analog with a C16 fatty (palmitic) acid chain via a glutamyl spacer off of the lysine residue and is represented as:

```
                                      (SEQ ID NO: 3)
HAEGTFTSDV SSYLEGQAAK(γ-Glu-palmitoyl)

EFIAWLVRGR G
``` wherein this sequence is an analog of amino acids 7-37 of the GLP-1 (1-37) polypeptide sequence.

```
Liraglutide fragment 1:
                                      (SEQ ID NO: 4)
HAEGTFTSDV SSYLEGQAAK EFIAWLVRGR G Liraglutide fragment 2:
                                      (SEQ ID NO: 5)
EGTFTSDV SSYLEGQAAK EFIAWLVRGR G Liraglutide fragment 3:
                                      (SEQ ID NO: 6)
TSDV SSYLEGQAAK EFIAWLVRGR G Liraglutide fragment 4:
                                      (SEQ ID NO: 7)
AK EFIAWLVRGR G
```

Dulaglutide (LY2189265, TRULICITY®), which is a molecule consisting of two identical, disulfide-linked chains, each containing a human GLP-1 analog sequence covalently linked to a modified human immunoglobulin G4 (IgG4) heavy chain fragment (Fc) by a small peptide linker.

The GLP-1 analog sequence is represented as:

```
                                      (SEQ ID NO: 8)
HGEGTFTSDV SSYLEEQAAK EFIAWLVKGG G
```

The immunoglobulin sequence is represented as:

```
                                      (SEQ ID NO: 9)
ESK YGPPCPPCPA PEAAGGPSVF LFPPKPKDTL MISRTPEVTC

VVVDVSQEDP EVQFNWYVDG VEVHNAKTKP REEQFNSTYR

VVSVLTVLHQ DWLNGKEYKC KVSNKGLPSS IEKTISKAKG

QPREPQVYTL PPSQEEMTKN QVSLTCLVKG FYPSDIAVEW

ESNGQPENNY KTTPPVLDSD GSFFLYSRLT VDKSRWQEGN

VFSCSVMHEA LHNHYTQKSL SLSLG
```

The small peptide linker is represented as:

```
                                      (SEQ ID NO: 10)
GGGGSGGGG SGGGGSA
```

The full sequence for one monomer of Dulaglutide (LY2189265, TRULICITY®) is represented as:

```
                                      (SEQ ID NO: 11)
HGEGTFTSDV SSYLEEQAAK EFIAWLVKGG GGGGGSGGGG

SGGGGSAESK YGPPCPPCPA PEAAGGPSVF LFPPKPKDTL

MISRTPEVTC VVVDVSQEDP EVQFNWYVDG VEVHNAKTKP

REEQFNSTYR VVSVLTVLHQ DWLNGKEYKC KVSNKGLPSS

IEKTISKAKG QPREPQVYTL PPSQEEMTKN QVSLTCLVKG

FYPSDIAVEW ESNGQPENNY KTTPPVLDSD GSFFLYSRLT

VDKSRWQEGN VFSCSVMHEA LHNHYTQKSL SLSLG*
*Disulfide bridges locations:
55-55' 58-58' 90-150 90'-150' 196-254 196'-254'
```

Exenatide (BYETTA®, BYDUREON, Exendin-4) and Exenatide LAR (GLP-1 portion is same):

(SEQ ID NO: 12)
HGEGTFTSDL SKQMEEEAVR LFIEWLKNGG PSSGAPPPS

Taspoglutide:

(SEQ ID NO: 13)
HXEGTFTSDV SSYLEGQAAK EFIAWLVKXR wherein X is 2-methyl alanine
Lixisenatide (LYXUMIA®):

(SEQ ID NO: 14)
HGEGTFTSDL SKQMEEEAVR LFIEWLKNGG PSSGAPPSKK KKKK wherein T is threonine and I is isoleucine
Albiglutide (TANZEUM®) is a polypeptide consisting of 645 proteinogenic amino acids with 17 disulfide bridges. Amino acids 1-30 and 31-60 constitute two copies of modified human GLP-1.
The GLP1 fragment is represented by:

(SEQ ID NO: 15)
HGEGTFTSDV SSYLEGQAAK EFIAWLVKGR

The full sequence of albiglutide is represented as:

(SEQ ID NO: 16)
HGEGTFTSDV SSYLEGQAAK EFIAWLVKGR HGEGTFTSDV

SSYLEGQAAK EFIAWLVKGR DAHKSEVAHR FKDLGEENFK

ALVLIAFAQY LQQCPFEDHV KLVNEVTEFA KTCVADESAE

NCDKSLHTLF GDKLCTVATL RETYGEMADC CAKQEPERNE

CFLQHKDDNP NLPRLVRPEV DVMCTAFHDN EETFLKKYLY

EIARRHPYFY APELLFFAKR YKAAFTECCQ AADKAACLLP

KLDELRDEGK ASSAKQRLKC ASLQKFGERA FKAWAVARLS

QRFPKAEFAE VSKLVTDLTK VHTECCHGDL LECADDRADL

AKYICENQDS ISSKLKECCE KPLLEKSHCI AEVENDEMPA

DLPSLAADFV ESKDVCKNYA EAKDVFLGMF LYEYARRHPD

YSVVLLLRLA KTYETTLEKC CAAADPHECY AKVFDEFKPL

VEEPQNLIKQ NCELFEQLGE YKFQNALLVR YTKKVPQVST

PTLVEVSRNL GKVGSKCCKH PEAKRMPCAE DYLSVVLNQL

CVLHEKTPVS DRVTKCCTES LVNRRPCFSA LEVDETYVPK

EFNAETFTFH ADICTLSEKE RQIKKQTALV ELVKHKPKAT

KEQLKAVMDD FAAFVEKCCK ADDKETCFAE EGKKLVAASQ

AALGL

Semaglutide (OZEMPIC®):

(SEQ ID NO: 17)
H-Aib-EGTFTSDV SSYLEGQAAK(AEEAc-AEEAc-γ-Glu-17- carboxyheptadecanoyl)EFIAWLVRGR G wherein Aib is α-aminoisobutyric acid.

Figure 8:
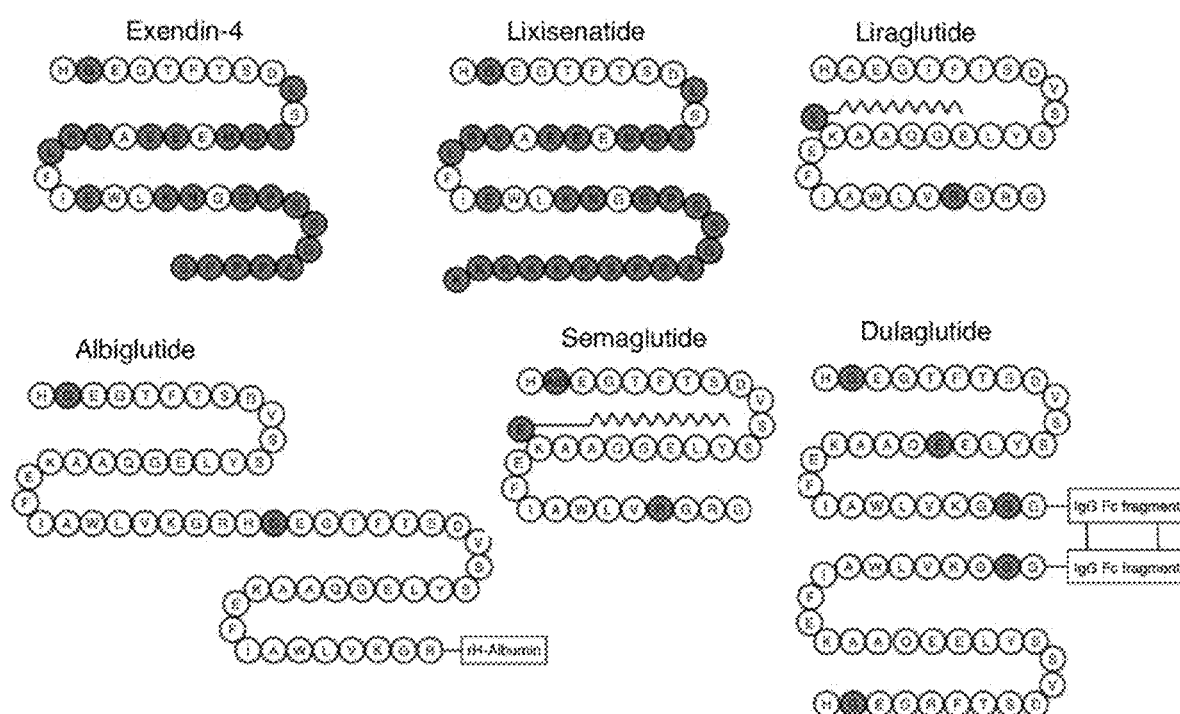
FIG. 8 provides non-limiting examples of GLP-1 analogs.

Illustrations of a selection of GLP-1 analogs are provided in FIG. 8. See also Dods, R. L. and Donnelly, D. *Bioscience Reports* 36(1) e2085 (Jan. 15, 2016); and Li, Y et al. *Reviews in Neurosciences* 27(7): 689-711 (2016).

In some embodiments, a glucagon-like-peptide 2 (GLP-2) or analogs thereof can be used in place of the GLP-1 polypeptide and analogs thereof described herein. Non-limiting examples of GLP-2 polypeptide and analogs thereof include:

GLP-2:

(SEQ ID NO: 18)
HADGSFSDEM NTILDNLAAR DFINWLIQTK ITD

Teduglutide (GATTEX®):

(SEQ ID NO: 19)
HGDGSFSDEM NTILDNLAAR DFINWLIQTK ITD

FE203799:

(SEQ ID NO: 20)
HGDGSFSDENle[d-Phe]TILDLLAARDFINWLIQTKITD

Glepaglutide (ZP1848):

(SEQ ID NO: 21)
HGEGTFSSEL ATILDALAAR DFIAWLIATK ITD-KKKKKK

Elsiglutide (ZP1846):

(SEQ ID NO: 22)
HGEGSFSSELSTILDALAARDFIAWLIATKITDKKKKKK

Any of the above sequences can be present in polypeptides having at least 80% sequence identity to any of the sequences above. For example, a compound provided herein can have comprise a polypeptide having at least 80%, at least 85%, at least 88%, at least 90%, at least 95%, at least 96%, at least 97%, at least 98%, at least 99% sequence identity to the recited sequence. For example, D comprises a residue of a GLP-1 polypeptide or an analog thereof wherein the GLP-1 polypeptide or analog thereof has at least 80% sequence identity (e.g., at least 85%, at least 88%, at least 90%, at least 95%, at least 96%, at least 97%, at least 98%, at least 99%) to a GLP-1 polypeptide or analog thereof as provided herein.

In some embodiments, the polypeptide is 30 to 100 amino acids in length. For example, 31 to 100 amino acids in length, 35 to 100 amino acids in length, 40 to 100 amino acids in length, 50 to 100 amino acids in length, 60 to 100 amino acids in length, 70 to 100 amino acids in length, 80 to 100 amino acids in length, 90 to 100 amino acids in length, 30 to 90 amino acids in length, 30 to 80 amino acids in length, 30 to 70 amino acids in length, 30 to 60 amino acids in length, 30 to 50 amino acids in length, 30 to 40 amino acids in length, 40 to 60 amino acids in length, 50 to 70 amino acids in length, 31 to 41 amino acids in length, or 31 to 50 amino acids in length. In some embodiments, the polypeptide is less than 50 amino acids in length. For example, less than 45 amino acids in length, less than 40 amino acids in length, or less than 35 amino acids in length. In some embodiments, the polypeptide is 30 to 300 amino acids in length. For example, 31 to 300 amino acids in length, 50 to 300 amino acids in length, 80 to 300 amino acids in length, 90 to 300 amino acids in length, 100 to 300 amino acids in length, 150 to 300 amino acids in length, or 200 to 300 amino acids in length.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2

Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B 12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\B12seq c:\seq1.txt -j c:\seq2.txt -p blastn -o c:\output. txt -q -1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2. txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, an amino acid sequence that has 25 matches when aligned with the sequence set forth in SEQ ID NO:1 is 95.6 percent identical to the sequence set forth in SEQ ID NO:1 (i.e., 25/31×100=80.6). It is noted that the percent sequence identity value is rounded to the nearest tenth. For example, 75.11, 75.12, 75.13, and 75.14 is rounded down to 75.1, while 75.15, 75.16, 7.17, 75.18, and 7.19 is rounded up to 7.2. It also is noted that the length value will always be an integer.

Analogs as provided herein include polypeptide variants having, for example, one or more amino acid substitutions, deletions, or insertions. In some embodiments, the variant has at least one amino acid substitutions, deletions, or insertions. In some embodiments, the variant has at least two amino acid substitutions, deletions, or insertions. In some embodiments, the variant has at least three amino acid substitutions, deletions, or insertions. Analogs as provided herein includes fragments. As used herein, "fragment," as applied to a polypeptide, will ordinarily be at least 10 residues, more typically at least 20 residues, and preferably at least 30 (e.g., 50) residues in length, but less than the entire, intact sequence. Analogs (e.g., variants and fragments) can be generated by methods known to those skilled in the art, e.g., by enzymatic digestion of naturally occurring or recombinant protein, by recombinant DNA techniques using an expression vector that encodes a defined fragment, or by chemical synthesis.

Figure 9:
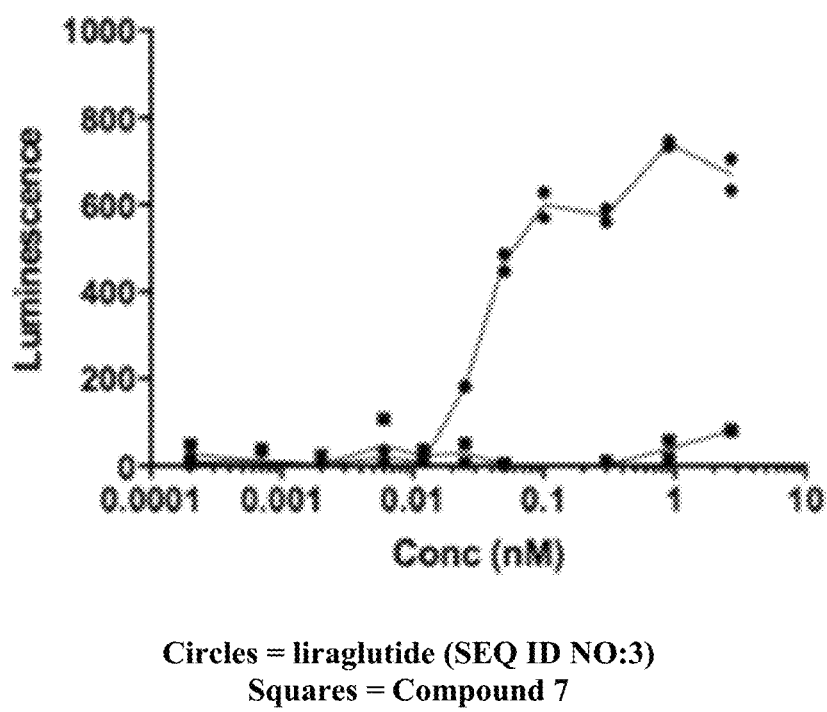
FIG. 9 is graph plotting the amount of biological activity of liraglutide detected for the indicated amounts of liraglutide (SEQ ID NO:3) and compound 7.

In some embodiments, GLP-1 polypeptides or analogs thereof, including those of SEQ ID NO:1-SEQ ID NO:22, are biologically inactive or only weakly biologically active when conjugated to an aliphatic moiety (e.g., PEG) as in Formula (I) or Formula (II), as compared to free, unconjugated forms of the polypeptides. The polypeptides can regain their biological activity after release from the aliphatic moiety (e.g., PEG moiety) of the compound of Formula (I) or Formula (II). For example, the compound of Formula (I) or Formula (II) has the ability to perform as a pro-drug within mammals (e.g., humans); remaining inactive compared to unconjugated GLP-1 polypeptide or an analog thereof, until the GLP-1 polypeptide or an analog thereof is released from the aliphatic moiety (e.g., PEG moiety) of Formula (I) or Formula (II). In some cases, as shown in FIG. 9, compound 7 (where polypeptide liraglutide is conjugated to a PEG moiety) remains inactive compared to unconjugated liraglutide, until the liraglutide is released from the aliphatic moiety (e.g., a PEG moiety) of compound 7 (See experimental results and discussion in Example 11).

Polymers

In some embodiments, the aliphatic moiety can be a polymer. A polymer, as described herein, can be branched or linear. For example, a polymer can have from 2 to 100 termini (e.g., 2 to 80, 2 to 75, 2 to 60, 2 to 50, 2 to 40, 2 to 35, 2 to 25, 2 to 10, 2 to 5, 4 to 20, 5 to 25, 10 to 50, 25 to 75, 3 to 6, 5 to 15 termini). In some embodiments, a polymer can have from 2 to 5, 4 to 6, 5 to 6, or 3 to 6 termini. In some embodiments, a polymer is linear and therefore has 2 termini. In some embodiments, one termini of a polymer is covalently bonded to the structure of any one of the formulae provided herein.

A polymer can be, for example, poly(alkylene glycol), poly(oxyethylated polyol), poly(olefinic alcohol), poly(β-hydroxy acid), poly(vinyl alcohol), polyoxazoline, or a copolymer thereof. A polyalkylene glycol includes linear or branched polymeric polyether polyols. Such polyalkylene glycols, include, but are not limited to, polyethylene glycol (PEG), polypropylene glycol, polybutylene glycol, and derivatives thereof. Other exemplary embodiments are listed, for example, in commercial supplier catalogs, such as Shearwater Corporation's catalog "Polyethylene glycol and Derivatives for Biomedical Applications" (2001).

In some embodiments, such polymeric polyether polyols have average molecular weights between about 0.1 kDa to about 100 kDa. For example, such polymeric polyether polyols include, but are not limited to, between about 500 Da and about 100,000 Da or more. The molecular weight of the polymer may be between about 500 Da and about 100,000 Da. For example, a polymer used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, and 500 Da. In some embodiments, the molecular weight of the polymer is between about 500 Da and about 50,000 Da. In some embodiments, the molecular weight of the polymer is between about 500 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

In some embodiments, a polymer is a linear or branched poly(ethylene glycol).

In some embodiments, the poly(ethylene glycol) molecule is a linear polymer. Linear PEG can be alkylated (e.g., methylated or ethylated), at one termini, but they can by incorporated to the conjugate of any one of the formulae disclosed herein using the free terminus in the non-derivatized hydroxyl form. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. For example, branched PEG can be V-shaped, or T-shaped, depending on the method by which PEG has been synthesized. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, the polyethylene glycol (linear or branched) has an average molecular weight from about 500 Da to about 40,000 Da, from about 1,000 Da to about 30,000 Da, from about 1,000 Da to about 20,000 Da, from about 5,000 Da to about 20,000 Da.

In some embodiments, the polymer (e.g., the polyethylene glycol) as provided herein has the following structural formula:

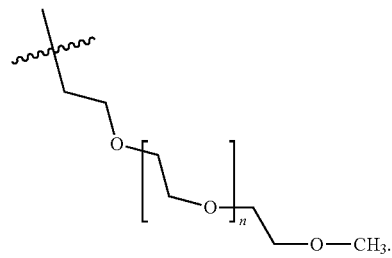

In some embodiments, n is an integer from 1 to 1,000, from 1 to 800, from 1 to 300, or from 1 to 100. In some embodiments, n is selected from 10, 20, 50, 100, 200, 250, 300, 500, 600, and 1000.

Further examples of suitable polymers can be found, for example, in Chen. S. et al. *Polymer* 51 (2010) 5283-5293, which is herein incorporated by reference in its entirety.

Exemplary Compounds

Non-limiting examples of the compounds provided herein include:

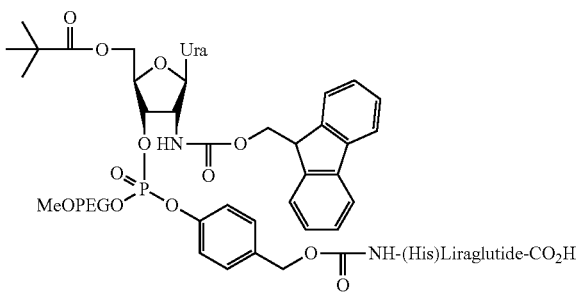

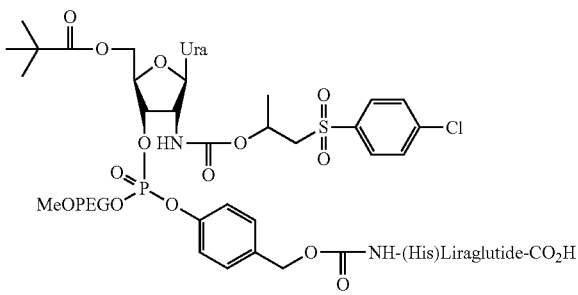

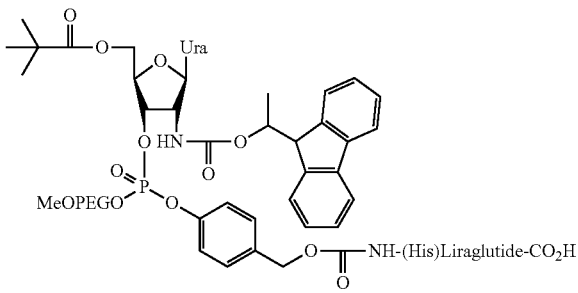

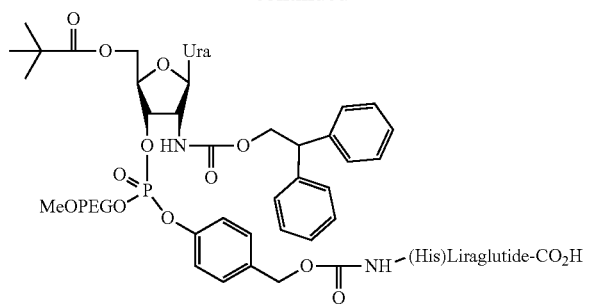

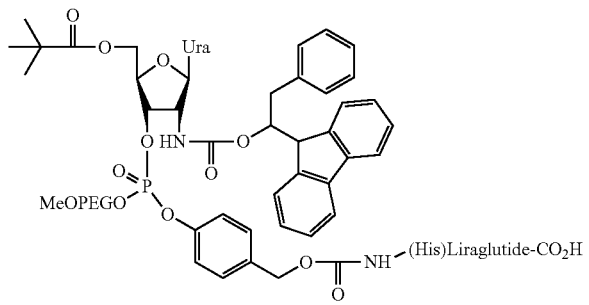

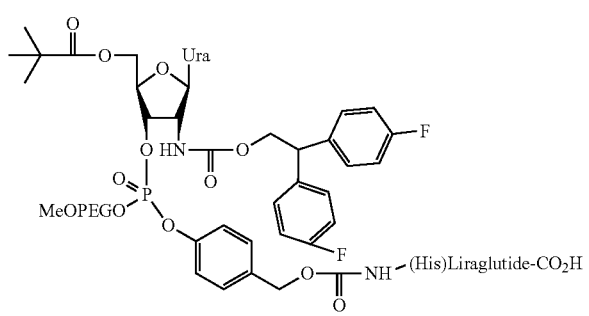

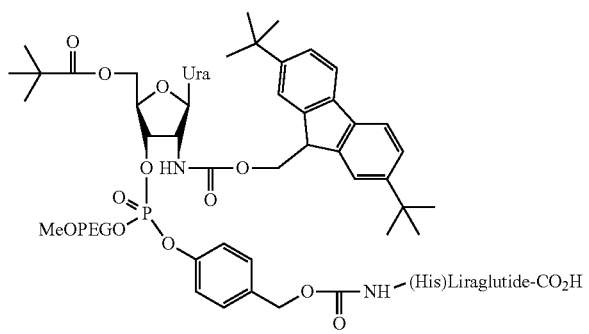

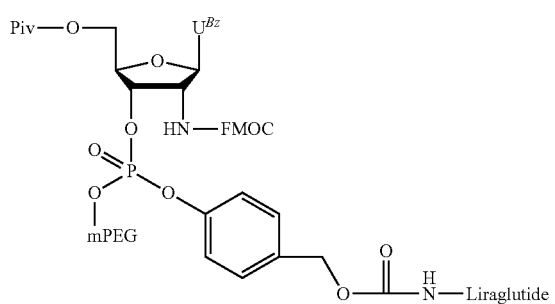

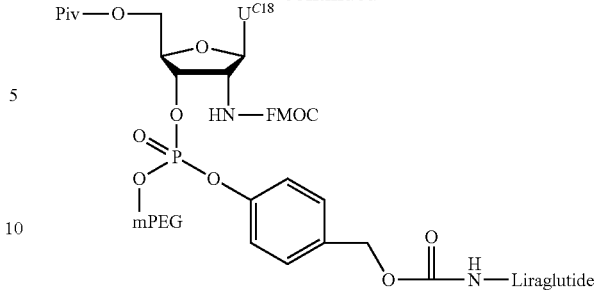

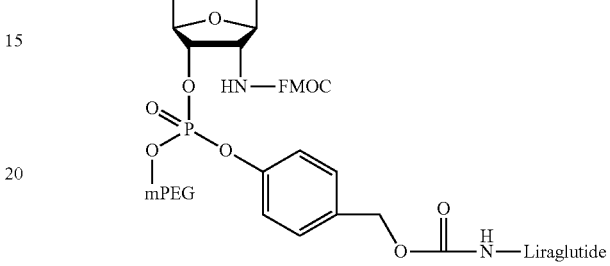

or a pharmaceutically acceptable salt thereof, wherein liragludide is the residue of liragludide; and Ura is uracil.

Pharmaceutically Acceptable Salts

In some embodiments, a salt of a compound of Formula (I) or Formula (II) disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula (I) or Formula (II) disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula (I) or Formula (II) disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formula (I) or Formula (II) disclosed herein, or pharmaceutically acceptable salts thereof, are substantially isolated.

In some embodiments, the present application provides a compounds of Formula (I) or Formula (II) disclosed herein, or pharmaceutically acceptable salts thereof, prepared by any one of the processes described herein.

Hydrolysis Cascade

The conjugates provided herein advantageously provide release of a GLP-1 polypeptide or analog thereof. In some embodiments, release of the drug occurs under physiological conditions. In some embodiments, the compound undergoes selective cleavage of one or more chemical bonds. Without being bound by any particular theory, it is believed that the conjugates may provide release of the GLP-1 polypeptide or analog thereof according to any one of the mechanisms described in the following Schemes.

The compounds of Formula (I) or Formula (II) may undergo a hydrolysis cascade and release the biologically active drug $HZ^3$-D or HO—(C=O)-D as described in Scheme 4. Referring to Scheme 4, when the compound of Formula (I) or Formula (II) is subjected to physiological pH, acidic pH or enzymatic conditions as described herein, the moiety E is selectively cleaved, leaving compound 2a-1 with a reactive nucleophilic group -AH (e.g., —OH), which, in turn, reacts with the phosphorus atom leading to the formation of a cyclic compound 2a-2 and the compound 2a-5 comprising the self-immolative group $M^4$. The breakdown of the self-immolative group in the compound 2a-5 leads to the formation of compound 2a-4 comprising the group $M^{4'}$, and a biologically active drug $HZ^3$-D or HO—(C=O)-D. The cyclic phosphotriester 2a-2 may be further hydrolyzed at physiological pH resulting in the opening of the 5-membered ring and formation of both isomeric phosphodiesters:

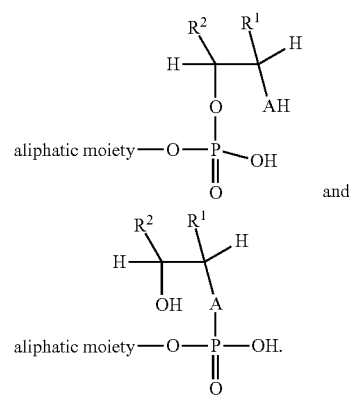

and

In some embodiments, the compound of Formula (I) or Formula (II) may undergo a hydrolysis cascade and release the biologically active drug as described in Scheme 5.

Scheme 4

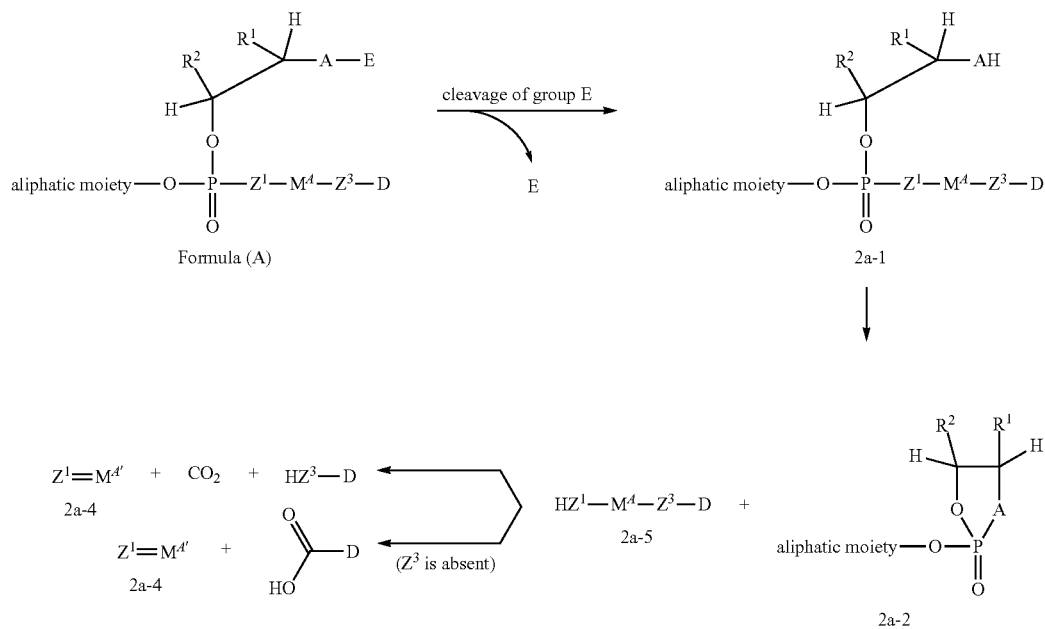

Scheme 5
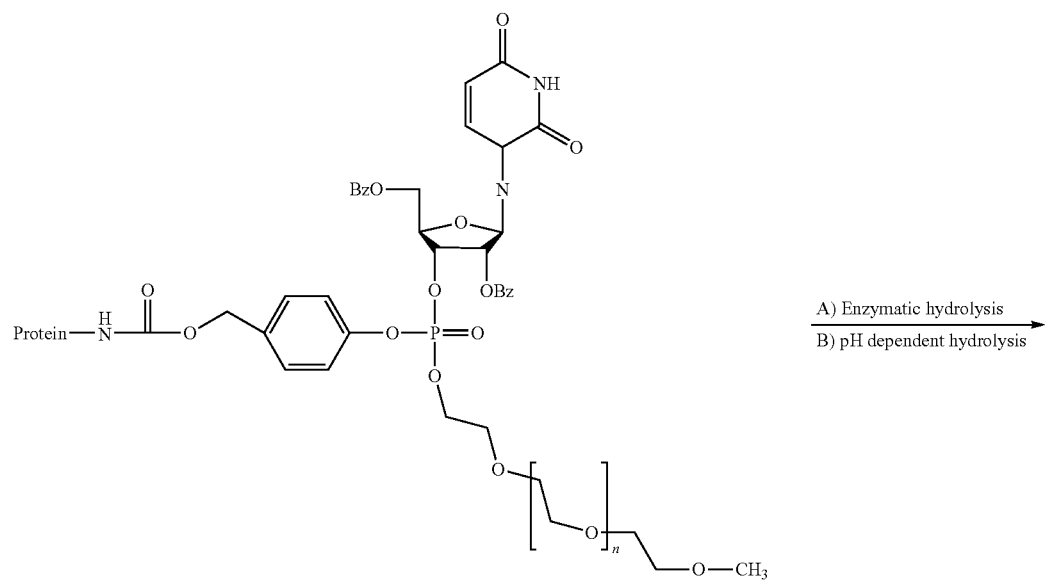
A) Enzymatic hydrolysis
B) pH dependent hydrolysis
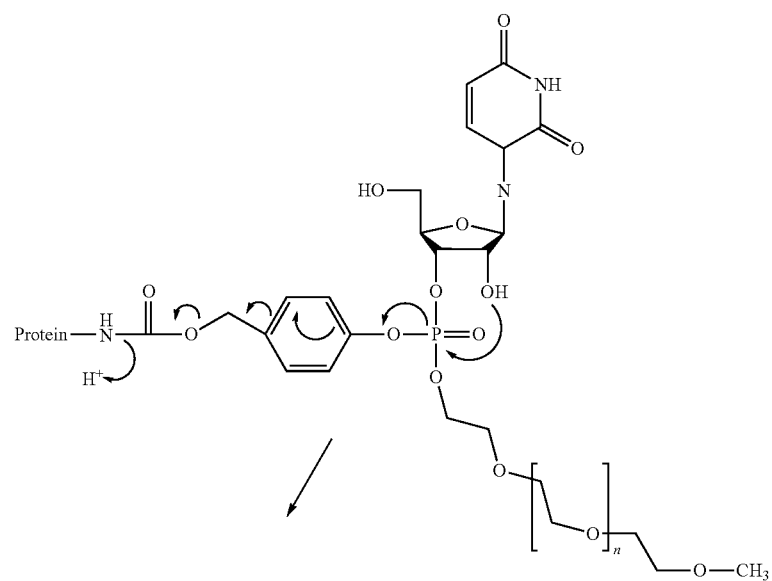

-continued
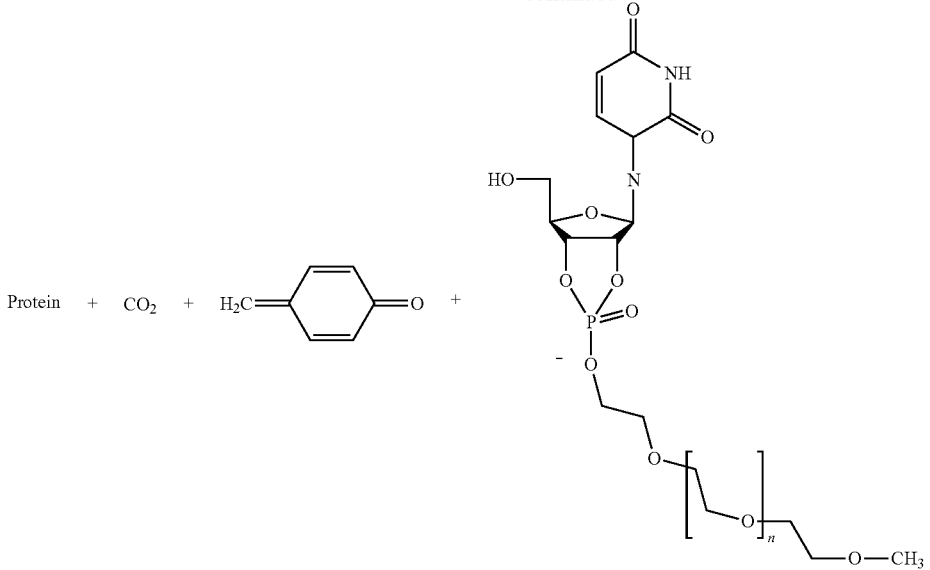
In some embodiments, the compound of Formula (I) or Formula (II) may undergo a hydrolysis cascade and release the GLP-1 polypeptide or analog thereof as described in Scheme 6.
Scheme 6
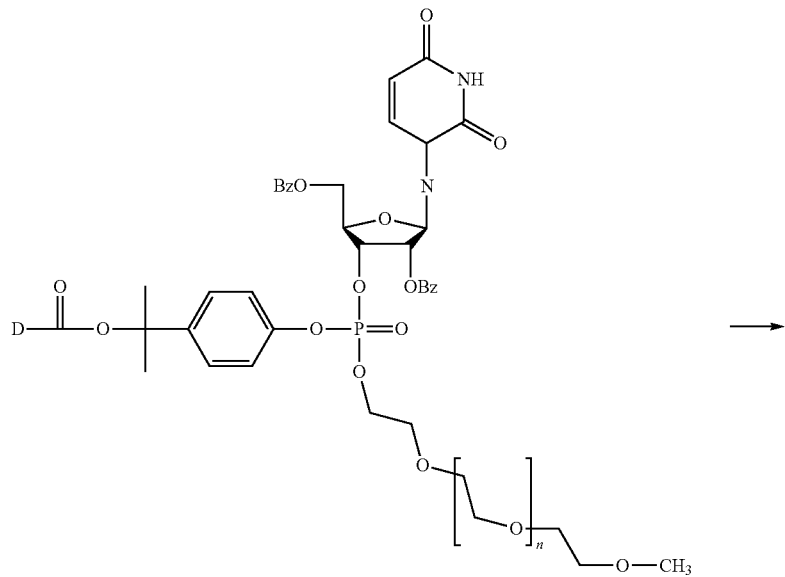

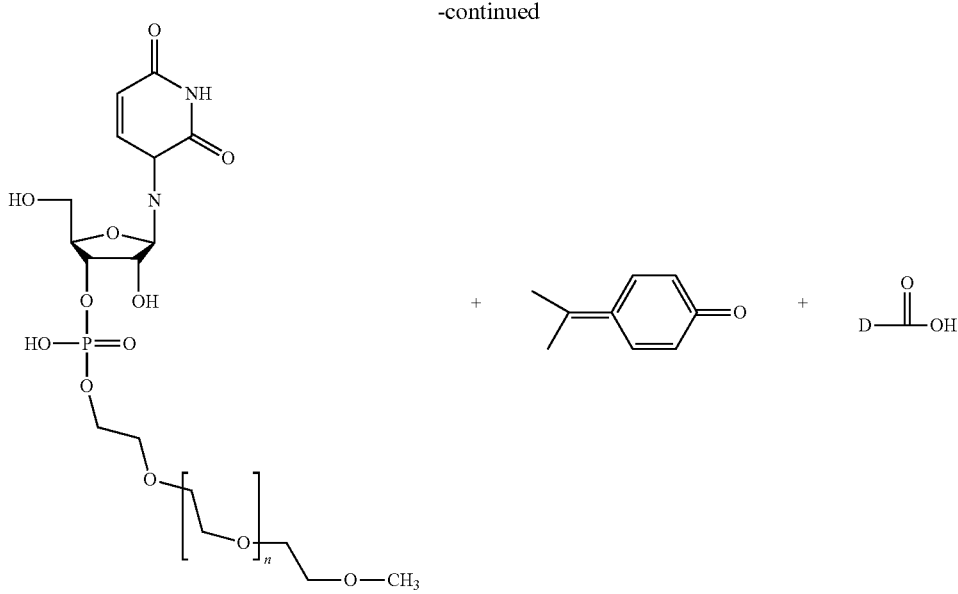

1) This represents the case when $Z^1$ and $Z^2$ oxygens and $Z^3$ is absent.
2) The functional group that is present on D is a carboxyl.
3) The secondary or tertiary ester thus formed is substanially more stable for hydrolysys than benzoyl - release kinetics is dependent on kinetics of Bz hydrolysis In some embodiments, when $M^A$ is Formula (I) or Formula (II) is a group of formula (i), the release cascade may occur according to the mechanism shown in Scheme 7:

Scheme 7

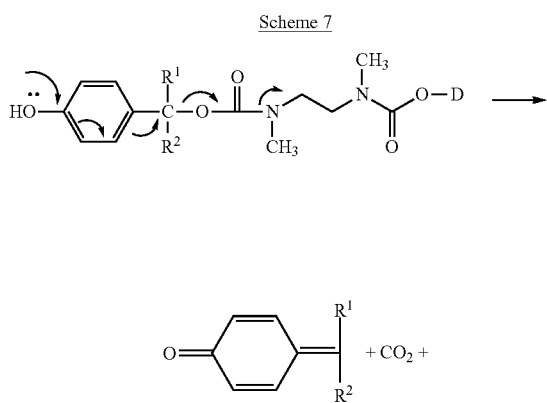

In some embodiments, when $M^A$ is Formula (I) is a stable diradical of formula (1), the release cascade may occur according to the mechanism shown in scheme 8:

Scheme 8

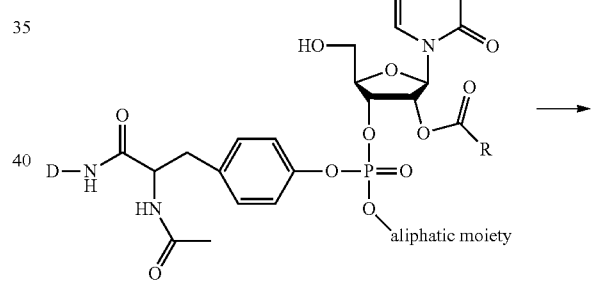

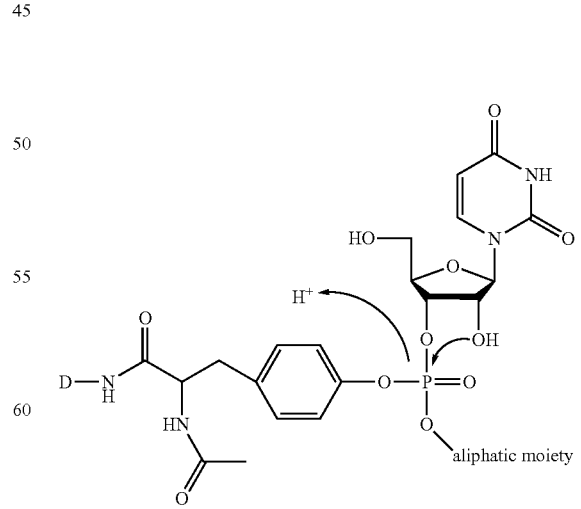

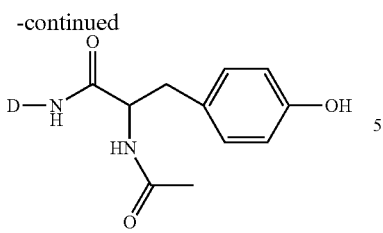

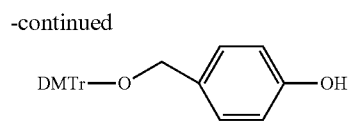

Exemplary Methods for Studies of Cleavage Reaction Ratios

Exemplary methods to study the extent of release of a biologically active drug from conjugates containing cleavable acyl groups are shown in the following schemes. In some embodiments of any of the compounds depicted in the schemes, U is an optionally substituted uracil.

Referring to scheme 9, the cleavage of the phosphotriester is followed by reverse phase (RP) HPLC separation and quantification of the liberated DMTr-hydroxybenzyl alcohol.

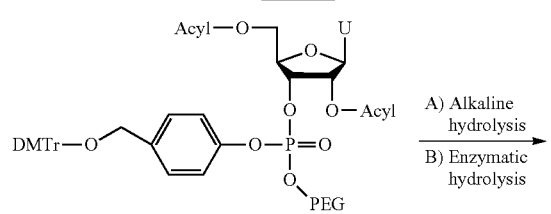

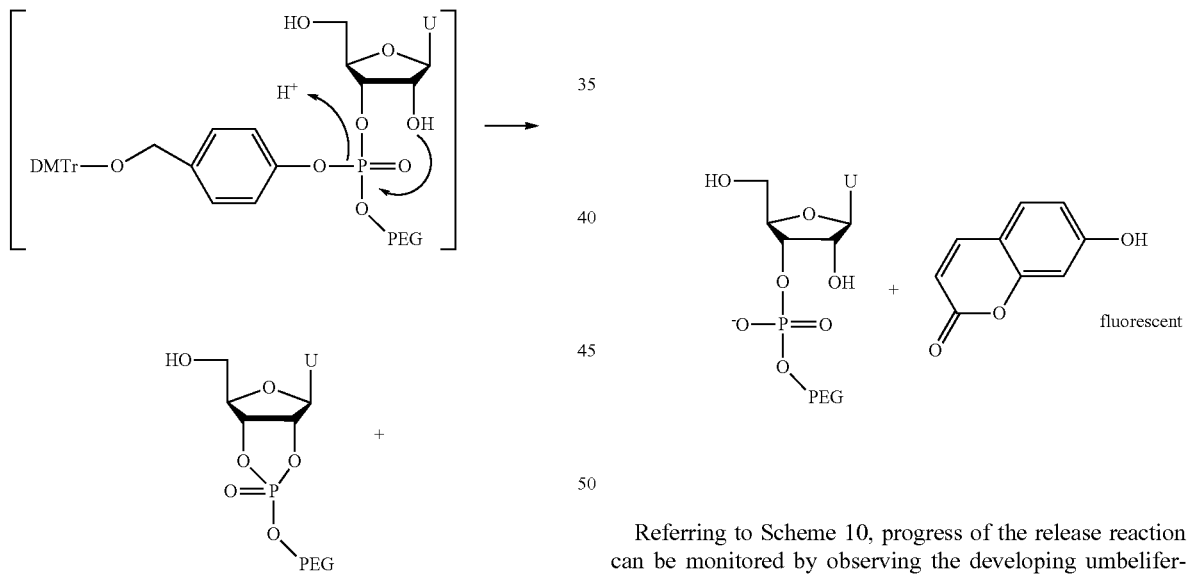

Referring to Scheme 10, progress of the release reaction can be monitored by observing the developing umbeliferrone fluorescence.

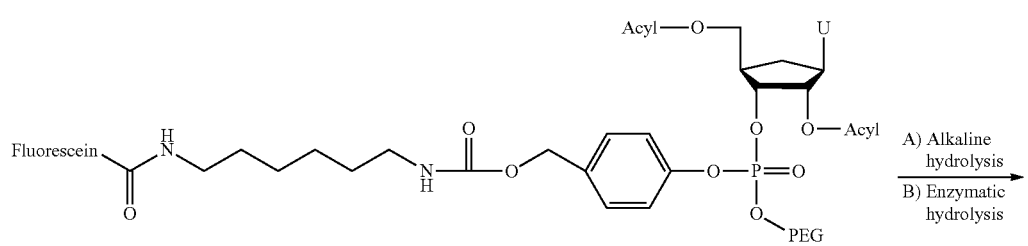

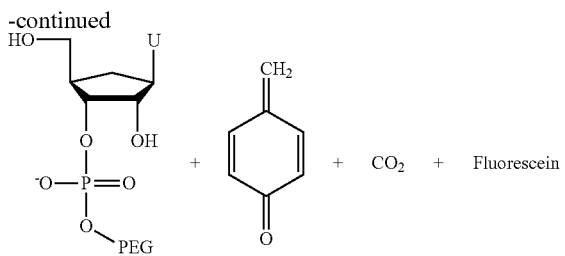

Referring to Scheme 11, disappearance of fluorescence from high MW starting material and formation of fluorescent low MW product may be monitored using Gel Permeation chromatography with fluorescence detection.

Methods of Making

Compounds of Formula (I) or Formula (II)

The compounds provided herein can be prepared using methods similar to those described in PCT/IB2018/051579 (WO 2018/163131), which is hereby incorporated by reference in its entirety herein.

Exemplary synthetic methods for preparing compounds of Formula (I) or Formula (II) of the present disclosure are described below.

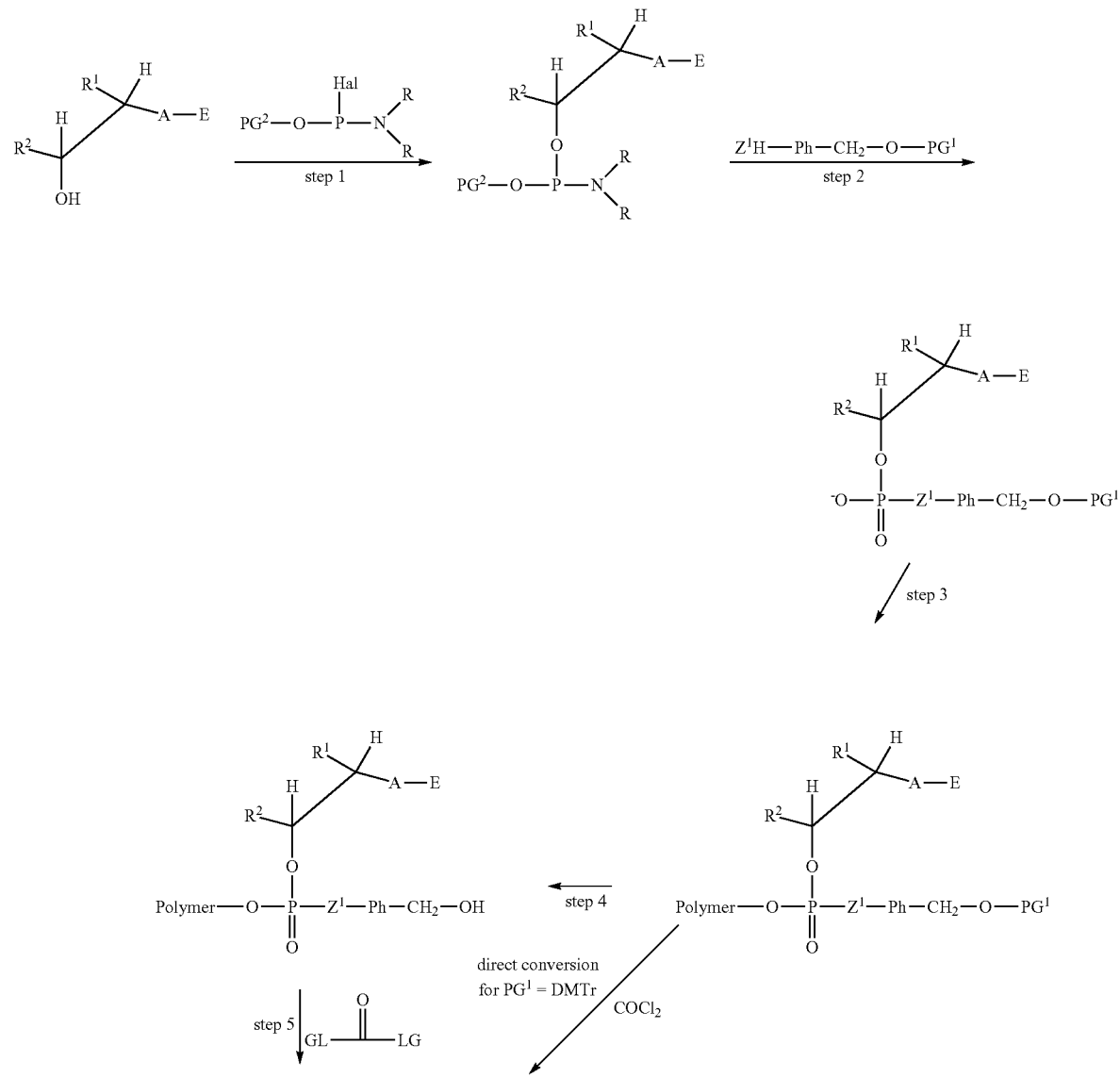

-continued

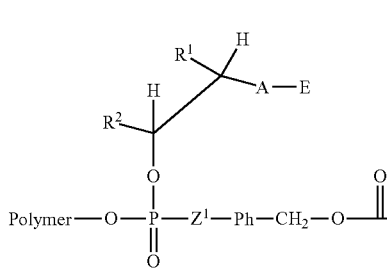
→ step 6
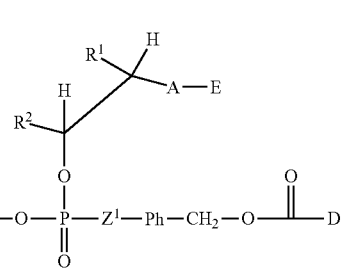

In some embodiments, the present application provides a method of making a compound of Formula (II):

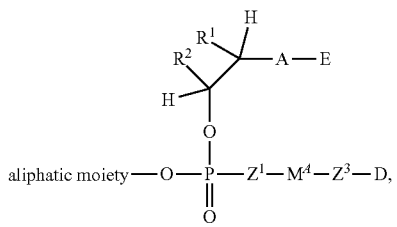
(II)

or a pharmaceutically acceptable salt thereof, comprising reacting a compound of Formula (II-IV):

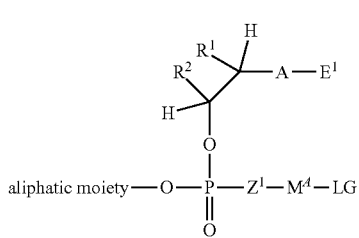
(II-IV)

with a biologically active drug of formula $HZ^3$-D, wherein $R^1$, $R^2$, $Z^1$, $Z^3$, D, $M^4$, A, E, $E^1$, LG, and aliphatic moiety are as described herein.

In some embodiments, the reaction is carried out in an aqueous solvent.

In some embodiments, the reaction is carried out in a 0.1 to 0.5 M phosphate buffer, HEPES (4-(2-hydroxyethyl)-1-piperazineethanesulfonic acid) or carbonate buffer. In some embodiments, the reaction is carried out at pH from about 7.2 to about 8.5, at about 0° C. to about room temperature, from about 30 min to about 12 h. In some embodiments, the reaction is carried out at ambient temperature.

In some embodiments, the compound of Formula (II-IV) is prepared by a method comprising:
i) deprotecting a compound of Formula (II-Va):

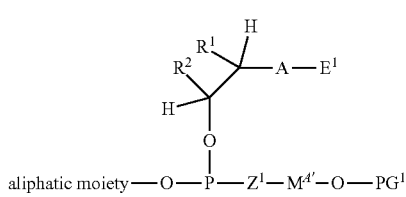
(II-Va)

to obtain a compound of Formula (II-Vb):

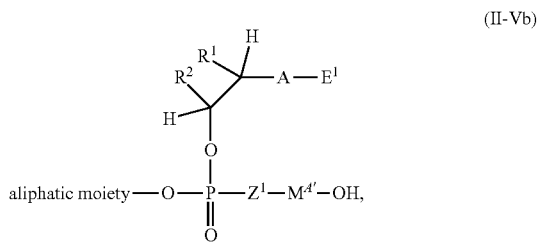
(II-Vb)

and
ii) reacting the compound of Formula (II-Vb) with a compound comprising a leaving group to prepare a compound of Formula (II-IV).

In some embodiments, the deprotecting comprises treating the compound of Formula (II-Va) with an acid.

In some embodiments, the compound comprising a leaving group is an activated carbonate. For example, the activated carbonate has the Formula (Vc) or Formula (Vd) as described herein:

(Vc)

(Vd)

In some embodiments, the compound of Formula (II-Va) is prepared by a method comprising reacting a compound of Formula (II-VIa):

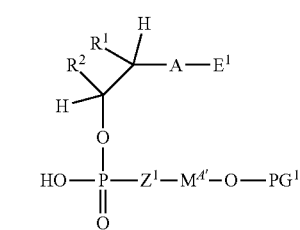
(II-VIa)

with an aliphatic moiety (e.g., polymer) comprising a reactive hydroxyl group.

In some embodiments, the reaction is carried out in the presence of an activating reagent (e.g., a reagent that reacts stoichiometrically with phosphate forming a mixed anhydride, which, in turn, is converted to, e.g., a methylimidazolide, that finally reacts with the OH group of the polymer). In some embodiments, the activating reagent is mesitylene sulfonyl chloride, mesitylene sulfonyl nitro triazole (MSNT) or tosyl chloride.

In some embodiments, the compound of Formula (II-VIa) is prepared by deprotecting the compound of Formula (II-VIb):

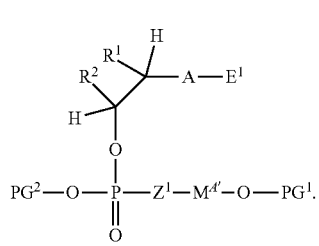
(II-VIb)

In some embodiments, the deprotection is carried out such that the phosphate protecting group $PG^1$ is removed selectively to yield the compound of Formula (II-VIa).

In some embodiments, the deprotection is carried out in the presence of a base. In some embodiments, the base is diisopropylethylamine, or 1,8-diazabicyclo[5.4.0]undec-7-ene (DBU) or triethylamine.

In some embodiments, wherein the compound of Formula (II-VIb) is prepared by a method comprising reacting a compound of Formula (II-VIIa):

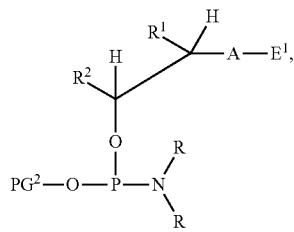
(II-VIIa)

with a compound of Formula (II-VIIb):

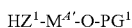
HZ$^1$-M$^{4'}$-O-PG$^1$ (VIIb), wherein each R is independently a $C_1$-$C_6$-alkyl, or the two R-groups jointly form a 5- or 6-membered ring with the N to which they are bonded. In some embodiments, each R is isopropyl. In some embodiments, the two R-groups together form a morpholine ring.

In some embodiments, the reaction is carried out in the presence of an activating reagent. For example, the activating reagent is selected from the group consisting of: tetrazole, 2-ethylthiotetrazole, 2-bezylthiotetrazole, 4,5-dicyanoimidazole, activator 42, pyridinium hydrochloride, and pyridinium trifluoroacetate.

In some embodiments, step 2 of this reaction is carried out in the presence of an oxidizing reagent. For example, the oxidizing reagent oxidizes the phosphorus atom from oxidation state $P^{+3}$ to oxidation state $P^{+5}$. Examples of oxidizing agents include iodine, hydrogen peroxide, t-butyl hydrogen peroxide, or acetone peroxide.

In some embodiments, the compound of Formula (II-VIIa) is prepared by a method comprising reacting a compound of Formula (II-VIIIa):

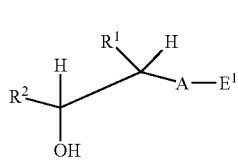
(II-VIIIa)

with a compound of Formula (VIIIb):

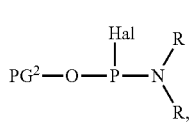
(II-VIIIb)

wherein Hal is a halogen atom (e.g., Cl, Br or I) and R is as described herein. In some embodiments, Hal is Cl.

In some embodiments, the reaction is carried out in the presence of a base.

In some embodiments, the compound of Formula (II) when $Z^3$ is absent may be prepared from the compound of formula (II-Vb), for example, according to Scheme 13:

Scheme 13

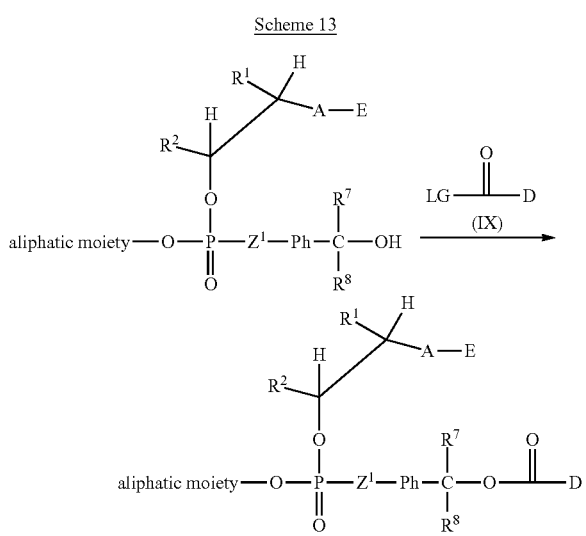

In some embodiments, the compounds of Formula (II) may be prepared as described in Scheme 14:

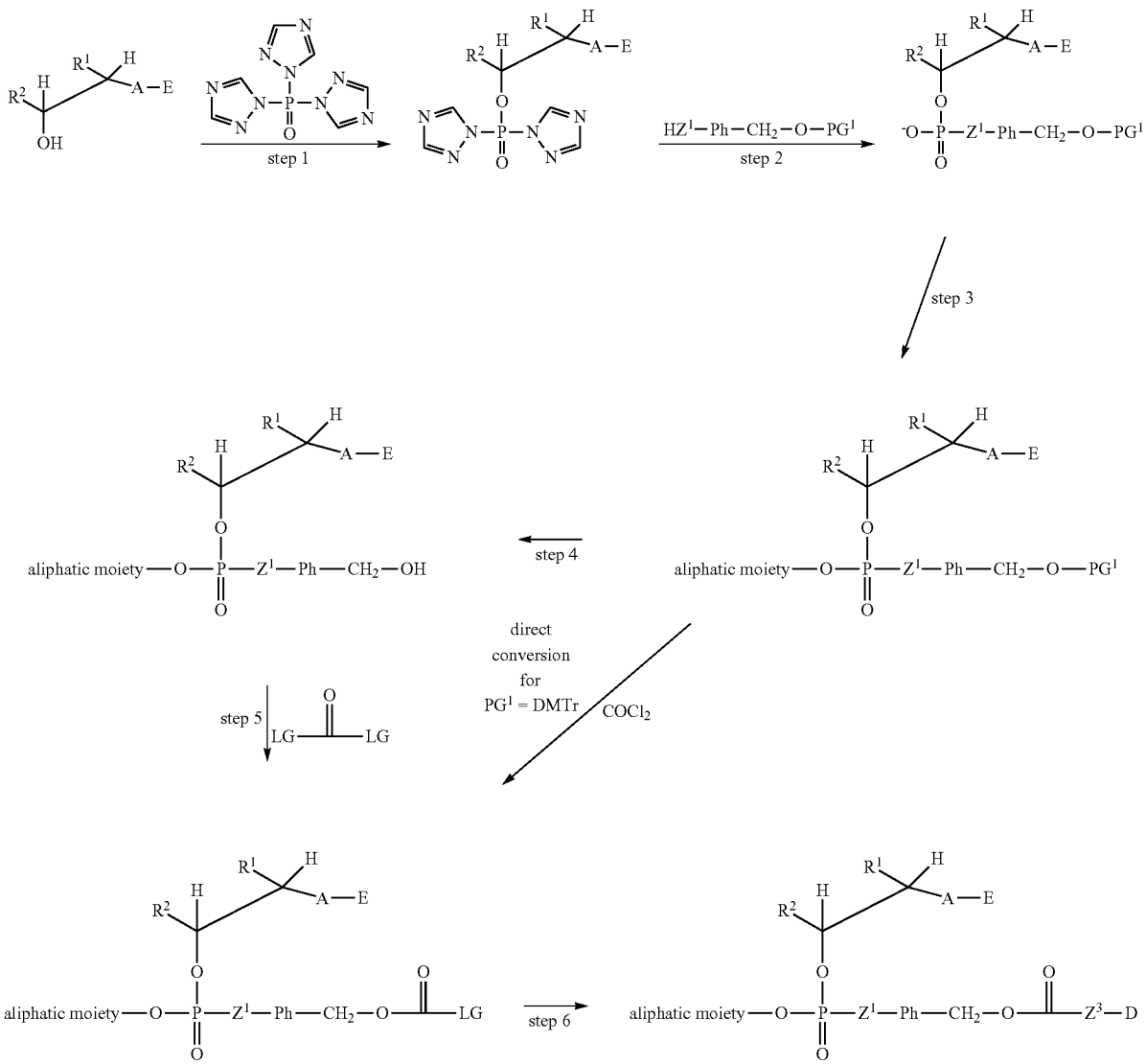
Scheme 14
In some embodiments, the compounds of Formula (II) may be prepared as described in Scheme 15:
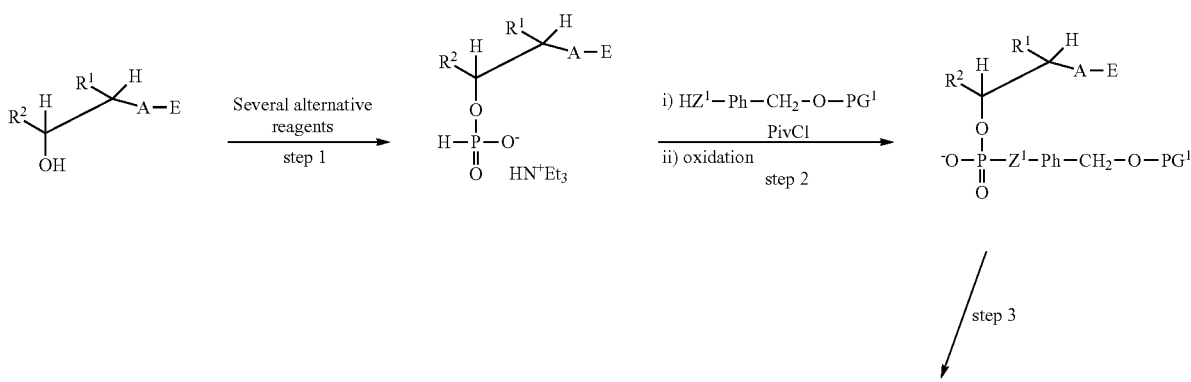
Scheme 15

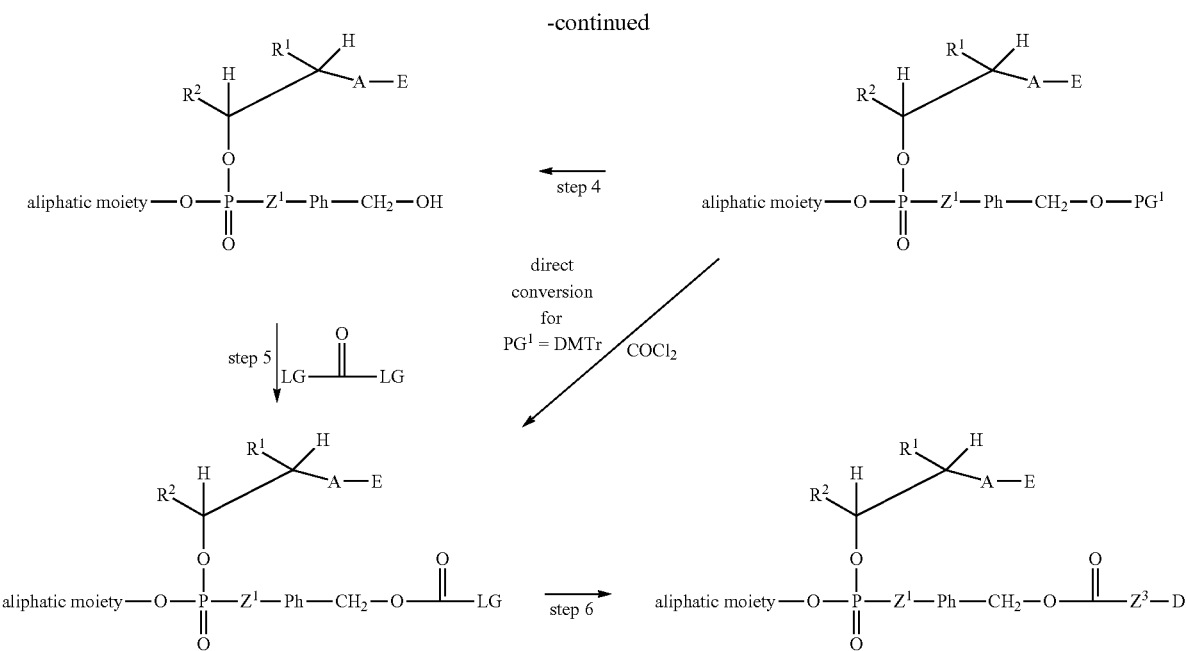
In some embodiments, the compounds of Formula (II) may be prepared as described in Scheme 16:
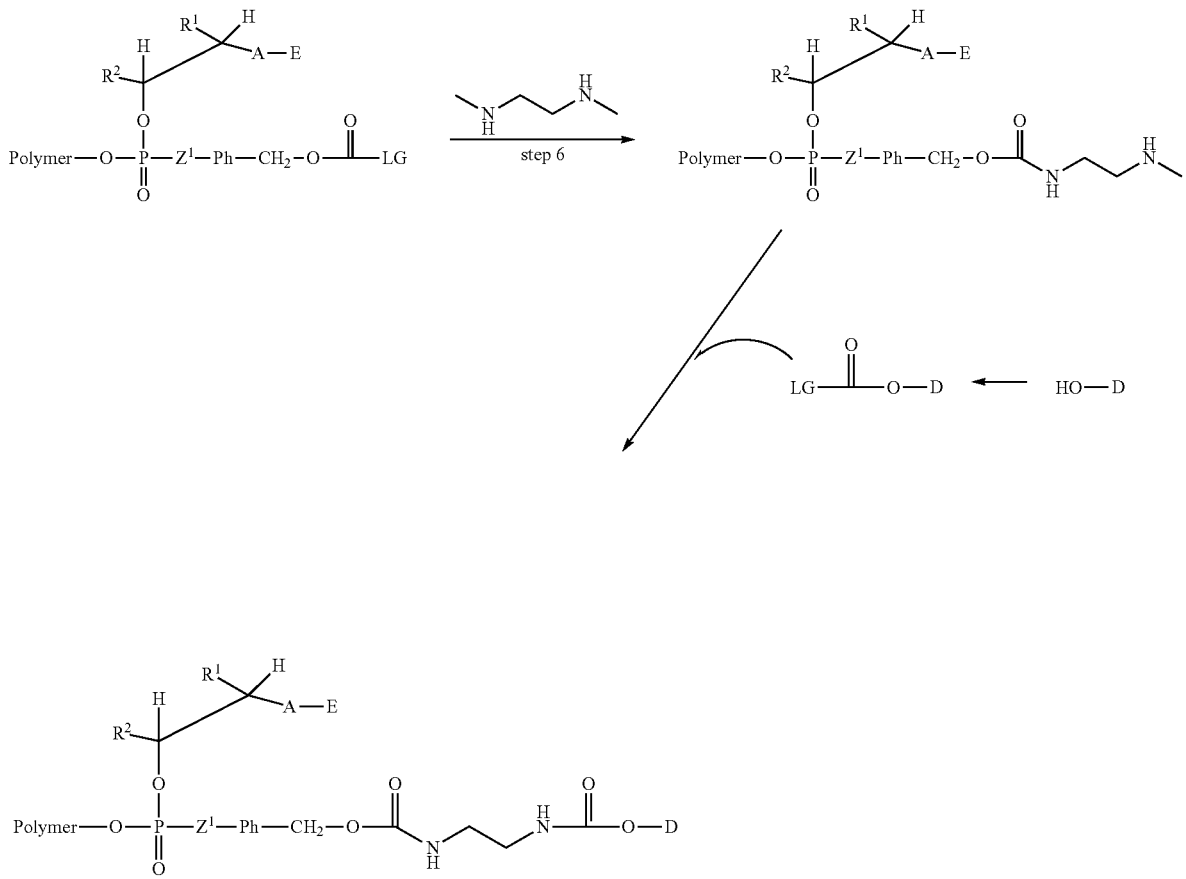

In some embodiments, when $M^4$ is a stable diradical of formula (k-1), the compounds of Formula (II) may be prepared as described in Scheme 17:

wherein LG is a leaving group as described herein, with a GLP-1 polypeptide or an analog thereof of formula $HZ^3$-D as described herein.

Scheme 17

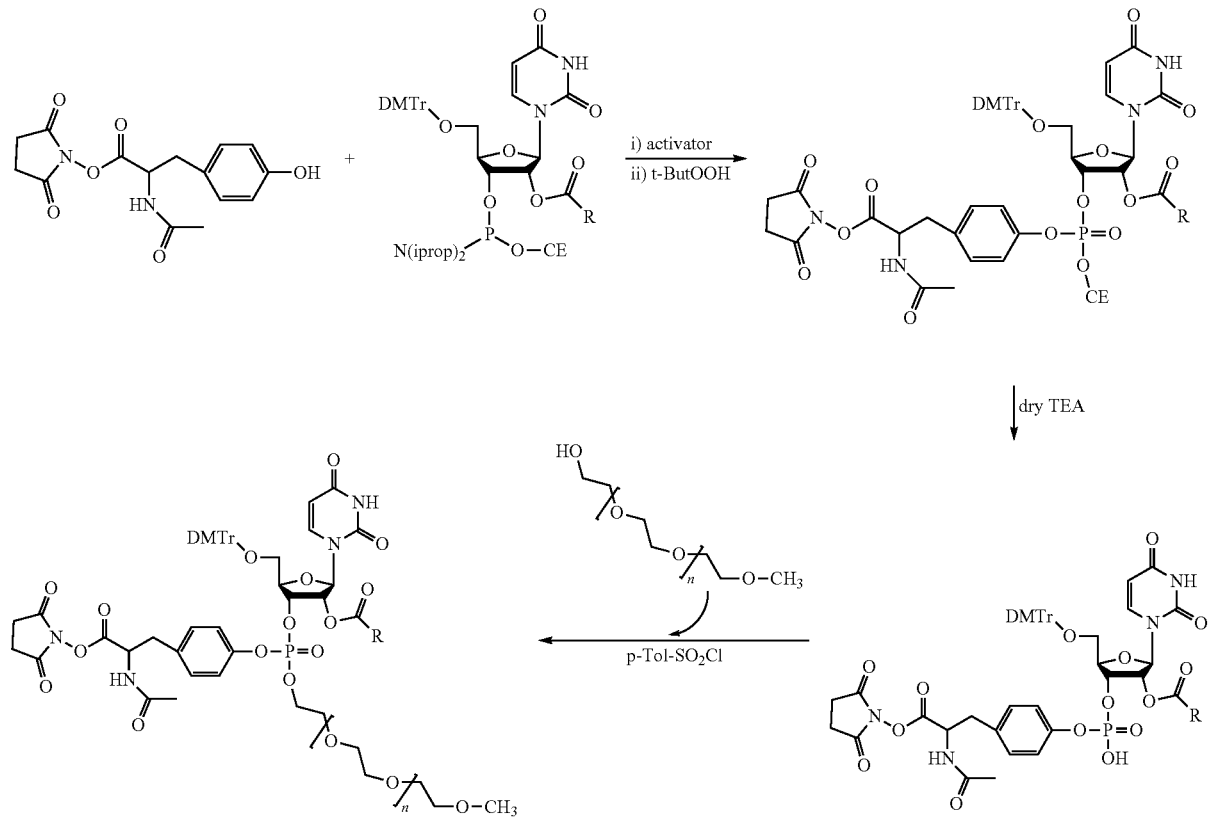

In some embodiments, this document provides a method of making a compound of Formula (I) or (II) having the formula:

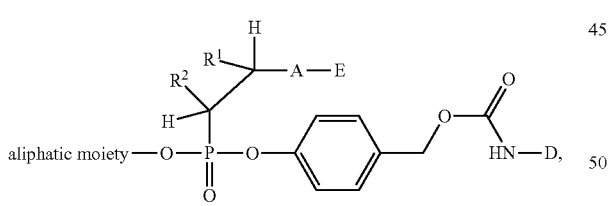

or a pharmaceutically acceptable salt thereof, wherein the aliphatic moiety, $R^1$, $R^2$, A, E, and D are as described herein, the method comprising:
reacting a compound of formula:

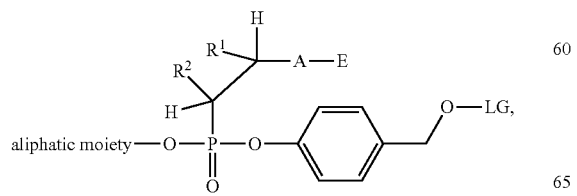

In some embodiments, the compound of formula:

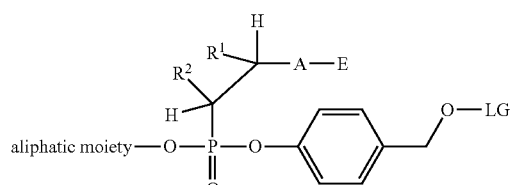

is obtained by a method comprising:
(i) deprotecting a compound of formula:

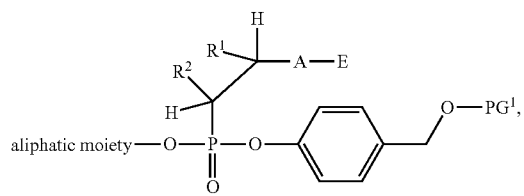

wherein PG¹ is a protecting group as described herein, to obtain a compound of formula:

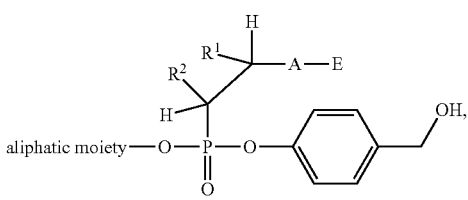

and
(ii) reacting the compound obtained in step (i) with a compound comprising a leaving group as described herein.

In some embodiments, the compound of formula:

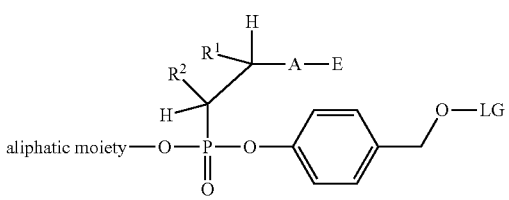

is obtained by a method comprising:
(i) reducing a compound of formula:

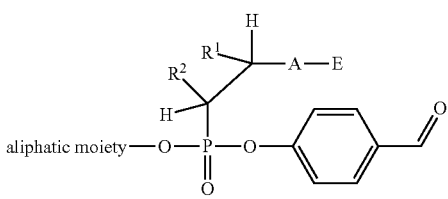

to obtain a compound of formula:

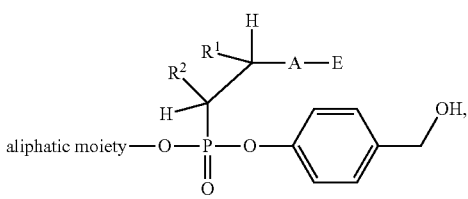

and
(ii) reacting the compound obtained in step (i) with a compound comprising a leaving group as described herein. Suitable examples of reagents to carry out the reducing of step (i) include, without limitation, NaBH₄ and LiAlH₄.

Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010); Katritzky et al. (Ed.); *Comprehensive Organic Functional Group Transformations II* (Elsevier, 2nd Edition, 2004); Smith et al., *March's Advanced Organic Chemistry: Reactions, Mechanisms, and Structure*, 6th Ed. (Wiley, 2007); Trost et al. (Ed.), *Comprehensive Organic Synthesis* (Pergamon Press, 1991).

Preparation of the compounds provided herein can involve the protection and deprotection of various chemical groups. The chemistry of protecting groups can be found, for example, in P. G. M. Wuts and T. W. Greene, *Protective Groups in Organic Synthesis*, 4th Ed., Wiley & Sons, Inc., New York (2006). The chemistry and protecting group strategy related to the nucleosides and nucleotides can be found in *Methods in Molecular Biology—Oligonucleotide Synthesis*, edited by Piet Herdewijn, Humana Press Inc. 2005 and also in *Protocols for oligonucleotide conjugate*, edited by Sudhir Agrawal, Humana Press Inc. 1994. Suitable starting materials and intermediates are readily available from various commercial sources.

Methods of Using the Compounds of the Present Disclosure
Methods of Treating a Disease or Condition In some embodiments, the disclosure provides a method for treating a disease, disorder or condition in a mammal (e.g., a human in need of such treatment), comprising the step of administering to the mammal a compound of Formula (I) or Formula (II) disclosed herein, or a pharmaceutically acceptable salt thereof, or a pharmaceutical composition comprising same.

For example, the compounds of the disclosure are useful in the treatment of a disease or condition beneficially treated by administration of a GLP-1 polypeptide or analogs thereof as described herein to a subject.

In some embodiments, the compounds of the disclosure are useful in decreasing food intake by the subject, for example by controlling or suppressing the subject's appetite.

In some embodiments, the disease or condition is obesity.

In some embodiments, the disease or condition is diabetes, which includes type 1, type 2, gestational, surgically induced, and chemically induced diabetes, and latent autoimmune diabetes in adults (LADA or type 1.5 diabetes).

Combination Therapies

One or more additional pharmaceutical agents or treatment methods can be used in combination with any one of the conjugates described herein for treatment of the diseases, disorders or conditions described herein. The pharmaceutical agents can be combined with the present compounds in a single dosage form, or the agents can be administered simultaneously or sequentially as separate dosage forms.

Suitable additional pharmaceutical agents contemplated for use in combination with the compounds of the present disclosure can comprise any one of the GLP-1 polypeptides or analogs thereof described herein.

Non-limiting examples of additional agents include insulin (e.g., rapid-acting insulin (taking effect within a few minutes and lasting 2-4 hours); regular or short-acting insulin (taking effect within 30 minutes and lasting 3-6 hours); intermediate-acting insulin (taking effect in 1-2 hours and lasting up to 18 hours); long-acting insulin (taking effect in 1-2 hours and lasting beyond 24 hours); ultra-long-acting insulin (taking effect in 1-2 hours and lasting 42 hours)); AFREZZA® (inhaled insulin); TRESIBA® (insulin degludec); RYZODEG® 70/30 (insulin degludec and insulin aspart injection); LEVEMIR® (insulin detemir); LANTUS® (insulin glargine); BYETTA® (exenatide, exenden-4); VICTOZA® (liraglutide); SAXENDA® (liraglutide); ALBIGLUTIDE® (tanzum, eperzan); TRULICITY® (duraglutide); OZEMPIC® (semaglutide); drugs that increase insulin production by the pancreas, including chlorpropamide (DIABINESE®), glimepiride, (AMARYL®), glipizide (GLUCOTROL®), glyburide (DIABETA®, GLYNASE®), nateglinide (STARLIX®), and repaglinide (PRANDIN®); drugs that decrease sugar absorption by the intestines, such as acarbose (PRECOSE®) and miglitol (GLYSET®); drugs that improve how the body uses insulin, such as pioglitazone (ACTOS®) and rosiglitazone (AVANDIA®); drugs that decrease sugar production by the liver and improve insulin resistance, like metformin (GLUCOPHAGE®); drugs that increase insulin production by the pancreas or its blood levels and/or reduce sugar production from the liver, including alogliptin (NESINA®), dulaglutide (TRULICITY®), linagliptin (TRADJENTA®), exenatide (BYETTA®, BYDUREON®), liraglutide (VICTOZA®), lixisenatide (ADLYXIN®), saxagliptin (ONGLYZA®), sitagliptin (JANUVIA®), and semaglutide (OZEMPIC®); drugs that block the reabsorption of glucose by the kidney and increase glucose excretions in urine, called sodium-glucose co-transporter 2 (SGLT2) inhibitors including canaglifozin (INVOKANA®), dapagliflozin (FARXIGA®), and empagliflozin (JARDIANCE®); pramlinitide (SYMLIN®); empagliflozin/linagliptin (GLYXAMBI®); orlistat (XENICAL®); lorcaserin (BELVIQ®); phentermine-topiramate (QSYMIA®); naltrexone-bupropion (CONTRAVE®)phentermine; benzphetamine; diethylpropion; and phendimetrazine.

In some embodiments, the methods provided herein may include more than one compound provided herein in combination. For example, the two compounds may have different release profiles (e.g., a longer T1/2 and a shorter T1/2).

Methods for the safe and effective administration of most of these pharmaceutical agents are known to those skilled in the art. In addition, their administration is described in the standard literature. For example, the administration of many of the pharmaceutical agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Compositions and Formulations

The present application also provides pharmaceutical compositions comprising an effective amount of a compound of any one of Formula (I) or Formula (II) disclosed herein, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain a compound of Formula (I) or Formula (II) described herein in the range of 0.005% to 100% with the balance made up from the suitable pharmaceutically acceptable excipients. The contemplated compositions may contain 0.001%400% of a compound of Formula (I) or Formula (II) provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compounds of Formula (I) or Formula (II) disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol*, 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of a compound of Formula (I) or Formula (II) disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a composition comprising a compound of the present application, such that said compound is released from said device and is therapeutically active.

Dosages and Regimens

In the pharmaceutical compositions of the present application, a compound of Formula (I) or Formula (II) disclosed herein is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of a compound of Formula (I) or Formula (II) disclosed herein can range, for example, from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weeks, once every two weeks, once a month).

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit.

EXAMPLES

Unless noted otherwise, all reagents were obtained from known commercial suppliers. Unless noted otherwise, standard laboratory and analytical procedures were employed.

Example 1—Synthesis of FMOC-Based Liraglutide Conjugate

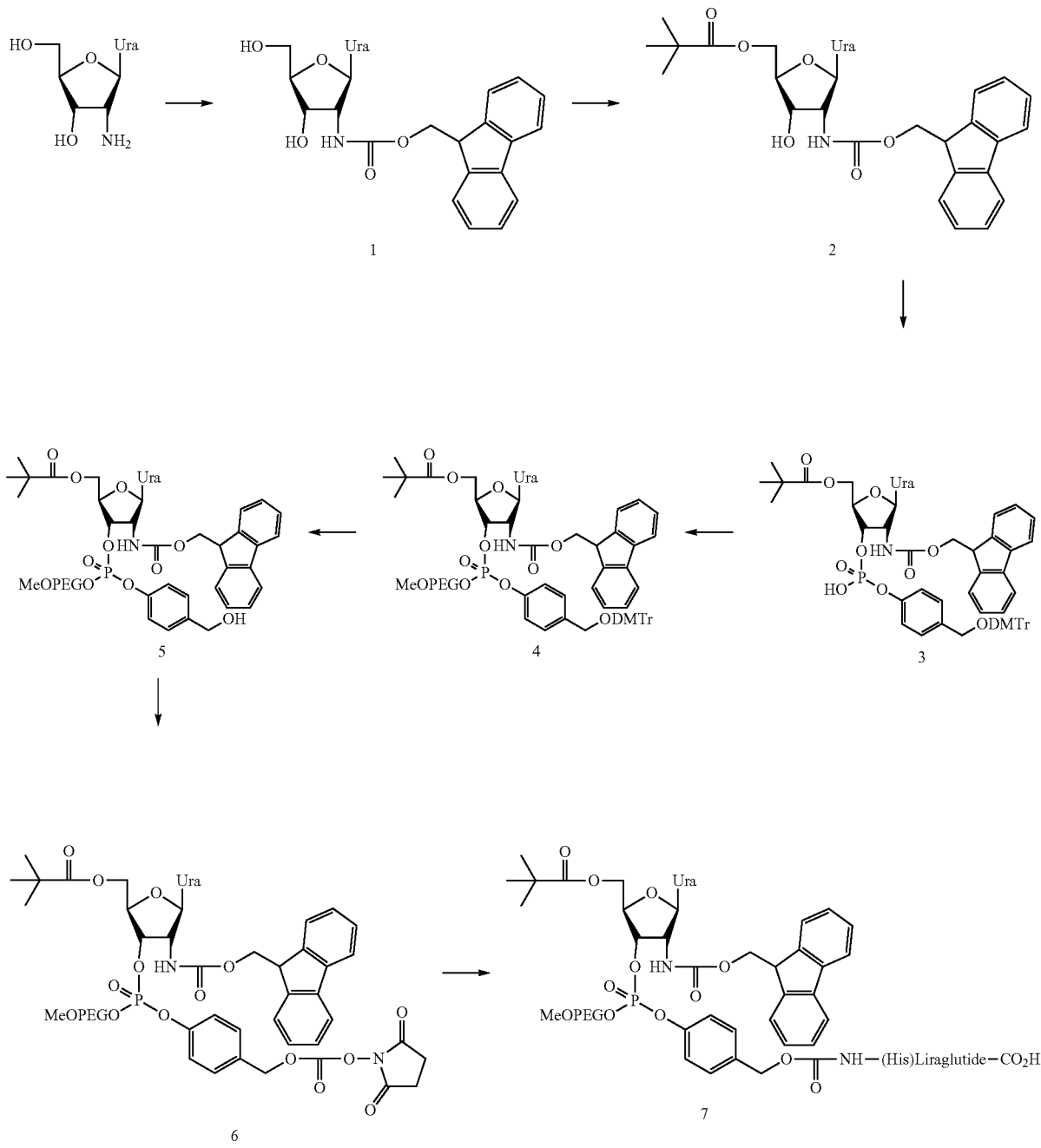

Step 1. Method for Reaction of FMOC-Cl with Aminouridine to give Carbamate 1

2'-aminouridine (1 mol eq.) was dissolved in water (10 ml/mmol) and a mixture of 1 M aqueous NaHCO$_3$ (3 mol eq.) with about 20% dioxane was added and the mixture cooled to 0° C. Fluorenylmethyl chloroformate (2 mol eq.) was dissolved in dry dioxane and added dropwise to the cooled solution. The solubility of the reaction mixture was adjusted by addition of dioxane. After stirring for 1 hour, chloroformate (1 mol eq.) was added and the mixture stirred for an additional hour. Cooling was removed and the aqueous reaction mixture was extracted thrice with 10% MeOH/DCM. The organic phase was evaporated to dryness. The residue was chromatographed through silica gel 60A using MeOH-DCM gradient (2-4-6%) to isolate the 2'-N-(Fluorenylmethylcarbamoyl)uridine (2'-N-(FMOC)uridine) as a white solid (yield 65-75%).

Step 2. The Method for 5'-O-pivaloylation of Uridine 2'-N-carbamate 1 to give the 5'-O-pivaloyluridine-2'-N-carbamate 2

Compound 1 (1 mol eq.) was dried by co-evaporation with dry pyridine and the residue dissolved in dry pyridine (2.5 mL/mmol) and cooled to 0° C. Pivaloyl chloride (1.2 mol eq.) was dissolved in dichloromethane (2.5 mL/mmol) and added slowly to the pyridine solution. After full addition, the mixture was stirred at RT for 15 hours (overnight). The reaction was quenched with MeOH, and after a few minutes, the mixture partitioned between 0.2 M phosphate pH 7.0 and dichloromethane. The oily residue was chromatographed evaporation of the organic phase and co-evaporation with toluene through silica gel 60A using a gradient of DCM/MeOH (0-2-3-4% MeOH/DCM, the product comes at 3-4% MeOH) to obtain product 2 in the form of a white foam (yield 70-80%).

Step 3. Method for Preparation of Phosphodiester Compound 3

Preparation of 4-(4, 4'-dimethoxytrityloxymethyl)phenol

A method similar to that published in Iyer, R. P. et al. *Tetrahedron Letters*, 2001, 42, 3669-3672, was used to produce compound 3. Briefly, 4-hydroxybenzyl alcohol (1 mol eq.) was dissolved in dry pyridine (10 mL/mol). 4,4'-dimethoxytrityl chloride (1.1 mol eq.) was dissolved in dry DCM (ca. 5 mL/mmol) and this solution was added dropwise from a dropping funnel to the pyridine solution with stirring. After full addition, the reaction solution was stirred at RT for at least 16 hours.

Work up and purification: the reaction was quenced by adding MeOH, and after stirring for a short while, the solvents were evaporated. The residue was dissolved in DCM and the organic phase extracted with saturated aqueous NaHCO$_3$. The aqueous phase was extracted two more times with DCM. The combined DCM phases were evaporated to dryness and the residue co-evaporated with toluene. The residue was chromatographed through silica gel 60A using a gradient of ethylacetate (EtAc)/petroleum ether (PetEt) (20-30-50% EtAc/PetEt+0.1% pyridine, the eluted at 30-50% EtAc) to obtain product phenol in high yield. $^1$H-NMR, 500 MHz (CDCl$_3$): 7.51-6.80 (m, 17H), 4.61 (br, s, 1H) OH, 4.07 (br s, 2H) CH$_2$, 3.78 (s, 6H) 2×OMe.

Triethylammonium Salt of Phosphodiester Compound 3.

A solution of (4-(4, 4'-dimethoxy trityloxy methyl)phenol (1.0 mol eq.) in dry MeCN (7 mL/mmol) plus dry pyridine (3.5 mL/mmol) was added slowly dropwise under nitrogen to a vigorously stirred 0.2 M solution of phosphorous tristriazolide (1.1 mol eq.) in dry MeCN. The resulting solution was stirred at RT for about 1-1½ hour under nitrogen.

A solution of compound 2 (0.95 mol eq.) in dry MeCN (9 mL/mmol) was added dropwise to the mixture and the new resulting mixture stirred at RT for ca. 2 hours. The reaction was quenched with 1 M triethylammonium hydrogen carbonate (~8 mL/mmol scale) and the mixture concentrated on a rotary evaporator. The remaining concentrate was poured into 1 M triethyl ammonium hydrogen carbonate and extracted three times with DCM. The solution was evaporated. The residue was chromatographed through silica gel 60A using a gradient of DCM/EtOH (0-4-8-10-15-20% EtOH/DCM+0.1% pyridine, the product eluted at 8-15% EtOH) to give the O-aryl-O-alkylphosphodiester 3 as a triethyl ammonium salt (yield 50-65%).

Step 4. Method for Preparation of MeOPEG Phosphotriester Compound 4.

The phosphodiester 3 (1 mol eq.), mPEG-OH (3 mol eq.) and N-methylimidazole (24 mol eq.) were dissolved in dry MeCN and evaporated to dryness. The residue was co-evaporated with dry MeCN once more and concentrated down to less than 5 mL/mmol of MeCN (semi-viscous). The viscous solution was swirled while a concentrated MeCN solution (1.25 mL/mmol) of 1-mesitylene sulfonyl chloride (12 mol eq.) was added dropwise. After the addition, the solution was rotated in the round bottle (to make sure all the material on the inside of the flask wall participate in the reaction. One can also use a shaking device) at RT for 66-72 hours.

The reaction mixture was quenched with MeOH and the mixture evaporated to dryness on a rotary evaporator. The residue was recrystallized from isopropanol (ca. 13 mL/g PEG used. Keeping the mixture at 55° C. dissolved the solid material and the pegylated material crystallized when cooled to RT). The solid mass was recrystallized on a P3 or P4 glass sinter filter, washed with cold isopropanol and finally washed with diethylether and dried under vacuum.

The crude solid was analyzed by C$_{18}$ RP-HPLC to verify presence of the triester product 4. The main UV-Vis side product was the mesitylenesulfonylated mPEG which had a shorter R$_t$ than the product triester 4. We have reason to believe that all free hydroxyls of the mPEG were consumed either by phosphorylation or by sulfonylation. Depending on the size of the C$_{18}$ RP HPCL column available to the organic chemist, one can batch wise separate the triester 4 from the side products with following solvent mixtures and gradient:

Sample diluent: 20% MeCN in water
Buffer A: 5% MeCN in 0.1M triethylammonium acetate/water.
Buffer B: 100% MeCN
Gradient: 30-60% B over 60 minutes
Monitoring: 270 nm The collected fractions were pooled and evaporated to dryness and the residue kept under high vacuum for some hours. The gummy residue (yield 45-55%) was used in step 5.

Step 5. Method for Preparation of MeOPEG Phosphotriester Hydroxyl Block Compound 5

Dissolve the 4-(4, 4'-dimethoxytrityloxymethyl)phenyl-phosphotriester compound 4 (1 mol eq.) in 80% acetic acid (~350 mL/mmol) and the solution was kept at RT for 2 hours. The volatile matters were evaporated and the residue co-evaporated with toluene. The residue was recrystallized from isopropanol as described in Step 4 to give the O-alkyl-O-(mpegyl)-O-[(4-hydroxymethyl)phenyl]phospho-triester 5 and was used directly in the next step 6.

Step 6. Method for Preparation of MeOPEG Phosphotriester NHS Carbonate Compound 6

The above hydroxyl block (1 mol eq.) was dissolved in dry DCM (140 μL/μmol) and then 15 wt % of phosgene (190 mol eq.) was added and the solution stirred for 2-3 hours at RT. The volatile matters were evaporated and the residue was then co-evaporated several times with toluene.

The crude chloroformate (1 mol eq.) was dissolved in dry THF (6 mL/mmol) and dry DCM (1.2 mL/mmol). N-hydroxysuccinimide (75 mol eq.) was then added, followed by addition of dry pyridine (100 mol eq.) and the mixture stirred for 2 hours at RT. The mixture was evaporated to dryness and the residue co-evaporated with toluene (at least three times) and then the residue triturated with diethyl ether, the supernatant was decanted, and the solid was dried under vacuum. This provided the O-alkyl-O-mpegyl-O-[4-(NHS-cabonyloxy-methyl)phenyl]phosphotriester 6. C18 RP-HPLC analysis showed one broad and homogenous peak corresponding to product 6. Another single peak at the front of the chromatogram was excess of NHS.

Sample diluent: 20% MeCN in water
Buffer A: 5% MeCN in 0.1% TFA/water.
Buffer B: 0.1% TFA in MeCN
Gradient: 30-60% B over 60 minutes (for column size 250×10 mm)
Monitoring: 270 nm (if parallel channel, also 254 nm)

Step 7. Method for Preparation of Releasable MeOPEG-Liraglutide Conjugate 7 (mPEG-Liraglutide)

Liraglutide (1 mg, 0.27 μmol; SEQ ID NO:3) was dissolved in 0.3M HEPES buffer pH 7.4 (400 μL) and MeCN (20 μL) in a 2 mL plastic screw cap vial. Solid compound 6 (24 mg, 0.81 μmol) was then added and the solid dissolved by occasional sonication (1-2 s at a time, approximately 3-4 times) and the solution stirred for 2-2½ hours at RT.

Work up: the reaction mixture was diluted up to 1 mL with deionized water (or distilled) and quenched by acidifying with 80% AcOH (pH 3-4). If necessary, the solution was diltered through 0.45 μm disc filters before injection onto the HPLC column. Using the column (RP 250×10 mm) and gradient system as in Step 6, the conjugate was identified as a broad peak in the region of 50-55 minutes. Unreacted liraglutide eluted close to 60 minutes. All other ingredients eluted earlier than 45 minutes.

The product fractions were collected, pooled and evaporated. The glassy residue was then dissolved in a small volume of 20% MeCN/water and lyophilized (94 nmol, 35%).

In the following experiment, the T1/2 at pH 8 is calculated to be approx. 11 h, which translates to 44 h at pH 7.4 (factor 4×). ~1 mg conjugate was dissolved in a volume of 20% MeCN in water. An appropriate amount of azidothymidine (AZT) was added as an internal reference and the hydrolysis was started by addition of a volume of 0.3 M TRIS buffer solution at pH 8.0. The reaction mixture was then kept at 37° C. 30 μL aliquots were taken at each time point and acidified by addition of 20 μL 1 M AcOH before injection to HPLC.

Example 2—CPSEC-based Liraglutide Conjugate 8

Using methods similar to that described in Example 1, CPSEC-based liraglutide conjugate 8 was prepared.

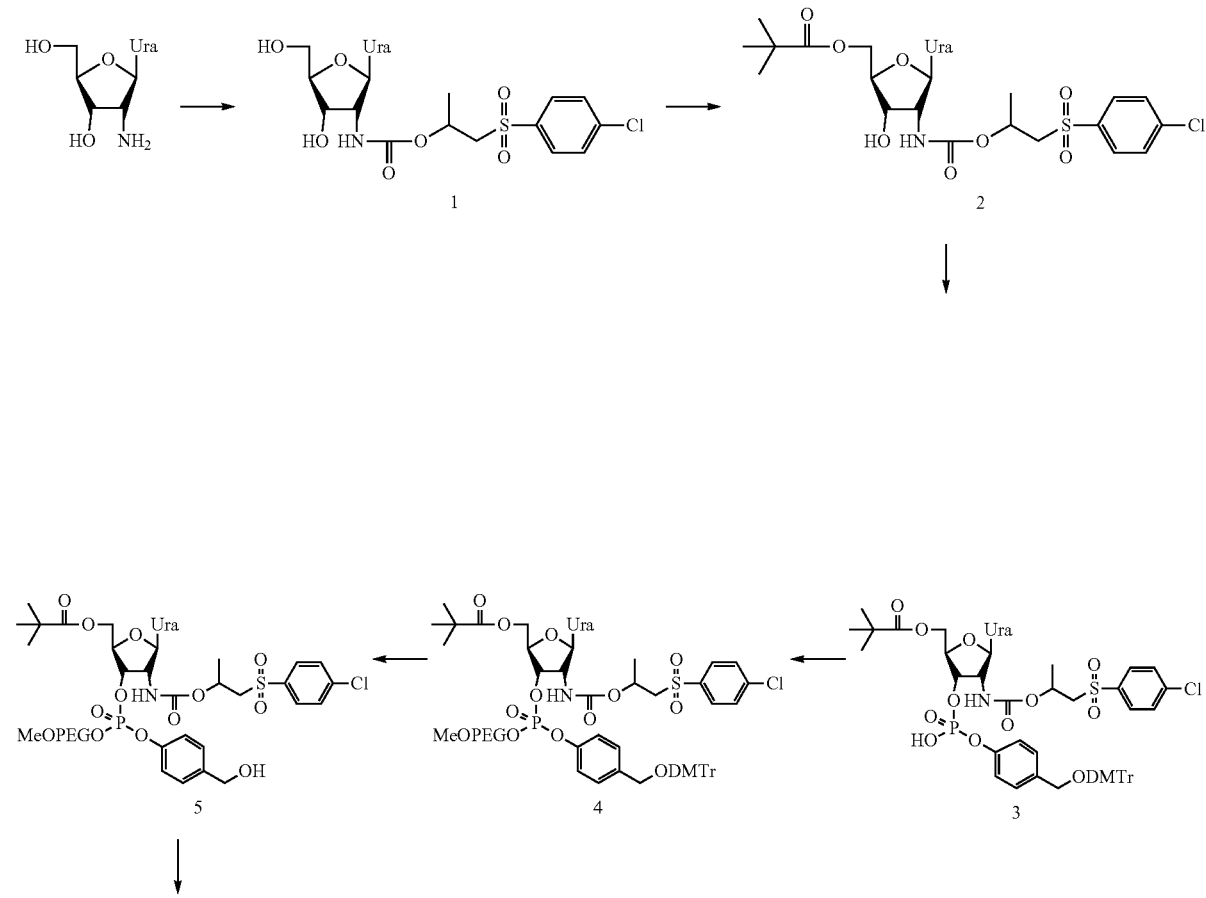

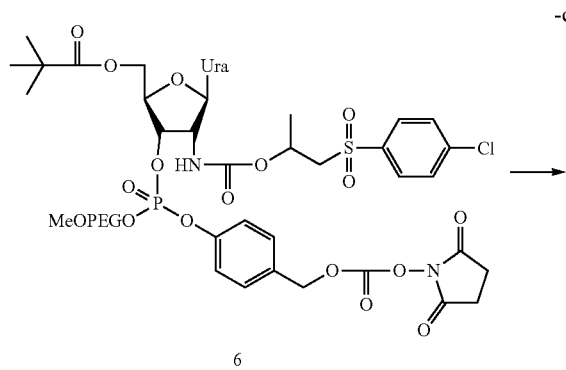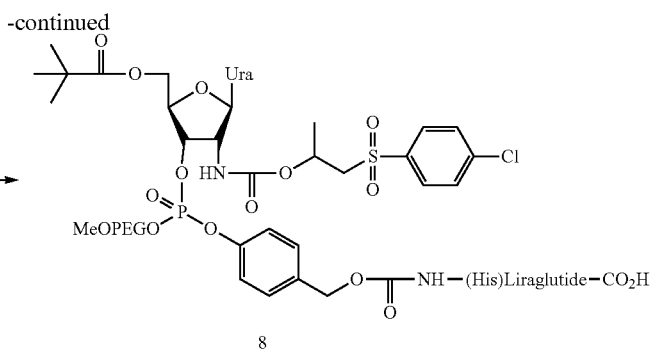
In Tris buffer at pH 8, 37° C., compound 8 has a pH triggered T1/2 of ~2.5 h (measured as in the method described in Example 1).
Example 3—FMOC Derivative (1-fluorenylethoxycarbonyl)-based Liraglutide Conjugate 9
Using methods similar to that described in Example 1, FMOC derivative (1-fluorenylethoxycarbonyl)-based liraglutide conjugate 9 was prepared.
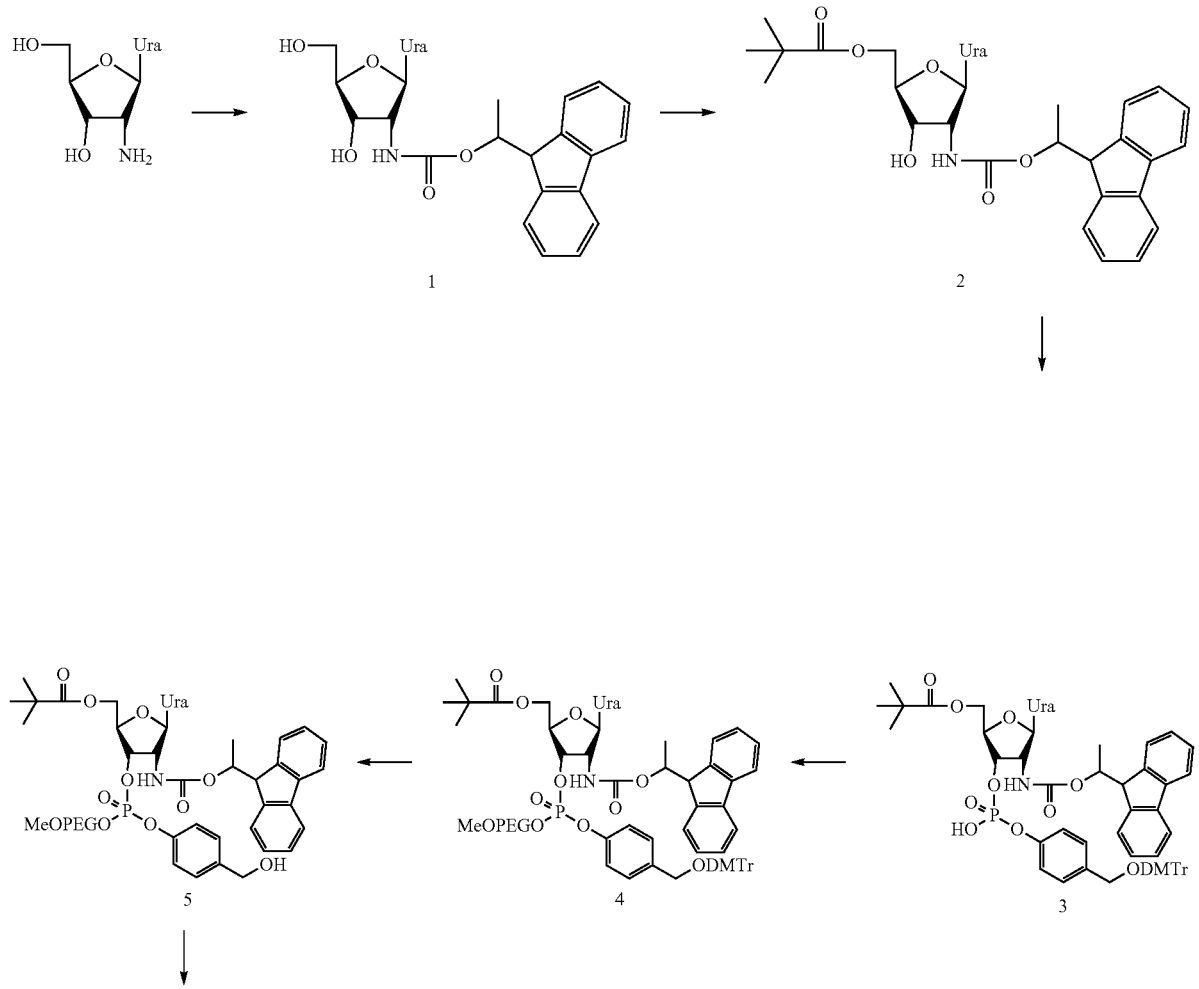

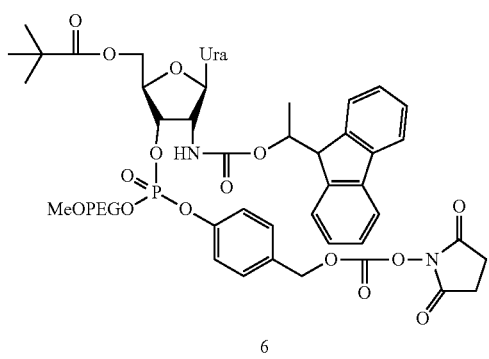

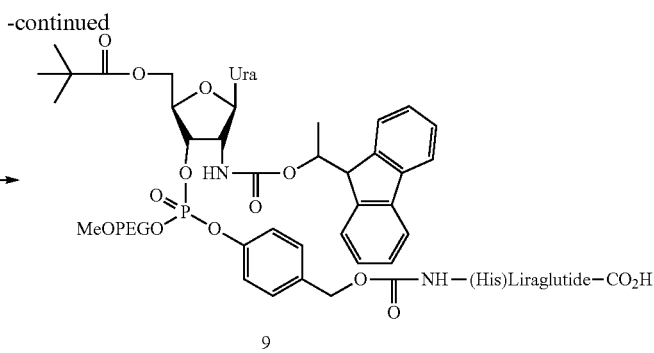

6 → 9

In Tris buffer at pH 7.4, 37° C., compound 9 is estimated to have a pH triggered T1/2 of ~36 days. This estimate is based on the hydrolysis (process outlined in Examiner 1) of compound 1 (FEC group). This resulted in a T1/2 at pH 8, which turned out to be close to 1 month (27 days). Multiplying by a factor of four (factor 4×) gives 4 months (2560 h) at pH 7.4. In previous experiments, it has been observed that there is an approximate factor 3× between T1/2 of aminouridine compounds like 1 and the T1/2 of the final conjugate (this is perhaps due to the influence of the phosphotriester group), so 2560 h/3=854 h (36 days).

Example 4—DPEC-based Liraglutide Conjugate 10

Using methods similar to that described in Example 1, DPEC-based liraglutide conjugate 10 was prepared.

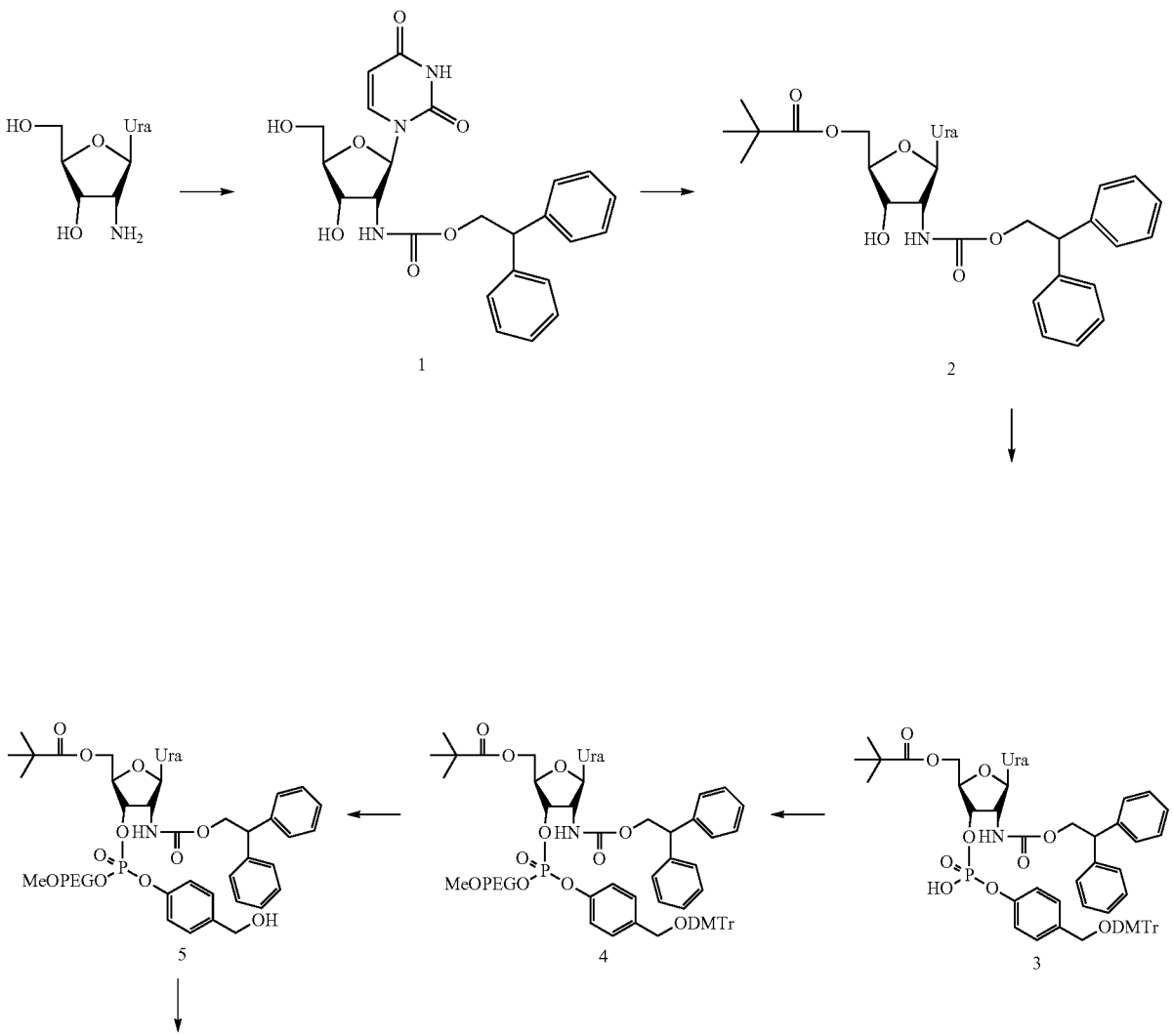

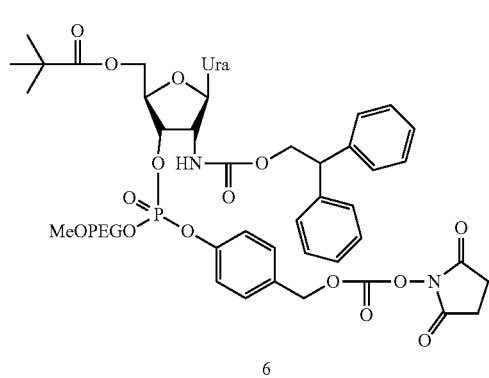
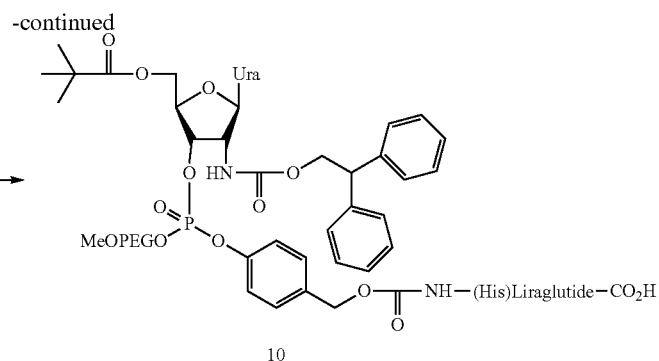

Hydrolysis of compound 1 gave a T1/2 of 12 days at pH 8, and based on the calculations as detailed in Example 3 resulted in an estimated T1/2 of 16 days for compound 10 at pH 7.4.

Example 5—FPEC (fluorenylphenylethoxycarbonyl)-based Liraglutide Conjugate 11

Using methods similar to that described in Example 1, FPEC (fluorenylphenylethoxycarbonyl)-based liraglutide conjugate 11 was prepared.

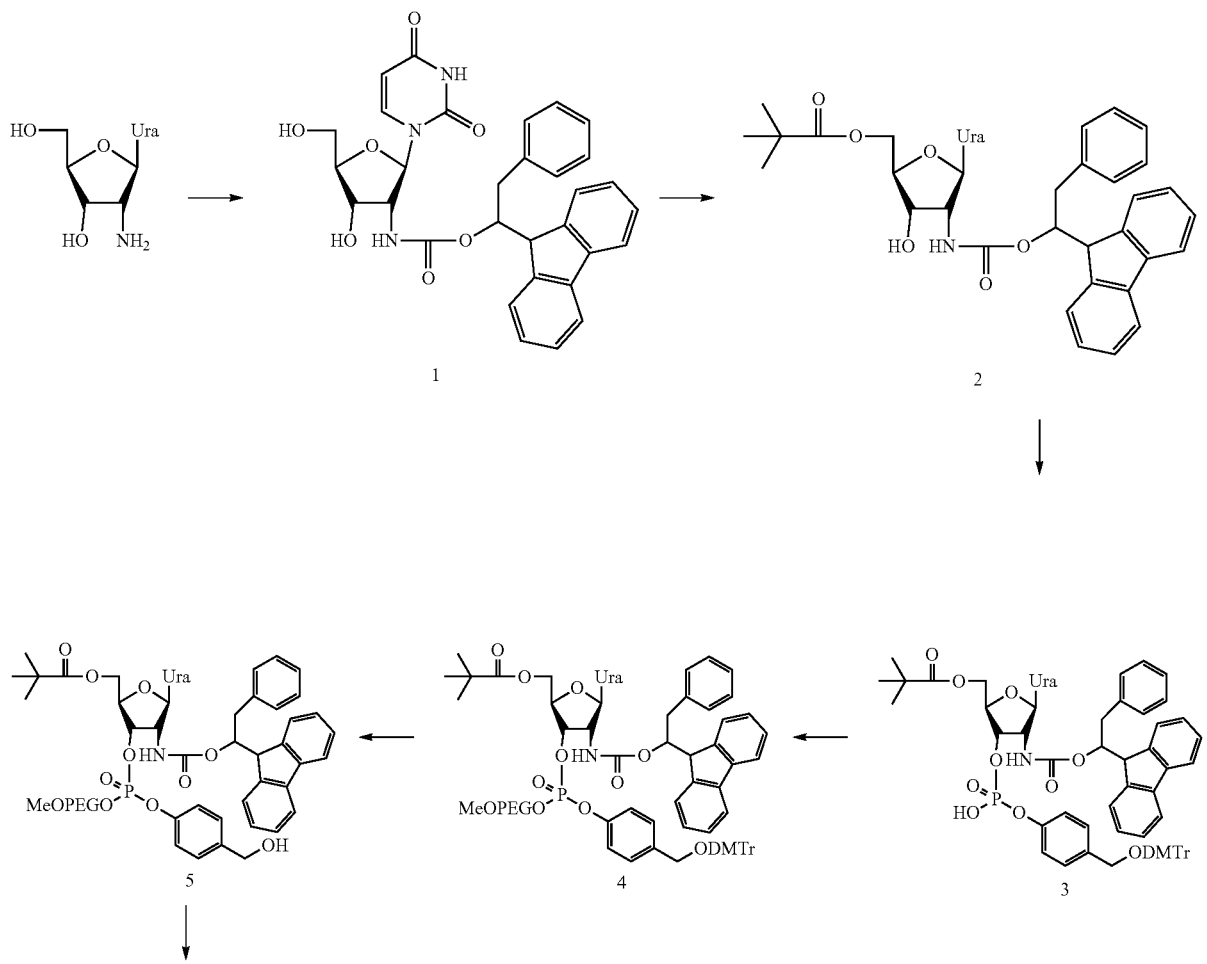

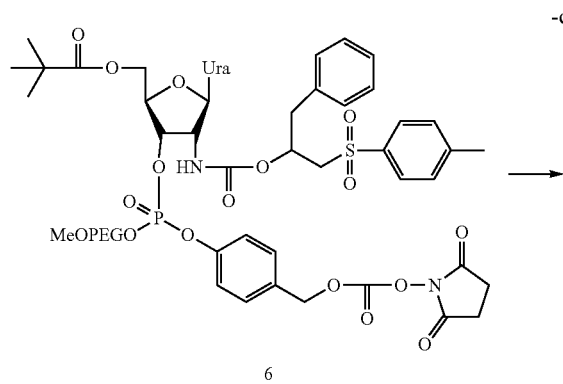
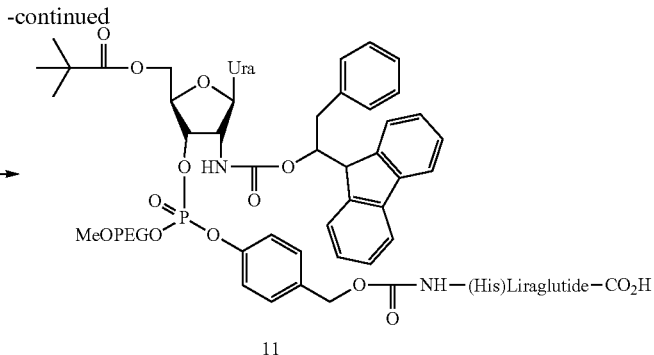
Example 6—DFDPEC-based Liraglutide Conjugate 12
Using methods similar to that described in Example 1, DFDPEC-based liraglutide conjugate 12 was prepared.
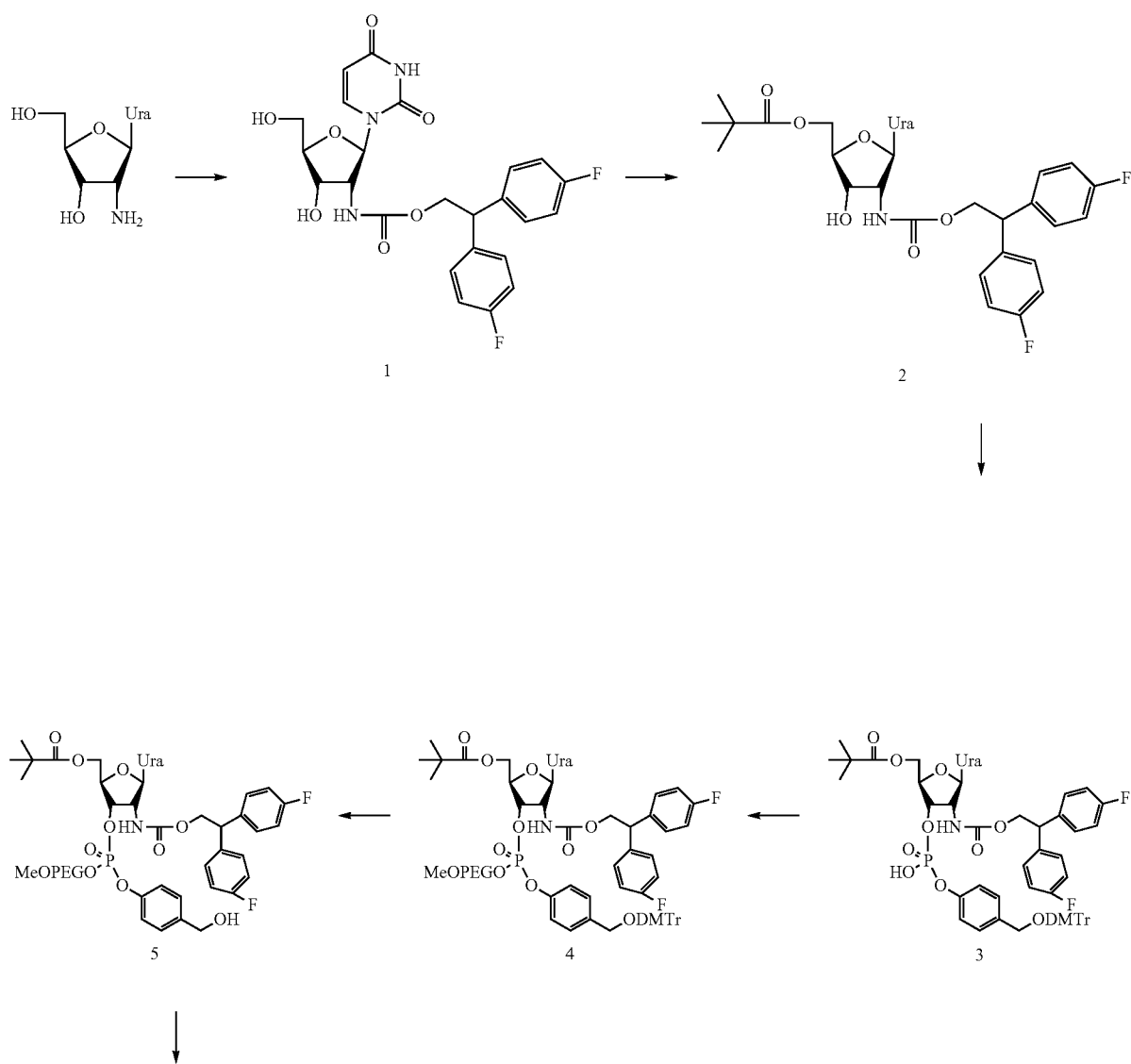

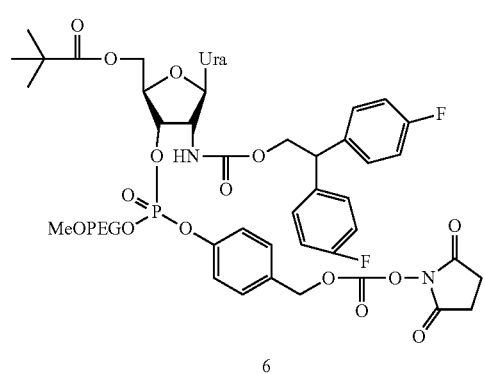
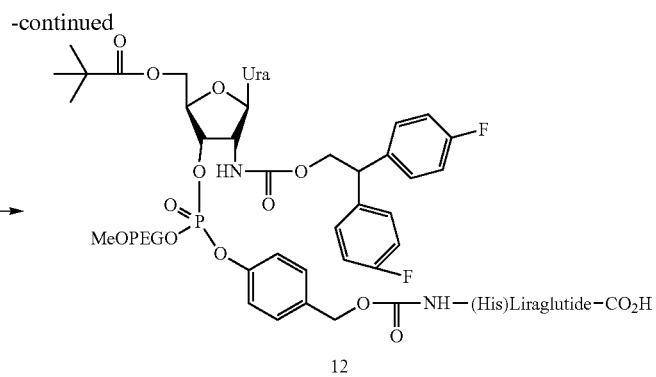
Example 7—DTBFMOC-based Liraglutide Conjugate 13
Using methods similar to that described in Example 1, DTBFMOC-based liraglutide conjugate 13 was prepared.
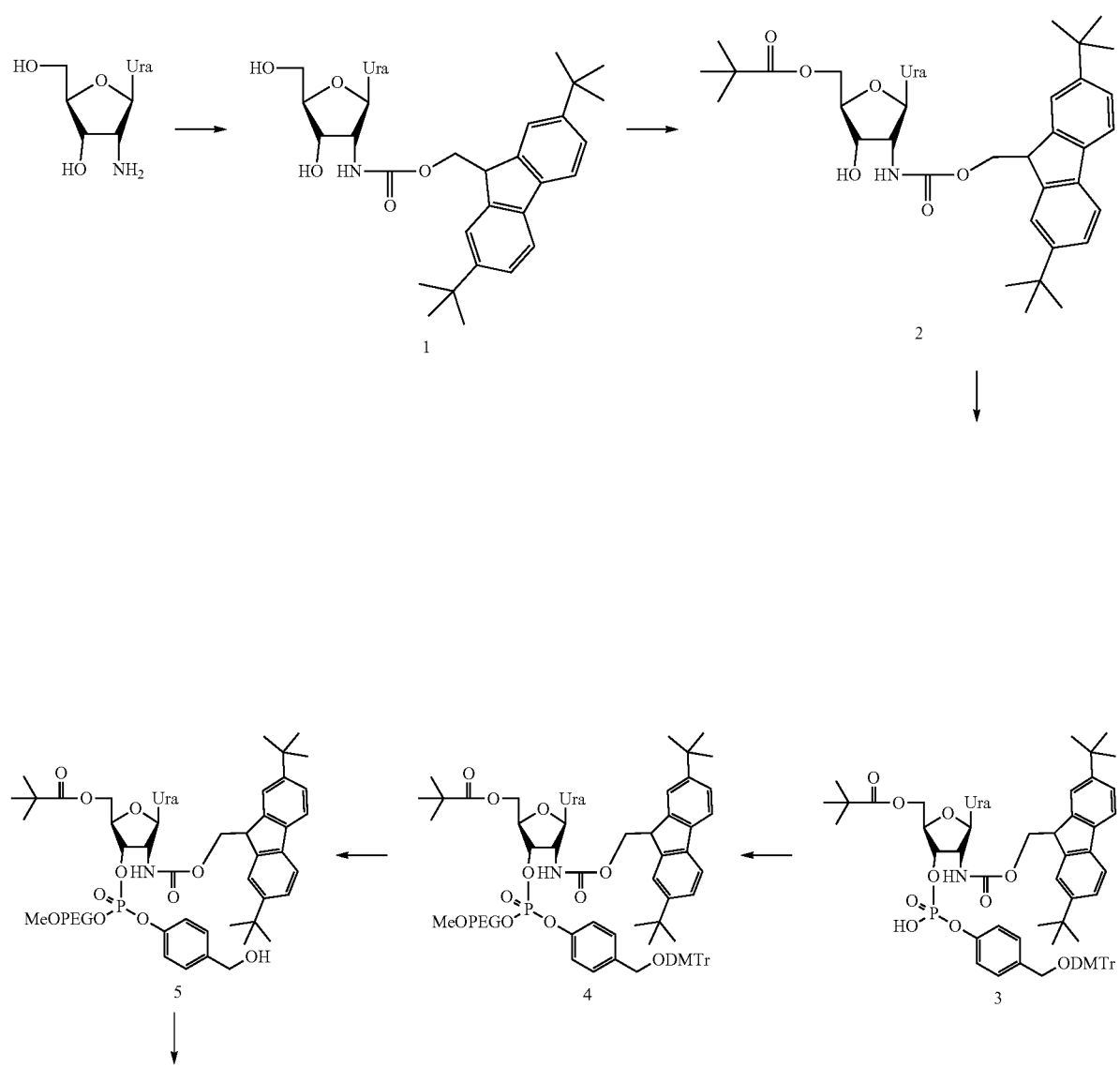

121
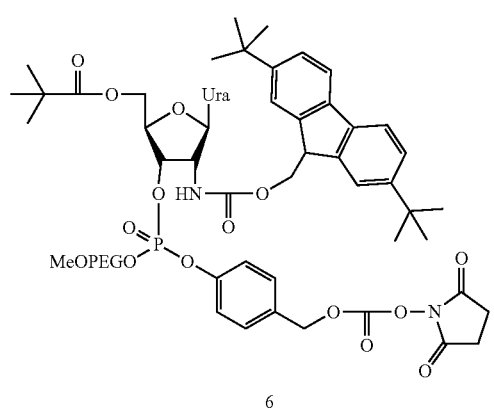
122
-continued
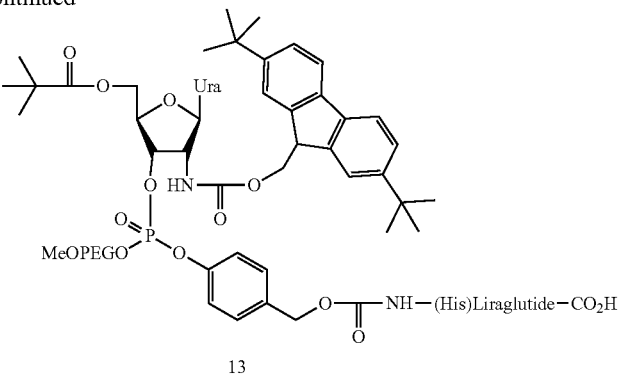
Example 8—Preparation of Liraglutide Conjugates Using Phosphodichloridate Methodology for PEG Reagent Synthesis
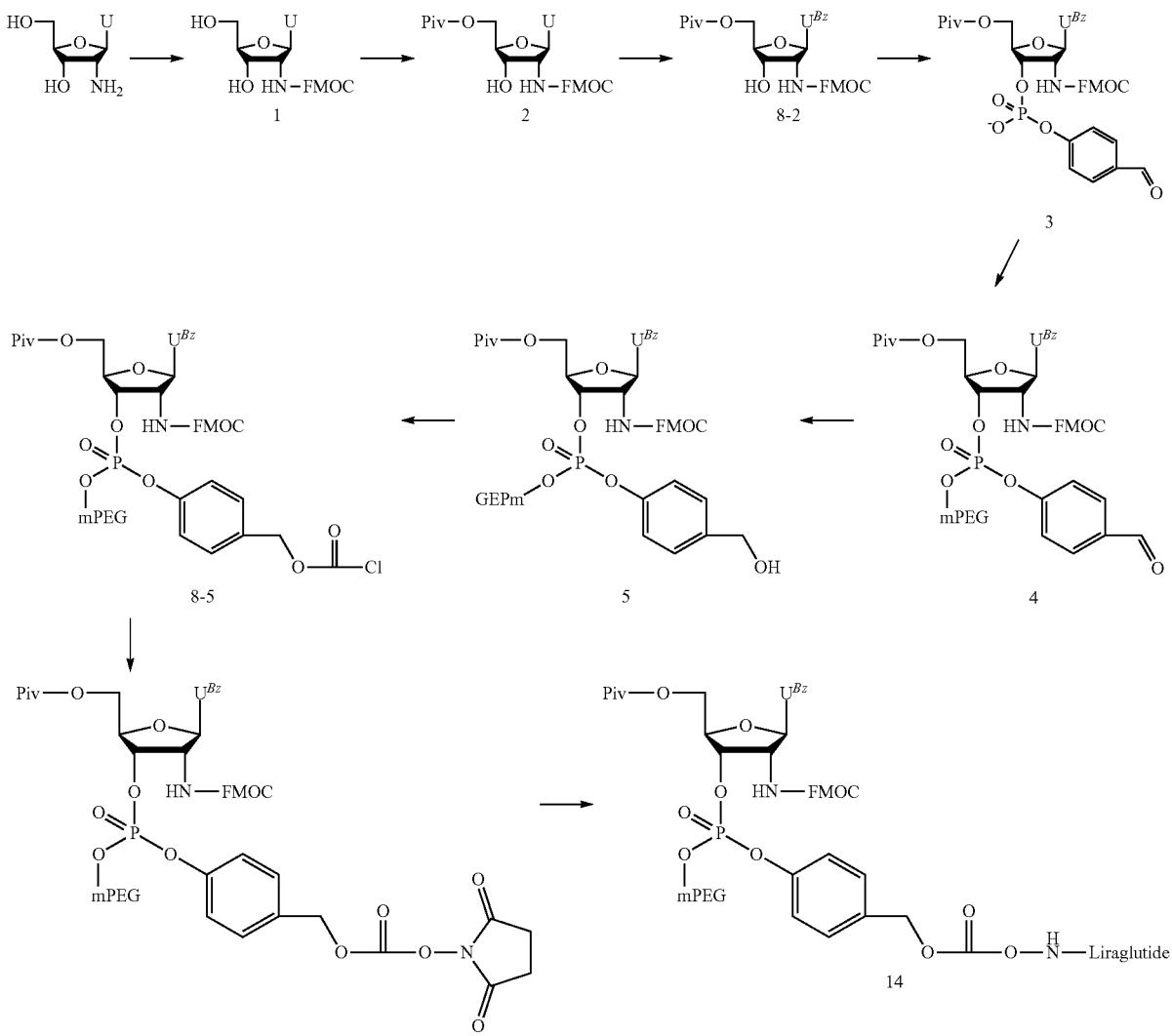

Steps 1-2. Steps 1 and 2 are carried out according to the methods and procedures similar to those of Example 1.

Step 3. Method for Preparation of the N3-benzoylated 5'-O-pivaloyluridine-2'-N-carbamate 8-2.

Compound 2 (1 eq.) was dissolved in dry pyridine (7 mL/mmol). Chlorotrimethylsilane (TMS-Cl, 3 eq.) was added to the pyridine solution at room temperature, and the mixture was stirred for 1 hour at room temperature. Next, benzoyl chloride (2 eq.) was added, and the mixture was stirred for 2 days. The reaction mixture was quenched with methanol, and after 15 minutes, it was concentrated on rotavapor and partitioned between saturated aqueous sodium bicarbonate and dichloromethane. After evaporation of the organic phase, the remaining oil was co-evaporated with toluene to remove traces of pyridine. The residue was dissolved in 80% AcOH (10 mL/mmol) and stirred for 10 minutes in order to cleave the silylether, followed by evaporation to dryness on rotavapor and coevaporation with toluene. The residue was chromatographed through silica gel 60A using gradient (0-2-4%) of MeOH in DCM to give the product 8-2 as a white solid. Isolated yield was usually around 80%.

Step 4. Method for Preparation of Triethylammonium Salt of Phosphodiester Compound 3.

A solution of 4-formylphenylphosphorodichloridate (2 eq.), prepared according to Engberts, J. B. F. N. et al. *Langmuir* 1996, 12, 5773-5780 and used crude without distillation, was dissolved in dry MeCN (1 mL/mmol) and added dropwise to the compound 8-2 (1 eq.) dissolved in dry pyridine (4 mL/mmol). The resulting mixture was stirred at room temperature for about 2 hours. The reaction was quenched by 1 M triethylammonium hydrogen carbonate and extracted three times with DCM. The organic phase was evaporated and dried by coevaporation with toluene, and the residue was chromatographed through silica gel 60A using a gradient of DCM/MeOH (0-2-4-6-8% MeOH/DCM+0.1% pyridine. The product was eluted with 4-6% MeOH to give the O-aryl-O-alkylphosphodiester 3 as a triethylammonium salt (isolated yield 50-65%).

Step 5. Method for Preparation of MeOPEG Phosphotriester Aldehyde 4.

The phosphodiester 3 (1 eq.), predried mPEG-OH (3 eq.) and N-methylimidazole (24 eq.) were dissolved in dry MeCN and evaporated to dryness. The residue was coevaporated with dry MeCN once more and concentrated down to a semi-viscous MeCN solution. To this solution, a solution of 1-mesitylenesulfonyl chloride (12 eq.) in a minimal amount of dry MeCN was added in one portion. After addition, the reaction mixture in the round bottom flask was shaken at room temperature for 16 hours.

The reaction mixture was quenched with MeOH and evaporated to dryness on a rotary evaporator. The residue was recrystallized from isopropanol (40 mL/3 g mPEG). The mixture was heated at 55° C. to dissolve the solid matter. The pegylated materials crystallized when cooled to room temperature. The crystallized material was filtered on a glass sinter filter, washed with cold isopropanol, followed by diethylether, and dried under vacuum (yield usually close to the amount mPEG-OH used in the reaction).

The crude solid was analyzed by $C_{18}$ RP-HPLC to verify presence of the phosphotriester product 4. The product appeared usually as the largest peak on the chromatogram, with a characteristic broadness typical for all PEG containing materials. The crude material was taken directly to the next step. It was not purified at this step due to the risk of being converted to a hydrate in a contact with water.

Step 6. Method for Preparation of MeOPEG Phosphotriester Hydroxyl Block Compound 5.

The crude aldehyde phosphotriester 4 (3.5 g, 0.059 mmol) was dissolved in MeCN (15 mL), and the solution was poured into water (70 mL) in a glass beaker with stirring. The glass rod from a pH meter was kept dipped in the resulting solution. Then immediately, $NaBH_4$ (5 eq.) was added portionwise with a spatula, and the rise of the pH was monitored. Gas evolution was also started. After full addition, the pH reached about 8.9 within a few minutes. At this time, 1 M citric acid was added dropwise in order to lower the pH to about 6.5-6.6.

The resulting clear solution was evaporated with addition of some n-butanol as anti-foaming agent. The residue was dissolved in MeCN and stirred for 5 minutes, and the fine suspension was filtered through Celite. The clear filtrate was then evaporated and dissolved in 30% acetonitrile/water solution.

Preparative RP HPLC (Lichrospher 100 RP-18) separated the triester 5 from the side products using the following solvent mixtures and gradient:

Buffer A: 0.1M triethylammonium acetate in 5% MeCN/water.
Buffer B: 100% MeCN
Gradient: 30-60% B over 60 minutes
Monitoring: 270 nm The collected fractions were pooled together and evaporated to dryness, and the residue kept under high vacuum for some hours. The gummy residue of pure compound 5 and residual triethylammonium acetate buffer was dissolved in warm isopropanol (55° C.), and compound 5 was crystallized upon cooling as a white solid. Yield was 60%.

Step 7-9.

Conversion of compound 5 into its NHS carbonate derivative 6 and its conjugation with liraglutide to produce the final conjugate 14 proceeded analogously to the appropriate steps presented in Example 1. The final conjugation mixture containing 0.3 M HEPES buffer was diluted with water (10×) and applied on an Anion Exchange column (OptioBio 40Q 10×100—Bio-Works, Uppsala Sweden) equilibrated in 20 mM phosphate buffer pH 7.0. The separation was performed starting with isocratic conditions and using Buffer A—20 mM phosphate buffer pH 7.0. This was continued for 15 minutes until uncharged excess of pegylating reagent was eluted out, following by a linear gradient of Buffer A to Buffer B (20 mM phosphate buffer pH 7.0+1.0 M NaCl. The fraction B—representing liraglutide conjugate—was collected, concentrated 10× by evaporation on a rotary evaporator, and acidified until pH 5 by addition of 1 M acetic acid. This material was further purified on Superdex 200 Increase 10/300 SEC column using 0.01 M phosphate buffer pH 7.4 containing 0.14 M NaCl operating at 0.5 mL/minute flow at room temperature. Samples as large as 2.5 mL were injected without substantial decrease of peak resolution. Collected fractions containing pure conjugate were stored by addition of 2 volumes of 0.3 M citrate buffer pH 4. Pure liraglutide—PEG conjugate 14 obtained during SEC separation. In the same system, the free liraglutide exhibited a retention time of 29 minutes.

Example 9—Preparation of Liraglutide Conjugates with Lipophilic Protection of Uracyl
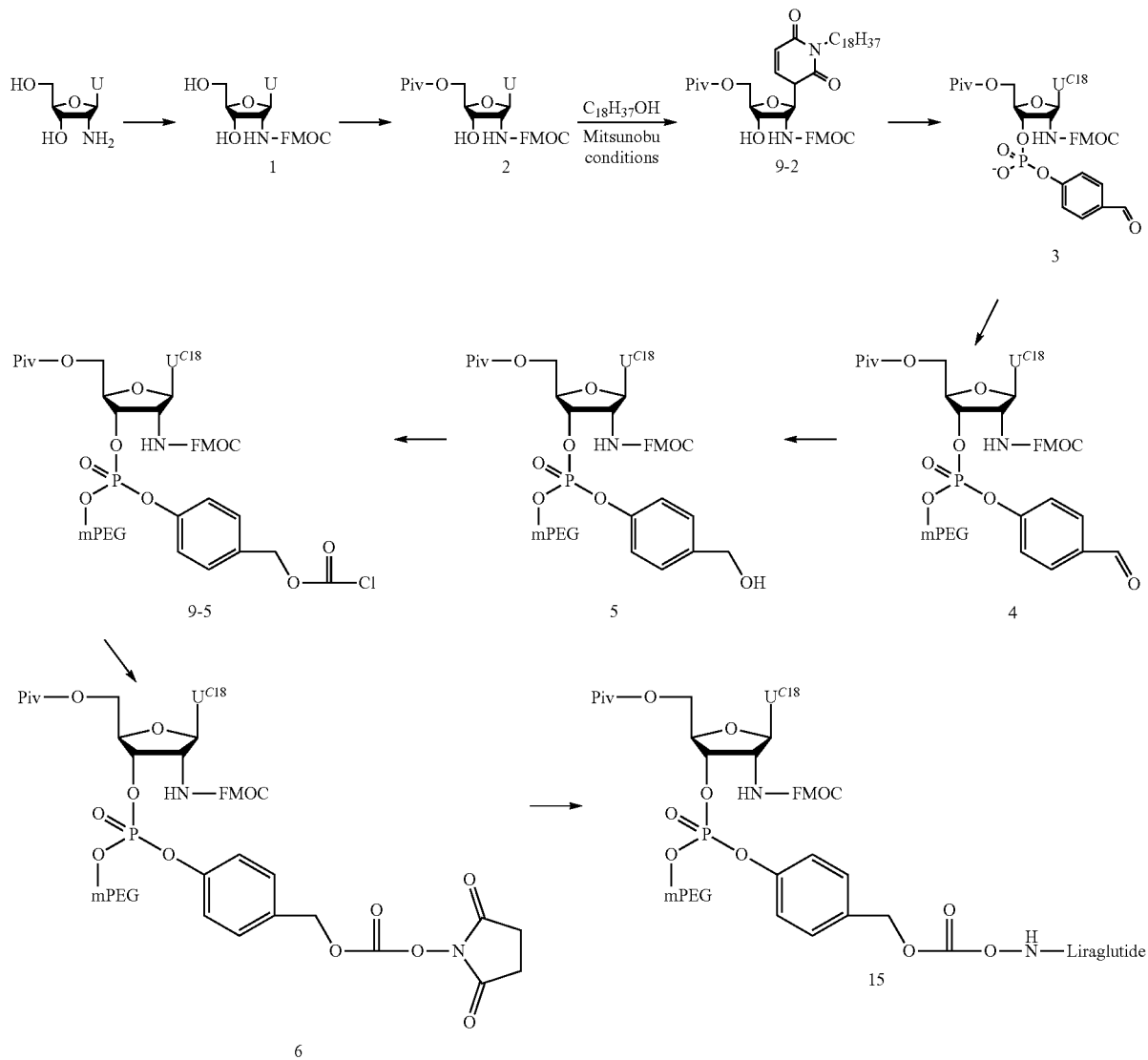
Conjugate 15 was obtained according to the methods and procedures similar to those described in Example 8.
Example 10—Preparation of Liraglutide Conjugate with Hydrophobic 5'-DMTr Group
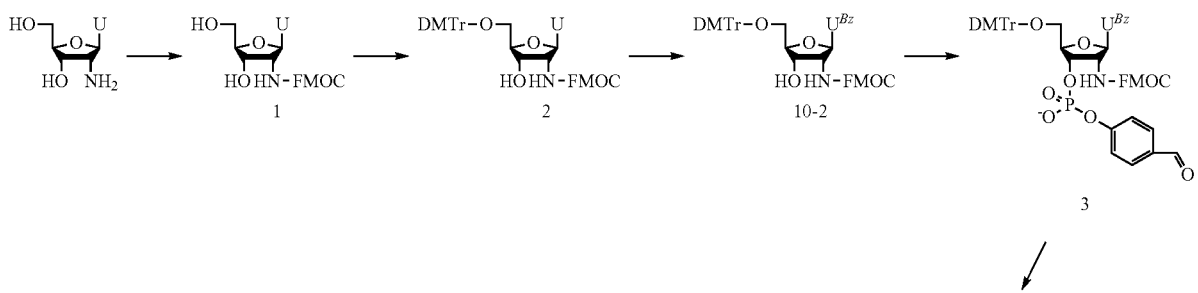

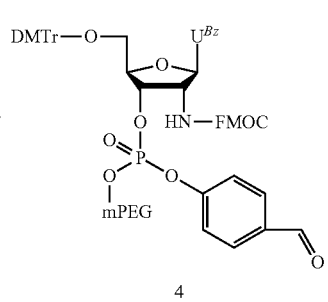
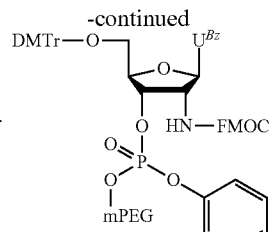
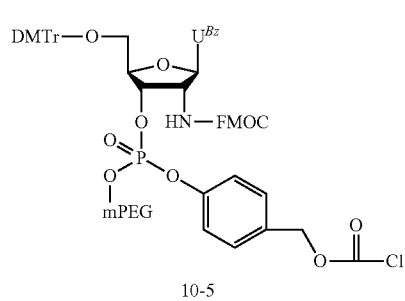
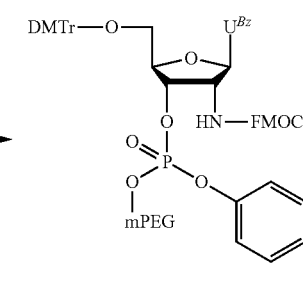
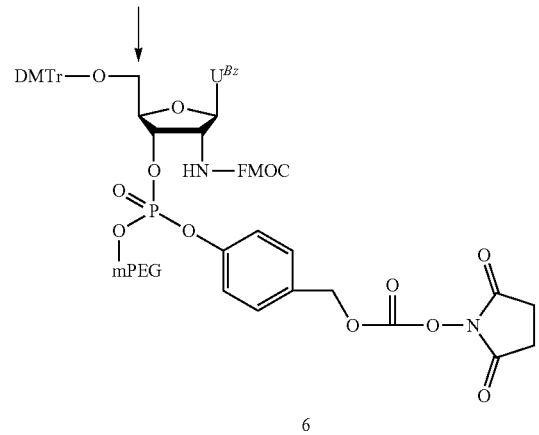

Conjugate 16 was obtained according to the methods and procedures similar to those described in Example 8.

Example 11—Proteolytic Stability and Biological Activity of Compound 7

The analysis of proteolytic stability of liraglutide and compound 7 in the presence of the protease dipeptidyl peptidase IV (DPP-IV) was analyzed by LC-ESI-MS.

Liraglutide (SEQ ID NO:3) was dissolved in 10 mM Na$_2$HPO$_4$ pH 7.4 to a concentration of 10 mg/mL. Compound 7 was dissolved in 50 mM ammonium acetate buffer pH 4.5 to a concentration of 10 mg/mL.

Both samples were diluted with 10 mM Na$_2$HPO$_4$ pH 7.4 to a protein concentration of 2.67 µM and digested in the presence of 50 mU/mL DPP-IV (from porcine kidney, Merck) at 37° C. Samples were taken 9-5 after 2 h, 10 h, 24 h, 34 h, 48 h, 72 h and 96 h. To stop the reaction, 57 µL of sample was acidified with 3 µL 10% TFA and stored at −20° C. until measurements were taken.

The samples were separated on a LaChrom Ultra HPLC system (VWR) using a reversed phase column (MAbPac RP 4 µm 2.1×100 mm, Thermo Scientific). Eluents were 0.1% FA in water and 0.1% FA in acetonitrile. The mass spectrometric analysis was performed with a micrOTOF-Q II (Bruker Daltonik).

The recorded LC-ESI-MS spectra were internally recalibrated on basis of the theoretical mass of liraglutide. Extracted ion chromatograms (EIC) were generated for the compounds shown in FIG. 1. The compounds observed in the EIC were integrated and the intensity was normalized to a compound observed at 382.86 m/z (unknown, specific for digestion as it was not observed in blank measurement). The relative intensity of each compound is shown in arbitrary units.

The digestion of liraglutide and compound 7 with DPP-IV led to generation of different liraglutide fragments (FIG. 1): liraglutide AA9-37 EGTFTSDV SSYLEGQAAK EFIAWLVRGR G (SEQ ID NO:5); liraglutide AA13-37 ((TSDV SSYLEGQAAK EFIAWLVRGR G (SEQ ID NO:6)); and liraglutide AA25-37 (AK EFIAWLVRGR G (SEQ ID NO:7)). FIG. 2 shows the results of a first test run, a digest performed at pH 7.6 with 50 mU/mL DPP-IV after 15 h at 37° C. Here, already, two liraglutide fragments were observed, liraglutide AA9-37 and liraglutide AA13-37. A third fragment (liraglutide AA25-37) was not observed yet in this sample. For the final experiment the pH was lowered to 7.4 to decrease the release of PEGylation from compound 7.

Figure 3:
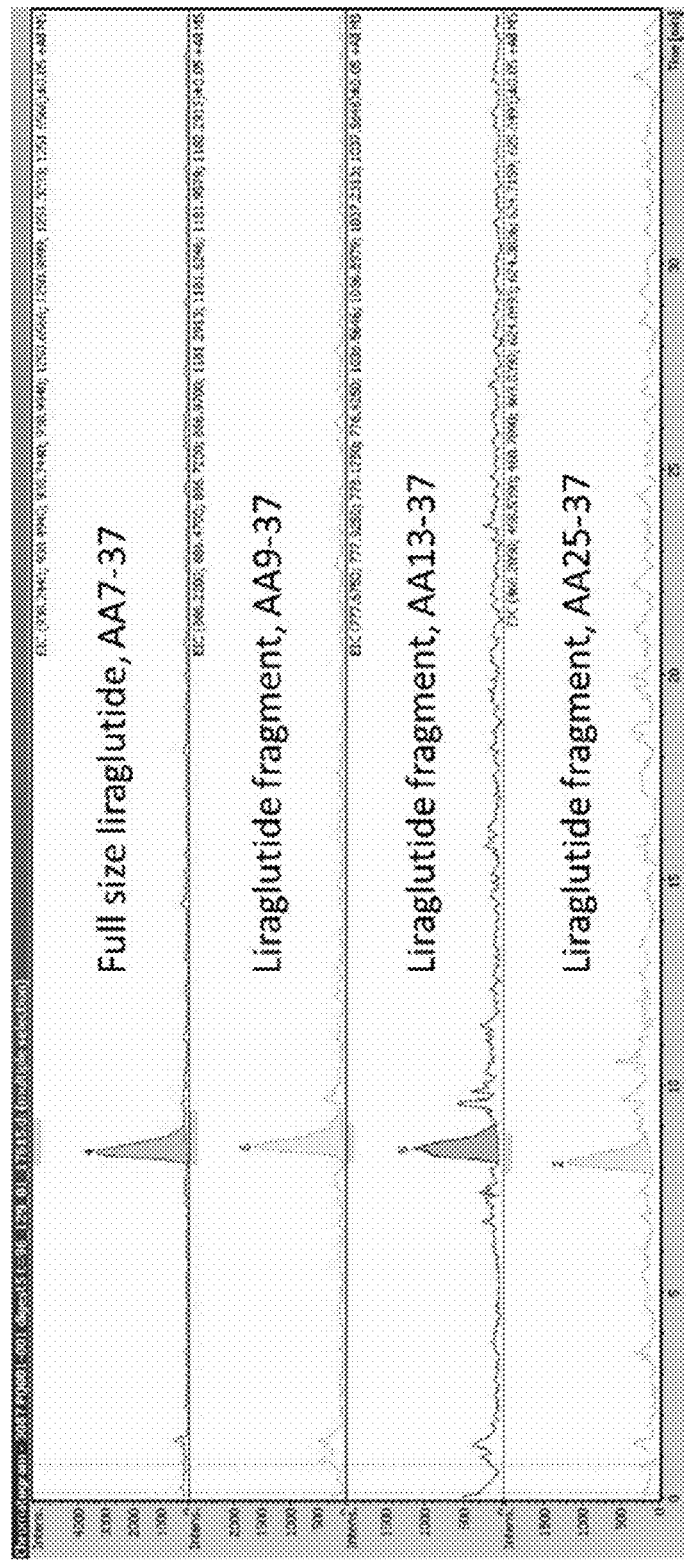
FIG. 3 shows exemplary data of the extracted ion chromatogram (EIC) traces of full size liraglutide and liraglutide fragments in sample liraglutide after 96 h digestion with DPP-IV at 37° C. and pH 7.4.

The proteolytic stability of liraglutide and compound 7 was successfully measured by LC-ESI-MS. FIG. 3 shows exemplary data of the extracted ion chromatogram (EIC) traces of full size liraglutide and liraglutide fragments in sample liraglutide after 96 h digestion with DPP-IV at 37° C. and pH 7.4. The peaks observed in the EIC were integrated, normalized and reported in arbitrary units.

Figure 4:
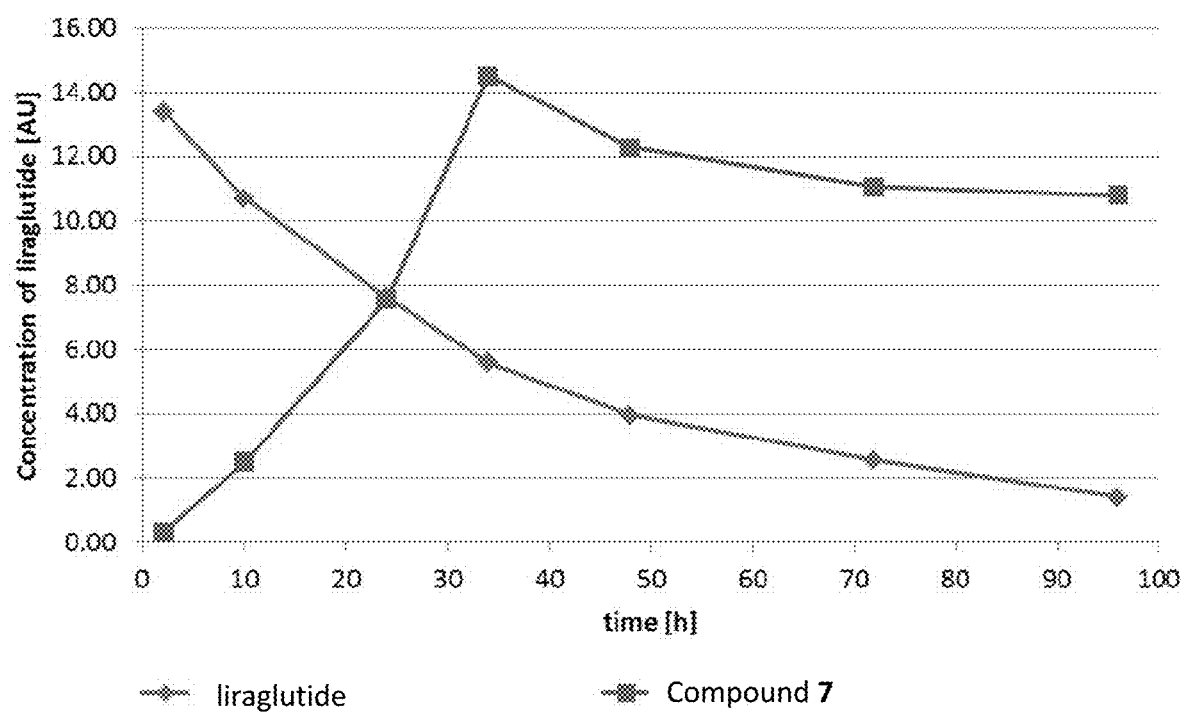
FIG. 4 is a line graph of the concentration of liraglutide shown in arbitrary units for liraglutide and compound 7 after digestion with 50 mU/mL DPP-IV in 10 mM $Na_2HPO_4$ pH 7.4 at 37° C.

FIG. 4 shows the concentration of non-PEGylated liraglutide after digestion with DPP-IV for the two samples. The following observations were made:

Liraglutide showed a half-life of approximately 25-35 hours.

Compound 7 showed an increase of non-PEGylated liraglutide in the first 34 hours which is generated by release of PEGylation due to the slightly alkaline pH.

After 34 hours, the released liraglutide in the sample of compound 7 showed a slower decline in concentration compared to liraglutide in the first 34 hours. This might be partly explained by a decline of enzyme activity after incubation at 37° C., however the unmodified liraglutide control study indicates that significant enzyme activity should still have been present. Therefore, the results appear to indicate proteolytic cleavage of the PEG-liraglutide was reduced.

The results indicate a much higher proteolytic stability of compound 7 compared to liraglutide.

Figure 5:
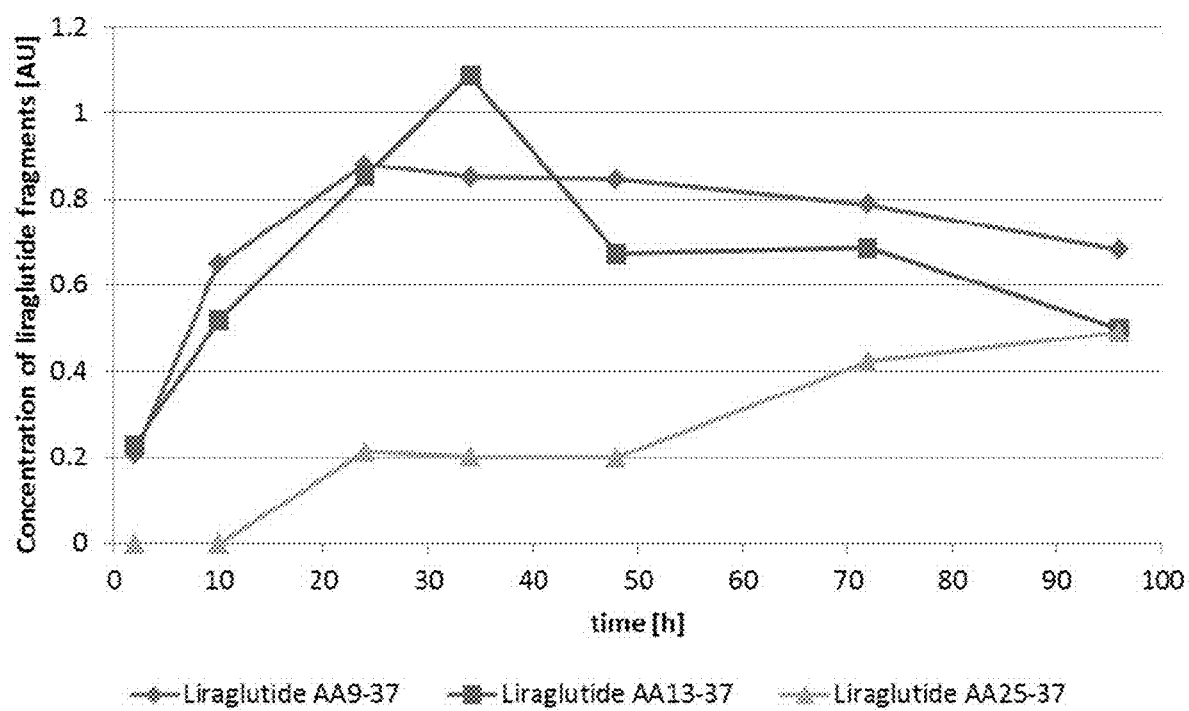
FIG. 5 is a line graph of the concentration of liraglutide fragments shown in arbitrary units for liraglutide after digestion with 50 mU/mL DPP-IV in 10 mM $Na_2HPO_4$ pH 7.4 at 37° C.

FIG. 5 shows the concentration of liraglutide fragments after digestion of liraglutide with DPP-IV. Apparently, liraglutide was first digested into liraglutide AA9-37 and liraglutide AA13-37. Later on during the digestion, a third liraglutide fragment (liraglutide AA25-37) was generated from digestion of the first two liraglutide fragments which showed a decline after 25-35 hours.

Figure 6:
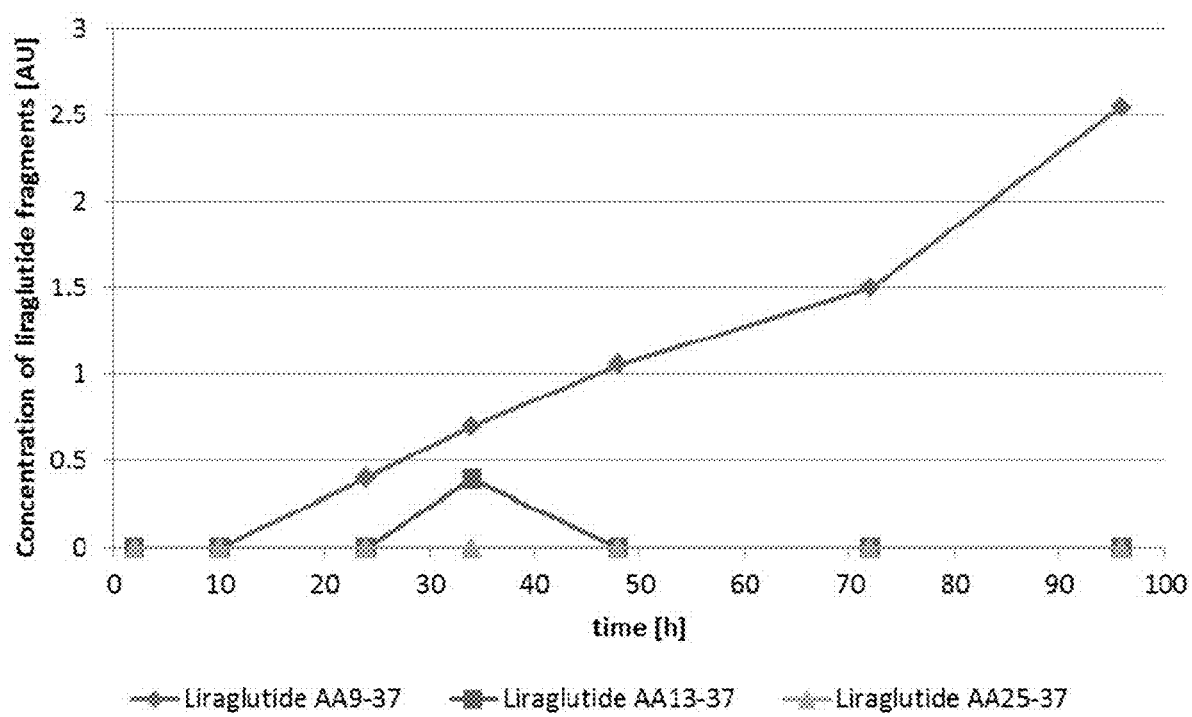
FIG. 6 is a line graph of the concentration of liraglutide fragments shown in arbitrary units for compound 7 after digestion with 50 mU/mL DPP-IV in 10 mM $Na_2HPO_4$ pH 7.4 at 37° C.

FIG. 6 shows the concentration of liraglutide fragments after digestion of compound 7 with DPP-IV. Here, mostly liraglutide AA9-37 was generated by digestion with DPP-IV. This observation suggests that compound 7 was digested differently than liraglutide. The generation of liraglutide AA13-37 and liraglutide AA25-37 was significantly reduced here.

Figure 7:
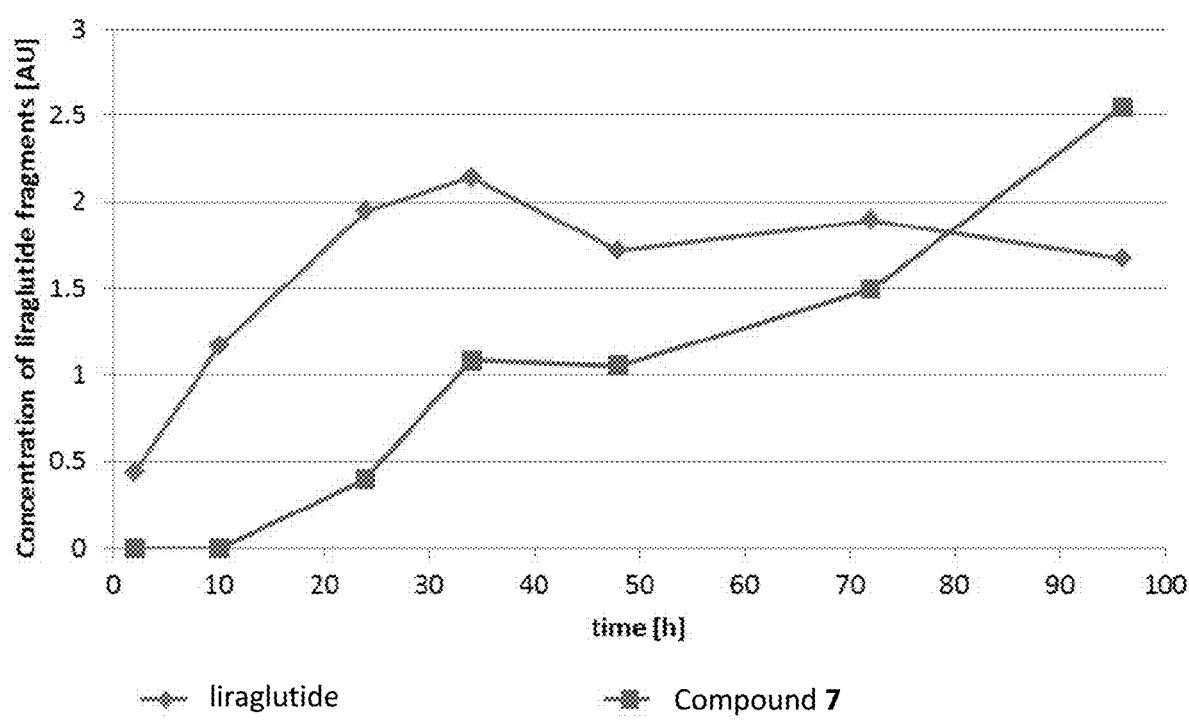
FIG. 7 is a line graph of the concentration of the sum of all observed liraglutide fragments shown in arbitrary units for liraglutide and compound 7 after digestion with 50 mU/mL DPP-IV in 10 mM $Na_2HPO_4$ pH 7.4 at 37° C.

FIG. 7 shows the concentration of the sum of all detected liraglutide fragments after digestion of liraglutide and compound 7 with DPP-IV (see, also, Tables 1 and 2). The apparent decline of digestion products in sample liraglutide after 34 hours is most probably due to liraglutide fragments being digested further into smaller fragments that were not detected by the method. The higher proteolytic stability of compound 7 is highly significant during the first 24 hours.

After 24 hours, liraglutide shows approximately five times more digestion products than an equimolar sample of compound 7. After 96 hours, compound 7 shows a higher concentration of observed digestion products. This was most probably due to the fact that the sample liraglutide was digested further into smaller fragments that were not analyzed by the method. The actual concentration of digestion products was most probably significantly higher in sample liraglutide. This was supported by the fact that liraglutide showed significantly less full-size liraglutide after 96 hours as shown in FIG. 4.

TABLE 1

Concentration of liraglutide and sum of all observed liraglutide fragments in arbitrary units for liraglutide (SEQ ID NO: 3; PQ001-2018-001) and Compound 7 (PEG-liraglutide; PQ001-2018-003) after digestion with 50 mU/mL DPP-IV in 10 mM Na2HPO4 pH 7.4 at 37° C.

| Time [h] | Concentration of full size liraglutide for liraglutide (PQ001-2018-001) [AU] | Concentration of full size liraglutide for PEG-liraglutide (PQ001-2018-0030) [AU] | Concentration of all liraglutide fragments for liraglutide (PQ001-2018-001) [AU] | Concentration of all liraglutide fragments for PEG-liraglutide (PQ001-2018-003) [AU] |
|---|---|---|---|---|
| 2 | 13.40 | 0.34 | 0.44 | 0.00 |
| 10 | 10.70 | 2.51 | 1.17 | 0.00 |
| 24 | 7.64 | 7.56 | 1.95 | 0.40 |
| 34 | 5.58 | 14.52 | 2.14 | 1.09 |
| 48 | 3.96 | 12.28 | 1.72 | 1.05 |
| 72 | 2.56 | 11.06 | 1.90 | 1.50 |
| 96 | 1.41 | 10.79 | 1.67 | 2.55 |

TABLE 2

Concentration of liraglutide fragments in arbitrary units for liraglutide (SEQ ID NO: 3; PQ001-2018-001) and Compound 7 (PEG-liraglutide; PQ001-2018-003) after digestion with 50 mU/mL DPP-IV in 10 mM $Na_2HPO_4$ pH 7.4 at 37° C.

| Time [h] | Concentration of liraglutide AA9-37 for liraglutide (PQ001-2018-001) [AU] | Concentration of liraglutide AA9-37 for liraglutide (PQ001-2018-003) [AU] | Concentration of liraglutide AA13-37 for liraglutide (PQ001-2018-001) [AU] | Concentration of liraglutide AA13-37 for PEG-liraglutide (PQ001-2018-003) [AU] | Concentration of liraglutide AA25-37 for liraglutide (PQ001-2018-001) [AU] | Concentration of liraglutide AA25-37 for PEG-liraglutide (PQ001-2018-003 [AU] |
|---|---|---|---|---|---|---|
| 2 | 0.21 | 0.00 | 0.23 | 0.00 | 0.00 | 0.00 |
| 10 | 0.65 | 0.00 | 0.52 | 0.00 | 0.00 | 0.00 |
| 24 | 0.88 | 0.40 | 0.85 | 0.00 | 0.21 | 0.00 |
| 34 | 0.85 | 0.69 | 1.09 | 0.39 | 0.20 | 0.00 |
| 48 | 0.85 | 1.05 | 0.67 | 0.00 | 0.20 | 0.00 |
| 72 | 0.79 | 1.50 | 0.69 | 0.00 | 0.42 | 0.00 |
| 96 | 0.68 | 2.55 | 0.50 | 0.00 | 0.49 | 0.00 |

The proteolytic stability of compound 7 was significantly higher than the stability of liraglutide. After 24 hours, liraglutide showed approximately five times more digestion product than an equimolar sample of compound 7. With increasing time, compound 7 showed loss of PEGylation and in consequence also increased generation of digestion products. After 96 hours, compound 7, however, still showed approximately seven to eight times more liraglutide under the described conditions.

In another experiment, liraglutide (SEQ ID NO:3) and compound 7 were successfully digested in vitro with pepsin and analyzed by mass spectrometry with MALDI-TOF-MS. The spectra for compound 7 digested with pepsin were compared to intact compound 7 and liraglutide (SEQ ID NO:3) digested with pepsin. From these comparisons, the N-terminus of liraglutide was determined to be the site of PEGylation for compound 7. Also, a significantly lower intensity for the N-terminal peptides for compound 7 confirmed that the N-terminus is protected by pegylation.

In sum, compound 7 provides for increased proteolytic stability and longer half-life of liraglutide as compared to conjugates of liraglutide with standard fatty acyl modification (e.g., γ-Glu-palmitoyl liraglutide modification, SEQ ID NO:3). In contrast with the γ-Glu-fatty acyl modification, compound 7 shows mechanistically different plasma breakdown (proteolysis) as the PEGylation site in compound 7 is in the viscinity of the normal plasma proteolysis site of liraglutide, which is not otherwise "protected" or "shielded" from proteolysis in any other form of liraglutide. In fact, in order for compound 7 to provide increased proteolytic stability of the polypeptide, the γ-Glu acyl tail modification in not necessary (although the acyl-modified GLP polypeptides may still be used in the conjugates of the present disclosure). The GLP polypeptide (e.g., liraglutide) without the acyl tail, after release from the conjugate, is in its native form, which advantageously leads to increase in hydrophilicity, better aqueous solubility, and reduction of side effects associated with fatty acyl modification. Hence, the conjugates provided herein are able to release a native ("biobetter") form of the GLP.

In addition, when compound 7 was analyzed by RP-HPLC, the purity was determined to be about 97%.

Figure 10:
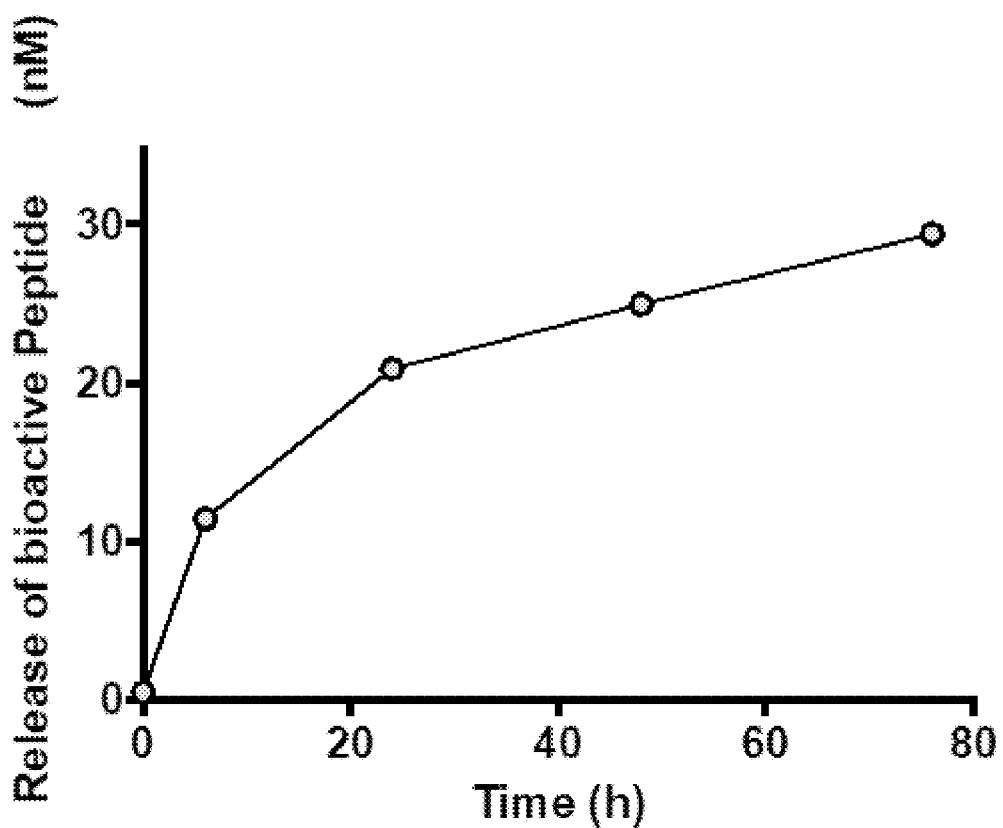
FIG. 10 is graph plotting the amount of biological activity of liraglutide released from compound 7 by incubation in rat plasma for the indicated times.

In another experiment, the biological activity of various amounts of liraglutide (SEQ ID NO:3) and compound 7 was assessed using a cell-based bioactivity assay (cAMP Hunter™ Liraglutide Bioassay Kit; DiscoverX). Increasing amounts of liraglutide (SEQ ID NO:3) resulted in the detection of increasing biological activity, while the biological activity of compound 7 remained low as the amounts of compound 7 were increased (FIG. 9). In another experiment, compound 7 was incubated in rat plasma at 37° C. (pH 7.4) for zero, 6, 24, 48, and 76 hours. After each timepoint, the material was tested for biological activity of any released liraglutide from compound 7 using the cell-based bioactivity assay (cAMP Hunter™ Liraglutide Bioassay Kit; DiscoverX). Biologically active liraglutide released from compound 7 was detected (FIG. 10). These results demonstrate that compound 7 has the ability to perform as a pro-drug within mammals (e.g., humans); remaining inactive compared to liraglutide (SEQ ID NO:3) until liraglutide is released from the PEGylation moiety of compound 7.

Example 12—In Vivo Performance of Compound 7

The liraglutide (SEQ ID NO:3) stock solution was prepared by dissolving liraglutide in 10 mM $Na_2HPO_4$ (pH 7.4) to a concentration of 10 mg/mL. The compound 7 stock solution was prepared by dissolving compound 7 in 50 mM ammonium acetate ($NH_4Ac$) buffer (pH 4.5) to a concentration of 10 mg/mL. Before dosing the animals, the stock solutions were dissolved in PBS (pH 7.4) to the final concentration (5.8 nmol/kg).

Two groups of six Sprague Dawley rats each were used. The first group (Group 1) received liraglutide (SEQ ID NO:3) at a dose of 5.8 nmol/kg administered intravenously in a volume of 1 mL/kg. The second group (Group 2) received compound 7 at a dose of 5.8 nmol/kg administered intravenously in a volume of 1 mL/kg. All injections were tail-vein bolus injections over 15 seconds.

Blood sample were collected from the sub-lingual vein into EDTA pre-coated vials. Eight blood samples containing 200 μL of blood were collected from each rat over a period of 48 hours (pre-dose, 0.08, 1, 3, 6, 24, 30, and 48 hours). The samples were centrifuged at 4500 g for five minutes, and 100 μL of the plasma was transferred to a new 1.5 mL vial. A fixed volume of 0.5 M ammonium acetate was added to reach a pH of 5.5 in the plasma. After acidification, the samples were stored at −80° C. until analyzed. The levels of liraglutide in plasma from both groups was determined using a high sensitivity GLP-1 ELISA kit (Merck EZGLPHS-35K), while a cell-based bioactivity assay was used to measure the amount of active liraglutide in the samples.

Figure 11:
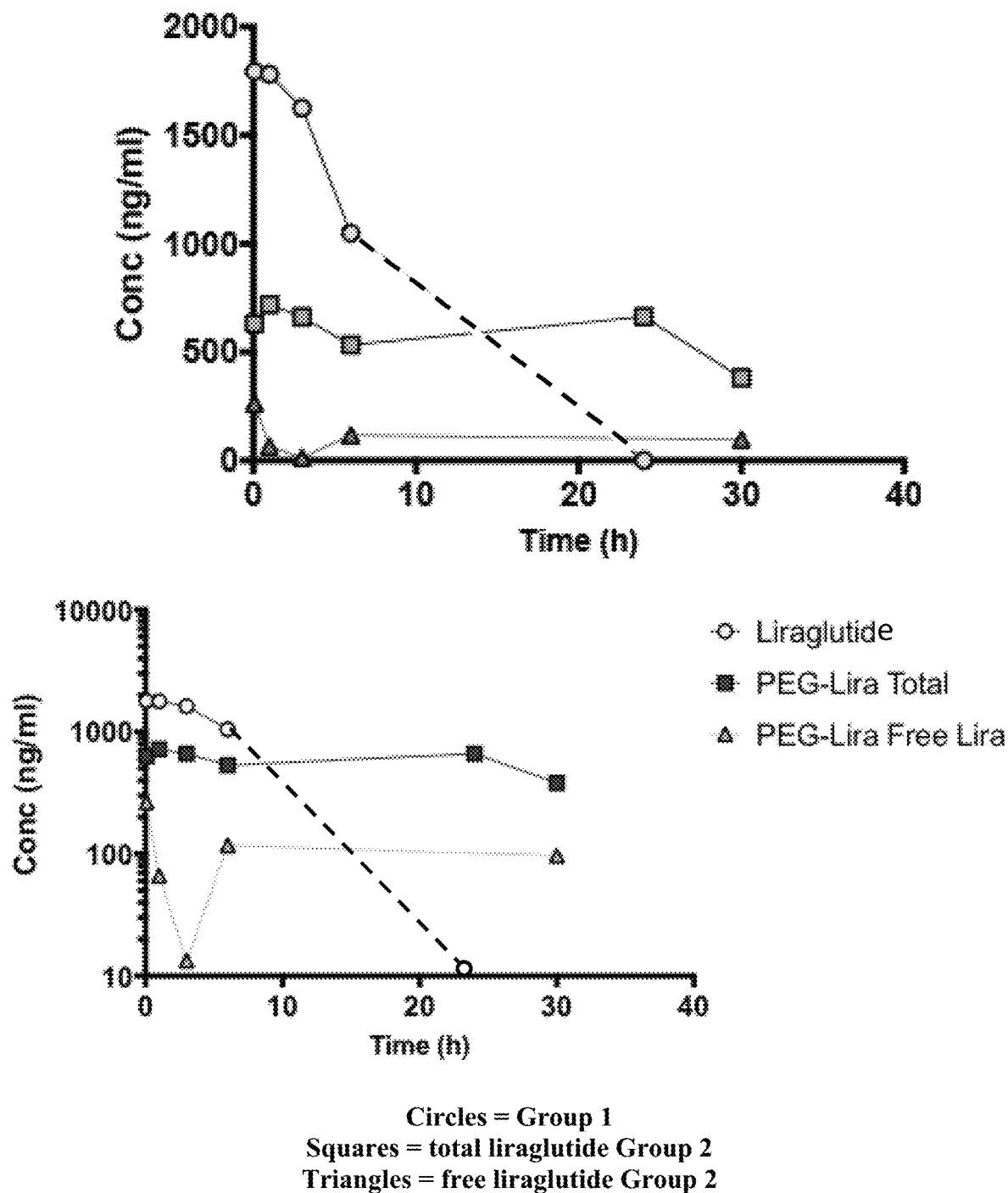
FIG. 11 contains graphs plotting the amount (ng/mL) of liraglutide detected in pooled samples collected at the indicated times from rats administered liraglutide (SEQ ID NO:3; Group 1) or compound 7 (Group 2).

The amounts of liraglutide measured in the pooled samples for each timepoint of Group 1 by ELISA were plotted in comparison to the amounts of total liraglutide and free liraglutide measured by ELISA in the pooled samples for each timepoint of Group 2 (FIG. 11). Likewise, the concentration of active liraglutide (nmol/L) measured in individual samples by the activity assay for Group 1 were compared to those measured for Group 2 (FIG. 12). These results demonstrate that compound 7 is more stable than liraglutide (SEQ ID NO:3), has a longer half-life than liraglutide (SEQ ID NO:3) (7.3 hours for compound 7 vs. 2.9 hours for non-pegylated liraglutide), and can perform like a pro-drug. These results also confirm the biological activity of the liraglutide released from compound 7 and demonstrate that compound 7 can be used as a once-weekly treatment in type 2 diabetes patients.

Taken together, the results provided herein demonstrate that drugs (e.g., liraglutide) linked to PEG as described herein can be formulated into pro-drugs having little or no biological activity until the drug is released from the PEG. This can allow for lower adverse side-effects in the drug treatment due to lower variation in plasma concentrations during the dosing interval. The results provided herein also demonstrate that drugs (e.g., liraglutide) can be linked to PEG as described herein to increase the drug's stability against degradation by enzymes such as dipeptidyl peptidase IV (DPP-IV). In addition, the results provided herein demonstrate that drugs (e.g., liraglutide) can be linked to PEG as described herein to provide for a controlled release of the drug with full biological activity. The linkers provided herein can allow one to select a desired release time or desired half-life for an administered drug.

Example 13. Evaluation of Various Cleavable Groups

The multi-step cleavage of the phosphotriester bond and release of free drug starts with hydrolysis of functional group E. This is usually the rate limiting step since all subsequent steps are much faster. In this example, carbamates obtained from 2'-aminouridine and chloroformates of different β-eliminative protecting groups, as presented in Example 15, were dissolved in acetonitrile and 200 μL of such solution was added to 0.3 M TRIS buffer (PBS) pH 8.0

(1.8 mL). This was quickly followed by addition of 3'-azido thymidine, used as the HPLC internal standard reference substance, and the sample was incubated at 37° C. Samples of this mixture, withdrawn at different time points were analyzed, monitoring disappearance of starting carbamate and formation of 2'-amino uridine. Results obtained at pH 8.0 could be simply recalculated for pH 7.4 (physiological conditions), by multiplication by 4 (i.e., the decrease in OH-concentration).

The results from these studies are presented in a table below.

| | $T_{1/2}$ at pH 8.0 | $T_{1/2}$ at pH 7.4 |
|---|---|---|
| (structure: 2'-carbamate uridine with –O–CH$_2$CH$_2$–SO$_2$–C$_6$H$_4$–Cl) | 1.6 h | 6.4 h (calculated) |
| (structure: 2'-carbamate uridine with –O–CH(CH$_3$)CH$_2$–SO$_2$–C$_6$H$_4$–Cl) | 2.4 h | 9.6 h (calculated) |
| (structure: 2'-carbamate uridine with –O–CH$_2$CH$_2$–SO$_2$–C$_6$H$_5$) | 3.2 h | 12.8 h (calculated) |
| (structure: 2'-carbamate uridine with –O–CH$_2$CH$_2$–SO$_2$–C$_6$H$_4$–OCH$_3$) | 3.3 h | 13 h (calculated) |
| (structure: 2'-carbamate uridine with –O–CH(CH$_3$)CH$_2$–SO$_2$–C$_6$H$_5$) | 8.0 h | 32 h (calculated) |
| (structure: 2'-carbamate uridine with –O–CH(CH$_3$)CH$_2$–SO$_2$–C$_6$H$_4$–CH$_3$ (p-tolyl)) | 12.5 h | 48 h (actual) |
| (structure: 2'-carbamate uridine with –O–CH(CH$_3$)CH$_2$–SO$_2$–2,4-dimethylphenyl) | — | 50 h (actual) |

| Structure | $T_{1/2}$ at pH 8.0 | $T_{1/2}$ at pH 7.4 |
|---|---|---|
| 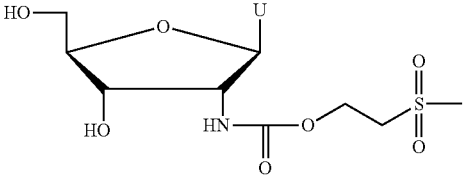 | — | 56 h (actual) |
| 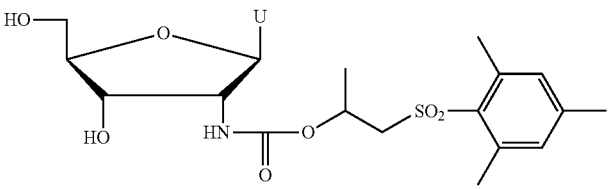 | 19 h | 77 h (actual) |
| 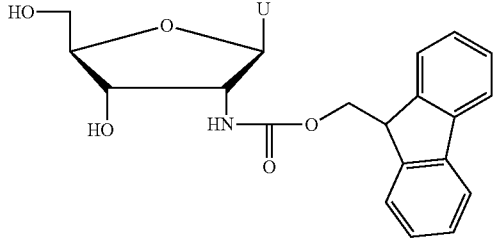 | 7.3 day | 29 day (calculated) |
| 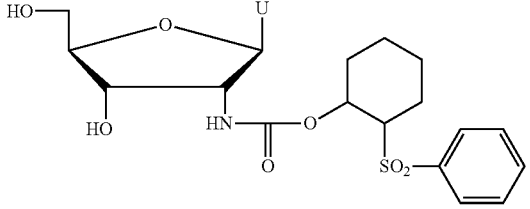 | Stable | Stable |

Certain Embodiments

In some embodiments, this document provides the compounds of Formula (I) and Formula (II), as well as pharmaceutical compositions and methods of using these compounds, as described in paragraphs 1-126.

Paragraph 1. A compound of Formula (I)

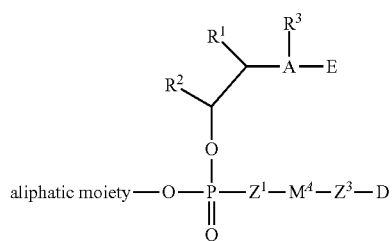

or a pharmaceutically acceptable salt thereof, wherein:

the aliphatic moiety is selected from a polymer, $R^P$, and a group selected from:

polymer-L-$(CH_2)_m$— and polymer-L-$(CH_2-CH_2-O)_p-(CH_2)_m$—;

$R^P$ is selected from optionally substituted $C_{1-6}$ alkyl, optionally substituted $C_{1-3}$ alkyl-O—$(CH_2-CH_2-O)_p-(CH_2)_m$—, and optionally substituted $C_{3-7}$ cycloalkyl;

L is a linking group;

m and p are each independently an integer from 1 to 10;

D is a residue of a GLP-1 polypeptide or an analog thereof;

$Z^1$ is selected from O, S, and $N(R^N)$;

$Z^3$ is selected from O and $N(R^N)$, or $Z^3$ is absent;

A is O or N, wherein when A is O then $R^3$ is absent;

$R^N$ is selected from H and optionally substituted $C_{1-6}$ alkyl;

$R^3$ is selected from H and $C_{1-6}$ alkyl, or $R^3$ and $R^1$, together with A and the carbon atom to which $R^1$ is attached, form an optionally substituted 4 to 7 membered aliphatic heterocyclic ring; or $R^3$ and $R^2$, together with A, the carbon atom to which $R^1$ is attached, and the carbon atom to which $R^2$ is attached, form an optionally substituted 4 to 8 membered aliphatic heterocyclic ring;

$M^A$ is a self-immolative group having any one of formulae (a)-(i):

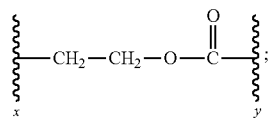
(a)

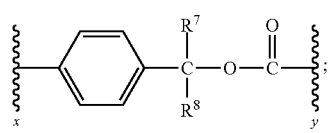
(b)

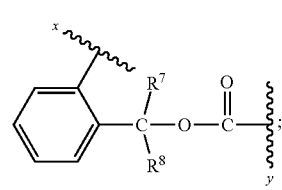
(c)

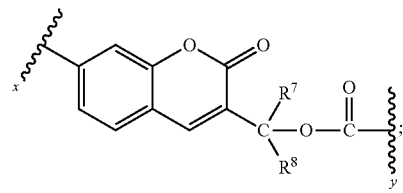
(d)

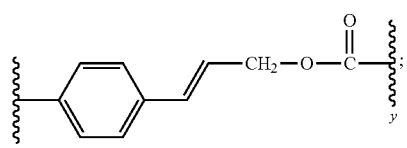
(e)

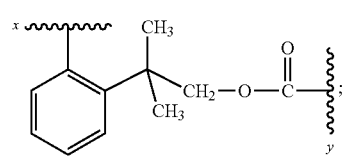
(f)

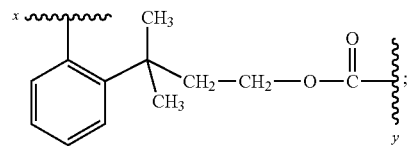
(g)

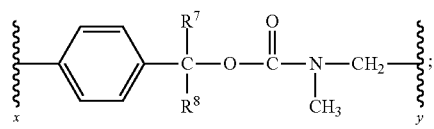
(h)

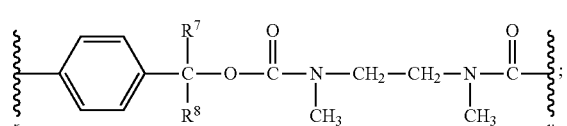
(i)

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H and $C_{1-6}$ alkyl; and

E is a cleavable moiety.

Paragraph 2. A compound of Formula (II):

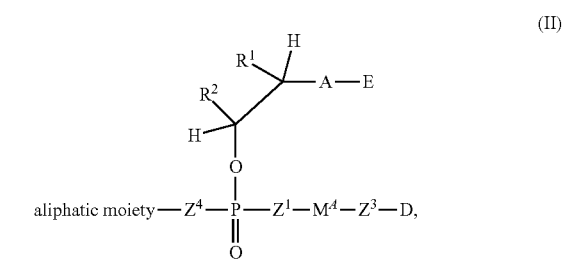
(II)

or a pharmaceutically acceptable salt thereof, wherein:

the aliphatic moiety is selected from a polymer, $R^P$, and a group selected from:

polymer-L-$(CH_2)_m$— and polymer-L-$(CH_2-CH_2-O)_p-(CH_2)_m$—;

$R^P$ is selected from optionally substituted $C_{1-6}$ alkyl, optionally substituted $C_{1-3}$ alkyl-O—$(CH_2-CH_2-O)_p-(CH_2)_m$—, and optionally substituted $C_{3-7}$ cycloalkyl;

L is a linking group;

m and p are each independently an integer from 1 to 10;

D is a residue of a biologically active drug;

$Z^1$ is selected from O, S, and $N(R^N)$;

$Z^3$ is selected from O and $N(R^N)$, or $Z^3$ is absent;

$Z^4$ is selected from O and S;

A is selected from O and $N(R^N)$;

$R^N$ is selected from H and optionally substituted $C_{1-4}$ alkyl;

$M^A$ is a diradical selected from:

i. a self-immolative group having any one of formulae (a)-(i):

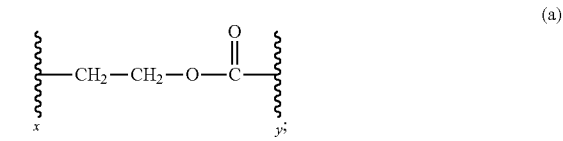
(a)

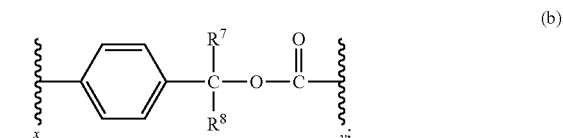
(b)

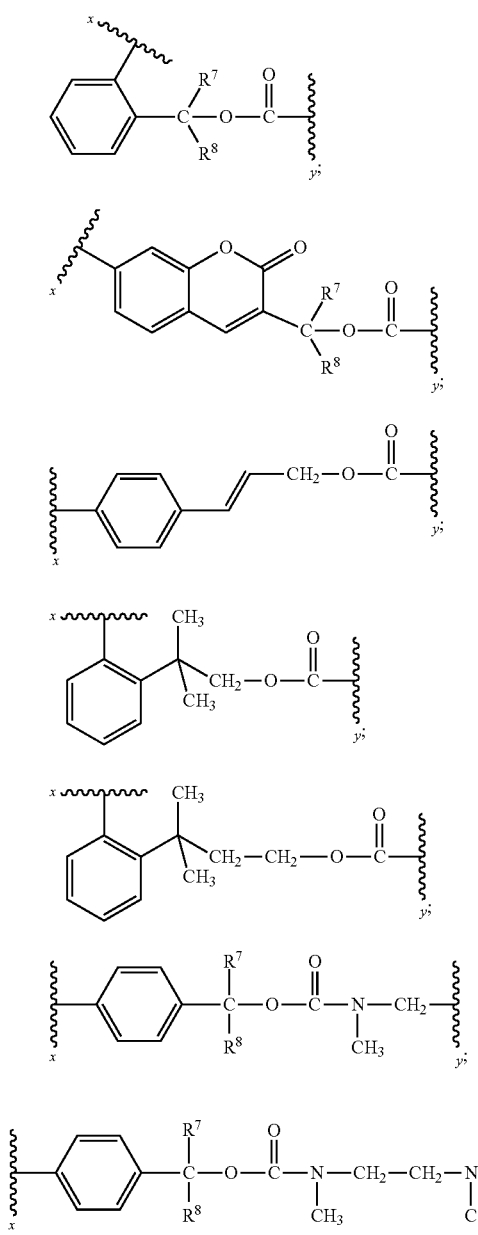

and
ii. a stable diradical selected from any one of formulae (j)-(l):

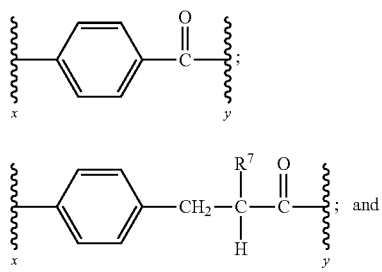

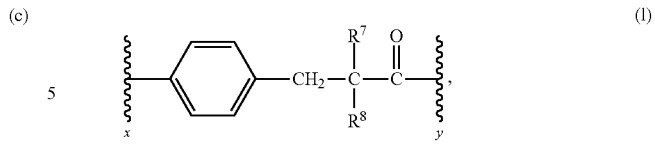

wherein x denotes a point of attachment to $Z^1$ and y denotes a point of attachment to $Z^3$;

$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;

or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5- to 14-membered heteroaryl;

or $R^1$ and $R^2$ are joined together to form a ribose ring system;

$R^7$ and $R^8$ are independently selected from H, $C_{1-6}$ alkyl, amino, ($C_{1-6}$ alkyl)amino, di-($C_{1-6}$ alkyl)amino, acylamino, and a protected amino group; and E is a cleavable moiety.

Paragraph 3. The compound of any one of the above paragraphs, wherein the aliphatic moiety is selected from a polymer, $R^P$, and a group of formula:

polymer-L-$(CH_2)_m$—;

$R^P$ is selected from optionally substituted $C_{1-6}$ alkyl and optionally substituted $C_{3-7}$ cycloalkyl; and m is an integer from 1 to 10.

Paragraph 4. The compound of any one of the above paragraphs, wherein the aliphatic moiety is a group of formula: polymer-L-$(CH_2)_m$—.

Paragraph 5. The compound of any one of the above paragraphs, wherein L is a linking group comprising a heterocycloakylene or a heteroarylene.

Paragraph 6. The compound of any one of the above paragraphs, wherein L is a linking group comprising a succinimide or a triazole.

Paragraph 7. The compound of any one of the above paragraphs, wherein L is a linking group of any one of the following formulae:

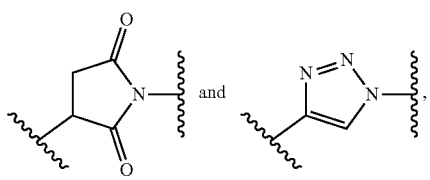 [SMILES: *C1CC(=O)N(*)C1=O ; *c1cn(*)nn1]

wherein ⁝ indicates a point of attachment of the linking group to the polymer or to the $CH_2$ group.

Paragraph 8. The compound of any one of the above paragraphs, wherein the linking group L is a linking group of formulae:

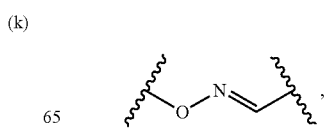

wherein ⁂ indicates a point of attachment of the linking group to the polymer or to the CH₂ group.

Paragraph 9. The compound of any one of the above paragraphs, wherein the linking group L comprises a group of formula (L¹):

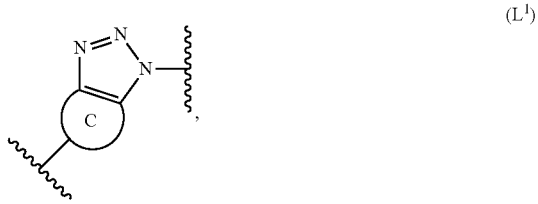

wherein ring C is selected from the group consisting of an optionally substituted $C_{8-16}$ cycloalkyl and an optionally substituted 8-16-membered heterocycloalkyl, and ⁂ indicates a point of attachment of the linking group to the polymer or to the CH₂ group.

Paragraph 10. The compound any one of the above paragraphs, wherein the group of formula (L¹) is selected from any one of the following formulae:

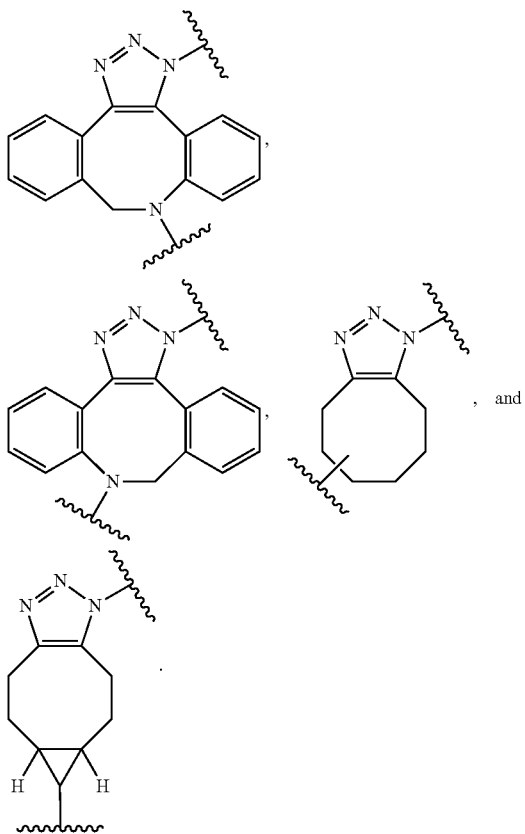

Paragraph 11. The compound of any one of the above paragraphs, wherein m is an integer from 1 to 6.
Paragraph 12. The compound of any one of the above paragraphs, wherein m is an integer from 1 to 4.
Paragraph 13. The compound of any one of the above paragraphs, wherein the aliphatic moiety is a polymer.
Paragraph 14. The compound of any one of the above paragraphs, wherein the polymer is selected from the group consisting of poly(alkylene glycol), poly(oxyethylated polyol), poly(olefinic alcohol), poly(α-hydroxy acid), poly (vinyl alcohol), polyoxazoline, and copolymers thereof.
Paragraph 15. The compound of any one of the above paragraphs, wherein the polymer is a polyethylene glycol.
Paragraph 16. The compound of any one of the above paragraphs, wherein the polyethylene glycol is linear.
Paragraph 17. The compound of any one of the above paragraphs, wherein the polyethylene glycol is branched.
Paragraph 18. The compound of any one of the above paragraphs, wherein the polyethylene glycol has an average molecular weight from about 500 Da to about 40,000 Da.
Paragraph 19. The compound of any one of the above paragraphs, wherein the polyethylene glycol has an average molecular weight from about 1,000 Da to about 30,000 Da.
Paragraph 20. The compound of any any one of the above paragraphs, wherein the polyethylene glycol has an average molecular weight from about 1,000 Da to about 20,000 Da.
Paragraph 21. The compound of any one of the above paragraphs, wherein the polyethylene glycol has an average molecular weight from about 5,000 Da to about 20,000 Da.
Paragraph 22. The compound of any one of the above paragraphs, wherein the polyethylene glycol has the following structural formula:

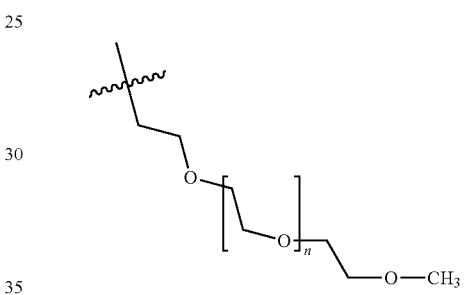

Paragraph 23. The compound of any one of the above paragraphs, wherein n is an integer from 1 to 1,000.
Paragraph 24. The compound of any one of the above paragraphs, wherein n is an integer from 1 to 800.
Paragraph 25. The compound of any one of the above paragraphs, wherein n is an integer from 1 to 300.
Paragraph 26. The compound of any one of the above paragraphs, wherein n is an integer from 1 to 100.
Paragraph 27. The compound of any one of the above paragraphs, wherein n is selected from 10, 20, 50, 100, 200, 250, 300, 500, 600, and 1000.
Paragraph 28. The compound of any one of the above paragraphs, wherein the aliphatic moiety is $R^P$.
Paragraph 29. The compound of any one of the above paragraphs, wherein $R^P$ is an optionally substituted $C_{1-6}$ alkyl.
Paragraph 30. The compound of any one of the above paragraphs, wherein $R^P$ is isopropyl.
Paragraph 31. The compound of any one of the above paragraphs, wherein $R^P$ is cyanoethyl.
Paragraph 32. The compound of any one of the above paragraphs, wherein $R^P$ is selected from the group of any one of the following formulae:

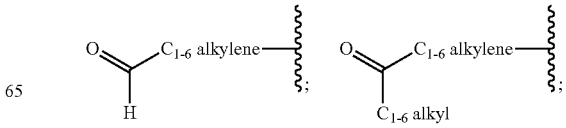

-continued

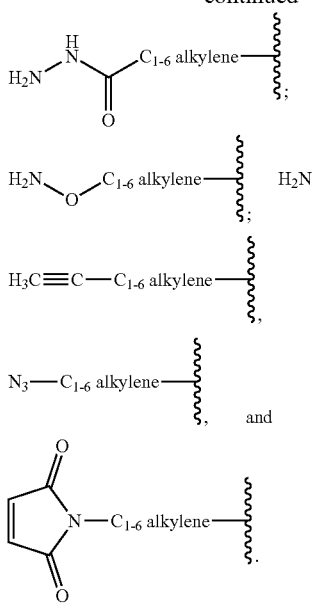

Paragraph 33. The compound of any one of the above paragraphs, wherein $R^P$ is selected from the group of any one of the following formulae:

Paragraph 34.

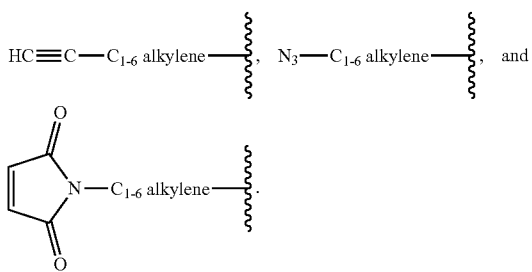

Paragraph 35. The compound of any one of the above paragraphs, wherein $R^P$ is selected from any one of the following formulae:

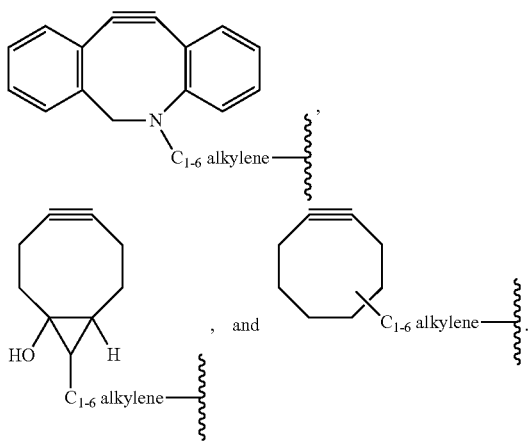

Paragraph 36. The compound of any one of the above paragraphs, wherein $Z^1$ is S and $M^4$ is a self-immolative group of formula (a):

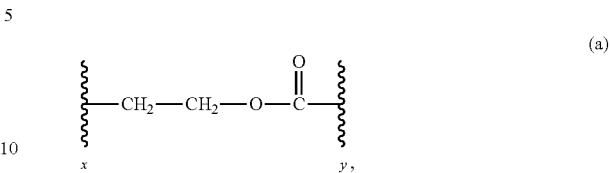

(a)

wherein x denotes a point of attachment to $Z^1$ and y denotes a point of attachment to $Z^3$.

Paragraph 37. The compound of any one of the above paragraphs, wherein $R^7$ and $R^8$ are independently selected from H and methyl.

Paragraph 38. The compound of any one of the above paragraphs, wherein $R^1$ and $R^2$ are each hydrogen.

Paragraph 39. The compound of any one of the above paragraphs, wherein $R^1$ and $R^2$ together form $C_{3-7}$ cycloalkyl ring.

Paragraph 40. The compound of any one of the above paragraphs, wherein the $C_{3-7}$ cycloalkyl ring is selected from the group consisting of cyclopropyl, cyclobutyl, cyclopentyl and cyclohexyl.

Paragraph 41. The compound of any one of the above paragraphs, wherein $R^1$ and $R^2$ together form a 4 to 7 membered aliphatic heterocyclic ring.

Paragraph 42. The compound of any one of the above paragraphs, wherein the 4 to 7 membered aliphatic heterocyclic ring is selected from the group consisting of pyrrolidine, piperidine, tetrahydrofuran and tetrahydropyran.

Paragraph 43. The compound of any one of the above paragraphs, wherein $R^1$ and $R^2$ together form a ribose ring system of a ribonucleoside.

Paragraph 44. The compound of any one of the above paragraphs, wherein $R^1$ and $R^2$ together form a ribose ring system of formula:

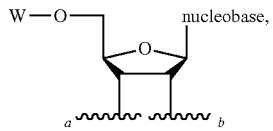

wherein either a denotes a point of attachment to O and b denotes a point of attachment to A, a denotes a point of attachment to A and b denotes a point of attachment to O, and wherein W is selected from the group consisting of H, an acyl group and a protecting group.

Paragraph 45. The compound of any one of the above paragraphs, wherein the nucleobase is selected from the group consisting of adenine, cytosine, guanine, thymine, uracil, and other natural and non-natural nucleobases.

Paragraph 46. The compound of any one of the above paragraphs, wherein the nucleobase is selected from the group consisting of adenine, cytosine, guanine, thymine and uracil.

Paragraph 47. The compound of any one of the above paragraphs, wherein the nucleobase is selected from the group consisting of 5-methylcytosine, pseudouridine, dihydrouridine, inosine, 7-methylguanosine, hypoxanthine and xanthine.

Paragraph 48. The compound of any one of the above paragraphs, wherein the nucleobase comprises a fluorescent group.

Paragraph 49. The compound of any one of the above paragraphs, wherein the nucleobase comprises a polymer.

Paragraph 50. The compound of any one of the above paragraphs, wherein $R^1$ and $R^2$ together form a ribose ring system of formula:

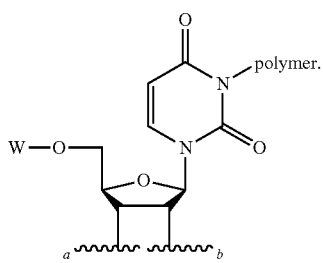

Paragraph 51. The compound of any one of the above paragraphs, wherein $R^1$ and $R^2$ together form a ribose ring system of formula:

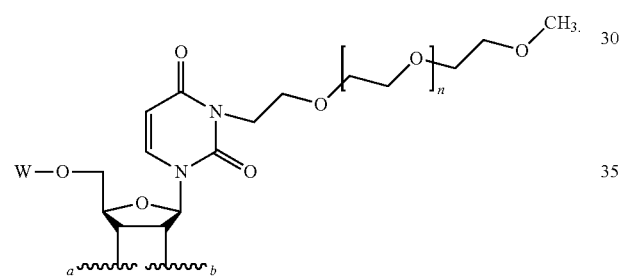

Paragraph 52. The compound of any one of the above paragraphs, wherein A is O.

Paragraph 53. The compound of any one of the above paragraphs, wherein A is $NR^3$.

Paragraph 54. The compound of any one of the above paragraphs, wherein $R^3$ and $R^1$, together with A and the carbon atom to which $R^1$ is attached, form an optionally substituted 4 to 7 membered aliphatic heterocyclic ring.

Paragraph 55. The compound of any one of the above paragraphs, wherein the 4 to 7 membered aliphatic heterocyclic ring is selected from the group consisting of:

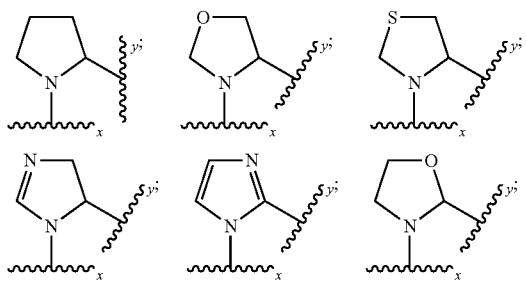

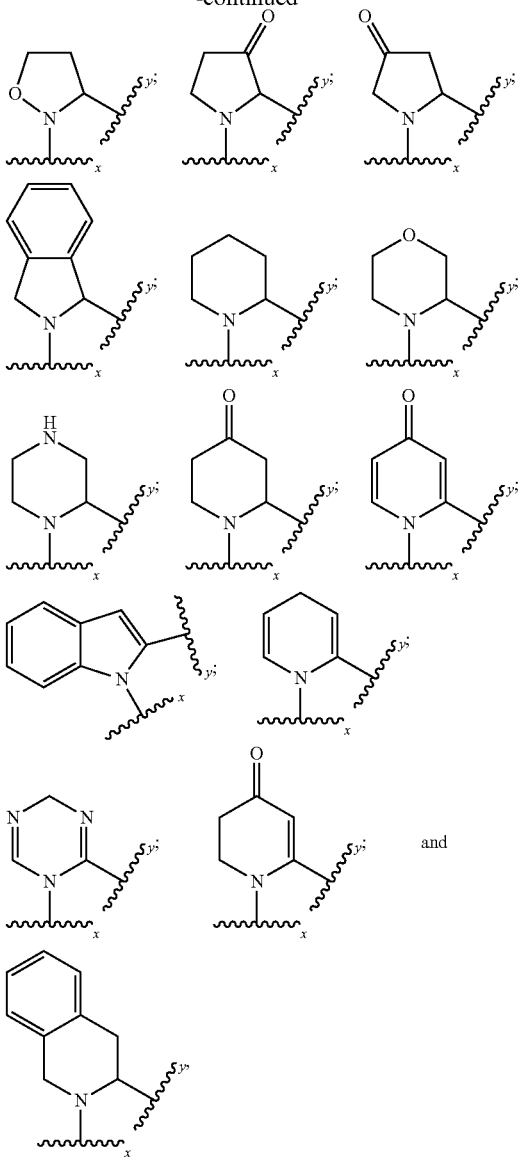

wherein x denotes a point of attachment to E, and y denotes a point of attachment to the carbon atom to which $R^1$ is attached.

Paragraph 56. The compound of any one of the above paragraphs, wherein $R^3$ and $R^2$, together with A, the carbon atom to which $R^1$ is attached, and the carbon atom to which $R^2$ is attached, form an optionally substituted 4 to 8 membered aliphatic heterocyclic ring.

Paragraph 57. The compound of any one of the above paragraphs, wherein A is NH.

Paragraph 58. The compound of any one of the above paragraphs, wherein A is $N(C_{1-6}$ alkyl).

Paragraph 59. The compound of any one of the above paragraphs, wherein E is cleavable by an enzyme selected from the group consisting of an esterase, a specific or an unspecific peptidase, a reductase, an oxidase, a glycosidase, a hydrolase, a glycosyl transferase, and a transaminase.

Paragraph 60. The compound of any one of the above paragraphs, wherein E is cleavable by an enzyme selected from the group consisting of an esterase, a reductase, an oxidase, a glycoside, a hydrolase and glycosyl transferase.

Paragraph 61. The compound of any one of the above paragraphs, wherein E is non-enzymatically cleavable at acidic or physiological pH.

Paragraph 62. The compound of any one of the above paragraphs, wherein E is an acyl group, a O-methyl-acyl group, a methyl azido group, a sugar residue, a protected acetal, or a carbonate ester.

Paragraph 63. The compound of any one of the above paragraphs, wherein E is cleavable by a reductase enzyme.

Paragraph 64. The compound of any one of the above paragraphs, wherein A is O and E is a group of formula:

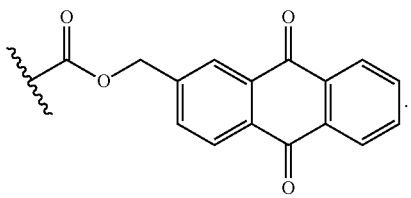 [SMILES: *C(=O)OCc1ccc2c(c1)C(=O)c1ccccc1C2=O]

Paragraph 65. The compound of any one of the above paragraphs, wherein E contains a dithio group which is cleavable by a biogenic thiol.

Paragraph 66. The compound of any one of the above paragraphs, wherein E is cleavable by a glutathione.

Paragraph 67. The compound of any one of the above paragraphs, wherein E is a group of any one of the following formulae:

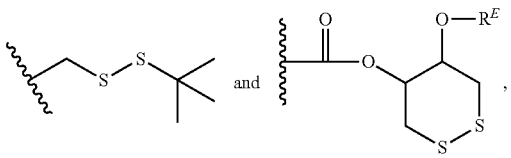

wherein $R^E$ is selected from the group consisting of $C_{1-6}$ alkyl and benzyl.

Paragraph 68. The compound of any one of the above paragraphs, wherein A is O, and E is a group of formula:

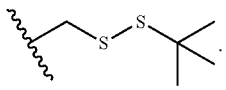 [SMILES: *CSSC(C)(C)C]

Paragraph 69. The compound of any one of the above paragraphs, wherein E is cleavable by glycoside hydrolase enzyme.

Paragraph 70. The compound of any one of the above paragraphs, wherein E is a residue of a sugar selected from glucose, galactose, mannose and glucuronic acid.

Paragraph 71. The compound of any one of the above paragraphs, wherein E is cleavable by an esterase enzyme.

Paragraph 72. The compound of any one of the above paragraphs, wherein E is selected from an acyl group, a carbonate ester and a O-methyl-acyl ester.

Paragraph 73. The compound of any one of the above paragraphs, wherein E is cleavable by hydrolysis at physiological pH.

Paragraph 74. The compound of any one of the above paragraphs, wherein E is an acyl group.

Paragraph 75. The compound of any one of the above paragraphs, wherein A is $NR^N$ or $NR^3$, and E is a cleavable moiety of formula:

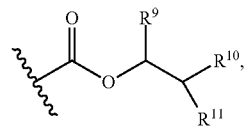

wherein:
$R^9$ is selected from H, an optionally substituted $C_{6-10}$ aryl, and an optionally substituted $C_{1-6}$ alkyl;

$R^{10}$ and $R^{11}$ are each independently selected from H, CN, $NO_2$, $COR^{12}$, $SOR^{12}$ or $SO_2R^{12}$, an optionally substituted $C_{1-6}$ alkyl, an optionally substituted $C_{6-10}$ aryl, and an optionally substituted 5- to 14-membered heteroaryl; or $R^{10}$ and $R^{11}$ together with the carbon atom to which they are attached form an optionally substituted $C_{3-7}$ cycloalkyl ring which is fused with one or more optionally substituted $C_{6-10}$ aryl rings;

$R^{12}$ is selected from an optionally substituted $C_{1-6}$ alkyl and an optionally substituted $C_{6-10}$ aryl.

Paragraph 76. The compound of any one of the above paragraphs, wherein A is NH, and $R^9$ is selected from H and an optionally substituted $C_{6-10}$ aryl.

Paragraph 77. The compound of any one of the above paragraphs, wherein E is a cleavable moiety of any one of the following formulae (E-1) to (E-12) and (E-37) to (E-42):

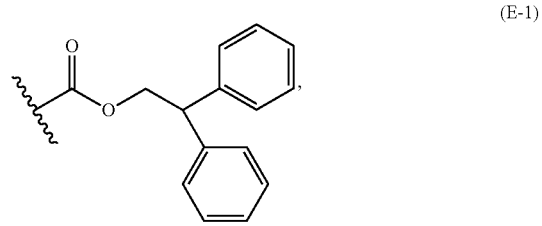
(E-1)

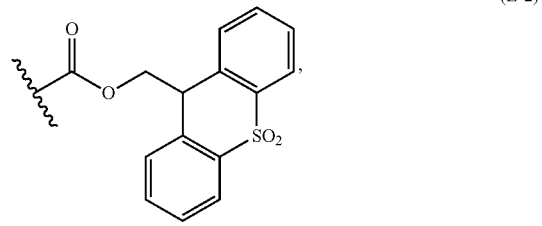
(E-2)

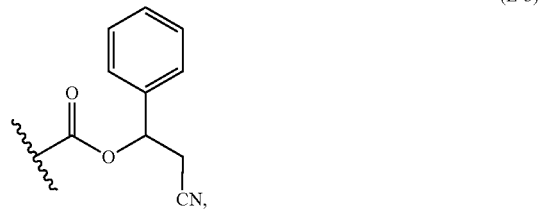
(E-3)

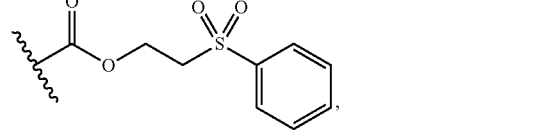
(E-4)

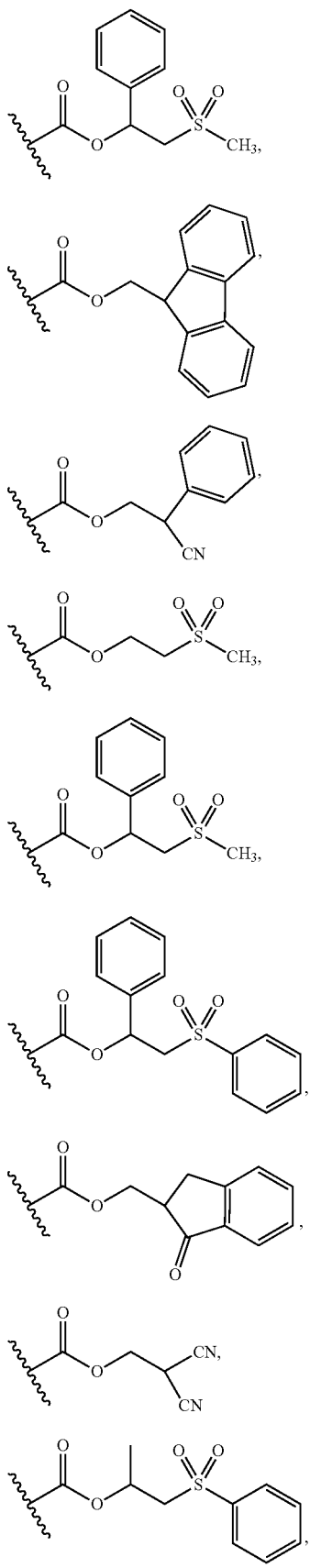
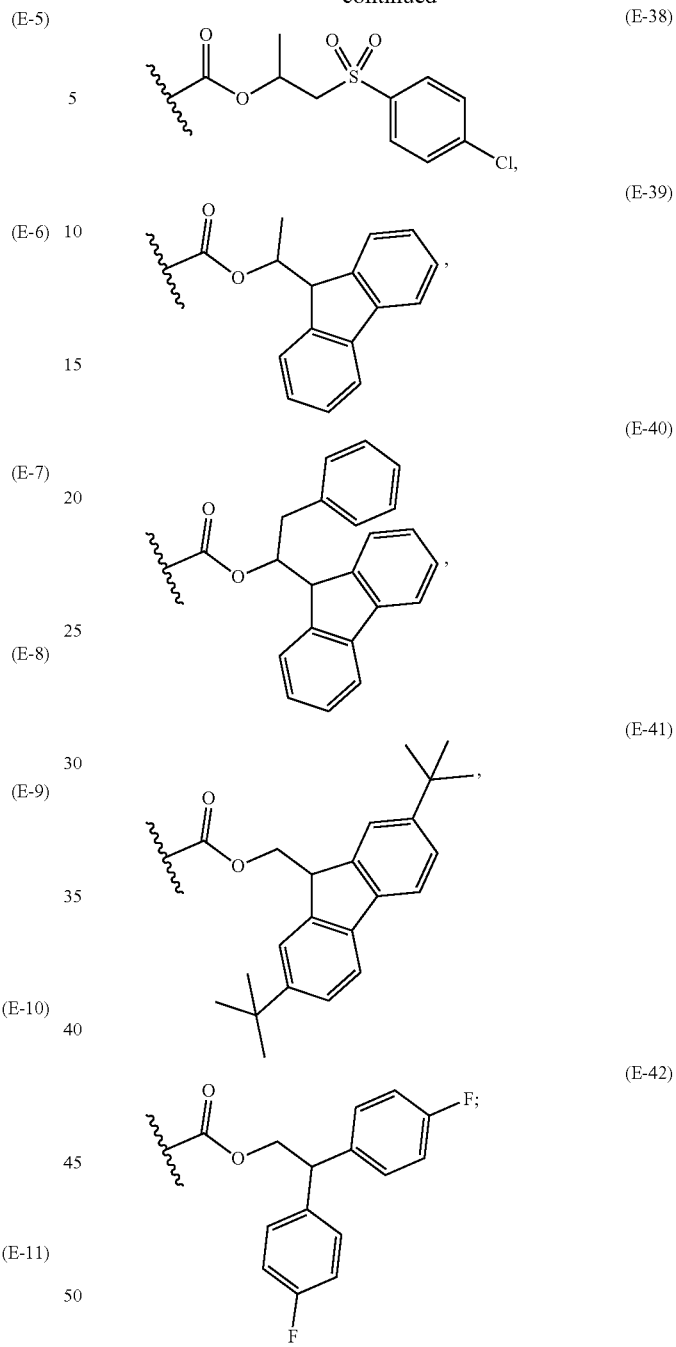

wherein any one of the phenyl rings in the formulae (E-1) to (E-12), (E-37) or (E-39) to (E-41) is optionally substituted with 1, 2, 3, 4, or 5 substituents selected from $C_{1-10}$ alkyl, $C_{1-10}$ haloalkyl, $C_{1-10}$ alkoxy, OH, $NO_2$, CN, halogen and acyl.

Paragraph 78. The compound of any one of the above paragraphs, wherein E is a cleavable moiety of any one of the following formulae (E-1) to (E-12), (E-37), or (E-39) to (E-41).

Paragraph 79. The compound of any one of the above paragraphs, wherein any one of the phenyl rings in the formulae (E-1) to (E-12), (E-37), or (E-39) to (E-41) is optionally substituted with 1, 2, 3, or 4 substituents selected from F, Cl, CN, acetyl, $NO_2$ and $CF_3$.

Paragraph 80. The compound of any one of the above paragraphs, wherein E is a group of any one of the following formulae (E-13) to (E-36):
(E-13)
(E-14)
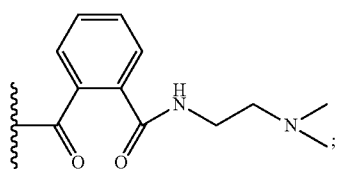
(E-15)
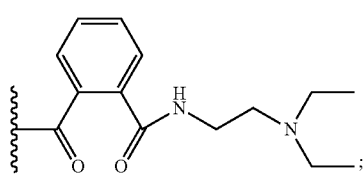
(E-16)
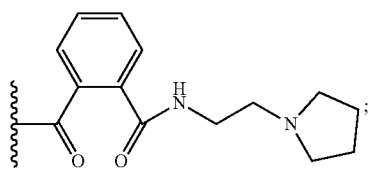
(E-17)
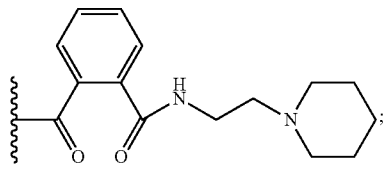
(E-18)
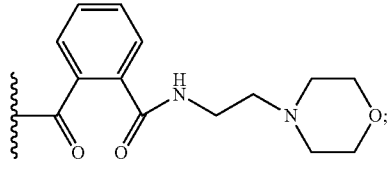
(E-19)
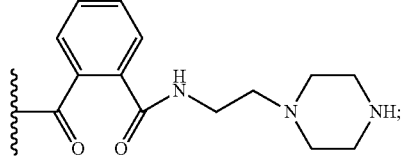
(E-20)
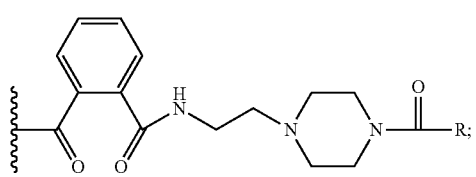
-continued
(E-21)
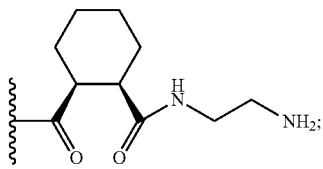
(E-22)
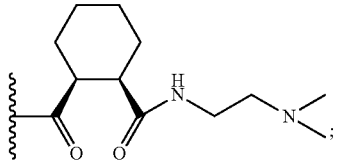
(E-23)
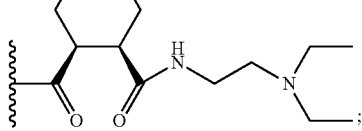
(E-24)
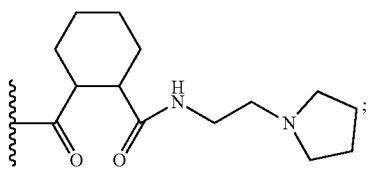
(E-25)
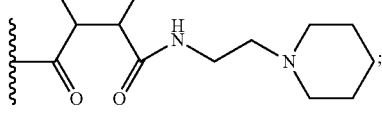
(E-26)
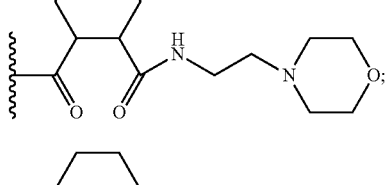
(E-27)
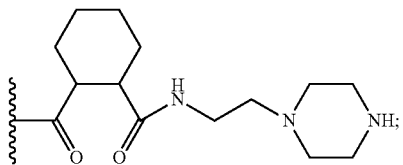
(E-28)
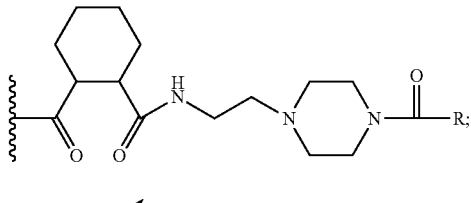
(E-29)
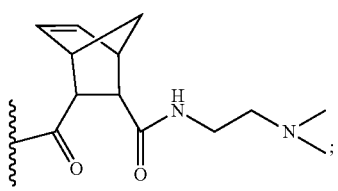

(E-30)
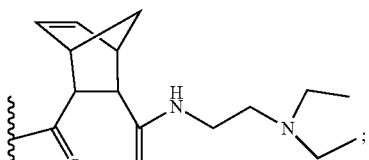

(E-31)
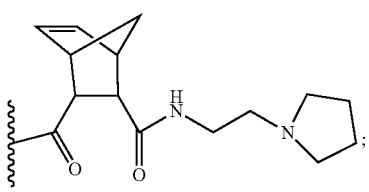

(E-32)
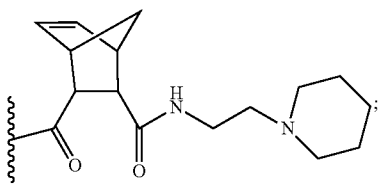

(E-34)
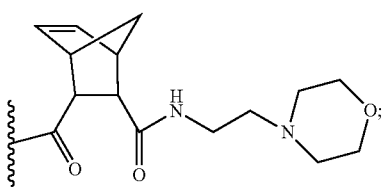

(E-35)
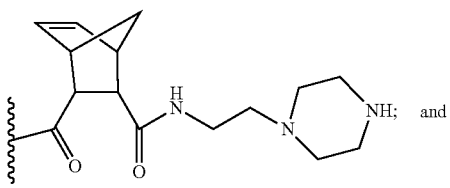

and (E-36)
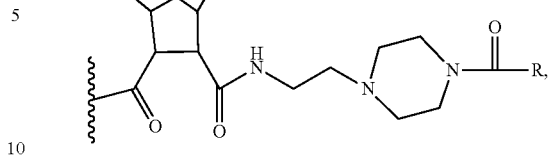

wherein R is $C_{1-6}$ alkyl.

Paragraph 81. The compound of any one of the above paragraphs wherein E is cleavable at acidic pH.

Paragraph 82. The compound of any one of the above paragraphs, wherein E is a group selected from an acetal, an ortho-ester, and substituted triphenyl methylethers.

Paragraph 83. The compound of any one of the above paragraphs, wherein E is selected from tetrahydrofuranyl, 4-methoxytetrahydropyran-4-yl, 1,5-dicarbo-methoxypentanyl, methoxy isopropyl acetal, methoxy cyclohexenyl acetal, dimethoxytrityl, trimethoxytrityl and pixyl.

Paragraph 84. The compound of any one of the above paragraphs, wherein a cleavable moiety E is attached to A using a group of formula ($L^E$):

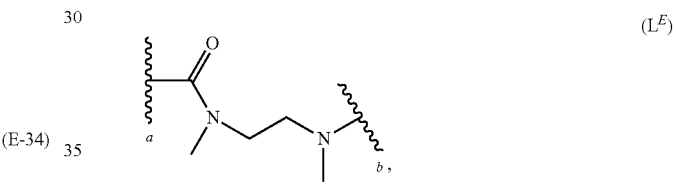

($L^E$)

wherein a denotes a point of attachment to A, and b denotes a point of attachment to E.

Paragraph 85. The compound of any one of the above paragraphs, wherein D is a residue of a GLP-1 polypeptide.

Paragraph 86. The compound of any one of the above paragraphs, wherein D is a residue of a GLP-1 polypeptide analog.

Paragraph 87. The compound of any one of the above paragraphs, wherein the GLP-1 polypeptide analog is liraglutide.

Paragraph 88. The compound of any one of the above paragraphs, wherein the compound of Formula (I) has any one of the following formulae:

(I-1)
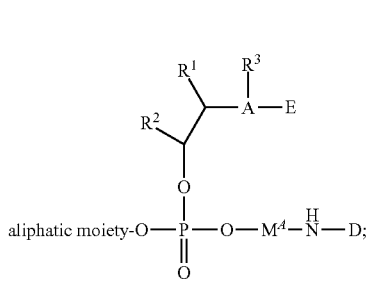

(I-2)
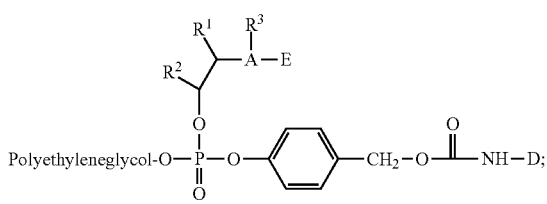

-continued
(I-3)
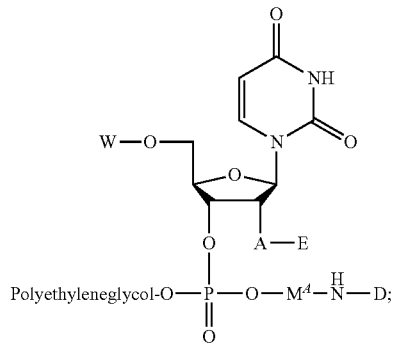
(I-4)
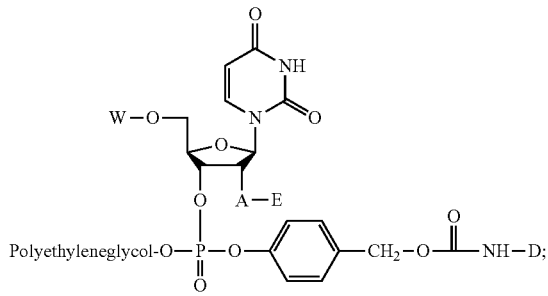
(I-5)
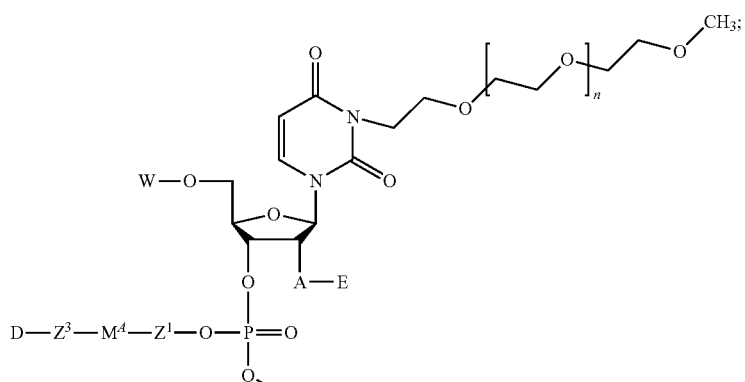
(I-6)
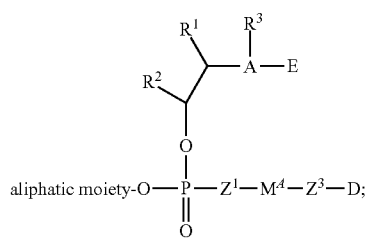
(I-7)
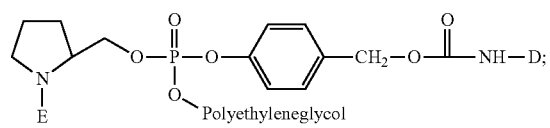
(I-8)
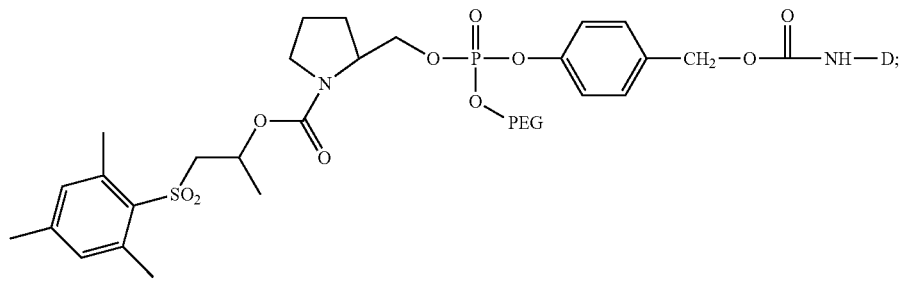
(I-9)
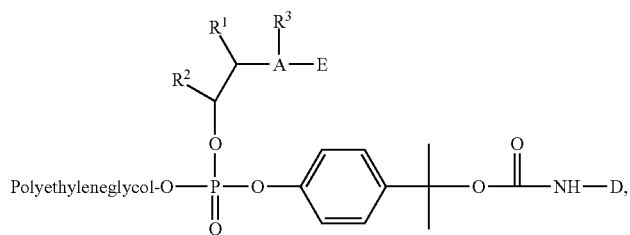
or a pharmaceutically acceptable salt thereof.

Paragraph 89. A compound of Formula (II-1):

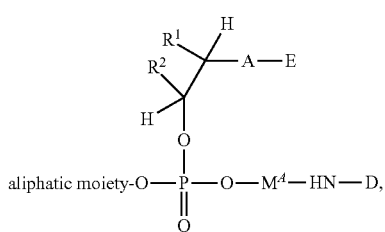
(II-1)

or a pharmaceutically acceptable salt thereof.

Paragraph 90. The compound of any one of the above paragraphs, wherein the compound of Formula (II) has Formula (II-2):

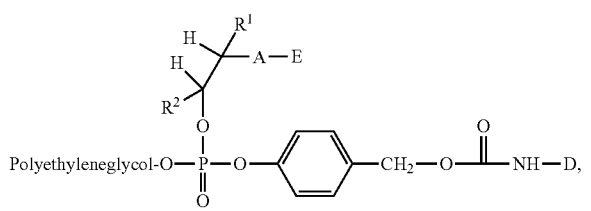
(II-2)

or a pharmaceutically acceptable salt thereof.

Paragraph 91. The compound of any one of the above paragraphs, wherein the compound of Formula (II) has Formula (II-3):

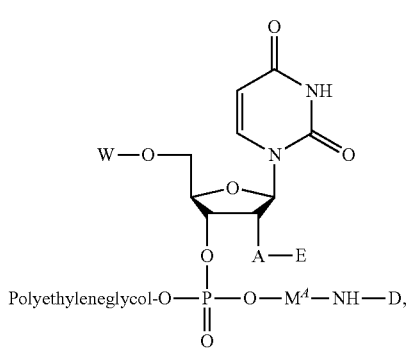
(II-3)

or a pharmaceutically acceptable salt thereof.

Paragraph 92. The compound of any one of the above paragraphs, wherein the compound of Formula (II) has Formula (II-4):

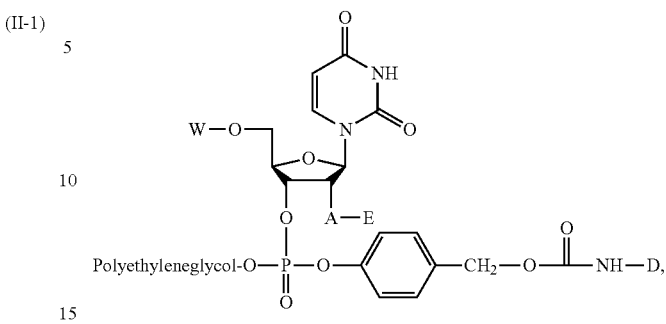
(II-4)

or a pharmaceutically acceptable salt thereof.

Paragraph 93. The compound of any one of the above paragraphs, wherein the compound of Formula (II) has any one of the following Formulae (II-5) to (II-7):

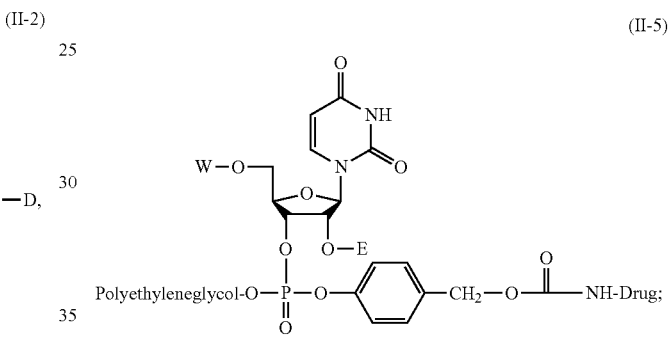
(II-5)

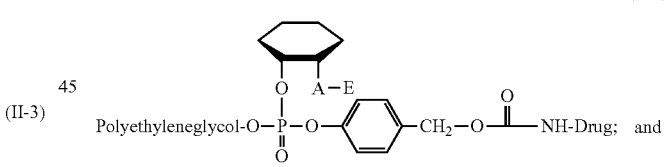
(II-6)

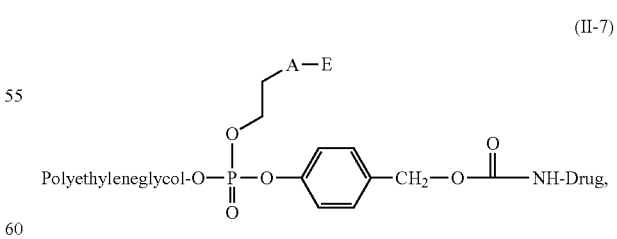
(II-7)

or a pharmaceutically acceptable salt thereof,
wherein when the compound has Formula 11-7, A is O.

Paragraph 94. The compound of any one of the above paragraphs, wherein the compound of Formula (II) has Formula (II-8):

(II-8)

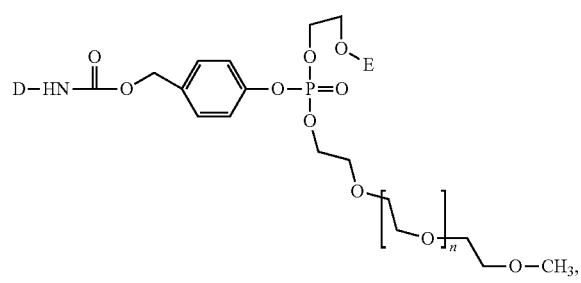

or a pharmaceutically acceptable salt thereof.

Paragraph 95. The compound of any one of the above paragraphs, wherein the compound of Formula (II) has any one of the following Formulae:

Paragraph 96. The compound of any one of the above paragraphs, wherein the compound of Formula (II) has Formula (II-10a):

(II-10a)

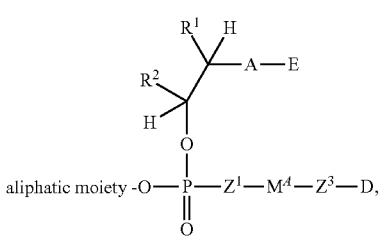

or a pharmaceutically acceptable salt thereof.

(II-9)

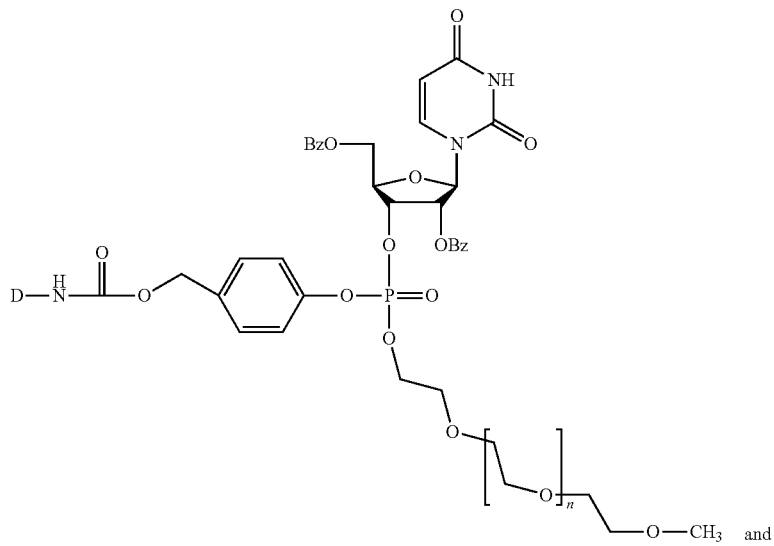

and (II-9b)

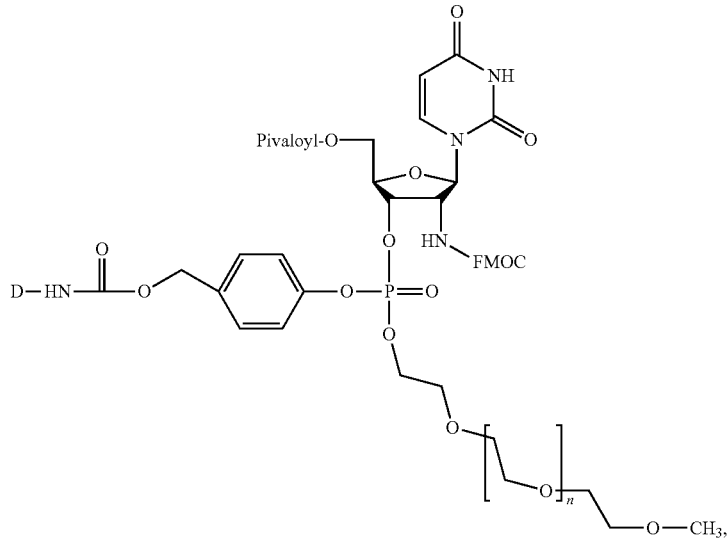

or a pharmaceutically acceptable salt thereof.

Paragraph 97. The compound of any one of the above paragraphs, wherein the compound of Formula (II) has Formula (II-10):

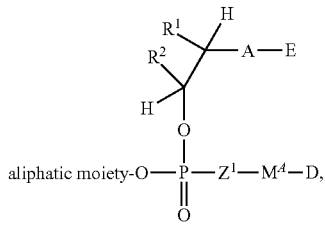
(II-10)

or a pharmaceutically acceptable salt thereof.

Paragraph 98. The compound of any one of the above paragraphs, wherein the compound of Formula (II) has Formula (II-11a):

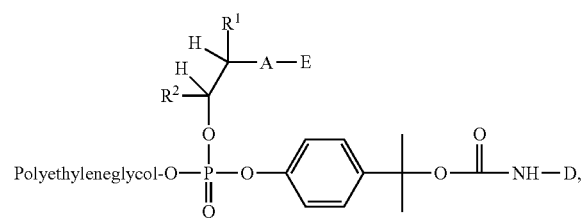
(II-11a)

or a pharmaceutically acceptable salt thereof.

Paragraph 99. The compound of any one of the above paragraphs, wherein the compound of Formula (II) has Formula (II-11):

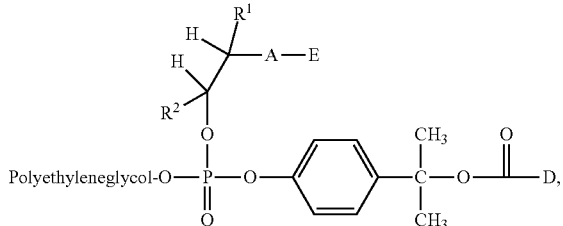
(II-11)

or a pharmaceutically acceptable salt thereof.

Paragraph 100. The compound of any one of the above paragraphs, wherein the compound of Formula (II) has Formula (II-12):

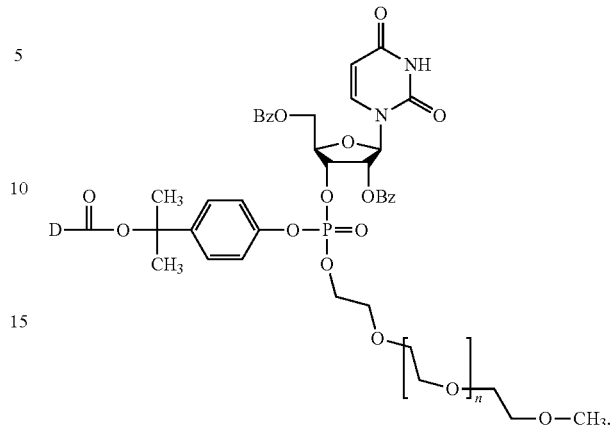
(II-12)

or a pharmaceutically acceptable salt thereof.

Paragraph 101. The compound of any one of the above paragraphs, wherein the compound of Formula (II) has Formula (II-14):

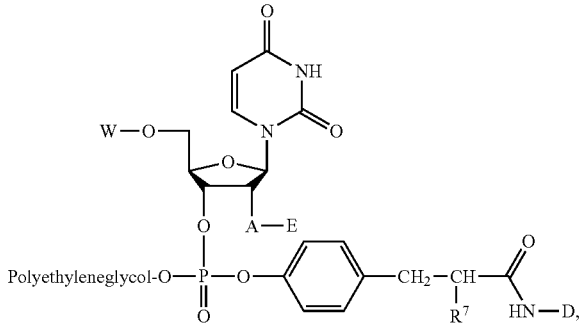
(II-14)

or a pharmaceutically acceptable salt thereof.

Paragraph 102. The compound of any one of the above paragraphs, wherein the compound of Formula (II) has Formula (II-15):

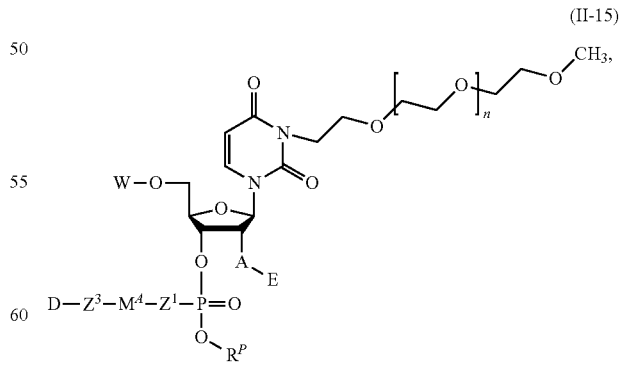
(II-15)

or a pharmaceutically acceptable salt thereof.

Paragraph 103. The compound of any one of the above paragraphs, wherein the compound of Formula (II) has Formula (II-16):

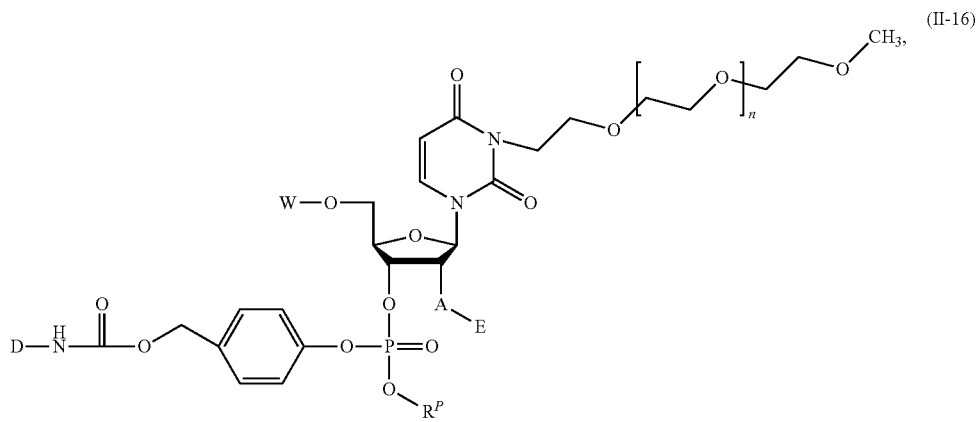

(II-16)

or a pharmaceutically acceptable salt thereof.
Paragraph 104. The compound of any one of the above paragraphs, wherein $R^P$ is $C_{1-6}$ alkyl.
Paragraph 105. The compound of any one of the above paragraphs, wherein $R^P$ is isopropyl.
Paragraph 106. The compound of any one of the above paragraphs, wherein $R^P$ is cyanoethyl.
Paragraph 107. The compound of any one of the above paragraphs wherein the compound of Formula (I) is:

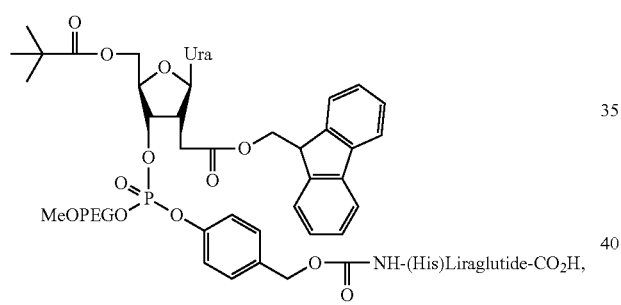

or a pharmaceutically acceptable salt thereof, wherein liragludide is the residue of liragludide.
Paragraph 108. The compound of any one of the above paragraphs, wherein the compound of Formula (I) is:

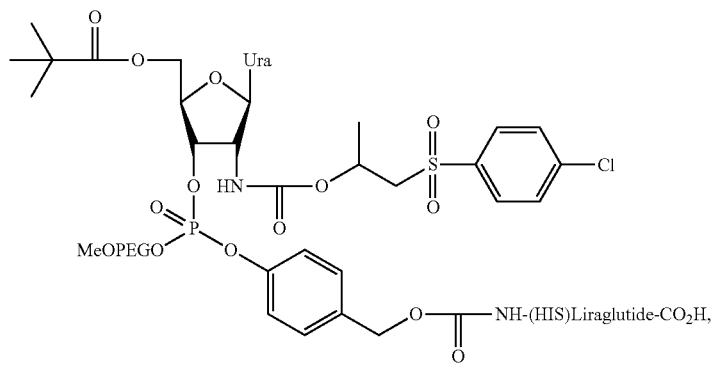

or a pharmaceutically acceptable salt thereof, wherein liragludide is the residue of liragludide.

Paragraph 109. The compound of any one of the above paragraphs, wherein the compound of Formula (I) is:

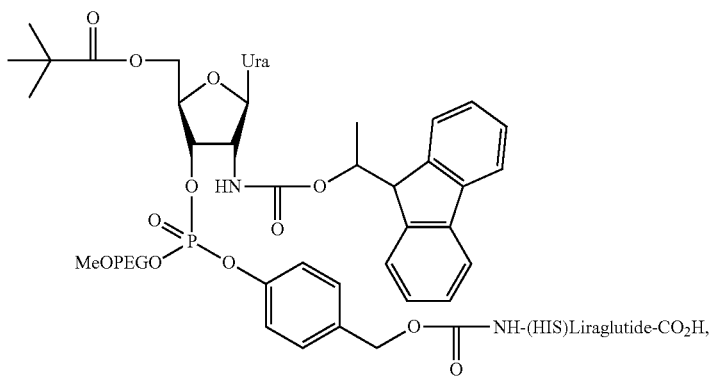

or a pharmaceutically acceptable salt thereof, wherein liragludide is the residue of liragludide.

Paragraph 110. The compound of any one of the above paragraphs, wherein the compound of Formula (I) is:

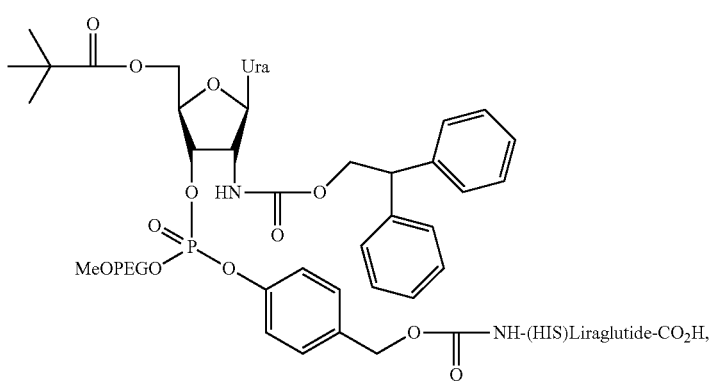

or a pharmaceutically acceptable salt thereof, wherein liragludide is the residue of liragludide.

Paragraph 111. The compound of any one of the above paragraphs, wherein the compound of Formula (I) is:

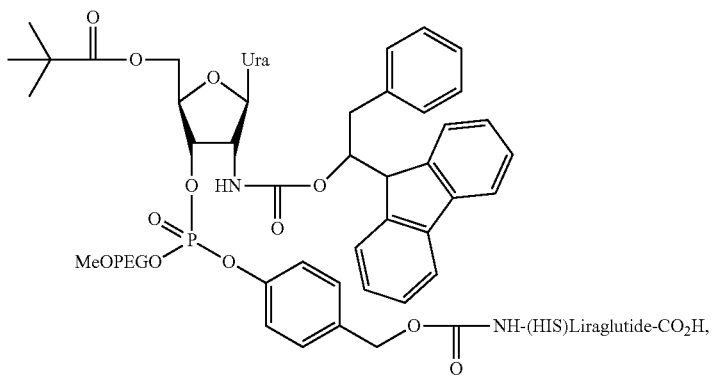

or a pharmaceutically acceptable salt thereof, wherein liragludide is the residue of liragludide.

Paragraph 112. The compound of any one of the above paragraphs, wherein the compound of Formula (I) is:

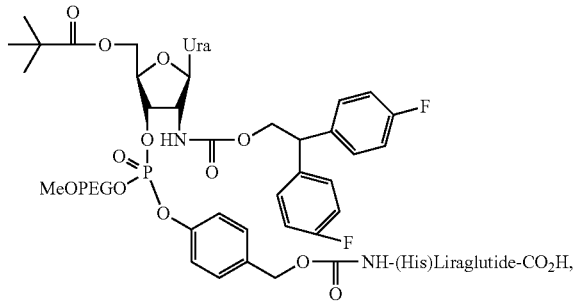

or a pharmaceutically acceptable salt thereof, wherein liragludide is the residue of liragludide.

Paragraph 113. The compound of any one of the above paragraphs, wherein the compound of Formula (I) is:

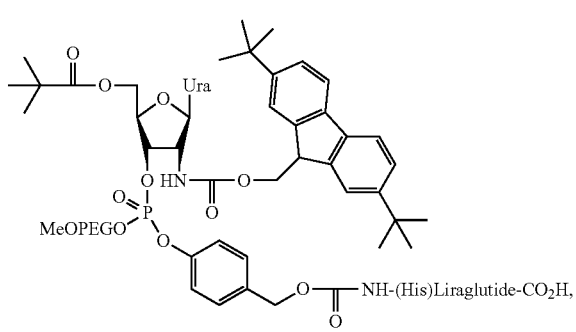

or a pharmaceutically acceptable salt thereof, wherein liragludide is the residue of liragludide.

Paragraph 114. The compound of any one of the above paragraphs, wherein the compound is not:

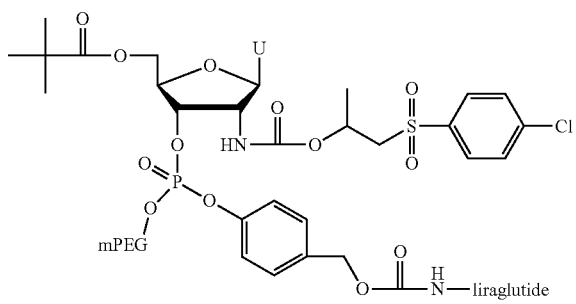

or a pharmaceutically acceptable salt thereof, wherein U is uracil.

Paragraph 115. The compound of any one of the above paragraphs, wherein E is not (E-38).

Paragraph 116. The compound of any one of the above paragraphs, wherein the compound is

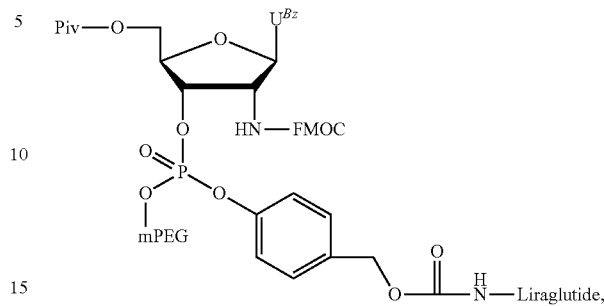

or a pharmaceutically acceptable salt thereof.

Paragraph 117. The compound of any one of the above paragraphs, wherein the compound is

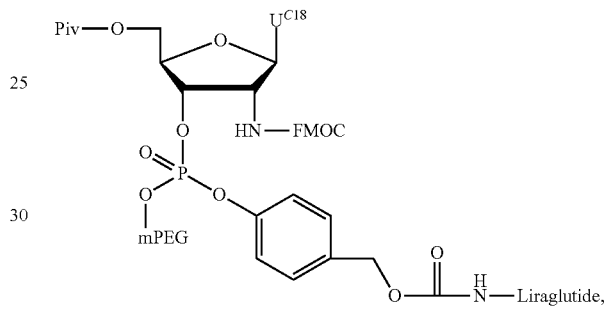

or a pharmaceutically acceptable salt thereof.

Paragraph 118. The compound of any one of the above paragraphs, wherein the compound is

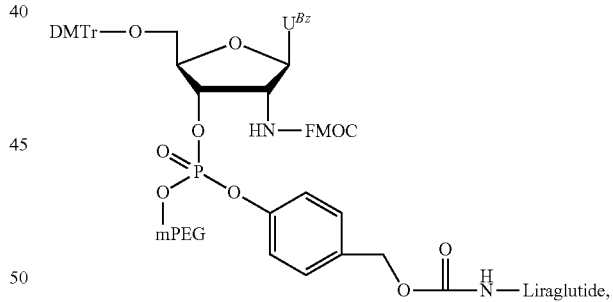

or a pharmaceutically acceptable salt thereof.

Paragraph 119. The compound of any one of the above paragraphs, wherein the Drug (e.g., liraglutide, a GLP-1 polypeptide, or an analog thereof) is inactive or weakly biologically active when conjugated in the compound Formula (I) or Formula (II), as compared to free, unconjugated form of the Drug, and regains its biological activity after the Drug is released from the compound of Formula (I) or Formula (II).

Paragraph 120. A pharmaceutical composition comprising the compound of any one of the above paragraphs, or a pharmaceutically acceptable salt thereof, and a pharmaceutically acceptable carrier.

Paragraph 121. A method of treating a disease or condition in a subject in need thereof, the method comprising administering to the subject a therapeutically effective amount of the compound of any one of any one of the above paragraphs, or a pharmaceutically acceptable salt thereof, or a pharmaceutical composition of paragraph 116.

Paragraph 122. The method of paragraph 117, wherein the disease or condition is selected from diabetes and obesity.

Paragraph 123. A method of making a compound of any one of the above paragraphs having the formula:

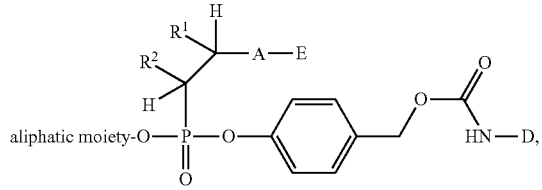

or a pharmaceutically acceptable salt thereof, the method comprising:
(i) reacting a compound of formula:

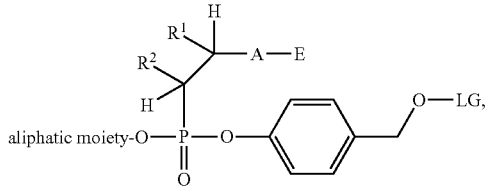

wherein LG is a leaving group, with the GLP-1 polypeptide or an analog thereof of formula $HZ^3$-D.

Paragraph 124. The method of the above paragraph, wherein the compound of formula:

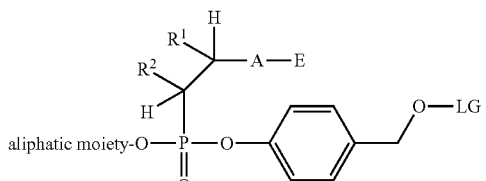

is obtained by the method comprising:
(i) deprotecting a compound of formula:

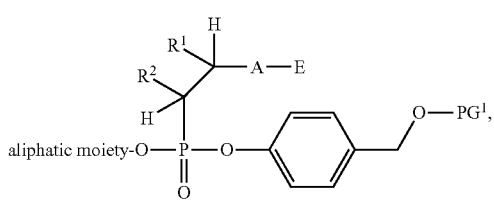

wherein $PG^1$ is a protecting group, to obtain a compound of formula:

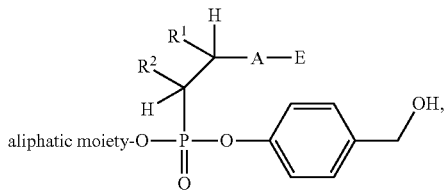

and
(ii) reacting the compound obtained in step (i) with a compound comprising a leaving group.

Paragraph 125. The method of the above paragraph, wherein the compound of formula:

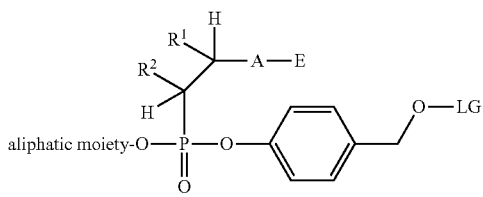

is obtained by the method comprising:
(i) reducing a compound of formula:

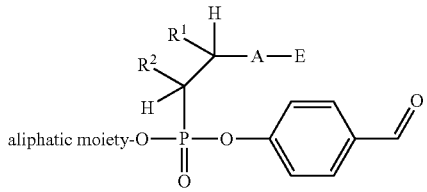

to obtain a compound of formula:

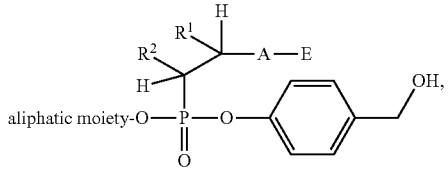

and
(ii) reacting the compound obtained in step (i) with a compound comprising a leaving group.

Paragraph 126. The method of any one of the above paragraphs, wherein D is a residue of liraglutide.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (I):

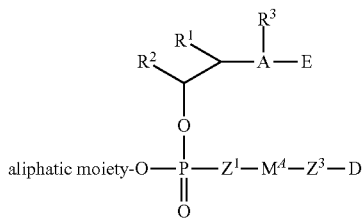

(I)

or a pharmaceutically acceptable salt thereof, wherein:
the aliphatic moiety is a polyethylene glycol having an average molecular weight from about 500 Da to about 40,000 Da;
D is a residue of a GLP-1 polypeptide or an analog thereof;
$Z^1$ is selected from O, S, and $N(R^N)$;
$Z^3$ is selected from O and $N(R^N)$, or $Z^3$ is absent;
A is O or N, wherein when A is O then $R^3$ is absent;
$R^N$ is selected from H and optionally substituted $C_{1-6}$ alkyl;
$R^3$ is selected from H and $C_{1-6}$ alkyl, or
$R^3$ and $R^1$, together with A and the carbon atom to which $R^1$ is attached, form an optionally substituted 4 to 7 membered aliphatic heterocyclic ring; or
$R^3$ and $R^2$, together with A, the carbon atom to which $R^1$ is attached, and the carbon atom to which $R^2$ is attached, form an optionally substituted 4 to 8 membered aliphatic heterocyclic ring;
$M^4$ is a self-immolative group having any one of formulae (a)-(i):

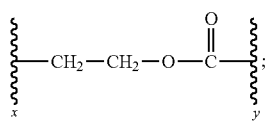

(a)

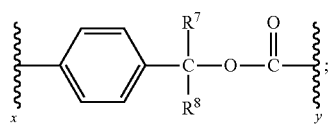

(b)

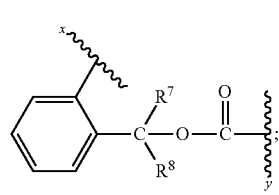

(c)

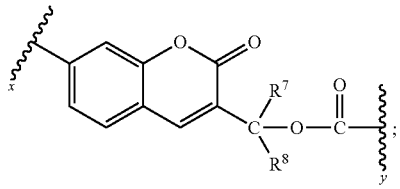

(d)

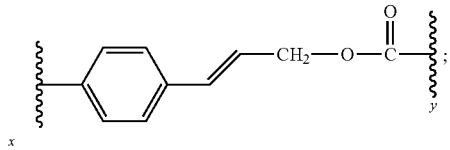

(e)

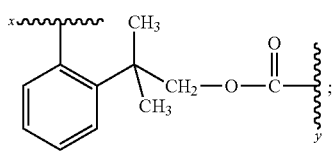

(f)

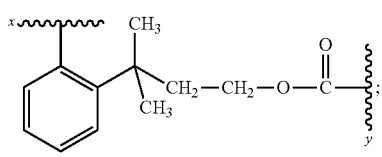

(g)

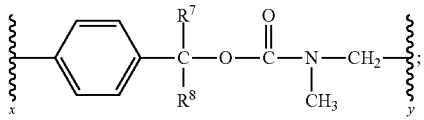

(h)

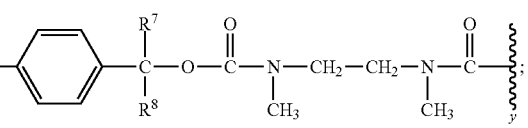

(i)

wherein x denotes a point of attachment to $Z^1$ and y denotes a point of attachment to $Z^3$;
$R^1$ and $R^2$ are independently selected from the group consisting of hydrogen, optionally substituted $C_{1-6}$ alkyl, optionally substituted $C_{6-10}$ aryl and optionally substituted 5- to 14-membered heteroaryl;
or $R^1$ and $R^2$ are joined together with the carbon atoms to which they are attached to form an optionally substituted $C_{3-7}$ cycloalkyl ring, an optionally substituted 4 to 7 membered aliphatic heterocyclic ring, an optionally substituted $C_{6-10}$ aryl or an optionally substituted 5-to 14-membered heteroaryl;
or $R^1$ and $R^2$ are joined together to form a ribose ring system;
$R^7$ and $R^8$ are independently selected from H and $C_{1-6}$ alkyl; and
E is a cleavable moiety.

2. The compound of claim 1, wherein the polyethylene glycol is linear.

3. The compound of claim 1, wherein the polyethylene glycol is branched.

4. The compound of claim 1, wherein the polyethylene glycol has an average molecular weight from about 1,000 Da to about 30,000 Da.

5. The compound of claim 1, wherein the polyethylene glycol has an average molecular weight from about 1,000 Da to about 20,000 Da.

6. The compound of claim 1, wherein the polyethylene glycol has an average molecular weight from about 5,000 Da to about 20,000 Da.

7. The compound of claim 1, wherein the polyethylene glycol has the following structural formula:

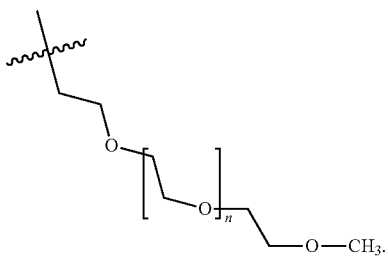

8. The compound of claim 7, wherein n is an integer from 1 to 1,000.

9. The compound of claim 8, wherein n is selected from 10, 20, 50, 100, 200, 250, 300, 500, 600, and 1000.

10. The compound of claim 1, wherein:
$Z^1$ is O;
$Z^2$ is O; and
$Z^3$ is NH.

11. The compound of claim 1, wherein $R^1$ and $R^2$ together form a ribose ring system of formula:

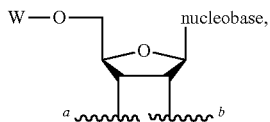

wherein either a denotes a point of attachment to O and b denotes a point of attachment to A, a denotes a point of attachment to A and b denotes a point of attachment to O, and wherein W is selected from the group consisting of H, an acyl group and a protecting group.

12. The compound of claim 11, wherein:
$Z^1$ is O;
$Z^2$ is O; and
$Z^3$ is NH.

13. The compound of claim 11, wherein the nucleobase is selected from the group consisting of adenine, cytosine, guanine, thymine, uracil, and other natural and non-natural nucleobases.

14. The compound of claim 1, wherein A is O or NH.

15. The compound of claim 1, wherein E is cleavable by an enzyme selected from the group consisting of an esterase, a specific or an unspecific peptidase, a reductase, an oxidase, a glycosidase, a hydrolase, a glycosyl transferase, and a transaminase, or E is non-enzymatically cleavable at acidic or physiological pH.

16. The compound of claim 1, wherein the compound of Formula (I) has any one of the following formulae:

(I-2)

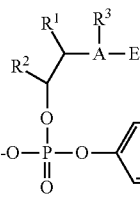

(I-3)

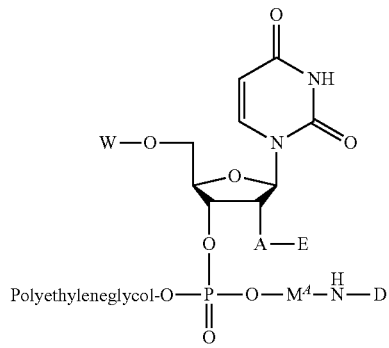

(I-4)

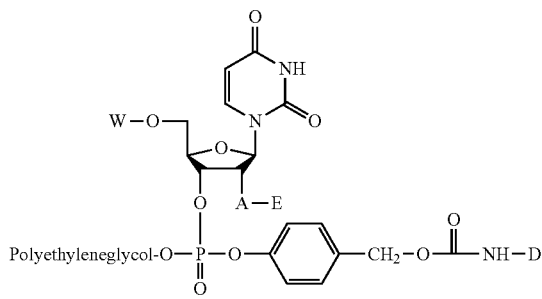

(I-7)

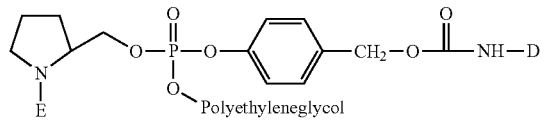

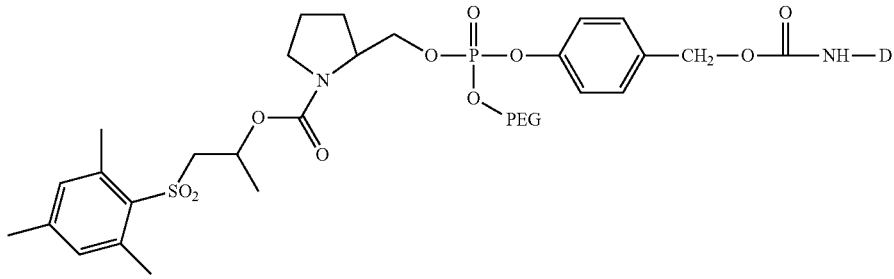
(I-8)

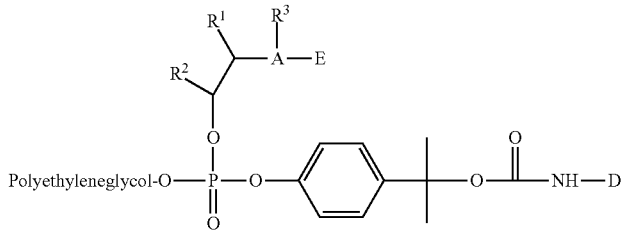
(I-9)

or a pharmaceutically acceptable salt thereof.

17. The compound of claim 1, wherein the GLP-1 polypeptide or an analog thereof is selected from liraglutide, dulaglutide, taspoglutide, albiglutide, semaglutide, teduglutide, glepaglutide, and elsiglutide.

18. The compound of claim 1, wherein the GLP-1 polypeptide analog is liraglutide.

19. A pharmaceutical composition comprising the compound of claim 1, or a pharmaceutically acceptable salt thereof, and a pharmaceutically acceptable carrier.

20. A method of treating a disease or condition selected from diabetes and obesity in a subject in need thereof, the method comprising administering to the subject a therapeutically effective amount of the compound of claim 1, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 11,957,735 B2 | Page 1 of 1 |
| APPLICATION NO. | : 17/559692 | |
| DATED | : April 16, 2024 | |
| INVENTOR(S) | : Marek Kwiatkowski and Christian Sund | |

It is certified that error appears in the above-identified patent and that said Letters Patent is hereby corrected as shown below:

In the Claims

Column 190, Line 61, Claim 1 – delete "5-to" and insert -- 5- to --.

Signed and Sealed this
Sixth Day of August, 2024

Katherine Kelly Vidal
*Director of the United States Patent and Trademark Office*

SEQUENCE LISTING

<160> NUMBER OF SEQ ID NOS: 25

<210> SEQ ID NO 1
<211> LENGTH: 37
<212> TYPE: PRT
<213> ORGANISM: Unknown
<220> FEATURE:
<221> NAME/KEY: source
<223> OTHER INFORMATION: /note="Description of Unknown:
      GLP-1 sequence"

<400> SEQUENCE: 1

His Asp Glu Phe Glu Arg His Ala Glu Gly Thr Phe Thr Ser Asp Val
1               5                   10                  15

Ser Ser Tyr Leu Glu Gly Gln Ala Ala Lys Glu Phe Ile Ala Trp Leu
            20                  25                  30

Val Lys Gly Arg Gly
        35

<210> SEQ ID NO 2
<211> LENGTH: 31
<212> TYPE: PRT
<213> ORGANISM: Unknown
<220> FEATURE:
<221> NAME/KEY: source
<223> OTHER INFORMATION: /note="Description of Unknown:
      GLP-1 sequence"

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (20)..(20)
<223> OTHER INFORMATION: Lys(gamma-Glu-palmitoyl)

<400> SEQUENCE: 3

His Ala Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
            20                  25                  30

<210> SEQ ID NO 4
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly

-continued

<210> SEQ ID NO 5
<211> LENGTH: 29
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 6
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Thr Ser Asp Val Ser Ser Tyr Leu Glu Gly Gln Ala Ala Lys Glu Phe
1               5                   10                  15

Ile Ala Trp Leu Val Arg Gly Arg Gly
            20                  25

<210> SEQ ID NO 7
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Ala Lys Glu Phe Ile Ala Trp Leu Val Arg Gly Arg Gly
1               5                   10

<210> SEQ ID NO 8
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 9
<211> LENGTH: 228
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 9

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225
```

<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
Gly Gly Gly Gly Ser Gly Gly Gly Ser Gly Gly Gly Ser Ala
1               5                   10                  15
```

<210> SEQ ID NO 11
<211> LENGTH: 275
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
His Gly Glu Gly Thr Phe Thr Ser Asp Val Ser Ser Tyr Leu Glu Glu
1               5                   10                  15
```

```
Gln Ala Ala Lys Glu Phe Ile Ala Trp Leu Val Lys Gly Gly Gly
                20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
            115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
            195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275

<210> SEQ ID NO 12
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
        35

<210> SEQ ID NO 13
<211> LENGTH: 30
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: 2-methyl alanine
<220> FEATURE:
<221> NAME/KEY: MOD_RES
<222> LOCATION: (29)..(29)
<223> OTHER INFORMATION: 2-methyl alanine

<400> SEQUENCE: 13

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Arg
            20                  25                  30

<210> SEQ ID NO 14
<211> LENGTH: 44
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 15
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 16
<211> LENGTH: 645
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45
```

-continued

```
Ala Lys Glu Phe Ile Ala Trp Leu Val Lys Gly Arg Asp Ala His Lys
 50                  55                  60

Ser Glu Val Ala His Arg Phe Lys Asp Leu Gly Glu Glu Asn Phe Lys
 65                  70                  75                  80

Ala Leu Val Leu Ile Ala Phe Ala Gln Tyr Leu Gln Gln Cys Pro Phe
                     85                  90                  95

Glu Asp His Val Lys Leu Val Asn Glu Val Thr Glu Phe Ala Lys Thr
                100                 105                 110

Cys Val Ala Asp Glu Ser Ala Glu Asn Cys Asp Lys Ser Leu His Thr
                115                 120                 125

Leu Phe Gly Asp Lys Leu Cys Thr Val Ala Thr Leu Arg Glu Thr Tyr
130                 135                 140

Gly Glu Met Ala Asp Cys Cys Ala Lys Gln Glu Pro Glu Arg Asn Glu
145                 150                 155                 160

Cys Phe Leu Gln His Lys Asp Asp Asn Pro Asn Leu Pro Arg Leu Val
                165                 170                 175

Arg Pro Glu Val Asp Val Met Cys Thr Ala Phe His Asp Asn Glu Glu
                180                 185                 190

Thr Phe Leu Lys Lys Tyr Leu Tyr Glu Ile Ala Arg Arg His Pro Tyr
                195                 200                 205

Phe Tyr Ala Pro Glu Leu Leu Phe Phe Ala Lys Arg Tyr Lys Ala Ala
210                 215                 220

Phe Thr Glu Cys Cys Gln Ala Ala Asp Lys Ala Ala Cys Leu Leu Pro
225                 230                 235                 240

Lys Leu Asp Glu Leu Arg Asp Glu Gly Lys Ala Ser Ser Ala Lys Gln
                245                 250                 255

Arg Leu Lys Cys Ala Ser Leu Gln Lys Phe Gly Glu Arg Ala Phe Lys
                260                 265                 270

Ala Trp Ala Val Ala Arg Leu Ser Gln Arg Phe Pro Lys Ala Glu Phe
                275                 280                 285

Ala Glu Val Ser Lys Leu Val Thr Asp Leu Thr Lys Val His Thr Glu
290                 295                 300

Cys Cys His Gly Asp Leu Leu Glu Cys Ala Asp Asp Arg Ala Asp Leu
305                 310                 315                 320

Ala Lys Tyr Ile Cys Glu Asn Gln Asp Ser Ile Ser Ser Lys Leu Lys
                325                 330                 335

Glu Cys Cys Glu Lys Pro Leu Leu Glu Lys Ser His Cys Ile Ala Glu
                340                 345                 350

Val Glu Asn Asp Glu Met Pro Ala Asp Leu Pro Ser Leu Ala Ala Asp
                355                 360                 365

Phe Val Glu Ser Lys Asp Val Cys Lys Asn Tyr Ala Glu Ala Lys Asp
370                 375                 380

Val Phe Leu Gly Met Phe Leu Tyr Glu Tyr Ala Arg Arg His Pro Asp
385                 390                 395                 400

Tyr Ser Val Val Leu Leu Leu Arg Leu Ala Lys Thr Tyr Glu Thr Thr
                405                 410                 415

Leu Glu Lys Cys Cys Ala Ala Ala Asp Pro His Glu Cys Tyr Ala Lys
                420                 425                 430

Val Phe Asp Glu Phe Lys Pro Leu Val Glu Glu Pro Gln Asn Leu Ile
                435                 440                 445

Lys Gln Asn Cys Glu Leu Phe Glu Gln Leu Gly Glu Tyr Lys Phe Gln
450                 455                 460

Asn Ala Leu Leu Val Arg Tyr Thr Lys Lys Val Pro Gln Val Ser Thr
```

```
                465                 470                 475                 480
        Pro Thr Leu Val Glu Val Ser Arg Asn Leu Gly Lys Val Gly Ser Lys
                        485                 490                 495

Cys Cys Lys His Pro Glu Ala Lys Arg Met Pro Cys Ala Glu Asp Tyr
                        500                 505                 510

Leu Ser Val Val Leu Asn Gln Leu Cys Val Leu His Glu Lys Thr Pro
                        515                 520                 525

Val Ser Asp Arg Val Thr Lys Cys Cys Thr Glu Ser Leu Val Asn Arg
                530                 535                 540

Arg Pro Cys Phe Ser Ala Leu Glu Val Asp Glu Thr Tyr Val Pro Lys
        545                 550                 555                 560

Glu Phe Asn Ala Glu Thr Phe Thr Phe His Ala Asp Ile Cys Thr Leu
                        565                 570                 575

Ser Glu Lys Glu Arg Gln Ile Lys Lys Gln Thr Ala Leu Val Glu Leu
                        580                 585                 590

Val Lys His Lys Pro Lys Ala Thr Lys Glu Gln Leu Lys Ala Val Met
                        595                 600                 605

Asp Asp Phe Ala Ala Phe Val Glu Lys Cys Cys Lys Ala Asp Asp Lys
                        610                 615                 620

Glu Thr Cys Phe Ala Glu Glu Gly Lys Lys Leu Val Ala Ala Ser Gln
        625                 630                 635                 640

Ala Ala Leu Gly Leu
                        645

<210> SEQ ID NO 17
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (20)..(20)
<223> OTHER INFORMATION: Lys(AEEAc-AEEAc-gamma-Glu-17-
      carboxyheptadecanoyl)

<400> SEQUENCE: 17

His Xaa Glu Gly Thr Phe Thr Ser Asp Val Ser Ser Tyr Leu Glu Gly
1               5                   10                  15

Gln Ala Ala Xaa Glu Phe Ile Ala Trp Leu Val Arg Gly Arg Gly
                20                  25                  30

<210> SEQ ID NO 18
<211> LENGTH: 33
<212> TYPE: PRT
<213> ORGANISM: Unknown
<220> FEATURE:
<221> NAME/KEY: source
<223> OTHER INFORMATION: /note="Description of Unknown:
      GLP-2 sequence"

<400> SEQUENCE: 18

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
                20                  25                  30
```

Asp

<210> SEQ ID NO 19
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 20
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (11)..(11)
<223> OTHER INFORMATION: D-Phe

<400> SEQUENCE: 20

His Gly Asp Gly Ser Phe Ser Asp Glu Xaa Xaa Thr Ile Leu Asp Leu
1               5                   10                  15

Leu Ala Ala Arg Asp Phe Ile Asn Trp Leu Ile Gln Thr Lys Ile Thr
            20                  25                  30

Asp

<210> SEQ ID NO 21
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

His Gly Glu Gly Thr Phe Ser Ser Glu Leu Ala Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 22
<211> LENGTH: 39
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"

<400> SEQUENCE: 22

His Gly Glu Gly Ser Phe Ser Ser Glu Leu Ser Thr Ile Leu Asp Ala
1               5                   10                  15

Leu Ala Ala Arg Asp Phe Ile Ala Trp Leu Ile Ala Thr Lys Ile Thr
            20                  25                  30

Asp Lys Lys Lys Lys Lys Lys
        35

<210> SEQ ID NO 23
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His Gly
            20                  25                  30

Glu Gly Thr Phe Thr Ser Asp Val Ser Ser Tyr Leu Glu Gly Gln Ala
        35                  40                  45

Ala Lys Glu Phe Ile Ala Trp Leu Val Lys Gly Arg
    50                  55                  60

<210> SEQ ID NO 24
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(2)
<223> OTHER INFORMATION: Alpha-aminoisobutyric acid

<400> SEQUENCE: 24

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 25
<211> LENGTH: 62
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: NON_CONS
<222> LOCATION: (31)..(32)

<400> SEQUENCE: 25

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
```

```
            20                  25                  30
Gly Gly Lys Val Leu Trp Ala Ile Phe Glu Lys Ala Ala Gln Glu Glu
            35                  40                  45
Leu Tyr Ser Ser Val Asp Ser Thr Phe Arg Gly Glu Gly His
50                  55                  60
```